(12) United States Patent
Goodman et al.

(10) Patent No.: US 12,221,472 B2
(45) Date of Patent: *Feb. 11, 2025

(54) COMPOSITIONS AND METHODS FOR THE REMOVAL OF BIOFILMS

(71) Applicant: Research Institute at Nationwide Children's Hospital, Columbus, OH (US)

(72) Inventors: Steven D. Goodman, Hilliard, OH (US); Lauren O. Bakaletz, Hilliard, OH (US)

(73) Assignee: Research Institute at Nationwide Children's Hospital, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/168,824

(22) Filed: Feb. 14, 2023

(65) Prior Publication Data

US 2023/0235030 A1    Jul. 27, 2023

Related U.S. Application Data

(60) Division of application No. 17/552,986, filed on Dec. 16, 2021, now Pat. No. 11,629,182, which is a continuation of application No. 15/999,215, filed on Aug. 16, 2018, now Pat. No. 11,274,144, which is a division of application No. 15/078,987, filed on Mar. 23, 2016, now abandoned, which is a continuation-in-part of application No. 14/967,228, filed on Dec. 11, 2015, now abandoned, which is a continuation of application No. PCT/US2014/042201, filed on Jun. 12, 2014.

(60) Provisional application No. 62/199,952, filed on Jul. 31, 2015, provisional application No. 61/834,846, filed on Jun. 13, 2013.

(51) Int. Cl.

| C07K 16/12 | (2006.01) |
|---|---|
| A01N 37/46 | (2006.01) |
| A61K 39/02 | (2006.01) |
| A61K 39/39 | (2006.01) |
| A61K 39/395 | (2006.01) |
| A61K 39/40 | (2006.01) |
| A61K 45/06 | (2006.01) |
| C07K 16/40 | (2006.01) |
| G01N 33/569 | (2006.01) |
| G01N 33/68 | (2006.01) |
| A61K 39/00 | (2006.01) |

(52) U.S. Cl.
CPC .......... *C07K 16/1242* (2013.01); *A01N 37/46* (2013.01); *A61K 39/0208* (2013.01); *A61K 39/39541* (2013.01); *A61K 39/40* (2013.01); *A61K 45/06* (2013.01); *C07K 16/12* (2013.01); *C07K 16/1232* (2013.01); *C07K 16/40* (2013.01); *G01N 33/56911* (2013.01); *G01N 33/6854* (2013.01); *G01N 33/6893* (2013.01); *A61K 2039/505* (2013.01); *C07K 2317/34* (2013.01); *C07K 2317/76* (2013.01); *G01N 2500/04* (2013.01); *G01N 2800/24* (2013.01)

(58) Field of Classification Search
None
See application file for complete search history.

(56) References Cited

U.S. PATENT DOCUMENTS

| 5,549,908 | A | 8/1996 | Smith et al. |
|---|---|---|---|
| 6,486,314 | B1 | 11/2002 | Van Geel-Schutten et al. |
| 6,551,795 | B1 | 4/2003 | Rubenfield et al. |
| 6,663,863 | B2 | 12/2003 | Horvath et al. |
| 6,696,550 | B2 | 2/2004 | Larosa et al. |
| 6,846,651 | B2 | 1/2005 | Fleischmann et al. |
| 7,241,867 | B2 | 7/2007 | Bakaletz et al. |
| 7,413,868 | B2 | 8/2008 | Kauvar et al. |
| 7,435,595 | B2 | 10/2008 | Boehm et al. |
| 7,638,282 | B2 | 12/2009 | Bakaletz et al. |
| 7,811,591 | B2 | 10/2010 | Bakaletz et al. |
| 7,816,086 | B2 | 10/2010 | Bakaletz et al. |
| 7,939,344 | B2 | 5/2011 | Kauvar et al. |
| 7,981,676 | B2 | 7/2011 | Boehm et al. |
| 7,998,490 | B2 | 8/2011 | Bakaletz et al. |
| 8,236,494 | B2 | 8/2012 | Bakaletz et al. |

(Continued)

FOREIGN PATENT DOCUMENTS

| JP | 2005-519998 A | 7/2005 |
|---|---|---|
| JP | 2006-506441 A | 2/2006 |

(Continued)

OTHER PUBLICATIONS

U.S. Appl. No. 15/649,352, filed Jul. 13, 2017.

(Continued)

*Primary Examiner* — Oluwatosin A Ogunbiyi

(74) *Attorney, Agent, or Firm* — Foley & Lardner LLP

(57) ABSTRACT

This disclosure provides isolated or recombinant polypeptides that are useful to vaccinate individuals suffering from chronic/recurrent biofilm disease or as a therapeutic for those with an existing infection. The individual's immune system will then naturally generate antibodies which prevent or clear these bacteria from the host by interfering with the construction and or maintenance of a functional protective biofilm. Alternatively, antibodies to the polypeptides can be administered to treat or prevent infection. Bacteria that cannot form functional biofilms are more readily cleared by the remainder of the host's immune system and/or traditional antibiotics.

11 Claims, 40 Drawing Sheets

Specification includes a Sequence Listing.

(56) References Cited

U.S. PATENT DOCUMENTS

| | | |
|---|---|---|
| 8,283,114 B2 | 10/2012 | Bakaletz et al. |
| 8,329,187 B2 | 12/2012 | Lazzari et al. |
| 8,628,917 B2 | 1/2014 | Bakaletz et al. |
| 8,652,773 B2 | 2/2014 | Bakaletz et al. |
| 8,758,764 B2 | 6/2014 | Masignani et al. |
| 8,933,029 B2 | 1/2015 | Mcnicol et al. |
| 8,999,291 B2 | 4/2015 | Goodman et al. |
| 9,017,656 B2 | 4/2015 | Hancock et al. |
| 9,034,642 B2 | 5/2015 | Bakaletz et al. |
| 9,155,792 B2 | 10/2015 | Cottarel et al. |
| 9,278,069 B2 | 3/2016 | Berkland et al. |
| 9,504,739 B2 | 11/2016 | Berkes et al. |
| 9,554,590 B2 | 1/2017 | Quintens et al. |
| 9,603,878 B2 | 3/2017 | Berry et al. |
| 9,610,307 B2 | 4/2017 | Berry et al. |
| 9,687,449 B2 | 6/2017 | Harel |
| 9,713,631 B2 | 7/2017 | Berkes et al. |
| 9,717,765 B2 | 8/2017 | Berkes et al. |
| 9,745,366 B2 | 8/2017 | Goodman et al. |
| 10,233,234 B2 | 3/2019 | Kauvar et al. |
| 10,369,176 B2 | 8/2019 | Goodman et al. |
| 10,570,193 B2 | 2/2020 | Kauvar et al. |
| 10,595,530 B2 | 3/2020 | Goodman et al. |
| 10,624,934 B2 | 4/2020 | Goodman et al. |
| 10,642,934 B2 | 5/2020 | Heck et al. |
| 11,248,040 B2 | 2/2022 | Kauvar et al. |
| 11,497,780 B2 | 11/2022 | Goodman et al. |
| 2002/0132753 A1 | 9/2002 | Rosen et al. |
| 2003/0060410 A1 | 3/2003 | Tracey et al. |
| 2003/0099602 A1 | 5/2003 | Levin et al. |
| 2003/0229065 A1 | 12/2003 | Levy et al. |
| 2004/0202670 A1 | 10/2004 | Apicella |
| 2005/0049402 A1 | 3/2005 | Babcook et al. |
| 2005/0059633 A1 | 3/2005 | Van Geel-Schuten |
| 2005/0112235 A1 | 5/2005 | Shefer et al. |
| 2005/0131222 A1 | 6/2005 | Fleischmann et al. |
| 2005/0170504 A1 | 8/2005 | Boehm et al. |
| 2005/0221439 A1 | 10/2005 | Bakaletz et al. |
| 2005/0266069 A1 | 12/2005 | Simmons et al. |
| 2006/0030539 A1 | 2/2006 | Nick et al. |
| 2006/0099207 A1 | 5/2006 | Wu et al. |
| 2006/0121047 A1 | 6/2006 | Tracey |
| 2006/0240045 A1 | 10/2006 | Berthet et al. |
| 2007/0154529 A1 | 7/2007 | Bullerdiek |
| 2007/0264256 A1 | 11/2007 | Bakaletz et al. |
| 2007/0286822 A1 | 12/2007 | Sanders et al. |
| 2008/0267966 A1 | 10/2008 | Masignani et al. |
| 2009/0029929 A1 | 1/2009 | Nakajima et al. |
| 2009/0155912 A1 | 6/2009 | Boehm et al. |
| 2009/0297555 A1 | 12/2009 | Kemble et al. |
| 2009/0324651 A1 | 12/2009 | Old et al. |
| 2010/0166771 A1 | 7/2010 | Bakaletz et al. |
| 2010/0291177 A1 | 11/2010 | Hermans et al. |
| 2010/0303723 A1 | 12/2010 | Farokhzad et al. |
| 2010/0310569 A1 | 12/2010 | Bakaletz et al. |
| 2011/0008493 A1 | 1/2011 | Zorea |
| 2011/0027328 A1 | 2/2011 | Baig et al. |
| 2011/0135646 A1 | 6/2011 | Bakaletz et al. |
| 2011/0236306 A1* | 9/2011 | Goodman ............ C07K 16/1203 424/257.1 |
| 2011/0293624 A1 | 12/2011 | Bakaletz et al. |
| 2012/0128701 A1 | 5/2012 | Goodman et al. |
| 2012/0148615 A1 | 6/2012 | Masignani et al. |
| 2012/0189558 A1 | 7/2012 | Prendergast |
| 2012/0247993 A1 | 10/2012 | Palazzi et al. |
| 2013/0017204 A1 | 1/2013 | Bakaletz et al. |
| 2013/0078254 A1 | 3/2013 | Bakaletz et al. |
| 2013/0183323 A1 | 7/2013 | Wang |
| 2014/0010918 A1 | 1/2014 | Quintens et al. |
| 2014/0120107 A1 | 5/2014 | Bakaletz et al. |
| 2014/0127221 A1 | 5/2014 | Bakaletz et al. |
| 2014/0287426 A1 | 9/2014 | Arnold et al. |
| 2014/0356389 A1 | 12/2014 | Masignani et al. |
| 2015/0010654 A1 | 1/2015 | Arnold et al. |
| 2015/0086542 A1 | 3/2015 | Goodman et al. |
| 2015/0086561 A1 | 3/2015 | Kauvar et al. |
| 2015/0110838 A1 | 4/2015 | Agrawal |
| 2015/0166641 A1 | 6/2015 | Goodman et al. |
| 2015/0197558 A1 | 7/2015 | Kauvar et al. |
| 2015/0216971 A1 | 8/2015 | Rotolo et al. |
| 2015/0218231 A1 | 8/2015 | Bakaletz et al. |
| 2015/0290140 A1 | 10/2015 | Singh et al. |
| 2015/0299298 A1 | 10/2015 | Kauvar et al. |
| 2015/0342848 A1 | 12/2015 | Bhushan et al. |
| 2016/0089363 A1 | 3/2016 | Borody |
| 2016/0095316 A1 | 4/2016 | Goodman et al. |
| 2016/0143961 A1 | 5/2016 | Berry et al. |
| 2016/0175440 A1 | 6/2016 | Goodman et al. |
| 2016/0193258 A1 | 7/2016 | Berry et al. |
| 2016/0194384 A1 | 7/2016 | Goodman et al. |
| 2016/0199424 A1 | 7/2016 | Berry et al. |
| 2016/0223553 A1 | 8/2016 | Sears et al. |
| 2016/0235792 A1 | 8/2016 | Berry et al. |
| 2016/0237145 A1 | 8/2016 | Kauvar et al. |
| 2016/0244489 A1 | 8/2016 | Masignani et al. |
| 2016/0271188 A1 | 9/2016 | Berry et al. |
| 2016/0289278 A1 | 10/2016 | Bakaletz et al. |
| 2016/0340650 A1 | 11/2016 | Wagner et al. |
| 2017/0056454 A1 | 3/2017 | Berkes et al. |
| 2017/0056455 A1 | 3/2017 | Berkes et al. |
| 2017/0128502 A1 | 5/2017 | Berkes et al. |
| 2017/0182205 A1 | 6/2017 | Zupancic et al. |
| 2017/0196914 A1 | 7/2017 | Mckenzie et al. |
| 2017/0196915 A1 | 7/2017 | Czarnecki-Maulden et al. |
| 2017/0197028 A1 | 7/2017 | Goldsmith |
| 2017/0209504 A1 | 7/2017 | Goodman et al. |
| 2017/0215417 A1 | 8/2017 | Bhushan et al. |
| 2017/0216377 A1 | 8/2017 | Berkes et al. |
| 2017/0281699 A1 | 10/2017 | Berkes et al. |
| 2017/0296600 A1 | 10/2017 | Rangavajla |
| 2018/0071344 A1 | 3/2018 | Berry et al. |
| 2018/0207067 A1 | 7/2018 | Goodman et al. |
| 2018/0221422 A1 | 8/2018 | Keshtmand et al. |
| 2018/0303900 A1 | 10/2018 | Bakaletz et al. |
| 2019/0040127 A1 | 2/2019 | Wadehra et al. |
| 2019/0055304 A1 | 2/2019 | Kauvar et al. |
| 2019/0337996 A1 | 11/2019 | Bakaletz et al. |
| 2019/0338018 A1 | 11/2019 | Bakaletz et al. |
| 2019/0388309 A1 | 12/2019 | Goodman et al. |
| 2020/0002409 A1 | 1/2020 | Goodman et al. |
| 2020/0155620 A1 | 5/2020 | Goodman et al. |
| 2020/0190170 A1 | 6/2020 | Kauvar et al. |
| 2021/0100854 A1 | 4/2021 | Goodman et al. |
| 2021/0139551 A1 | 5/2021 | Goodman et al. |
| 2021/0228716 A1 | 7/2021 | Bakaletz et al. |
| 2021/0340198 A1 | 11/2021 | Goodman et al. |
| 2022/0259294 A1 | 8/2022 | Kauvar et al. |

FOREIGN PATENT DOCUMENTS

| | | | |
|---|---|---|---|
| JP | 2006-506467 A | 2/2006 | |
| JP | 2008-520552 A | 6/2008 | |
| JP | 2013-529893 A | 7/2013 | |
| WO | WO-98/50018 A1 | 11/1998 | |
| WO | WO-00/47104 A2 | 8/2000 | |
| WO | WO-02/077183 A2 | 10/2002 | |
| WO | WO-02/085295 | 10/2002 | |
| WO | WO-03/026691 A1 | 4/2003 | |
| WO | WO-03/026691 A2 | 4/2003 | |
| WO | WO-03/083045 A2 | 10/2003 | |
| WO | WO-2004/014418 A2 | 2/2004 | |
| WO | WO-2004/044001 A2 | 5/2004 | |
| WO | WO-2004/072094 A2 | 8/2004 | |
| WO | WO-2004078949 A2 * | 9/2004 | ............ A61P 27/16 |
| WO | WO-2005/025604 A2 | 3/2005 | |
| WO | WO-2005/111066 A2 | 11/2005 | |
| WO | WO-2006/017816 A2 | 2/2006 | |
| WO | WO-2006/083301 A2 | 8/2006 | |
| WO | WO-2006/114805 A2 | 11/2006 | |
| WO | WO-2006/138527 | 12/2006 | |
| WO | WO-2007/001422 A2 | 1/2007 | |
| WO | WO-2009/006699 A1 | 1/2009 | |
| WO | WO-2010/138522 A2 | 12/2010 | |
| WO | WO-2011/123396 A1 | 10/2011 | |

(56) References Cited

FOREIGN PATENT DOCUMENTS

| WO | WO-2012/034090 A1 | 3/2012 |
|---|---|---|
| WO | WO-2013/088045 A1 | 6/2013 |
| WO | WO-2013/177596 A2 | 11/2013 |
| WO | WO-2014/067976 A1 | 5/2014 |
| WO | WO-2014/121304 A1 | 8/2014 |
| WO | WO-2014/201305 A1 | 12/2014 |
| WO | WO-2015/038339 A1 | 3/2015 |
| WO | WO-2015/048484 A2 | 4/2015 |
| WO | WO-2016/154491 A1 | 9/2016 |
| WO | WO-2017/192594 A1 | 11/2017 |
| WO | WO-2018/042385 A2 | 3/2018 |
| WO | WO-2018/187615 A1 | 10/2018 |
| WO | WO-2019/112978 A2 | 6/2019 |
| WO | WO-2020/038963 A1 | 2/2020 |
| WO | WO-2020/092554 A1 | 5/2020 |
| WO | WO-2021/007260 A2 | 1/2021 |

OTHER PUBLICATIONS

U.S. Appl. No. 16/746,708, filed Jan. 17, 2020.
U.S. Appl. No. 17/150,731, filed Jan. 15, 2021.
Adams et al., "D-158. Epitope-mapping the immune response of children with otitis media and adults with chronic obstructive pulmonary disease to the PilA protein of nontypeable Haemophilus influenzae type IV pilus," 107th General Meeting, American Society for Microbiology; Toronto, ON, 2007, 1 page.
Adams et al., "Epitope-mapping the immune response of children with otitis media and adults with chronic obstructive pulmonary disease to the PilA protein of nontypeable Haemophilus influenzae type IV pilus," Immunology, 9th International Symposium on Recent Advances in Otitis Media; St. Pete Beach, FL, 2007, p. 356, 1 page.
Allaker et al., "Non-conventional therapeutics for oral infections," Virulence, vol. 6, No. 3, Apr. 2015, pp. 196-207.
Andersson et al. (2011) "HMGB1 Is a Therapeutic Target for Sterile Inflammation and Infection," Annu. Rev. Immunol. 29:139-162.
Bakaletz et al., "New strategies to target bacterial biofilms", 28th Annual North American Cystic Fibrosis Conference (NACFC), Atlanta, GA, Oct. 9-11, 2014 (presentation), 2 pages.
Bakaletz et al., "Relative immunogenicity and efficacy of two synthetic chimeric peptides of fimbrin as vaccinogens against nasopharyngeal colonization by nontypeable Haemophilus influenzae in the chincilla," Vaccine, vol. 15, No. 9, 1997, pp. 955-961.
Bakaletz et al., "Protection against Development of Otitis Media Induced by Nontypeable Haemophilus influenzae by Both Active and Passive Immunization in a Chinchilla Model of Virus-Bacterium Superinfection," Infection and Immunity, vol. 67, No. 6, Jun. 1999, pp. 2746-2762.
Bakaletz, "Biofilms can be dispersed by focusing the immune system on a common family of bacterial nucleoid associated proteins", 6th ASM Conference on Biofilms, Miami, FL, Sep. 29-Oct. 4, 2012 (presentation), 5 pages.
Bakaletz, L.O., Targeting the biofilm for development of novel preventative and therapeutic vaccine candidates to prevent otitis media, 6th ASM Conference on Biofilms, Miami, FL, Sep. 29-Oct. 4, 2012 (presentation), 5 pages.
Barve et al., "Cloning and characterization of the mating type (MAT) locus from Ascochyta rabiei (teleomorph: Didymella rabiei) and a MAT phylogeny of legume-associated *Ascochyta* spp.," Fungal Genetics and Biology, vol. 39, No. 2, Feb. 10, 2003, pp. 151-167.
Bass, et al. "Extracellular DNA: A Major Proinflammatory Component of Pseudomonas aeruginosa Biofilms," The Journal of Immunology, (2010) 184:6386-6395.
Beech, et al. "Microbe-surface interactions in biofouling and biocorrosion processes," International Microbiology (2005) 8:157-168.
Ben et al., "Low level of galacto-oligosaccharide in infant formula stimulates growth of intestinal Bifidobacteria and Lactobacilli," World Journal of Gastroenterology, vol. 14, No. 42, Nov. 14, 2008, pp. 6564-6568.
Bjarnsholt, "The role of bacterial biofilms in chronic infections," APMIS (2013) 121(Suppl. 136):1-51.
Boles et al., "Staphylococcal biofilm disassembly," Trends in Microbiology (2011) 19(9):449-455.
Brady et al., "Identification of Staphylococcus aureus Proteins Recognized by the Antibody-Mediated Immune Response to a Biofilm Infection," Infection and Immunity (2006) 74(6):3415-3426.
Brandstetter et al., "Antibodies Directed Against Integration Host Factor Mediate Biofilm Clearance From Nasopore," The Laryngoscope, vol. 12, No. 11, Nov. 2013, pp. 2626-2632.
Brinkmann et al., "Neutrophil extracellular traps kill bacteria", Science. 2004; 303(5663):1532-5. doi: 10.1126/science. 1092385.
Brockson et al., "Evaluation of the kinetics and mechanism of action anti-integration host factor-mediated disruption of bacterial biofilms: Anti-IHF-mediated biofilm collapse", Molecular Microbiology, Epub Aug. 19, 2014, 93(6):1246-1258.
Brockson et al., "Evaluation of the kinetics and mechanism of action of anti-integration host factor-mediated disruption of bacterial biofilms," Molecular Microbiology, vol. 93, No. 6, Aug. 19, 2014, pp. 1246-1258, Supplementary Material.
Brockson et al., "Evaluation of the kinetics and mechanism of action of anti-integration host factor-mediated disruption of bacterial biofilms," Molecular Microbiology, vol. 93, No. 6, Aug. 19, 2014, pp. 1246-1258.
Brockson, et al., "Evaluation of the kinetics and mechanism of action of anti-integration host factor-mediated disruption of bacterial biofilms", Molecular microbiology. 2014; 93(6): 1246-58. Epub Jul. 30, 2014.
Catlin, "Extracellular Deoxyribonucleic Acid of Bacteria and a Deoxyribonuclease Inhibitor," Science, vol. 124, Sep. 7, 1956, pp. 441-442.
Ceri, et al., "The Calgary Biofilm Device: New Technology for Rapid Determination of Antibiotic Susceptibilities of Bacterial Biofilms," Journal of Clinical Microbiology (1999) 37(6):1771-1776.
Chen et al., "Novel Strategies for the Prevention and Treatment of Biofilm Related Infections," Int. J. Mol. Sci., vol. 14, Sep. 6, 2013, pp. 18488-18501.
Chen et al., "Substrate specificity of Helicobacter pylori histone-like HU protein is determined by insufficient stabilization of DNA flexure points," Biochem J. (2004) 383:343-351.
Cho et al., "The modulation of the biological activities of mitochondrial histone Abf2p by yeast PKA and its possible role in the regulation of mitochondrial DNA content during glucose repression," Biochimica et Biophysica Acta, vol. 1522, No. 3, Oct. 4, 2001, pp. 175-186.
Coenye et al., "In vitro and in vivo model systems to study microbial biofilm formation," Journal of Microbiological (2010) Methods 83:89-105.
Cohavy et al. "Identification of a Novel Mycobacterial Histone H1 Homologue (HupB) as an Antigenic Target of pANCA Monoclonal Antibody and Serum Immunoglobulin A from Patients with Cohn's Disease," Infection and Immunity (1999) 67(12):6510-6517.
Collarini, et al., "Potent High-Affinity Antibodies for Treatment and Prophylaxis of Respiratory Syncytial Virus Derived from B Cells of Infected Patients," J Immunol (2009) 183:6338-6345.
Dalai, et al. "Histone-like protein H-NS regulates biofilm formation and virulence of Actinobacillus pheuropneumonia," (2009) Microbial Pathogenesis 46:128-134.
Darouiche et al., "Treatment of Infections Associated with Surgical Implants," N Engl J Med (2004) 350:1422-1429.
Darvaj et al., "DNABII proteins play a central role in UPEC biofilm structure", Molecular microbiology. Jun. 2015. 96(6):1119-35, doi: 10.1111/mmi. 12994. Epub Apr. 16, 2015.
Darveau, "Periodontitis: a polymicrobial disruption of host homeostasis", Nature reviews Microbiology, vol. 8, No. 7, Jul. 2010, pp. 481-490.
Darveau, "The oral microbial consortium's interaction with the periodontal innate defense system", DNA and cell biology. 2009; 28(8):389-95. Epub May 14, 2009. doi:10.1089/dna.2009.0864.
De La Fuente-Nunez et al., "Broad-Spectrum Anti-biofilm Peptide That Targets a Cellular Stress Response," PLoS Pathog., vol. 10, No. 5, May 2014, pp. 1-12.

(56) References Cited

OTHER PUBLICATIONS

Devaraj et al., "DNABII proteins play a central role in UPEC biofilm structure", Molecular Microbiology, 2015, vol. 96, vol. 6, Jun. 2015, pp. 1119-1135.
Dominguez-Herrera, et al., "Efficacy of Daptomycin versus Vancomycin in an Experimental Model of Foreign-Body and Systemic Infection Caused by Biofilm Producers and Methicillin-Resistant *Staphylococcus epidermidis*," Antimicrobial Agents and Chemotherapy (2011) 56(2):613-617.
Donlan, et al. "Biofilms: Survival Mechanisms of Clinically Relevant Microorganisms," Clinical Microbiology Reviews (2002) 15(2):167-193.
Durocher et al., "High-level and high-throughput recombinant protein production by transient transfection of suspension-growing human 293-EBNA1 cells," Nucleic Acids Research, vol. 30, No. 2, e9, Nov. 11, 2001, 9 pages.
Dzink et al., "The predominant cultivable microbiota of active and inactive lesions of destructive periodontal diseases", Journal of clinical periodontology, vol. 15, No. 5, Sep. 8, 1987, pp. 316-323.
Eboigbodin, et al., "Characterization of the Extracellular Plymeric Substances Produced by *Escherichia coli* Using Infrared Spectroscopic, Proteomic, and Aggregation Studies," (2008) Biomacromolecules 9:686-695.
Eke et al., "Prevalence of periodontitis in adults in the United States: 2009 and 2010," Journal of dental research. 2012; 91(10):914-20. Epub Sep. 1, 2019. doi: 10.1177/0022034512457373.
Estelles et al., "A High-Affinity Native Human Antibody Disrupts Biofilm from Staphylococcus aureus Bacteria and Potentiates Antibiotic Efficacy in a Mouse Implant Infection Model," Antimicrobial Agents and Chemotherapy, vol. 60, No. 4, Apr. 2016, pp. 2292-2301.
Estrela et al., "Combining Biofilm-Controlling Compounds and Antibiotics as a Promising New Way to Control Biofilm Infections," Pharmaceuticals, vol. 3, May 11, 2010, pp. 1374-1393.
Falciola et al., "Mutational analysis of the DNA binding domain A of chromosomal protein HMG1," Nucleic Acids Research, vol. 22, No. 3, Jan. 10, 1994, pp. 285-292.
Fan, et al., "HMG2 Interacts with the Nucleosome Assembly Protein SET and Is a Target of the Cytotoxic T-Lymphocyte Protease Granzyme A," Molecular and Cellular Biology (2002) 22(8):2810-2820.
Fedorov, et al., "Kinase Inhibitor Selectivity Profiling Using Differential Scanning Fluorimetry," Kinase Inhibitors: Methods and Protocols, Methods in Molecular Biology (2012) 795:109-118.
Final Office Action in U.S. Appl. No. 15/078,987 dated Dec. 28, 2016, 12 pages.
Final Office Action on U.S. Appl. No. 14/967,228 dated Nov. 22, 2017, 26 pages.
First Examination Report on AU Application No. 2014324761 dated May 31, 2019, 4 pages.
Foreign Search Report on EP 19219328.2 DTD Jul. 15, 2020.
Garcia-Contreras et al., "Protein Translation and Cell Death: The Role of Rare tRNAs in Biofilm Formation and in Activating Dormant Phage Killer Genes," PLoS ONE, vol. 3, No. 6, Jun. 11, 2008, e2394, 17 pages.
Gerstel et al., "Complex Regulation of csgD Promoter Activity by Global Regulatory Proteins," Molecular Microbiology, vol. 49, No. 3, Aug. 2003, pp. 639-654.
Goldenberg et al., "Genetic and biochemical analysis of IHF/HU hybrid proteins", BioChimie, vol. 76, No. 10-11, Jan. 1, 1994, pp. 941-950.
Goodman et al., "Biofilms can be dispersed by focusing the immune system on a common family of bacterial nucleoid-associated proteins", Advances in Mucosal Immunology, Jun. 29, 2011, pp. 1-13.
Goodman et al., "Biofilms can be dispersed by focusing the immune system on a common family of bacterial nucleoid-associated proteins", Mucosal Immuno, Nature Publishing Group, vol. 4, No. 6, Nov. 1, 2011, pp. 625-637.
Goodman et al., "In Vitro Selection of Integration Host Factor Binding Sites," Journal of Bacteriology, vol. 181, No. 10, May 1999, pp. 3246-3255.
Goodman et al., "Replacement of Integration Host Factor Protein-induced DNA Bending by Flexible Regions of DNA," The Journal of Biological Chemistry, vol. 274, No. 52, Aug. 6, 1999, pp. 37004-37011.
Goodman, "A new immunotherapeutic approach that disperses biofilms, Banff Conference on Infectious Diseases", Banff, Alberta, Canada, May 18, 2012 (presentation), 9 pages.
Goodman, "Making and breaking biofilms", Ohio Branch American Society for Microbiology Annual Meeting, Columbus, OH, Apr. 11-12, 2014 (presentation), 12 pages.
Goodman, "Nucleoprotein complexes in the extracellular matrix are critical for the structural integrity of bacterial biofilms", 112th General Meeting, American Society for Microbiology, San Francisco, CA, Jun. 18, 2012 (presentation), 9 pages.
Goodman, "The DNABII family of proteins: Diagnostic markers and therapeutic targets of bacterial biofilms", International Congress on Bacteriology and Infectious Disease, Baltimore, MD, Nov. 21, 2013, 7 pages.
Goshima et al., "Chimeric HU-IHF proteins that alter DNA-binding ability," GENE, vol. 118, No. 1, Sep. 1, 1992, pp. 97-102.
Govan et al., "Microbial pathogenesis in cystic fibrosis: mucoid Pseudomonas aeruginosa and Burkholderia cepacia," Microbiol. Rev., vol. 60, No. 3, Sep. 1996, pp. 539-574.
Granston et al., "Characterization of a Set of Integration Host Factor Mutants Deficient for DNA Binding," J. Mol. Biol., vol. 234, Jun. 21, 1993, pp. 45-59.
Greenspan et al., "Defining epitopes: It's not as easy as it seems," Nature Biotechnology, vol. 17, Oct. 1999, pp. 936-937.
Gustave et al., "Targeting bacterial integration host factor to disrupt biofilms associated with cystic fibrosis", Journal of cystic fibrosis: official journal of the European Cystic Fibrosis Society. 2013; 12(4):384-9. Epub Nov. 22, 2012. doi:10.1016/j.jcf.2012.10.011.
Gustave et al., "Targeting bacterial integration host factor to disrupt biofilms associated with cystic fibrosis," Journal of Cystic Fibrosis, vol. 12, No. 4, Nov. 17, 2012, pp. 384-389.
Gustave et al., Biofilms recovered from the sputum of CF patients contain the bacterial protein integration host factor (IHF), 25th Annual North American Cystic Fibrosis Conference, Anaheim, CA, Nov. 3-5, 2011 (poster), 1 page.
Hall-Stoodley et al., "Bacterial Biofilms: From the Natural Environment to Infectious Diseases," Nature Reviews, Microbiology, vol. 2, Feb. 2004, pp. 95-108.
Hall-Stoodley et al., "Direct Detection of Bacterial Biofilms on the Middle-Ear Mucosa of Children With Chronic Otitis Media," JAMA, vol. 296, No. 2, Jun. 1, 2007, pp. 202-211.
Hall-Stoodley et al., "Evolving concepts in biofilm infections", Cellular Microbiology, vol. 11, No. 7, 2009, pp. 1034-1043.
Hall-Stoodley et al., "Characterization of biofilm matrix, degradation by DNase treatment and evidence of capsule downregulation in *Streptococcus pneumoniae* clinical isolates," BMC Microbiology, vol. 8, No. 173, Oct. 8, 2008, 16 pages.
Haluzi et al., "Genes Coding for Integration Host Factor Are Conserve in Gram-Negative Bacteria," Journal of Bacteriology, vol. 173, No. 19, Oct. 1991, pp. 6297-6299.
Harley et al., "The Molecular Action and Regulation of the Testis-Determining Factors, SRY (Sex-Determining Region on the Y Chromosome) and SOX9 [SRY-Related High-Mobility Group (HMG) Box 9]," Endocrine Reviews, vol. 24, No. 4, Aug. 2003, pp. 466-487.
Harriman, et al., "Antibody discovery via multiplexed single cell characterization," Journal of Immunological Methods (2008) 341:135-145.
Harrison et al., "Microtiter susceptibility testing of microbes growing on peg lids: a miniaturized biofilm model for high-throughput screening," Nature Protocols (2010) 5(7):1236-1254.
Haruta et al., "A possible role of histone-like DNA-binding protein of *Streptococcus intermedius* in the pathogenesis of bile duct damage in primary biliary cirrhosis," Clinical Immunology, vol. 127, No. 2, Mar. 11, 2008, pp. 245-251.

(56) References Cited

OTHER PUBLICATIONS

Haruta et al., "Long-term bacterial exposure can trigger nonsuppurative destructive cholangitis associated with multifocal epithelial inflammation," Laboratory Investigation, vol. 90, Apr. 2010, pp. 577-588.
Haurum. "Recombinant polyclonal antibodies: the next generation of antibody therapeutics?" Drug Discovery Today. Jul. 2006; 11(13-14):655-60.
Hoyle et al., "Bacterial Resistance to Antibiotics: The Role of Biofilms," Prog. Drug Res., vol. 37, 1991, pp. 91-105.
Idicula, et al. "Identification of Biofilms in Post-tympanostomy Tube Otorrhea," The Laryngoscope (2016) 126(8):1946-1951.
International Search Report and Written Opinion for PCT Patent Application No. PCT/US2014/042201, dated Nov. 28, 2014, 16 pages.
Janeway, "Manipulating the immune response to fight infection," Immunobiology: The Immune System in Health and Disease, 5th ed.; retrieved online from https://www.ncbi.nlm.nih.gov/books/NBK27131/, 2001, 13 pages.
Jiao et al., "Identification of Biofilm Matrix-Associated Proteins from an Acid Mine Drainage Microbial Community," Appl & Environ Microbiol., vol. 77, Aug. 2011, pp. 5230-5237.
Jodar et al., "Development of vaccines against meningococcal disease," Lancet, vol. 359, Apr. 27, 2002, pp. 1499-1508.
John, et al., "Reversible Daptomycin Tolerance of Adherent Staphylococci in an Implant Infection Model," Antimicrobial Agents and Chemotherapy (2011) 55(7):3510-3516.
Johnson et al., "Chapter 8: Bending and Compaction of DNA by Proteins," Protein-Nucleic Acid Interactions: Structural Biology, 2008, pp. 176-220.
Joo, et al., "Molecular Basis of In Vivo Formation by Bacterial Pathogens," Chemistry & Biology (2012) 19:1503-1513.
Jurcisek et al., "Biofilms formed by nontypeable Haemophilus influenzae in vivo contain both double-stranded DNA and type IV pilin protein", Journal of bacteriology. 2007; 189(10):3868-75. Epub Feb. 27, 2007. doi: 10.1128/JB.01935-06.
Jurcisek et al., "Role of Sialic Acid and Complex Carbohydrate Biosynthesis in Biofilm Formation by Nontypeable Haemophilus influenzae in the Chinchilla Middle Ear," Infection and Immunity, vol. 73, Jun. 2005, pp. 3210-3218.
Jurcisek et al., "Biofilms Formed by Nontypeable Haemophilus influenzae In Vivo Contain both Double-Stranded DNA and Type IV Pilin Protein," Journal of Bacteriology, vol. 189, No. 10, Feb. 15, 2007, pp. 3868-3875.
Justice et al., "Aberrant Community Architecture and Attenuated Persistence of Uropathogenic *Escherichia coli* in the Absence of Individual IHF Subunits," PLoS ONE, vol. 7, No. 10, Oct. 2012, pp. 1-11.
Kamashev et al., "The histone-like protein HU binds specifically to DNA recombination and repair intermediates", The EMBO journal. 2000; 19(23):6527-35.
Kamashev et al., "The histone-like protein HU binds specifically to DNA recombination and repair intermediates," The EMBO Journal, vol. 19, No. 23, Oct. 13, 2000, pp. 6527-6535.
Kennedy et al., "Passive Transfer of Antiserum Specific for Immunogens Derived from a Nontypeable Haemophilus influenzae Adhesin and Lipoprotein D Prevents Otitis Media after Heterologous Challenge," Infection and Immunity, vol. 68, No. 5, May 2000, pp. 2756-2765.
Khrapunov, et al., (2006) "Binding then bending: A mechanism for wrapping DNA," PNAS 103(51):19217-19218.
Kim et al., "Beta-Arm flexibility of HU from *Staphylococcus aureus* dictates the DNA-binding and recognition mechanism," Acta Cryst., D70, Oct. 30, 2014, pp. 3273-3289.
Kim et al., "Proteins Released by Helicobacter pylori In Vitro," Journal of Bacteriology, vol. 184, No. 22, Nov. 2002, pp. 6155-6162.
Kirketerp-Moller et al., "Distribution, Organization, and Ecology of Bacteria in Chronic Wounds," Journal of Clinical Microbiology, vol. 46, No. 8, Aug. 2008, pp. 2717-2722.
Kornblit et al., "The genetic variation of the human HMG1 gene," Tissue Antigens, vol. 70, Apr. 12, 2007, pp. 151-156.
Kristian et al., (2003) "Alanylation of Teichoic Acids Protects *Staphylococcus aureus* against Toll-like Receptor 2-Dependent Host Defense in a Mouse Tissue Cage Infection Model," The Journal of Infectious Diseases 188:414-423.
Kyd et al., "Efficacy of the 26-Kilodalton Outer Membrane Protein and Two P5 Fimbrin-Derived Immunogens To Induce Clearance of Nontypeable Haemophilus influenzae from the Rat Middle Ear and Lungs as Well as from the Chinchilla Middle Ear and Nasopharynx," Infection and Immunity, vol. 71, No. 8, Aug. 2003, pp. 4691-4699.
Labbé et al., "Association of Smads with lymphoid enhancer binding factor 1/T cell-specific factor mediates cooperative signaling by the transforming growth factor-β and Wnt pathways," Proc. Natl. Acad. Sci. USA, vol. 97, No. 15, Jul. 18, 2000, pp. 8358-8363.
Lappann et al., "A dual role of extracellular DNA during biofilm formation of Neisseria meningitidis", Molecular microbiology. 2010; 75(6):1355-71. doi: 10.1111/j.1365-2958.2010.07054.x.
Lebeaux et al., "From in vitro to in vivo Models of Bacterial Biofilm-Related Infections," Pathogens, vol. 2, May 13, 2013, pp. 288-356.
Li et al., "Retroviral cDNA Integration: Stimulation by HMG I Family Proteins," Journal of Virology, vol. 74, No. 23, Dec. 2000, pp. 10965-10974.
Liu et al., "Histone-like DNA binding protein of *Streptococcus intermedius* induces the expression of pro-inflammatory cytokines in human monocytes via activation of ERK1/2 and JNK pathways," Cellular Microbiology (2008) 10(1):262-276.
Liu et al., "The essentiality and involvement of Streptococcus intermedius histone-like DNA-binding protein in bacterial viability and normal growth," Molecular Microbiology, vol. 68, No. 5, Apr. 21, 2008, pp. 1268-1282.
Lunsford et al., "DNA-Binding Activities in *Streptococcus gordonii*: Indentification of a Receptor-Nickase and a Histonelike Protein," Current Microbiology, vol. 32, 1996, pp. 95-100.
Lutz, et al., "Covalent binding of detergent-solubilized membrane glycoproteins to 'Chemobond' plates for ELISA," Journal of Immunological Methods (1990) 129:211-220.
Mahdi et al., "Holliday Junction Resolvases Encoded by Homologous rusA Genes in *Escherichia coli* K-12 and Phage 82", J. Mol. Biol., vol. 257, Jan. 19, 1996, pp. 561-573.
Malhotra et al., "Defining the functional epitopes of Integration Host Factor (IHF) to develop a novel biofilm-focused immunotherapeutic against nontypeable Haemophilus influenzae-induced chronic and recurrent otitis media", 18th International Symposium on Recent Advances in Otitis Media, National Harbor, MD, Jun. 7-11, 2015 (poster), 1 page.
Malhotra et al., "Fine mapping the functional epitopes within integration host factor, a novel therapeutic target for nontypeable Haemophilus influenza-induced diseases of the respiratory tract", Abst. 12th Annual AMA Research Symposium, Dallas, TX, Nov. 7, 2014, 1 page.
Malhotra et al., Identification of immunoprotective domains within the bacterial DNA-binding protein, integration host factor, 20th Annual Midwest Microbial Pathogenesis Meeting. The Ohio State University, Columbus, OH, Aug. 23-25, 2013 (poster), 1 page.
Malhotra et al., Identification of immunoprotective domains within the bacterial DNA-binding protein, integration host factor, Abst. Seventh Extraordinary International Symposium on Recent Advances in Otitis Media, Stockholm, Sweden, Jun. 12, 2013, 20 pages.
Malhotra et al., Identification of immunoprotective domains within the bacterial DNA-binding protein, integration host factor, Seventh Extraordinary International Symposium on Recent Advances in Otitis Media, Stockholm, Sweden, Jun. 15, 2013 (presentation).
Mann, et al., "Modulation of eDNA Release and Degradation Affects *Staphylococcus aureus* Biofilm Maturation," PLoS ONE (2009) 4(6):e5822, 1-12.
Martinez-Antonio et al. "Functional organization of *Escherichia coli* transcriptional regulatory network", J. Mol. Biol. (2008) vol. 381, p. 238-247.
Meluleni et al., "Mucoid Pseudomonas aeruginosa Growing in a Biofilm In Vitro Are Killed by Opsonic Antibodies to the Mucoid

(56) References Cited

OTHER PUBLICATIONS

Exopolysaccharide Capsule but Not by Antibodies Produced During Chronic Lung Infection in Cystic Fibrosis Patients," J. Immunology (1995) 155:2029-2038.

Mouw et al., "Shaping the *Borrelia burgdorferi* genome: crystal structure and binding properties of the DNA-bending protein Hbb," Molecular Microbiology, vol. 63, No. 5, Jan. 22, 2007, pp. 1319-1330.

Mukherjee et al., "Quantitative protein expression and cell surface characteristics of *Escherichia coli* MG1655 biofilms," Proteomics, vol. 11, Nov. 1, 2010, pp. 339-351.

Murphy et al., "Microbial Interactions in the Respiratory Tract," The Pediatric Infectious Disease Journal, vol. 28, No. 10, Oct. 2009, pp. S121-S126.

Murphy, et al., "Biofilm formation by nontypeable Haemophilus influenzae: strain variablitiy, outer membrane antigen expression and role of pili," BMC (2002) Microbiology 2:7, 1-8.

Nakamura et al., "HMG Box A in HMG3 Protein Functions as a Mediator of DNA Structural Alteration Together with Box B," J. Biochem., vol. 129, No. 4, Feb. 5, 2001, pp. 643-651.

Nash et al., "Overproduction of *Escherichia coli* Integration Host Factor, a Protein with Nonidentical Subunits," Journal of Bacteriology, vol. 169, No. 9, Sep. 1987, pp. 4124-4127.

NCBI GenBank AAC74782.1 (Jul. 28, 2009).

NCBI Genebank: POA6Y1 (Sep. 13, 2005), 7 pages.

NCBI Sequence NP_415432.1 (Jul. 30, 2009).

Non-Final Office Action in U.S. Appl. No. 15/078,987 dated Jul. 14, 2016, 15 pages.

Non-Final Office Action in U.S. Appl. No. 15/078,987, mailed Mar. 16, 2018, 18 pages.

Non-Final Office Action on U.S. Appl. No. 14/967,228 dated May 19, 2017, 21 pages.

Novotny et al., "Epitope mapping immunodominant regions of the PilA protein of nontypeable Haemophilus influenzae (NTHI) to facilitate the design of two novel chimeric vaccine candidates," Vaccine, vol. 28, No. 1, pp. 279-289 (Dec. 10, 2009).

Novotny et al., "Monoclonal antibodies against DNA-binding tips of DNABII proteins disrupt biofilms in vitro and induce bacterial clearance in vivo", EBIOMEDICINE, Aug. 1, 2016, vol. 10, pp. 33-44.

Novotny et al., "Structural stability of Burkholderia cenocepacia biofilms is reliant on eDNA structure and presence of a bacterial nucleic acid binding protein", PLoS ONE. 2013; 8(6):e67629. Epub Jun. 27, 2013. doi: 10.1371/journal.pone.0067629.

Novotny et al., "Structural Stability of Burkholderia cenocepacia Biofilms Is Reliant on eDNA Structure and Presence of a Bacterial Nucleic Acid Binding Protein," PLoS ONE, vol. 8, No. 6, e67629, Jun. 2013, 15 pages.

Novotny et al., "Detection and characterization of pediatric serum antibody to the OMP P5-homologous adhesin of nontypeable Haemophilus influenzae during acute otitis media," Vaccine, vol. 20, No. 29-30, Jun. 8, 2002, pp. 3590-3597.

Novotny et al., "Epitope mapping immunodominant regions of the PilA protein of nontypeable Haemophilus influenzae (NTHI) to facilitate the design of two novel chimeric vaccine candidates," Vaccine, vol. 28, No. 1, Aug. 22, 2009, pp. 279-289.

Novotny et al., "Epitope mapping of the Outer Membrane Protein P5-Homologous Fimbrin Adhesin of Nontypeable Haemophilus influenzae," Infection and Immunity, vol. 68, No. 4, Apr. 2000, pp. 2119-2128.

Novotny et al., "Passive immunization with human anti-protein D antibodies induced by polysaccharide protein D conjugates protects chinchillas against otitis media after intranasal challenge with Haemophilus influenzae," Vaccine, vol. 24, No. 22, Mar. 27, 2006, pp. 4804-4811.

Novotny et al., "The Fourth Surface-Exposed Region of the Outer Membrane Protein P5-Homologous Adhesin of the Nontypable Haemophilus influenzae Is an Immunodominant But Nonprotective Decoying Epitope," The Journal of Immunology, vol. 171, No. 4, Jun. 10, 2003, pp. 1978-1983.

Novotny, "Development of a novel biofilm-focused immunotherapeutic against NTHI-induced otitis media", 18th International Symposium on Recent Advances in Otitis Media, National Harbor, MD, Jun. 7-11, 2015 (presentation), 3 pages.

Novotny, et al., "Monoclonal antibodies against DNA-binding tips of DNABII proteins disrupt biofilms in vitro and induce bacterial clearance in vivo," 2016, EBioMedicine 10:33-44.

Nowakowska, J. et al. (2014) "Foreign Body Infection Models to Study Host-Pathogen Response and Antimicrobial Tolerance of Bacterial Biofilm," Antibiotics 3:378-397, Aug. 2014.

Oberto et al., "Histones, HMG, HU, IHF: Même combat," Biochimie, vol. 76, 1994, pp. 901-908.

Ordway et al., "Evaluation of Standard Chemotherapy in the Guinea Pig Model of Tuberculosis," Antimicrobial Agents and Chemotherapy, vol. 54, May 2010, pp. 1820-1833.

Otto, "*Staphylococcus epidermidis*—the 'accidental' pathogen," Nature Reviews Microbiology, vol. 7, Aug. 2009, pp. 555-567.

Pedulla et al., "A novel host factor for integration of mycobacteriophage L5," Proc. Natl. Acad. Sci. USA, vol. 93, Dec. 1996, pp. 15411-15416.

Percival, S.L. et al. (2015) "Biofilms and Wounds: An Overview of the Evidence," Advances in Wound Care 4(7):373-381.

Petersen et al., "Biofilm Mode of Growth of *Streptococcus intermedius* Favoreed by a Competence-Stimulating Signaling Peptide," Journal of Bacteriology, vol. 186, No. 18, Sep. 2004, pp. 6327-6331.

Pethe et al., "Mycobacterium smegmatis laminin-binding glycoprotein shares epitopes with *Mycobacterium tuberculosis* heparin-binding haemagglutinin," Molecular Microbiology, vol. 39, No. 1, 2001, pp. 89-99.

Priyadarshini et al., "The nucleoid-associated protein HUß affects global gene expression in Porphyromonas gingivalis", Microbiology. 2013; 159(Pt 2):219-29. First Published: Feb. 1, 2013.

Prymula et al., "Pneumococcal capsular polysaccharides conjugated to protein D for prevention of acute otitis media caused by both Streptococcus pneumoniae and non-typable Haemophilus influenzae: a randomized double-blind efficacy study," Lancet, vol. 367, No. 9512, Mar. 4, 2006, pp. 740-748.

Reffuveille et al., "A Broad-Spectrum Antibiofilm Peptide Enhances Antibiotic Action against Bacterial Biofilms", Antimicrobial Agents and Chemotherapy, vol. 58, No. 9, Sep. 2014, pp. 5363-5371.

Restriction Requirement on U.S. Appl. No. 14/967,228 dated Dec. 23, 2016, 7 pages.

Rice et al., "1IHF Integration Host Factor/DNA Complex," PDB ID: 1IHF: Rice, P.A. et al. (1996), 1 page; retrieved online from http://www.rcsb.org/pdb/explore.do?structureId=IHF, 2 pages.

Rice et al., "Crystal Structure of an IHF-DNA Complex: A Protein-Induced DNA U-Turn," CELL, vol. 87, No. 7, pp. 1295-1306 (Dec. 27, 1996).

Rice et al., "Crystal Structure of an IHF-DNA Complex: A Protein-Induced DNA U-Turn," Cell, vol. 87, No. 7, Dec. 27, 1996, pp. 1295-1306.

Rouviere-Yaniv et al., "Characterization of a novel, low-molecular-weight DNA-binding protein from *Escherichia coli*", Proceedings of the National Academy of Sciences of the United States of America. 1975; 72(9):3428-32. Epub Sep. 1, 1975.

Rudikoff et al., "Single amino acid substitution altering antigen-binding specificity," Proc. Natl. Acad. Sci. USA, vol. 79, No. 6, Mar. 1982, pp. 1979-1983.

Sapi et al., "Characterization of Biofilm Formation by Borrelia burgdorferi In Vitro," PLOS One, vol. 7, No. 10, Oct. 2012, pp. 1-11.

Schwartz et al., (2012) "Functional Amyloids Composed of Phenol Soluble Modulins Stabilize *Staphylococcus aureus* Biofilms," PLOS Pathogens 8:e1002744, 1-11.

Segall et al., "Architectural elements in nucleoprotein complexes: interchangeability of specific and non-specific DNA binding proteins," The EMBO Journal, vol. 13, No. 19, 1994, pp. 4536-4548.

Shahrooei et al., "Inhibition of *Staphylococcus epidermidis* Biofilm Formation by Rabbit Polyclonal Antibodies against the SesC Protein," Infection and Immunity, vol. 77, No. 9, Sep. 2009, pp. 3670-3678.

(56) References Cited

OTHER PUBLICATIONS

Shields, R.C. et al. (2013) "Efficacy of a Marine Bacterial Nuclease against Biofilm Forming Microorganisms Isolated from Chronic Rhinosinusitis," PLoS ONE 8(2):e55339, 1-13.
Singh et al., "Quorum-sensing signals indicate that cystic fibrosis lungs are infected with bacterial biofilms," Nature, vol. 407, No. 12, Oct. 12, 2000, pp. 762-764.
Skolnick, J. et al. (2000) "From genes to protein structure and function: novel applications of computational approaches in the genomic era," Trends in Biotechnology 18:34-39.
Smith et al., "Cystic Fibrosis Airway Epithelia Fail to Kill Bacteria Because of Abnormal Airway Surface Fluid," Cell, vol. 85, Apr. 19, 1996, pp. 229-236.
Stinson, et al. "Streptococcal Histone-Like Protein: Primary Structure of hlpA and Protein Binding to Lipoteichoic Acid and Epithelial Cells," Infection and Immunity, 1998, 66(1):259-265.
Stoltz et al., "Cystic Fibrosis Pigs Develop Lung Disease and Exhibit Defective Bacterial Eradication at Birth," www.ScienceTranslationMedicine.org, vol. 2, No. 29, Apr. 28, 2010, pp. 1-8.
Stros et al., "The HMG-box: a versatile protein domain occurring in a wide variety of DNA-binding proteins," Cell. Mol. Life Sci., vol. 64, No. 19-20, Jun. 29, 2007, pp. 2590-2606.
Sun et al., "Inhibition of Biofilm Formation by Monoclonal Antibodies against Staphylococcus epidermindis RP62A Accumulation-Associated Protein," Clinical & Diagnostic Laboratory Immunology, vol. 12, No. 1, Jan. 2005, pp. 93-100.
Swinger et al., "IHF and HU: flexible architects of bent DNA," Current Opinion in Structural Biology, vol. 14, No. 1, 2004, pp. 28-35.
Takeda, "Polyhistidine Affinity Chromatography for Purification and Biochemical Analysis of Fungal Cell Wall-Degrading Enzymes," Affinity Chromatography, Dr. Sameh Magdeldin (Ed.), ISBN: 978-953-51-0325-7, In Tech, 2012, pp. 177-186.
Taudte et al., "Alanine mutagenesis of high-mobility-group-protein-1 box B (HMG1-B)," Biochem. J., vol. 347, Feb. 25, 2000, pp. 807-814.
Teter et al., "DNA Bending and Twisting Properties of Integration Host Factor Determined by DNA Cyclization," Plasmid, vol. 43, 2000, pp. 73-84.
Tetz et al., "Effect of DNase and Antibiotics on Biofilm Characteristics," Antimicrobial Agents and Chemotherapy, vol. 53, No. 3, Mar. 2009, pp. 1204-1209.
Thomas, "HMG1 and 2: architectural DNA-binding proteins," Biochemical Society Transactions, vol. 29, Pt. 4, Apr. 12, 2001, pp. 395-401.
Thurnheer et al., "Colonisation of gingival epithelia by subgingival biofilms in vitro: role of 'red complex' bacteria", Arch Oral Biol., vol. 59, No. 9, Sep. 2014, pp. 1-24.
Tsaras et al., "Incidence, Secular Trends, and Outcomes of Prosthetic Joint Infection: A Population-Based Study, Olmsted County, Minnesota, 1969-2007," Infect Control Hosp Epidemiol., vol. 33, No. 12, Dec. 2012, pp. 1207-1212.
Van Schaik et al., "DNA Binding: a Novel Function of Pseudomonas aeruginosa Type IV Pili," Journal of Bacteriology, vol. 187, No. 4, Feb. 2005, pp. 1455-1464.
Whitchurch et al., "Extracellular DNA Required for Bacterial Biofilm Formation," Science, vol. 295, No. 5559, Feb. 22, 2002, p. 1487, 1 page.
Whitchurch et al., "Extracellular DNA Required for Bacterial Biofilm Formation," Science, vol. 295, No. 5559, Feb. 22, 2002, Supplementary Material, 2 pages.
Winters et al., "Isolation and Characterization of a Streptococcus pyogenes Protein that Binds to Basal Laminae of Human Cardiac Muscle," Infection and Immunity, vol. 61, No. 8, Aug. 1993, pp. 3259-3264.
Winther et al., "Location of Bacterial Biofilm in the Mucus Overlying the Adenoid by Light Microscopy," Head & Neck Surgery, vol. 135, No. 12, Dec. 2009, pp. 1239-1245.
Woischnig et al., "High Affinity Native Human Monoclonal Antibody with Broad Cross-Species Biofilm Disrupting Activity" poster presented at ICAAC Meeting on Sep. 20, 2015, available at www.trellisbio.com/assets/docs/ICAAC%20Biofilm%20Poster%2020150920.pdf., 1 page.
Yoshida, "HMG box proteins: general architectural elements in the assembly of active transcription complex," SEIKAGAKU Biochemistry (1996) 68(12):1829-1834.
Zimmerli et al., "Pathogenesis of Foreign Body Infection," J. Clin. Invest (1984) 73(4):1191-1200.
Zimmerli et al., "Pathogenesis of Foreign Body Infection: Description and Characteristics of an Animal Model," The Journal of Infectious Diseases, vol. 146, No. 4, Oct. 1982, pp. 487-497.
Zulianello et al., "The HimA and HimD subunits of integration host factor can specifically bind to DNA as homodimers," The EMBO Journal, vol. 13, No. 4, Apr. 1, 1994, pp. 1534-1540.
Devaraj et al., "The DNABII family of proteins is comprised of the only nucleoid associated proteins required for nontypeable Haemophilus influenzae biofilm structure", MicrobiologyOpen, 2018, 13 pages.
Trifiro et al., "Ghost Mycobacteria on Gram Stain," Journal of Clinical Microbiology, Jan. 1990, vol. 28, No. 1, pp. 146-147.
U.S. Notice of Allowance dated Jun. 24, 2024, for U.S. Appl. No. 16/475,654.

\* cited by examiner

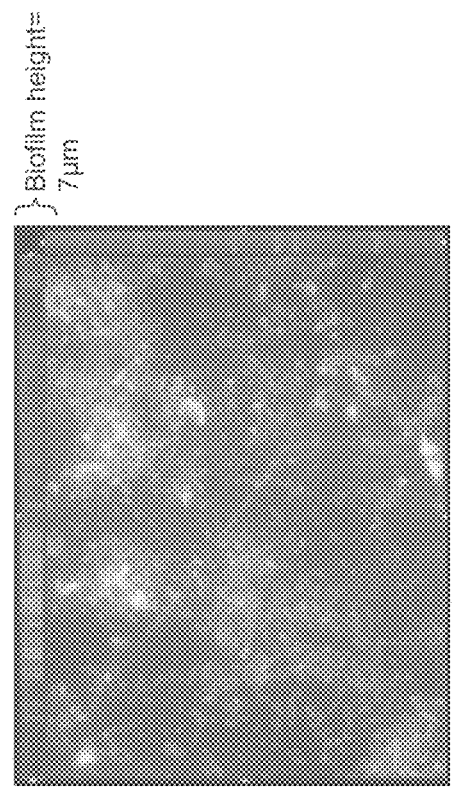
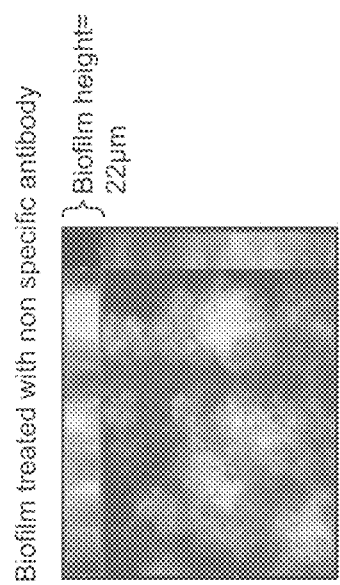
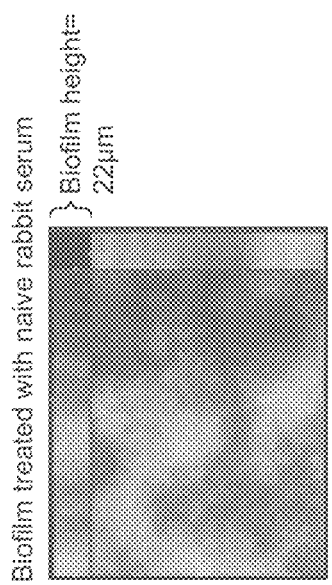
FIG. 3A
FIG. 3B
FIG. 3C

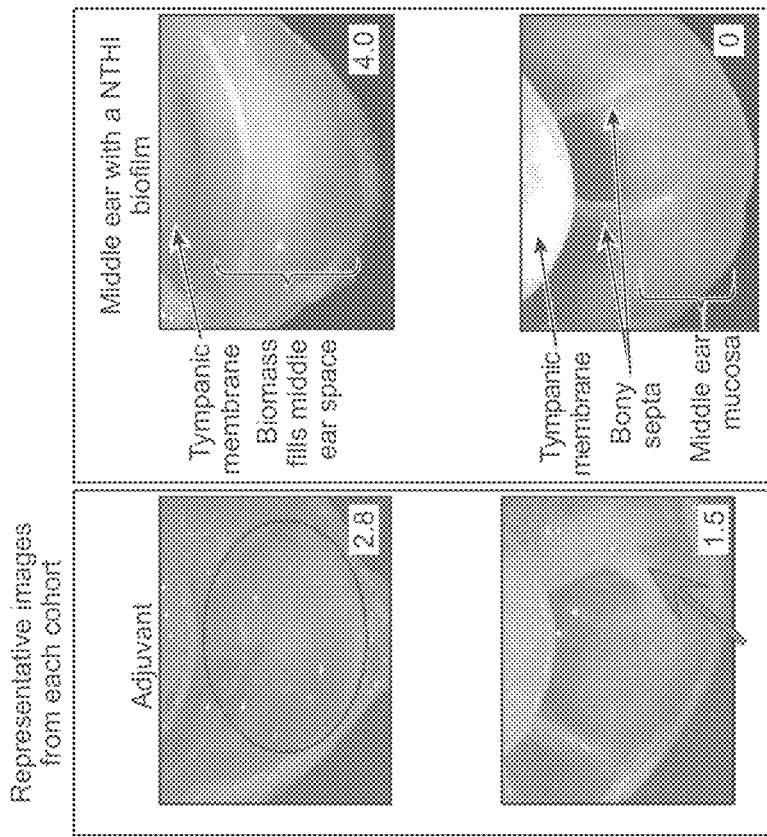
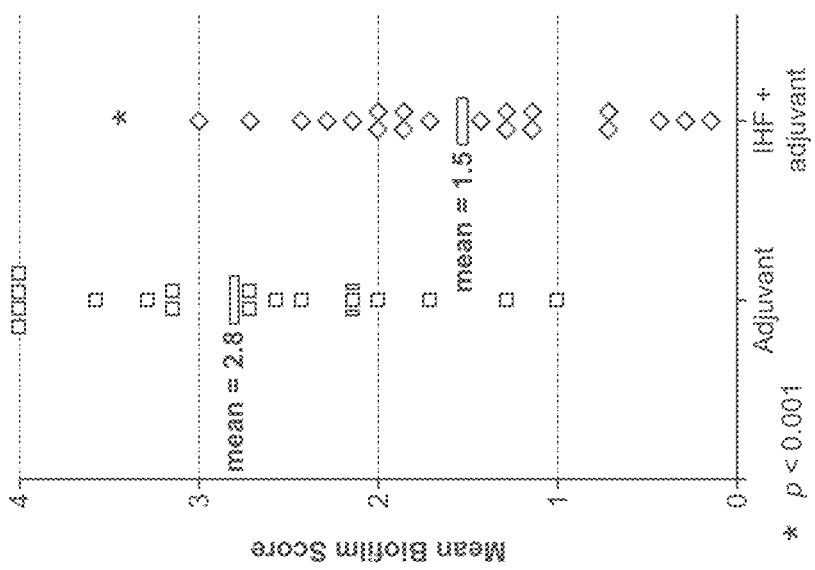
FIG. 9A
FIG. 9B

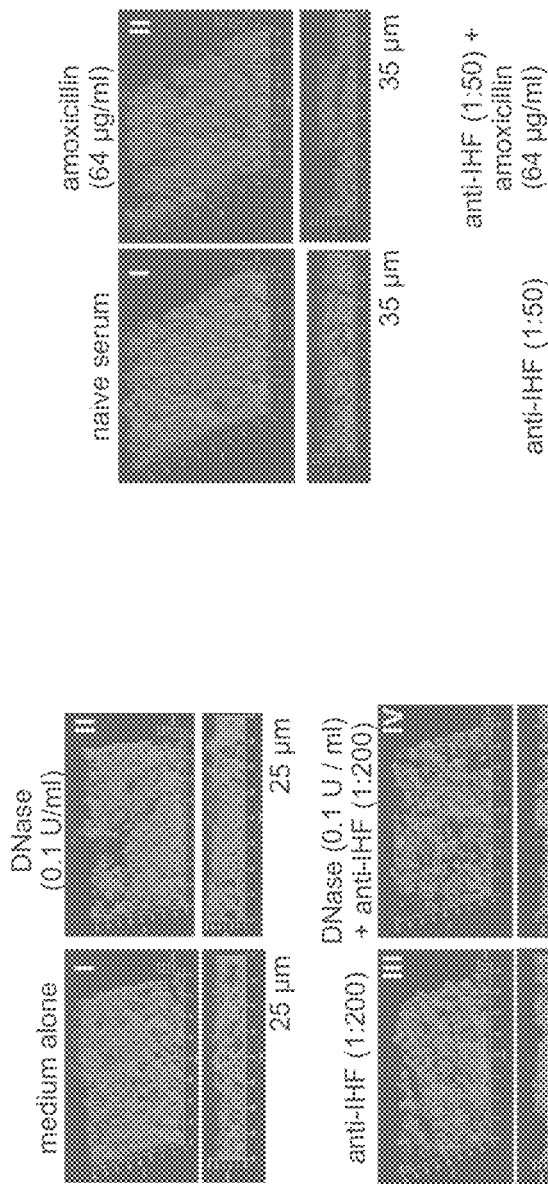
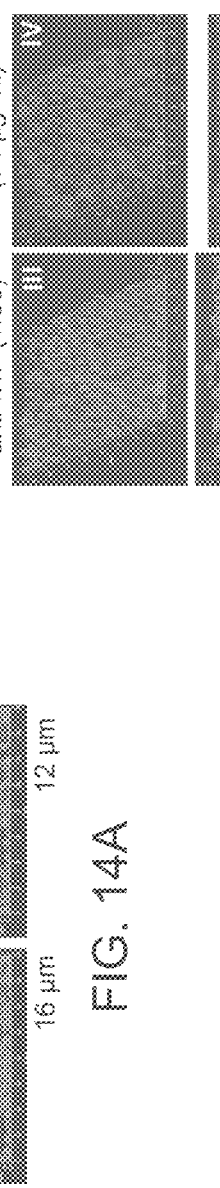
FIG. 14A
FIG. 14B
FIG. 14C

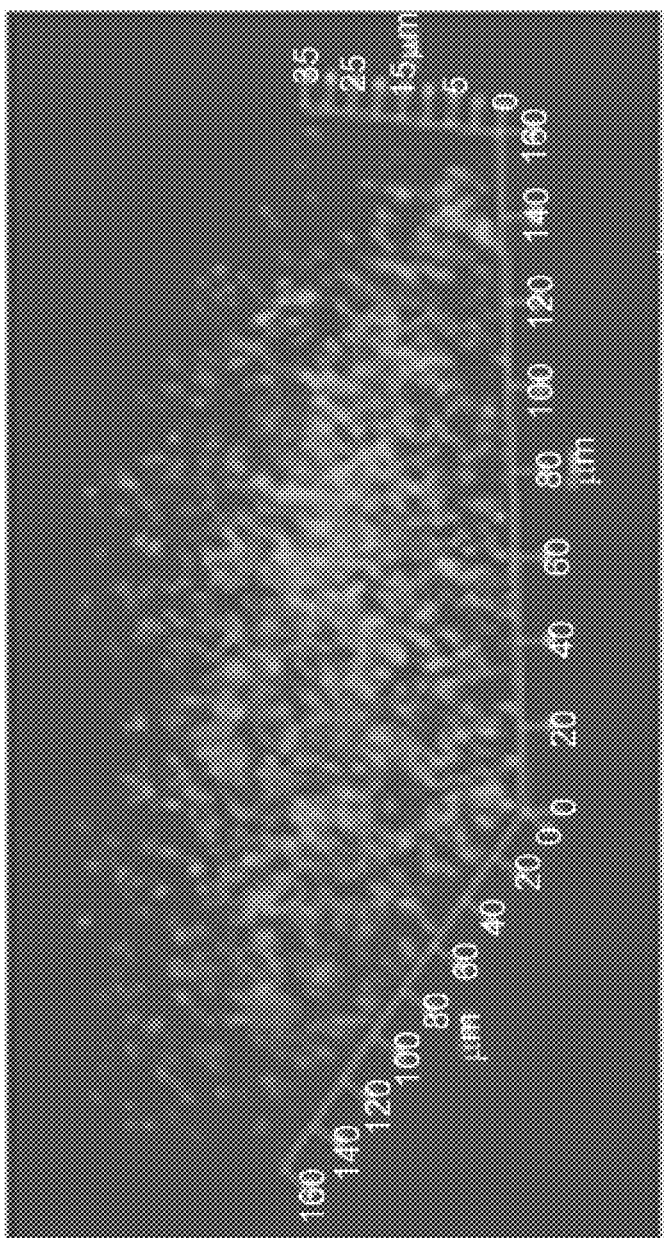
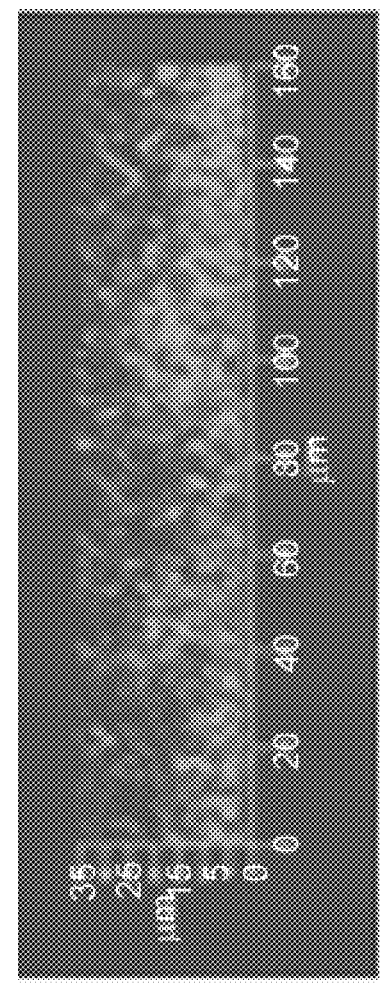
FIG. 15 (CONT.)

| 9A | 9A (cont.) | SEQ ID NOS 42-72, respectively, in order of appearance |
|----|------------|--------------------------------------------------------|

| | | | | |
|---|---|---|---|---|
| Ec_HimA | ------MALTKAEMSEYLFDK | LG-LS-----KR | DAKELVELFFEEIRRAL | EN |
| Salm_HimA | ------MALTKAEMSEYLFDK | LG-LS-----KR | DAKELVELFFEEIRRAL | EN |
| Vc_HimA | ------MALTKAELAEALFEQ | LG-MS-----KR | DAKDTVEVFFEEIRKAL | ES |
| Pa_HimA | -----MGALTKAEIAERLYEE | LG-LN-----KR | EAKELVELFFEEIRQAL | EH |
| Hi_HimA | -----MATITKLDIIEYLSDK | YH-LS-----KQ | DTKNVVENFLEEIRLSL | ES |
| Aa_IHFalpha | ------MTLTKVELAENLIEK | FH-LS-----KR | EAKDLVESFFEEIRVAL | ET |
| Mc_HimA | -----MGALTKADMVDELTIR | LR-LT-----RQ | QARKLVDGFFEEISQSL | AQ |
| Ng_IHFalpha | ------MTLTKAELADILVDK | VSNVT-----KN | DAKEIVELFFEEIRSTL | AS |
| Nm_HimA | ------MTLTKAELADILVDK | VSNVT-----KN | DAKEIVELFFEEIRSTL | AS |
| Bc_IHFA | +30aa ASTE-TPTLTKAELAELLFDS | VG-LN-----KR | EAKDMVEAFFEVIRDAL | EN |
| Bp_IHFA | +27aa TSAGDTPTLTKAELAELLFDS | VG-LN-----KR | EAKDMVEAFFEVIRDAL | EN |
| Bpert_IhfA | MGTTMLAEPRTLTKAELAELLFER | VG-LN-----KR | EAKDIVDTFFEEIRDAL | AR |
| Pm_HimA | ---------MNNKEFIAALAAR | TGYT------QD | ESQKMVKTVVDMMGKSF | ET |
| Pi_HimA | ---------MNNKEFITALANR | VGRS------QD | ETQKLVKTALQAMGDNF | ES |
| Tp_Dbp_II | ----MKRVRRTRSFVVDALCD | EVDLS-----RR | HVARVVDSFVSVVTAAL | ER |
| Pm_Hup | ------MAKSAIQLITSALAK | QHNLS-----ADD | AAAFVDAFFDIISSELK | N- |
| Pi_hypo | ------MAKTALQLIADAVAK | KHKIT-----VK | EAEKFVSAIFDVVNEGL | KT |
| Sa_HU | --------MNKTDLINAVAEQ | ADLT------KK | EAGSAVDAVFESIQNSL | AK |
| Ec_hupA | --------MNKTQLIDVIAEK | AELS------KT | QAKAALESTLAAITESL | KE |
| Se_Hup | --------MNKTDLINAVAEQ | ADLT------KK | EAGSAVDAVFESIQNSL | AK |
| Ss_Hu | -------MANKQDLIAKVAEA | TELT------KK | DSAAAVDIVFSSIEGFL | SK |
| Spyog_HU | -------MANKQDLIAKVAEA | TELT------KK | DSAAAVDAVFSTIEAFL | AE |
| Sgall_HlpA | -------MANKQDLIAKVAEA | TELT------KK | DSAAAVDAVFSAIESFL | SE |
| GBS_Hup | -------MANKQDLIAKVAEA | TELT------KK | DSAAAVDAVFAAVADYL | AE |
| Spneu_HU | -------MANKQDLIAKVAEA | TELT------KK | DSAAAVEAVFAAVADYL | AA |
| Sg_HlpA | -------MANKQDLIAKVAAA | TELT------KK | DSAAAVDAVFAAVTEYL | SK |
| Sm_HU | -------MANKQDLIAKVAEA | TELT------KK | DSAAAVDAVFSAVSSYL | AK |
| Ef_Hup | -------MANKAELIENVASS | TGLT------KK | DATAAVDAVFSTIQETL | AK |
| Hi_HupA | --------MNKTDLIDAIANA | AELN------KK | QAKAALEATLDAITASL | KE |
| Vc_HupA | --------MNKTQLIDFIAEK | ADLT------KV | QAKAALEATLGAVEGAL | KD |
| Pa_HupB | --------MNKSELIDAIAAS | ADIP------KA | VAGRALDAVIESVTGAL | KA |

α-1    Turn    α-2    T

Table 9A1

FIG. 19

| β-1 | T | β-2 | Binding domain | Turn | Returning strand | β-3 | α-3 | |
|---|---|---|---|---|---|---|---|---|
| GEQVK | LSG | FGNFD | LRDKNQRP-GR | NPKT | GEDIPITARRVV | TFRPGQ | KLKSRV | ENASPKDE- |
| GEQVK | LSG | FGNFD | LRDKNQRP-GR | NPKT | GEDIPITARRVV | TFRPGQ | KLKSRV | ENASPKEE- |
| GEQVK | LSG | FGNFD | LRDKNERP-GR | NPKT | GEDIPITARRVV | TFRPGQ | KLKARV | ENIKVEK-- |
| NEQVK | LSG | FGNFD | LRDKRQRP-GR | NPKT | GEEIPITARRVV | TFRPGQ | KLKARV | EAYAGTKS- |
| GQDVK | LSG | FGNFE | LRDKSSRP-GR | NPKT | GDVIPVSARRVV | TFKPGQ | KLRARV | EKTK----- |
| GNDVK | LSG | FGNFE | LRDKASRP-GR | NPST | GESVPVSARRVV | VFKPGQ | KLRNRV | EKVKPKA- |
| GHEVK | LSG | FGNFE | LKDKKPRP-GR | NPKT | GESVPIQARRVV | TFKAGQ | KLRGWI | DSQNEG |
| GEEIK | VSG | FGNFQ | LRDKPQRP-GR | NPKT | GEEVPITARRVV | TFHASQ | KLKGMV | EHYYDKQR- |
| GEEIK | VSG | FGNFQ | LRDKPQRP-GR | NPKT | GEEVPITARRVV | TFHASQ | KLKSMV | EHYYDKQR |
| GESVK | LSG | FGNFQ | LRDKPQRP-GR | NPKT | GEAIPIAARRVV | TFHASQ | KLKALV | ENGAE |
| GESVK | LSG | FGNFQ | LRDKPQRP-GR | NPNT | GEAIPIAARRVV | TFHASQ | KLKALV | ENGAEPDLAR |
| GDSVK | LSG | FGNFQ | VRDKPPRP-GR | NPKT | GETIPIAARRVV | TFHASQ | KLKSVV | EQPNSPPDPASAE |
| GDPVP | VIG | FGTFE | VKKRLERV-MV | NPST | GLRMLVPPKLVL | NFKPAA | TIKGHV | RKGGQDNG |
| GEPVL | VSG | FGSFE | VKKRLERI-MT | NPAT | GLRMLVPPKLVL | NFRATA | SVKEKL | KKGGAE |
| GETVE | LRD | FGVFE | SRVRKASV-GK | SNT | GEVVSIPSHCVV | VFRPSK | RLKSAV | RGYRSGEVGAD |
| GNQVK | VKG | LGTFK | VQAVKPR-ESV | NVNT | GERVLIEGHDKI | SFTPDT | MVKELV | NKPFSQFET +354aa |
| GEKVQ | LIG | FGNFE | VRERAARK-GR | NPQT | GKEIDIPASKVP | AFKAGK | ALKDAV | K-------- |
| GDAVQ | LVG | FGTFK | VNHRAERT-GR | NPQT | GKEIKIAAANVP | AFVSGK | ALKDAV | K |
| GEKVQ | LIG | FGNFE | VRERAARK-GR | NPQT | GKEIDIPASKVP | AFKAGK | ALKDAV | K-------- |
| GEKVQ | LIG | FGNFE | VRERAARK-GR | NPQT | GAEIKIAASKVP | AFKAGK | ALKDAV | K-------- |
| GEKVQ | LIG | FGNFE | VRERAARK-GR | NPQT | GAEIEIAASKVP | AFKAGK | ALKDAV | K-------- |
| GEKVQ | LIG | FGNFE | VRERAARK-GR | NPQT | GEEIEIAASKVP | AFKAGK | ALKDAV | K-------- |
| GEKVQ | LIG | FGNFE | VRERAARK-GR | NPQT | GAEIEIAASKVP | AFKAGK | ALKDAV | K-------- |
| GEKVQ | LIG | FGNFE | VRERAERK-GR | NPQT | GKEMTIAASKVP | AFKAGK | ALKDAV | K-------- |
| GEKVQ | LIG | FGNFE | VRERAARK-GR | NPQT | GKEIKIAASKVP | AFKAGK | ALKDAV | K-------- |
| GEKVQ | LIG | FGNFE | VRERAARK-GR | NPQT | GEEIKIKASKVP | AFKAGK | ALKDAV | K-------- |
| GEKVQ | LIG | FGNFE | VRERAARK-GR | NPQT | GQEIQIAASKVP | AFKPGK | ALKDAV | K |
| GEPVQ | LIG | FGTFK | VNERAART-GR | NPQT | GAEIQIAASKVP | AFVSGK | ALKDAI | K-------- |
| GDQVQ | LIG | FGTFK | VNHRSART-GR | NPQT | GEEIKIAAANVP | AFVAGK | ALKDAI | K-------- |
| GDSVV | LVG | FGTFA | VKERAART-GR | NPQT | GKPIKIAAAKIP | GFKAGK | ALKDAV | N-------- |

----------ARM----------

Table 9A1 (continued)

FIG. 19 (continued)

| 9A2 | 9A2 (cont.) | SEQ ID NOS 73-76, respectively, in order of appearance |
|---|---|---|

| | | | | |
|---|---|---|---|---|
| Aa HU | --------MN | KTDLIDAIASS | AELN------KK | QAKAALEATLDAITGSL | KK |
| Vc_HupB | ---------MN | KTQLVEQIAAN | ADIS-------KA | SAGRALDAFIEAVSGTL | QS |
| Ec hupB | ---------MN | KSQLIDKIAAG | ADIS-------KA | AAGRALDAIIASVTESL | KE |
| Mc HupB | ---------MN | KSELVDSIAQS | AGLT------KE | QAAKAVNAFTESVQGAL | QR |
| | | α-1 | Turn | α-2 | T |

Table 9A2

| | | | | | | | | | |
|---|---|---|---|---|---|---|---|---|---|
| GEAVQ | LIG | FGTFK | VNARKART-GR | NPQT | GAEIKIAASKVP | AFVSGK | ALKDAV | K | - |
| GDQVA | LVG | FGTFS | VRTRAART-GR | NPQT | GEEIKIAEAKVP | SFKAGK | ALKDAC | N------ | |
| GDDVA | LVG | FGTFA | VKERAART-GR | NPQT | GKEITIAAAKVP | SFRAGK | ALKDAV | N | |
| GDDVV | LVG | FGTFS | VKERAARM-GR | NPQT | GEAIQIAASKVP | SFKAGK | VLKESV | N | |
| | | | Binding | | Returning | | | | |
| β-1 | T | β-2 | domain | Turn | strand | β-3 | α-3 | | |
| | | | --------ARM-------- | | | | | | |

Table 9A2 (continued)

FIG. 19 (continued)

| | 9A3 (cont.) | SEQ ID NOS 77-100, respectively, in order of appearance |

| Name | α-1 | Turn | α-2 | T |
|---|---|---|---|---|
| Bpert HupB | --------MNKTELIDHIASK | ADIS--------KA | AAGRSLDALIGAVKTTL | KK |
| Mc HimD | ----MQAVINKSNLIANLASV | CEEL--------EED | VVDEAVRLMIAMMVNEL | VY |
| Pm HupB | --------MNKTELIEKIAAN | AEVS--------KA | AAKKALDATTEAIKEAL | AA |
| Pi Hup | --------MNKTELIEKIAAG | AGLS--------KA | DSKKALDAMTAAIKEAL | VA |
| Td HU | --------MKQKRSKIDIIDS | VYRNNPQYQLKQ | INAIANLFLDELSVLLQ | QG |
| Pg_Hup-1 | --------MNKTDFIAAVAEK | ANLT--------KA | DAQRAVNAFAEVITEQM | NA |
| Hp_Hup | --------MNKAEFIDLVKEA | GKYNS-------KR | EAEEAISAFTLAVETAL | SK |
| Pm HupA | --------MTKADIINEIATS | TGIA--------KK | DVSAVVESFMETIKDSL | LE |
| Pi Hup-2 | --------MTKADIINEIASS | TGIS--------KK | DVSAVVESFMDAIKDSL | LE |
| Pg_Hup-2 | --------MTKADVINAIAKS | TGID--------KE | TTLKVVESFMDTIKDSL | SE |
| Mt HU | --------MNKAELIDVLTQK | LGSD--------RR | QATAAVENVVDTIVRAV | HK |
| Ms Hup | --------MNKAELIDVLTTK | MGTD--------RR | QATTAVENVVDTIVRAV | HK |
| Ec_HimD | --------MTKSELIERLATQ | QS----------HIPAK | TVEDAVKEMLEHMASTL | AQ |
| Salm_HimD | --------MTKSELIERLATQ | QS----------HIPAK | AVEDAVKEMLEHMASTL | AQ |
| Vc_HipB | --------MTKSELIERLCAE | QT----------HLSAK | EIEDAVKNILEHMASTL | EA |
| Pa_HimD | --------MTKSELIERIVTH | QG----------QLSAK | DVELAIKTMLEQMSQAL | AT |
| Hi_HimD | --------MTKSELMEKLSAK | QP----------TLPAK | EIENMVKGILEFISQSL | EN |
| Aa-IHFB | --------MTKSELIELLVQK | NS----------NIPVK | HVEEAVKAILEQMSYVL | EH |
| Ng_IHFβ | -------------MVRLAEV | FAAKNGTHLLAK | DVEYSVKVLVDTMTRSL | AR |
| Nm HimD | --------MTKSELMVRLAEV | FAAKNGTHLLAK | DVEYSVKVLVDTMTRSL | AR |
| Bc IHFB | --------MTKSELFAQLASR | FP----------QLVLK | DADFAVKTMLDAMSDAL | AK |
| Bp IHFB | --------MTKSELFAQLASR | FP----------QLVLK | DADFAVKTMLDAMSDAL | SK |
| Bpert IhfB | --------MTKSELIAALAAR | YP----------QLAAR | DTDYAVKTMLDAMTQAL | AS |
| Bb_Hbb | MSFSRRPKVTKSDIVDQISLN | IKNNL---KLEKK | YIRLVIDAFFEELKSNL | CS |

Table 9A3

| β-1 | T | β-2 | Binding domain | Turn | Returning strand | β-3 | α-3 |
|---|---|---|---|---|---|---|---|
| GGTVT | LVG | FGTFA | VSARAART-GR | NPRT | GETIKIKKAKVP | KFRPGK | ALKDAV N |
| DGRIE | VRG | FGSFC | LHHRSARI-AR | NPRT | GESVSVKAKATP | YFKPGK | ALRESV NLVND |
| GDKVQ | LVG | FGTFA | TTERPAHE-GI | NPRS | KEKIKIAAKVA | KFKAGA | ELADAV NK |
| GDKVQ | LVG | FGTYS | VTERPAHE-GI | NPAT | KQKIQIAAKKVA | KFKPGA | ELADAV NA |
| IPVEI | RGL | GSFDF | AVLHGR-KNAR | NPST | GEAVLTADRCKV | RFKPGK | ELKEAL HKIDTQELIES |
| GEKIA | LIG | FGTFS | VSERAARK-GI | NPST | KKSISIPARKVV | RFKPGS | TLELK- --------- |
| GESVE | LIG | FGKFE | TAEQKGKE-GK | VPGS | DKTYKTEDKRVP | KFKFGK | TLKQKV EEGK------ |
| KKENV | YLR | GFGSF | IVKHRAEKTAR | NISK | NTTITIPAHDFP | SFKPAK | TFIEDM KK |
| NKENV | YLR | GFGSF | IVKHRAEKTAR | NISK | NTTITIPAHDFP | SFKPAK | TFIEDM KK |
| GDNVY | LRG | FGSFI | VKERAEKT-AR | NISK | QTTHIPKRNIP | AFKPSK | IFMSQM KQD------ |
| GDSVT | ITG | FGVFE | QRRRAAR-VAR | NPRT | GETIKIKPTSVP | AFRFGA | QFKAVV SGAQRLPAEGP +114aa |
| GDSVT | ITG | FGVFE | QRRRAAR-VAR | NPRT | GETIKIKPTSVP | AFRFGA | QFKAVI SGAQKLPADGP +108aa |
| GERIE | IRG | FGSFS | LHYRAPRT-GR | NPST | GDKVELEGKYVP | HFKPGK | ELRDRA NIYG----- |
| GERIE | IRG | FGSFS | LHYRAPRT-GR | NPKT | GDKVELEGKYVP | HFKPGK | ELRDRA NIYG----- |
| GERIE | IRG | FGSFS | LHYREPRV-GR | NPKT | GDKVELEGKYVP | HFKPGK | ELRERV NL------- |
| GDRIE | IRG | FGSFS | LHYRAPRV-GR | NPKT | GESVRLDGKFVP | HFKPGK | ELRDRV NEPE----- |
| GDRVE | VRG | FGSFS | LHHRQPRL-GR | NPKT | GDSVNLSAKSVP | YFKAGK | ELKARV DVQA----- |
| GERIE | VRG | FGSFS | LHCRQPRI-GR | NPST | GEQVKLDAKCVP | YFKAGK | ELRERV DVYAA---- |
| GQRIE | IRG | FGSFD | LNHRPARI-GR | NPKT | GERVEVPEKHVP | HFKPGK | ELRERV DLALKENAN |
| GQRIE | IRG | FGSFD | LNHRPARI-GR | NPST | GERVEVPEKHVP | HFKPGK | ELRERV DLALKENAN |
| GHRIE | IRG | FGSFG | LNRRPARV-GR | NPKS | GEKVQVPEKFVP | HFKPGK | ELRERV DGRAGEPLKADDPDDDR |
| GHRIE | IRG | FGSFG | LNRRPARV-GR | NPKS | GEKVQVPEKHVP | HFKPGK | ELRERV DGRAGEPLKNDEPEDAQ |
| GQRIE | IRG | FGSFS | LSQRSPRI-GR | NPKS | GEQVLVPGKQVP | HFKPGK | ELREWV DLVGNDQGDDS +18aa |
| NNVIE | FRS | FGTFE | VRKRKGRLNAR | NPQT | GEYVKVLDHHVA | YFRPGK | DLKERV WGIKG---- |

-----------ARM-------------

Table 9A3 (continued)

FIG. 19 (continued)

SEQ ID NOS 101-128, respectively, in order of appearance

Comparison to Liu et al 16 as peptide motif

| | |
|---|---|
| *Strep inter* HU | EVRERAARK-GRNPQTG |
| Ec_HimA | DLRDKNQRP-GRNPKTG |
| SalmHimA | DLRDKNQRP-GRNPKTG |
| Vc_HimA | DLRDKNERP-GRNPKTG |
| Pa_HimA | DLRDKRQRP-GRNPKTG |
| Hi_HimA | ELRDKSSRP-GRNPKTG |
| Aa_IHFalpha | ELRDKASRP-GRNPKTG |
| Mc HimA | ELKDKKPRP-GRNPKTG |
| Ng_IHFalpha | QLRDKPQRP-GRNPKTG |
| Nm HimA | QLRDKPQRP-GRNPKTG |
| Bc IHFA | QLRDKPQRP-GRNPKTG |
| Bp IHFA | QLRDKPQRP-GRNPNTG |
| Bpert IhfA | QVRDKPPRP-GRNPKTG |
| Pm HimA | EVKKRLERV-MVNPSTG |
| Pi HimA | EVKKRLERI-MTNPATG |
| Tp Dbp II | ESRVRKASV-GKSINTG |
| Pm Hup | KVQAVKPR-ESVNVNTG |
| Pi hypo | KVQAVKPR-ESVNVNTG |
| Sa_HU | EVRERAARK-GRNPQTG |
| Ec hupA | KVNHRAERT-GRNPQTG |
| Se_Hup | EVRERAARK-GRNPQTG |
| Ss Hu | EVRERAARK-GRNPQTG |
| Spyog_HU | EVRERAARK-GRNPQTG |
| Sgall_HlpA | EVRERAARK-GRNPQTG |
| GBS_Hup | EVRERAARK-GRNPQTG |
| Spneu_HU | EVRERAERK-GRNPQTG |
| Sg_HlpA | EVRERAARK-GRNPQTG |
| Sm_HU | EVRERAARK-GRNPQTG |

Table 9B

FIG. 20

SEQ ID NOS 129-139, respectively, in order of appearance

| | |
|---|---|
| Ef Hup | EVRERAARK-GRNPQTG |
| Hi_HupA | KVNERAART-GRNPQTG |
| Vc_HupA | KVNHRSART-GRNPQTG |
| Bper HupB | AVSARAART-GRNPRTG |
| Pa_HupB | AVKERAART-GRNPQTG |
| Aa HU | SVRTRAART-GRNPKTG |
| Pm HupB | ATTERPAHE-GINPRSK |
| Pi Hup | SVTERPAHE-GINPATK |
| Td HU | FAVLHGR-KNARNPKTG |
| Pg_Hup-1 | SVSERAARK-GINPKTK |
| Hp_Hup | ETAEQKGKE-GKVPGSD |

Table 9B (continued)

FIG. 20 (continued)

SEQ ID NOS 140-159, respectively, in order of appearance

**Comparison to Liu *et al* 16 as peptide motif**

| | |
|---|---|
| *Pm* HupA | FIVKHRAEKTARNISKN |
| *Pi* Hup-2 | FIVKHRAEKTARNISKN |
| *Pg*_Hup-2 | IVKERAEKT-*A*RNISKQ |
| *Mt* HU | EQRRRAAR-VARNPRT**G |
| *Ms* Hup | EQRRRAAR-VARNPRT**G |
| Ec_HimD | *SLH*YRAPRT-GRNPKTG |
| | |
| Salm_HimD | *SLH*YRAPRT-GRNPKTG |
| Vc_HipB | *SLH*YREPRV-GRNPKTG |
| Ec hupB | AVKERAART-GRNPQTG |
| Mc HupB | SVKERAARM-GRNPKTG |
| Pa_HimD | *SLH*YRAPRV-GRNPKTG |
| Hi_HimD | *SLH*HRQPRL-GRNPKTG |
| Aa_IHFB | *SLH*CRQPRI-GRNPKTG |
| Ng_IHFβ | *DL*NHRPARI-GRNPKTG |
| | |
| *Nm* HimD | *DL*NHRPARI-GRNPKTG |
| *Bc* IHFB | *GL*NRRPARV- GRNPKSG |
| *Bp* IHFB | *GL*NRRPARV-GRNPKSG |
| Bpert IhfB | *SLS*QRSPRI- GRNPKSG |
| *Mc* HimD | *CLH*HRSARI-ARNPRT**G |
| Bb_Hbb | EVRKRKGRLN*A*RNPQT**G |

Table 9B (continued)

FIG. 20 (continued)

SEQUENCE LISTING

```
Sequence total quantity: 458
SEQ ID NO: 1            moltype =   length =
SEQUENCE: 1
000

SEQ ID NO: 2            moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 2
VKKSGFGNF                                                                          9

SEQ ID NO: 3            moltype =   length =
SEQUENCE: 3
000

SEQ ID NO: 4            moltype = AA  length = 5
FEATURE                 Location/Qualifiers
REGION                  1..5
                        note = Description of Artificial Sequence: Synthetic peptide
MOD_RES                 3
                        note = Lys or Gln
source                  1..5
                        mol_type = protein
                        organism = synthetic construct
SEQUENCE: 4
NPXTG                                                                              5

SEQ ID NO: 5            moltype = AA  length = 7
FEATURE                 Location/Qualifiers
REGION                  1..7
                        note = Description of Artificial Sequence: Synthetic peptide
MOD_RES                 5
                        note = Lys or Gln
source                  1..7
                        mol_type = protein
                        organism = synthetic construct
SEQUENCE: 5
GRNPXTG                                                                            7

SEQ ID NO: 6            moltype = AA  length = 96
FEATURE                 Location/Qualifiers
source                  1..96
                        mol_type = protein
                        organism = Haemophilus influenzae
SEQUENCE: 6
MATITKLDII EYLSDKYHLS KQDTKNVVEN FLEEIRLSLE SGQDVKLSGF GNFELRDKSS                  60
RPGRNPKTGD VVPVSARRVV TFKPGQKLRA RVEKTK                                            96

SEQ ID NO: 7            moltype = AA  length = 136
FEATURE                 Location/Qualifiers
source                  1..136
                        mol_type = protein
                        organism = Haemophilus influenzae
SEQUENCE: 7
MRFVTIFINH AFNSSQVRLS FAQFLRQIRK DTFKESNFLF NRRYKFMNKT DLIDAIANAA                  60
ELNKKQAKAA LEATLDAITA SLKEGEPVQL IGFGTFKVNE RAARTGRNPQ TGAEIQIAAS                 120
KVPAFVSGKA LKDAIK                                                                136

SEQ ID NO: 8            moltype = AA  length = 96
FEATURE                 Location/Qualifiers
source                  1..96
                        mol_type = protein
                        organism = Haemophilus influenzae
SEQUENCE: 8
MATITKLDII EYLSDKYHLS KQDTKNVVEN FLEEIRLSLE SGQDVKLSGF GNFELRDKSS                  60
RPGRNPKTGD VVPVSARRVV TFKPGQKLRA RVEKTK                                            96

SEQ ID NO: 9            moltype = AA  length = 96
FEATURE                 Location/Qualifiers
source                  1..96
                        mol_type = protein
                        organism = Haemophilus influenzae
SEQUENCE: 9
MATITKLDII EYLSDKYHLS KQDTKNVVEN FLEEIRLSLE SGQDVKLSGF GNFELRDKSS                  60
```

```
RPGRNPKTGD VVPVSARRVV TFKPGQKLRA RVEKTK                                     96

SEQ ID NO: 10           moltype = AA   length = 99
FEATURE                 Location/Qualifiers
source                  1..99
                        mol_type = protein
                        organism = Escherichia coli
SEQUENCE: 10
MALTKAEMSE YLFDKLGLSK RDAKELVELF FEEIRRALEN GEQVKLSGFG NFDLRDKNQR           60
PGRNPKTGED IPITARRVVT FRPGQKLKSR VENASPKDE                                  99

SEQ ID NO: 11           moltype = AA   length = 100
FEATURE                 Location/Qualifiers
source                  1..100
                        mol_type = protein
                        organism = Pseudomonas aeruginosa
SEQUENCE: 11
MGALTKAEIA ERLYEELGLN KREAKELVEL FFEEIRQALE HNEQVKLSGF GNFDLRDKRQ           60
RPGRNPKTGE EIPITARRVV TFRPGQKLKA RVEAYAGTKS                                 100

SEQ ID NO: 12           moltype = AA   length = 6
FEATURE                 Location/Qualifiers
source                  1..6
                        mol_type = protein
                        organism = Escherichia coli
SEQUENCE: 12
TFRPGQ                                                                      6

SEQ ID NO: 13           moltype = AA   length = 14
FEATURE                 Location/Qualifiers
source                  1..14
                        mol_type = protein
                        organism = Escherichia coli
SEQUENCE: 13
KLKSRVENAS PKDE                                                             14

SEQ ID NO: 14           moltype = AA   length = 6
FEATURE                 Location/Qualifiers
source                  1..6
                        mol_type = protein
                        organism = Escherichia coli
SEQUENCE: 14
HFKPGK                                                                      6

SEQ ID NO: 15           moltype = AA   length = 10
FEATURE                 Location/Qualifiers
source                  1..10
                        mol_type = protein
                        organism = Escherichia coli
SEQUENCE: 15
ELRDRANIYG                                                                  10

SEQ ID NO: 16           moltype = AA   length = 6
FEATURE                 Location/Qualifiers
source                  1..6
                        mol_type = protein
                        organism = Haemophilus influenzae
SEQUENCE: 16
TFKPGQ                                                                      6

SEQ ID NO: 17           moltype = AA   length = 10
FEATURE                 Location/Qualifiers
source                  1..10
                        mol_type = protein
                        organism = Haemophilus influenzae
SEQUENCE: 17
KLRARVEKTK                                                                  10

SEQ ID NO: 18           moltype = AA   length = 6
FEATURE                 Location/Qualifiers
source                  1..6
                        mol_type = protein
                        organism = Haemophilus influenzae
SEQUENCE: 18
TFKPGQ                                                                      6

SEQ ID NO: 19           moltype = AA   length = 10
FEATURE                 Location/Qualifiers
source                  1..10
```

```
                            mol_type = protein
                            organism = Haemophilus influenzae
SEQUENCE: 19
KLRARVENTK                                                              10

SEQ ID NO: 20               moltype = AA   length = 6
FEATURE                     Location/Qualifiers
source                      1..6
                            mol_type = protein
                            organism = Haemophilus influenzae
SEQUENCE: 20
TFKPGQ                                                                  6

SEQ ID NO: 21               moltype = AA   length = 10
FEATURE                     Location/Qualifiers
source                      1..10
                            mol_type = protein
                            organism = Haemophilus influenzae
SEQUENCE: 21
KLRARVEKTK                                                              10

SEQ ID NO: 22               moltype = AA   length = 6
FEATURE                     Location/Qualifiers
source                      1..6
                            mol_type = protein
                            organism = Haemophilus influenzae
SEQUENCE: 22
TFKPGQ                                                                  6

SEQ ID NO: 23               moltype = AA   length = 10
FEATURE                     Location/Qualifiers
source                      1..10
                            mol_type = protein
                            organism = Haemophilus influenzae
SEQUENCE: 23
KLRARVEKTK                                                              10

SEQ ID NO: 24               moltype = AA   length = 6
FEATURE                     Location/Qualifiers
source                      1..6
                            mol_type = protein
                            organism = Escherichia coli
SEQUENCE: 24
TFRPGQ                                                                  6

SEQ ID NO: 25               moltype = AA   length = 14
FEATURE                     Location/Qualifiers
source                      1..14
                            mol_type = protein
                            organism = Escherichia coli
SEQUENCE: 25
KLKSRVENAS PKDE                                                         14

SEQ ID NO: 26               moltype = AA   length = 6
FEATURE                     Location/Qualifiers
source                      1..6
                            mol_type = protein
                            organism = Pseudomonas aeruginosa
SEQUENCE: 26
TFRPGQ                                                                  6

SEQ ID NO: 27               moltype = AA   length = 14
FEATURE                     Location/Qualifiers
source                      1..14
                            mol_type = protein
                            organism = Pseudomonas aeruginosa
SEQUENCE: 27
KLKARVEAYA GTKS                                                         14

SEQ ID NO: 28               moltype = AA   length = 90
FEATURE                     Location/Qualifiers
source                      1..90
                            mol_type = protein
                            organism = Escherichia coli
SEQUENCE: 28
MNKTQLIDVI AEKAELSKTQ AKAALESTLA AITESLKEGD AVQLVGFGTF KVNHRAERTG        60
RNPQTGKEIK IAAANVPAFV SGKALKDAVK                                        90

SEQ ID NO: 29               moltype = AA   length = 90
```

```
FEATURE              Location/Qualifiers
source               1..90
                     mol_type = protein
                     organism = Escherichia coli
SEQUENCE: 29
MNKSQLIDKI AAGADISKAA AGRALDAIIA SVTESLKEGD DVALVGFGTF AVKERAARTG   60
RNPQTGKEIT IAAAKVPSFR AGKALKDAVN                                   90

SEQ ID NO: 30        moltype = AA   length = 6
FEATURE              Location/Qualifiers
source               1..6
                     mol_type = protein
                     organism = Escherichia coli
SEQUENCE: 30
AFVSGK                                                              6

SEQ ID NO: 31        moltype = AA   length = 7
FEATURE              Location/Qualifiers
source               1..7
                     mol_type = protein
                     organism = Escherichia coli
SEQUENCE: 31
ALKDAVK                                                             7

SEQ ID NO: 32        moltype = AA   length = 6
FEATURE              Location/Qualifiers
source               1..6
                     mol_type = protein
                     organism = Escherichia coli
SEQUENCE: 32
SFRAGK                                                              6

SEQ ID NO: 33        moltype = AA   length = 7
FEATURE              Location/Qualifiers
source               1..7
                     mol_type = protein
                     organism = Escherichia coli
SEQUENCE: 33
ALKDAVN                                                             7

SEQ ID NO: 34        moltype = AA   length = 20
FEATURE              Location/Qualifiers
source               1..20
                     mol_type = protein
                     organism = Escherichia coli
SEQUENCE: 34
TFRPGQKLKS RVENASPKDE                                              20

SEQ ID NO: 35        moltype = AA   length = 20
FEATURE              Location/Qualifiers
source               1..20
                     mol_type = protein
                     organism = Escherichia coli
SEQUENCE: 35
KYVPHFKPGK ELRDRANIYG                                              20

SEQ ID NO: 36        moltype =    length =
SEQUENCE: 36
000

SEQ ID NO: 37        moltype = AA   length = 6
FEATURE              Location/Qualifiers
REGION               1..6
                     note = Description of Artificial Sequence: Synthetic peptide
source               1..6
                     mol_type = protein
                     organism = synthetic construct
SEQUENCE: 37
GPSLKL                                                              6

SEQ ID NO: 38        moltype = AA   length = 4
FEATURE              Location/Qualifiers
REGION               1..4
                     note = Description of Artificial Sequence: Synthetic peptide
source               1..4
                     mol_type = protein
                     organism = synthetic construct
SEQUENCE: 38
GPSL                                                                4
```

```
SEQ ID NO: 39          moltype = AA   length = 4
FEATURE                Location/Qualifiers
REGION                 1..4
                       note = Description of Artificial Sequence: Synthetic peptide
source                 1..4
                       mol_type = protein
                       organism = synthetic construct
SEQUENCE: 39
PSLK                                                                        4

SEQ ID NO: 40          moltype = AA   length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 40
GPSLK                                                                       5

SEQ ID NO: 41          moltype = AA   length = 4
FEATURE                Location/Qualifiers
REGION                 1..4
                       note = Description of Artificial Sequence: Synthetic peptide
source                 1..4
                       mol_type = protein
                       organism = synthetic construct
SEQUENCE: 41
SLKL                                                                        4

SEQ ID NO: 42          moltype = AA   length = 99
FEATURE                Location/Qualifiers
source                 1..99
                       mol_type = protein
                       organism = Escherichia coli
SEQUENCE: 42
MALTKAEMSE YLFDKLGLSK RDAKELVELF FEEIRRALEN GEQVKLSGFG NFDLRDKNQR            60
PGRNPKTGED IPITARRVVT FRPGQKLKSR VENASPKDE                                  99

SEQ ID NO: 43          moltype = AA   length = 99
FEATURE                Location/Qualifiers
source                 1..99
                       mol_type = protein
                       organism = Salmonella enterica
SEQUENCE: 43
MALTKAEMSE YLFDKLGLSK RDAKELVELF FEEIRRALEN GEQVKLSGFG NFDLRDKNQR            60
PGRNPKTGED IPITARRVVT FRPGQKLKSR VENASPKEE                                  99

SEQ ID NO: 44          moltype = AA   length = 98
FEATURE                Location/Qualifiers
source                 1..98
                       mol_type = protein
                       organism = Vibrio cholerae
SEQUENCE: 44
MALTKAELAE ALFEQLGMSK RDAKDTVEVF FEEIRKALES GEQVKLSGFG NFDLRDKNER            60
PGRNPKTGED IPITARRVVT FRPGQKLKAR VENIKVEK                                   98

SEQ ID NO: 45          moltype = AA   length = 100
FEATURE                Location/Qualifiers
source                 1..100
                       mol_type = protein
                       organism = Pseudomonas aeruginosa
SEQUENCE: 45
MGALTKAEIA ERLYEELGLN KREAKELVEL FFEEIRQALE HNEQVKLSGF GNFDLRDKRQ            60
RPGRNPKTGE EIPITARRVV TFRPGQKLKA RVEAYAGTKS                                 100

SEQ ID NO: 46          moltype = AA   length = 96
FEATURE                Location/Qualifiers
source                 1..96
                       mol_type = protein
                       organism = Haemophilus influenzae
SEQUENCE: 46
MATITKLDII EYLSDKYHLS KQDTKNVVEN FLEEIRLSLE SGQDVKLSGF GNFELRDKSS            60
RPGRNPKTGD VVPVSARRVV TFKPGQKLRA RVEKTK                                     96

SEQ ID NO: 47          moltype = AA   length = 98
FEATURE                Location/Qualifiers
source                 1..98
```

```
                              mol_type = protein
                              organism = Aggregatibacter actinomycetemcomitans
SEQUENCE: 47
MTLTKVELAE NLIEKFHLSK REAKDLVESF FEEIRVALET GNDVKLSGFG NFELRDKASR     60
PGRNPKTGES VPVSARRVVV FKPGQKLRNR VEKVKPKA                            98

SEQ ID NO: 48                 moltype = AA   length = 98
FEATURE                       Location/Qualifiers
source                        1..98
                              mol_type = protein
                              organism = Moraxella catarrhalis
SEQUENCE: 48
MGALTKADMV DELTIRLRLT RQQARKLVDG FFEEISQSLA QGHEVKLSGF GNFELKDKKP     60
RPGRNPKTGE SVPIQARRVV TFKAGQKLRG WIDSQNEG                            98

SEQ ID NO: 49                 moltype = AA   length = 100
FEATURE                       Location/Qualifiers
source                        1..100
                              mol_type = protein
                              organism = Neisseria gonorrhoeae
SEQUENCE: 49
MTLTKAELAD ILVDKVSNVT KNDAKEIVEL FFEEIRSTLA SGEEIKISGF GNFQLRDKPQ     60
RPGRNPKTGE EVPITARRVV TFHASQKLKG MVEHYYDKQR                         100

SEQ ID NO: 50                 moltype = AA   length = 100
FEATURE                       Location/Qualifiers
source                        1..100
                              mol_type = protein
                              organism = Neisseria meningitidis
SEQUENCE: 50
MTLTKAELAD ILVDKVSNVT KNDAKEIVEL FFEEIRSTLA SGEEIKISGF GNFQLRDKPQ     60
RPGRNPKTGE EVPITARRVV TFHASQKLKS MVEHYYDKQR                         100

SEQ ID NO: 51                 moltype = AA   length = 101
FEATURE                       Location/Qualifiers
source                        1..101
                              mol_type = protein
                              organism = Burkholderia cenocepacia
SEQUENCE: 51
ASTETPTLTK AELAELLFDS VGLNKREAKD MVEAFFEVIR DALENGESVK LSGFGNFQLR     60
DKPQRPGRNP KTGEAIPIAA RRVVTFHASQ KLKALVENGA E                       101

SEQ ID NO: 52                 moltype = AA   length = 107
FEATURE                       Location/Qualifiers
source                        1..107
                              mol_type = protein
                              organism = Burkholderia pseudomallei
SEQUENCE: 52
TSAGDTPTLT KAELAELLFD SVGLNKREAK DMVEAFFEVI RDALENGESV KLSGFGNFQL     60
RDKPQRPGRN PNTGEAIPIA ARRVVTFHAS QKLKALVENG AEPDLAR                 107

SEQ ID NO: 53                 moltype = AA   length = 113
FEATURE                       Location/Qualifiers
source                        1..113
                              mol_type = protein
                              organism = Bordetella pertussis
SEQUENCE: 53
MGTTMLAEPR TLTKAELAEL LFERVGLNKR EAKDIVDTFF EEIRDALARG DSVKLSGFGN     60
FQVRDKPPRP GRNPKTGETI PIAARRVVTF HASQKLKSVV EQPNSPPDPA SAE          113

SEQ ID NO: 54                 moltype = AA   length = 97
FEATURE                       Location/Qualifiers
source                        1..97
                              mol_type = protein
                              organism = Prevotella melaninogenica
SEQUENCE: 54
MNNKEFIAAL AARTGYTQDE SQKMVKTVVD MMGKSFETGD PVPVIGFGTF EVKKRLERVM     60
VNPSTGLRML VPPKLVLNFK PAATIKGHVR KGGQDNG                            97

SEQ ID NO: 55                 moltype = AA   length = 95
FEATURE                       Location/Qualifiers
source                        1..95
                              mol_type = protein
                              organism = Prevotella intermedia
SEQUENCE: 55
MNNKEFITAL ANRVGRSQDE TQKLVKTALQ AMGDNFESGE PVLVSGFGSF EVKKRLERIM     60
TNPATGLRML VPPKLVLNFR ATASVKEKLK KGGAE                              95

SEQ ID NO: 56                 moltype = AA   length = 105
```

```
FEATURE                 Location/Qualifiers
source                  1..105
                        mol_type = protein
                        organism = Treponema palladium
SEQUENCE: 56
MKRVRRTRSF VVDALCDEVD LSRRHVARVV DSFVSVVTAA LERGETVELR DFGVFESRVR   60
KASVGKSINT GEVVSIPSHC VVVFRPSKRL KSAVRGYRSG EVGAD                  105

SEQ ID NO: 57           moltype = AA   length = 101
FEATURE                 Location/Qualifiers
source                  1..101
                        mol_type = protein
                        organism = Prevotella melaninogenica
SEQUENCE: 57
MAKSAIQLIT SALAKQHNLS ADDAAAFVDA FFDIISSELK NGNQVKIKGL GTFKVQAVKP   60
RESVNVNTGE RVLIEGHDKI SFTPDTVMKE LVNKPFSQFE T                     101

SEQ ID NO: 58           moltype = AA   length = 101
FEATURE                 Location/Qualifiers
source                  1..101
                        mol_type = protein
                        organism = Prevotella intermedia
SEQUENCE: 58
MAKTALQLIA DAVAKKHKIT VKEAEKFVSA IFDVVNEGLK TDKLVKVKGL GTFKVQAVKP   60
RESVNVNTGE RVLIEGHEKV SFTPDATMKE LVNKPFAQFE T                     101

SEQ ID NO: 59           moltype = AA   length = 90
FEATURE                 Location/Qualifiers
source                  1..90
                        mol_type = protein
                        organism = Staphylococcus aureus
SEQUENCE: 59
MNKTDLINAV AEQADLTKKE AGSAVDAVFE SIQNSLAKGE KVQLIGFGNF EVRERAARKG   60
RNPQTGKEID IPASKVPAFK AGKALKDAVK                                   90

SEQ ID NO: 60           moltype = AA   length = 90
FEATURE                 Location/Qualifiers
source                  1..90
                        mol_type = protein
                        organism = Escherichia coli
SEQUENCE: 60
MNKTQLIDVI AEKAELSKTQ AKAALESTLA AITESLKEGD AVQLVGFGTF KVNHRAERTG   60
RNPQTGKEIK IAAANVPAFV SGKALKDAVK                                   90

SEQ ID NO: 61           moltype = AA   length = 90
FEATURE                 Location/Qualifiers
source                  1..90
                        mol_type = protein
                        organism = Staphylococcus epidermidis
SEQUENCE: 61
MNKTDLINAV AEQADLTKKE AGSAVDAVFE SIQNSLAKGE KVQLIGFGNF EVRERAARKG   60
RNPQTGKEID IPASKVPAFK AGKALKDAVK                                   90

SEQ ID NO: 62           moltype = AA   length = 91
FEATURE                 Location/Qualifiers
source                  1..91
                        mol_type = protein
                        organism = Streptococcus sobrinus
SEQUENCE: 62
MANKQDLIAK VAEATELTKK DSAAAVDTVF SSIEGFLSKG EKVQLIGFGN FEVRERAARK   60
GRNPQTGAEI KIAASKVPAF KAGKALKDAV K                                 91

SEQ ID NO: 63           moltype = AA   length = 91
FEATURE                 Location/Qualifiers
source                  1..91
                        mol_type = protein
                        organism = Streptococcus pyogeneses
SEQUENCE: 63
MANKQDLIAK VAEATELTKK DSAAAVDAVF STIEAFLAEG EKVQLIGFGN FEVRERAARK   60
GRNPQTGAEI EIAASKVPAF KAGKALKDAV K                                 91

SEQ ID NO: 64           moltype = AA   length = 91
FEATURE                 Location/Qualifiers
source                  1..91
                        mol_type = protein
                        organism = Streptococcus gallolyticus
SEQUENCE: 64
MANKQDLIAK VAEATELTKK DSAAAVDAVF SAIESFLSEG EKVQLIGFGN FEVRERAARK   60
GRNPQTGEEI EIAASKVPAF KAGKALKDAV K                                 91
```

-continued

```
SEQ ID NO: 65         moltype = AA   length = 91
FEATURE               Location/Qualifiers
source                1..91
                      mol_type = protein
                      organism = Streptococcus agalactiae
SEQUENCE: 65
MANKQDLIAK VAEATELTKK DSAAAVDAVF AAVADYLAEG EKVQLIGFGN FEVRERAARK   60
GRNPQTGAEI EIAASKVPAF KAGKALKDAV K                                 91

SEQ ID NO: 66         moltype = AA   length = 91
FEATURE               Location/Qualifiers
source                1..91
                      mol_type = protein
                      organism = Streptococcus pneumoniae
SEQUENCE: 66
MANKQDLIAK VAEATELTKK DSAAAVEAVF AAVADYLAAG EKVQLIGFGN FEVRERAERK   60
GRNPQTGKEM TIAASKVPAF KAGKALKDAV K                                 91

SEQ ID NO: 67         moltype = AA   length = 91
FEATURE               Location/Qualifiers
source                1..91
                      mol_type = protein
                      organism = Streptococcus gordonii
SEQUENCE: 67
MANKQDLIAK VAEATELTKK DSAAAVDAVF AAVTEYLSKG EKVQLIGFGN FEVRERAARK   60
GRNPQTGKEI KIAASKVPAF KAGKALKDAV K                                 91

SEQ ID NO: 68         moltype = AA   length = 91
FEATURE               Location/Qualifiers
source                1..91
                      mol_type = protein
                      organism = Streptococcus mutans
SEQUENCE: 68
MANKQDLIAK VAEATELTKK DSAAAVDAVF SAVSSYLAKG EKVQLIGFGN FEVRERAARK   60
GRNPQTGEEI KIKASKVPAF KAGKALKDAV K                                 91

SEQ ID NO: 69         moltype = AA   length = 91
FEATURE               Location/Qualifiers
source                1..91
                      mol_type = protein
                      organism = Enterococcus faecalis
SEQUENCE: 69
MANKAELIEN VASSTGLTKK DATAAVDAVF STIQETLAKG EKVQLIGFGN FEVRERAARK   60
GRNPQTGQEI QIAASKVPAF KPGKALKDAV K                                 91

SEQ ID NO: 70         moltype = AA   length = 90
FEATURE               Location/Qualifiers
source                1..90
                      mol_type = protein
                      organism = Haemophilus influenzae
SEQUENCE: 70
MNKTDLIDAI ANAAELNKKQ AKAALEATLD AITASLKEGE PVQLIGFGTF KVNERAARTG   60
RNPQTGAEIQ IAASKVPAFV SGKALKDAIK                                   90

SEQ ID NO: 71         moltype = AA   length = 90
FEATURE               Location/Qualifiers
source                1..90
                      mol_type = protein
                      organism = Vibrio cholerae
SEQUENCE: 71
MNKTQLIDFI AEKADLTKVQ AKAALEATLG AVEGALKDGD QVQLIGFGTF KVNHRSARTG   60
RNPQTGEEIK IAAANVPAFV AGKALKDAIK                                   90

SEQ ID NO: 72         moltype = AA   length = 90
FEATURE               Location/Qualifiers
source                1..90
                      mol_type = protein
                      organism = Pseudomonas aeruginosa
SEQUENCE: 72
MNKSELIDAI AASADIPKAV AGRALDAVIE SVTGALKAGD SVVLVGFGTF AVKERAARTG   60
RNPQTGKPIK IAAAKIPGFK AGKALKDAVN                                   90

SEQ ID NO: 73         moltype = AA   length = 90
FEATURE               Location/Qualifiers
source                1..90
                      mol_type = protein
                      organism = Aggregatibacter actinomycetemcomitans
SEQUENCE: 73
```

```
MNKTDLIDAI ASSAELNKKQ AKAALEATLD AITGSLKKGE AVQLIGFGTF KVNARKARTG    60
RNPQTGAEIK IAASKVPAFV SGKALKDAVK                                   90

SEQ ID NO: 74         moltype = AA   length = 90
FEATURE               Location/Qualifiers
source                1..90
                      mol_type = protein
                      organism = Vibrio cholerae
SEQUENCE: 74
MNKTQLVEQI AANADISKAS AGRALDAFIE AVSGTLQSGD QVALVGFGTF SVRTRAARTG   60
RNPKTGEEIK IAEAKVPSFK AGKALKDACN                                   90

SEQ ID NO: 75         moltype = AA   length = 90
FEATURE               Location/Qualifiers
source                1..90
                      mol_type = protein
                      organism = Escherichia coli
SEQUENCE: 75
MNKSQLIDKI AAGADISKAA AGRALDAIIA SVTESLKEGD DVALVGFGTF AVKERAARTG   60
RNPQTGKEIT IAAAKVPSFR AGKALKDAVN                                   90

SEQ ID NO: 76         moltype = AA   length = 90
FEATURE               Location/Qualifiers
source                1..90
                      mol_type = protein
                      organism = Moraxella catarrhalis
SEQUENCE: 76
MNKSELVDSI AQSAGLTKEQ AAKAVNAFTE SVQGALQRGD DVVLVGFGTF SVKERAARMG   60
RNPKTGEAIQ IAASKVPSFK AGKVLKESVN                                   90

SEQ ID NO: 77         moltype = AA   length = 90
FEATURE               Location/Qualifiers
source                1..90
                      mol_type = protein
                      organism = Bordetella pertussis
SEQUENCE: 77
MNKTELIDHI ASKADISKAA AGRSLDALIG AVKTTLKKGG TVTLVGFGTF AVSARAARTG   60
RNPRTGETIK IKKAKVPKFR PGKALKDAVN                                   90

SEQ ID NO: 78         moltype = AA   length = 99
FEATURE               Location/Qualifiers
source                1..99
                      mol_type = protein
                      organism = Moraxella catarrhalis
SEQUENCE: 78
MQAVINKSNL IANLASVCEE LEEDVVDEAV RLMIAMMVNE LVYDGRIEVR GFGSFCLHHR   60
SARIARNPRT GESVSVKAKA TPYFKPGKAL RESVNLVND                         99

SEQ ID NO: 79         moltype = AA   length = 91
FEATURE               Location/Qualifiers
source                1..91
                      mol_type = protein
                      organism = Prevotella melaninogenica
SEQUENCE: 79
MNKTELIEKI AANAEVSKAA AKKALDATTE AIKEALAAGD KVQLVGFGTF ATTERPAHEG   60
INPRSKEKIK IAAKKVAKFK AGAELADAVN K                                 91

SEQ ID NO: 80         moltype = AA   length = 91
FEATURE               Location/Qualifiers
source                1..91
                      mol_type = protein
                      organism = Prevotella intermedia
SEQUENCE: 80
MNKTELIEKI AAGAGLSKAD SKKALDAMTA AIKEALVAGD KVQLVGFGTY SVTERPAHEG   60
INPATKQKIQ IAAKKVAKFK PGAELADAVN A                                 91

SEQ ID NO: 81         moltype = AA   length = 106
FEATURE               Location/Qualifiers
source                1..106
                      mol_type = protein
                      organism = Treponema denticola
SEQUENCE: 81
MKQKRSKIDI IDSVYRNNPQ YQLKQINAIA NLFLDELSVL LQQGIPVEIR GLGSFDFAVL   60
HGRKNARNPK TGEAVLTADR CKVRFKPGKE LKEALHKIDT QELIES                106

SEQ ID NO: 82         moltype = AA   length = 88
FEATURE               Location/Qualifiers
source                1..88
                      mol_type = protein
```

```
                         organism = Porphyromonas gingivalis
SEQUENCE: 82
MNKTDFIAAV AEKANLTKAD AQRAVNAFAE VVTEQMNAGE KIALIGFGTF SVSERAARKG    60
INPKTKKSIS IPARKVVRFK PGSTLELK                                      88

SEQ ID NO: 83            moltype = AA   length = 94
FEATURE                  Location/Qualifiers
source                   1..94
                         mol_type = protein
                         organism = Helicobacter pylori
SEQUENCE: 83
MNKAEFIDLV KEAGKYNSKR EAEEAISAFT LAVETALSKG ESVELIGFGK FETAEQKGKE    60
GKVPGSDKTY KTEDKRVPKF KFGKTLKQKV EEGK                                94

SEQ ID NO: 84            moltype = AA   length = 92
FEATURE                  Location/Qualifiers
source                   1..92
                         mol_type = protein
                         organism = Prevotella melaninogenica
SEQUENCE: 84
MTKADIINEI ATSTGIAKKD VSAVVESFME TIKDSLLEKK ENVYLRGFGS FIVKHRAEKT    60
ARNISKNTTI TIPAHDFPSF KPAKTFIEDM KK                                  92

SEQ ID NO: 85            moltype = AA   length = 92
FEATURE                  Location/Qualifiers
source                   1..92
                         mol_type = protein
                         organism = Prevotella intermedia
SEQUENCE: 85
MTKADIINEI ASSTGISKKD VSAVVESFMD AIKDSLLENK ENVYLRGFGS FIVKHRAEKT    60
ARNISKNTTI TIPAHDFPSF KPAKTFIEDM KK                                  92

SEQ ID NO: 86            moltype = AA   length = 92
FEATURE                  Location/Qualifiers
source                   1..92
                         mol_type = protein
                         organism = Porphyromonas gingivalis
SEQUENCE: 86
MTKADVVNAI AKSTGIDKET TLKVVESFMD TIKDSLSEGD NVYLRGFGSF IVKERAEKTA    60
RNISKQTTII IPKRNIPAFK PSKIFMSQMK QD                                  92

SEQ ID NO: 87            moltype = AA   length = 100
FEATURE                  Location/Qualifiers
source                   1..100
                         mol_type = protein
                         organism = Mycobacterium tuberculosis
SEQUENCE: 87
MNKAELIDVL TQKLGSDRRQ ATAAVENVVD TIVRAVHKGD SVTITGFGVF EQRRRAARVA    60
RNPRTGETVK VKPTSVPAFR FGAQFKAVVS GAQRLPAEGP                          100

SEQ ID NO: 88            moltype = AA   length = 100
FEATURE                  Location/Qualifiers
source                   1..100
                         mol_type = protein
                         organism = Mycobacterium smegmatis
SEQUENCE: 88
MNKAELIDVL TTKMGTDRRQ ATAAVENVVD TIVRAVHKGD SVTITGFGVF EQRRRAARVA    60
RNPRTGETVK VKPTSVPAFR FGAQFKAVIS GAQKLPADGP                          100

SEQ ID NO: 89            moltype = AA   length = 94
FEATURE                  Location/Qualifiers
source                   1..94
                         mol_type = protein
                         organism = Escherichia coli
SEQUENCE: 89
MTKSELIERL ATQQSHIPAK TVEDAVKEML EHMASTLAQG ERIEIRGFGS FSLHYRAPRT    60
GRNPKTGDKV ELEGKYVPHF KPGKELRDRA NIYG                                94

SEQ ID NO: 90            moltype = AA   length = 94
FEATURE                  Location/Qualifiers
source                   1..94
                         mol_type = protein
                         organism = Salmonella enterica
SEQUENCE: 90
MTKSELIERL ATQQSHIPAK AVEDAVKEML EHMASTLAQG ERIEIRGFGS FSLHYRAPRT    60
GRNPKTGDKV ELEGKYVPHF KPGKELRDRA NIYG                                94

SEQ ID NO: 91            moltype = AA   length = 92
FEATURE                  Location/Qualifiers
```

```
source                        1..92
                              mol_type = protein
                              organism = Vibrio cholerae
SEQUENCE: 91
MTKSELIERL CAEQTHLSAK EIEDAVKNIL EHMASTLEAG ERIEIRGFGS FSLHYREPRV    60
GRNPKTGDKV ELEGKYVPHF KPGKELRERV NL                                 92

SEQ ID NO: 92                 moltype = AA   length = 94
FEATURE                       Location/Qualifiers
source                        1..94
                              mol_type = protein
                              organism = Pseudomonas aeruginosa
SEQUENCE: 92
MTKSELIERI VTHQGQLSAK DVELAIKTML EQMSQALATG DRIEIRGFGS FSLHYRAPRV    60
GRNPKTGESV RLDGKFVPHF KPGKELRDRV NEPE                               94

SEQ ID NO: 93                 moltype = AA   length = 94
FEATURE                       Location/Qualifiers
source                        1..94
                              mol_type = protein
                              organism = Haemophilus influenzae
SEQUENCE: 93
MTKSELMEKL SAKQPTLPAK EIENMVKGIL EFISQSLENG DRVEVRGFGS FSLHHRQPRL    60
GRNPKTGDSV NLSAKSVPYF KAGKELKARV DVQA                               94

SEQ ID NO: 94                 moltype = AA   length = 95
FEATURE                       Location/Qualifiers
source                        1..95
                              mol_type = protein
                              organism = Aggregatibacter actinomycetemcomitans
SEQUENCE: 94
MTKSELIELL VQKNSNIPVK HVEEAVKAIL EQMSYVLEHG ERIEVRGFGS FSLHCRQPRI    60
GRNPKTGEQV KLDAKCVPYF KAGKELRERV DVYAA                              95

SEQ ID NO: 95                 moltype = AA   length = 98
FEATURE                       Location/Qualifiers
source                        1..98
                              mol_type = protein
                              organism = Neisseria gonorrhoeae
SEQUENCE: 95
MVRLAEVFAA KNGTHLLAKD VEYSVKVLVD TMTRSLARGQ RIEIRGFGSF DLNHRPARIG    60
RNPKTGERVE VPEKHVPHFK PGKELRERVD LALKENAN                           98

SEQ ID NO: 96                 moltype = AA   length = 104
FEATURE                       Location/Qualifiers
source                        1..104
                              mol_type = protein
                              organism = Neisseria meningitidis
SEQUENCE: 96
MTKSELMVRL AEVFAAKNGT HLLAKDVEYS VKVLVDTMTR SLARGQRIEI RGFGSFDLNH    60
RPARIGRNPK TGERVEVPEK HVPHFKPGKE LRERVDLALK ENAN                    104

SEQ ID NO: 97                 moltype = AA   length = 107
FEATURE                       Location/Qualifiers
source                        1..107
                              mol_type = protein
                              organism = Burkholderia cenocepacia
SEQUENCE: 97
MTKSELVAQL ASRFPQLVLK DADFAVKTML DAMSDALAKG HRIEIRGFGS FGLNRRPARV    60
GRNPKSGEKV QVPEKFVPHF KPGKELRERV DGRAGEPLKA DDPDDDR                 107

SEQ ID NO: 98                 moltype = AA   length = 107
FEATURE                       Location/Qualifiers
source                        1..107
                              mol_type = protein
                              organism = Burkholderia pseudomallei
SEQUENCE: 98
MTKSELVAQL ASRFPQLVLK DADFAVKTML DAMSDALSKG HRIEIRGFGS FGLNRRPARV    60
GRNPKSGEKV QVPEKHVPHF KPGKELRERV DGRAGEPLKN DEPEDAQ                 107

SEQ ID NO: 99                 moltype = AA   length = 101
FEATURE                       Location/Qualifiers
source                        1..101
                              mol_type = protein
                              organism = Bordetella pertussis
SEQUENCE: 99
MTKSELIAAL AARYPQLAAR DTDYAVKTML DAMTQALASG QRIEIRGFGS FSLSQRSPRI    60
GRNPKSGEQV LVPGKQVPHF KPGKELREWV DLVGNDQGDD S                       101
```

```
SEQ ID NO: 100          moltype = AA  length = 108
FEATURE                 Location/Qualifiers
source                  1..108
                        mol_type = protein
                        organism = Borrelia burgdorferi
SEQUENCE: 100
MSFSRRPKVT KSDIVDQISL NIKNNNLKLE KKYIRLVIDA FFEELKSNLC SNNVIEFRSF  60
GTFEVRKRKG RLNARNPQTG EYVKVLDHHV AYFRPGKDLK ERVWGIKG            108

SEQ ID NO: 101          moltype = AA  length = 16
FEATURE                 Location/Qualifiers
source                  1..16
                        mol_type = protein
                        organism = Streptococcus sp.
SEQUENCE: 101
EVRERAARKG RNPQTG                                                 16

SEQ ID NO: 102          moltype = AA  length = 16
FEATURE                 Location/Qualifiers
source                  1..16
                        mol_type = protein
                        organism = Escherichia coli
SEQUENCE: 102
DLRDKNQRPG RNPKTG                                                 16

SEQ ID NO: 103          moltype = AA  length = 16
FEATURE                 Location/Qualifiers
source                  1..16
                        mol_type = protein
                        organism = Salmonella enterica
SEQUENCE: 103
DLRDKNQRPG RNPKTG                                                 16

SEQ ID NO: 104          moltype = AA  length = 16
FEATURE                 Location/Qualifiers
source                  1..16
                        mol_type = protein
                        organism = Vibrio cholerae
SEQUENCE: 104
DLRDKNERPG RNPKTG                                                 16

SEQ ID NO: 105          moltype = AA  length = 16
FEATURE                 Location/Qualifiers
source                  1..16
                        mol_type = protein
                        organism = Pseudomonas aeruginosa
SEQUENCE: 105
DLRDKRQRPG RNPKTG                                                 16

SEQ ID NO: 106          moltype = AA  length = 16
FEATURE                 Location/Qualifiers
source                  1..16
                        mol_type = protein
                        organism = Haemophilus influenzae
SEQUENCE: 106
ELRDKSSRPG RNPKTG                                                 16

SEQ ID NO: 107          moltype = AA  length = 16
FEATURE                 Location/Qualifiers
source                  1..16
                        mol_type = protein
                        organism = Aggregatibacter actinomycetemcomitans
SEQUENCE: 107
ELRDKASRPG RNPKTG                                                 16

SEQ ID NO: 108          moltype = AA  length = 16
FEATURE                 Location/Qualifiers
source                  1..16
                        mol_type = protein
                        organism = Moraxella catarrhalis
SEQUENCE: 108
ELKDKKPRPG RNPKTG                                                 16

SEQ ID NO: 109          moltype = AA  length = 16
FEATURE                 Location/Qualifiers
source                  1..16
                        mol_type = protein
                        organism = Neisseria gonorrhoeae
SEQUENCE: 109
```

```
QLRDKPQRPG RNPKTG                                                        16

SEQ ID NO: 110          moltype = AA   length = 16
FEATURE                 Location/Qualifiers
source                  1..16
                        mol_type = protein
                        organism = Neisseria meningitidis
SEQUENCE: 110
QLRDKPQRPG RNPKTG                                                        16

SEQ ID NO: 111          moltype = AA   length = 16
FEATURE                 Location/Qualifiers
source                  1..16
                        mol_type = protein
                        organism = Burkholderia cenocepacia
SEQUENCE: 111
QLRDKPQRPG RNPKTG                                                        16

SEQ ID NO: 112          moltype = AA   length = 16
FEATURE                 Location/Qualifiers
source                  1..16
                        mol_type = protein
                        organism = Burkholderia pseudomallei
SEQUENCE: 112
QLRDKPQRPG RNPNTG                                                        16

SEQ ID NO: 113          moltype = AA   length = 16
FEATURE                 Location/Qualifiers
source                  1..16
                        mol_type = protein
                        organism = Bordetella pertussis
SEQUENCE: 113
QVRDKPPRPG RNPKTG                                                        16

SEQ ID NO: 114          moltype = AA   length = 16
FEATURE                 Location/Qualifiers
source                  1..16
                        mol_type = protein
                        organism = Prevotella melaninogenica
SEQUENCE: 114
EVKKRLERVM VNPSTG                                                        16

SEQ ID NO: 115          moltype = AA   length = 16
FEATURE                 Location/Qualifiers
source                  1..16
                        mol_type = protein
                        organism = Prevotella intermedia
SEQUENCE: 115
EVKKRLERIM TNPATG                                                        16

SEQ ID NO: 116          moltype = AA   length = 16
FEATURE                 Location/Qualifiers
source                  1..16
                        mol_type = protein
                        organism = Treponema palladium
SEQUENCE: 116
ESRVRKASVG KSINTG                                                        16

SEQ ID NO: 117          moltype = AA   length = 16
FEATURE                 Location/Qualifiers
source                  1..16
                        mol_type = protein
                        organism = Prevotella melaninogenica
SEQUENCE: 117
KVQAVKPRES VNVNTG                                                        16

SEQ ID NO: 118          moltype = AA   length = 16
FEATURE                 Location/Qualifiers
source                  1..16
                        mol_type = protein
                        organism = Prevotella intermedia
SEQUENCE: 118
KVQAVKPRES VNVNTG                                                        16

SEQ ID NO: 119          moltype = AA   length = 16
FEATURE                 Location/Qualifiers
source                  1..16
                        mol_type = protein
                        organism = Staphylococcus aureus
```

```
SEQUENCE: 119
EVRERAARKG RNPQTG                                                        16

SEQ ID NO: 120          moltype = AA  length = 16
FEATURE                 Location/Qualifiers
source                  1..16
                        mol_type = protein
                        organism = Escherichia coli
SEQUENCE: 120
KVNHRAERTG RNPQTG                                                        16

SEQ ID NO: 121          moltype = AA  length = 16
FEATURE                 Location/Qualifiers
source                  1..16
                        mol_type = protein
                        organism = Staphylococcus epidermidis
SEQUENCE: 121
EVRERAARKG RNPQTG                                                        16

SEQ ID NO: 122          moltype = AA  length = 16
FEATURE                 Location/Qualifiers
source                  1..16
                        mol_type = protein
                        organism = Streptococcus sobrinus
SEQUENCE: 122
EVRERAARKG RNPQTG                                                        16

SEQ ID NO: 123          moltype = AA  length = 16
FEATURE                 Location/Qualifiers
source                  1..16
                        mol_type = protein
                        organism = Streptococcus pyogeneses
SEQUENCE: 123
EVRERAARKG RNPQTG                                                        16

SEQ ID NO: 124          moltype = AA  length = 16
FEATURE                 Location/Qualifiers
source                  1..16
                        mol_type = protein
                        organism = Streptococcus gallolyticus
SEQUENCE: 124
EVRERAARKG RNPQTG                                                        16

SEQ ID NO: 125          moltype = AA  length = 16
FEATURE                 Location/Qualifiers
source                  1..16
                        mol_type = protein
                        organism = Streptococcus agalactiae
SEQUENCE: 125
EVRERAARKG RNPQTG                                                        16

SEQ ID NO: 126          moltype = AA  length = 16
FEATURE                 Location/Qualifiers
source                  1..16
                        mol_type = protein
                        organism = Streptococcus pneumoniae
SEQUENCE: 126
EVRERAERKG RNPQTG                                                        16

SEQ ID NO: 127          moltype = AA  length = 16
FEATURE                 Location/Qualifiers
source                  1..16
                        mol_type = protein
                        organism = Streptococcus gordonii
SEQUENCE: 127
EVRERAARKG RNPQTG                                                        16

SEQ ID NO: 128          moltype = AA  length = 16
FEATURE                 Location/Qualifiers
source                  1..16
                        mol_type = protein
                        organism = Streptococcus mutans
SEQUENCE: 128
EVRERAARKG RNPQTG                                                        16

SEQ ID NO: 129          moltype = AA  length = 16
FEATURE                 Location/Qualifiers
source                  1..16
                        mol_type = protein
```

```
                        organism = Enterococcus faecalis
SEQUENCE: 129
EVRERAARKG RNPQTG                                                    16

SEQ ID NO: 130          moltype = AA   length = 16
FEATURE                 Location/Qualifiers
source                  1..16
                        mol_type = protein
                        organism = Haemophilus influenzae
SEQUENCE: 130
KVNERAARTG RNPQTG                                                    16

SEQ ID NO: 131          moltype = AA   length = 16
FEATURE                 Location/Qualifiers
source                  1..16
                        mol_type = protein
                        organism = Vibrio cholerae
SEQUENCE: 131
KVNHRSARTG RNPQTG                                                    16

SEQ ID NO: 132          moltype = AA   length = 16
FEATURE                 Location/Qualifiers
source                  1..16
                        mol_type = protein
                        organism = Bordetella pertussis
SEQUENCE: 132
AVSARAARTG RNPRTG                                                    16

SEQ ID NO: 133          moltype = AA   length = 16
FEATURE                 Location/Qualifiers
source                  1..16
                        mol_type = protein
                        organism = Pseudomonas aeruginosa
SEQUENCE: 133
AVKERAARTG RNPQTG                                                    16

SEQ ID NO: 134          moltype = AA   length = 16
FEATURE                 Location/Qualifiers
source                  1..16
                        mol_type = protein
                        organism = Aggregatibacter actinomycetemcomitans
SEQUENCE: 134
SVRTRAARTG RNPKTG                                                    16

SEQ ID NO: 135          moltype = AA   length = 16
FEATURE                 Location/Qualifiers
source                  1..16
                        mol_type = protein
                        organism = Prevotella melaninogenica
SEQUENCE: 135
ATTERPAHEG INPRSK                                                    16

SEQ ID NO: 136          moltype = AA   length = 16
FEATURE                 Location/Qualifiers
source                  1..16
                        mol_type = protein
                        organism = Prevotella intermedia
SEQUENCE: 136
SVTERPAHEG INPATK                                                    16

SEQ ID NO: 137          moltype = AA   length = 16
FEATURE                 Location/Qualifiers
source                  1..16
                        mol_type = protein
                        organism = Treponema denticola
SEQUENCE: 137
FAVLHGRKNA RNPKTG                                                    16

SEQ ID NO: 138          moltype = AA   length = 16
FEATURE                 Location/Qualifiers
source                  1..16
                        mol_type = protein
                        organism = Porphyromonas gingivalis
SEQUENCE: 138
SVSERAARKG INPKTK                                                    16

SEQ ID NO: 139          moltype = AA   length = 16
FEATURE                 Location/Qualifiers
source                  1..16
```

```
                        mol_type = protein
                        organism = Helicobacter pylori
SEQUENCE: 139
ETAEQKGKEG KVPGSD                                                     16

SEQ ID NO: 140          moltype = AA  length = 17
FEATURE                 Location/Qualifiers
source                  1..17
                        mol_type = protein
                        organism = Prevotella melaninogenica
SEQUENCE: 140
FIVKHRAEKT ARNISKN                                                    17

SEQ ID NO: 141          moltype = AA  length = 17
FEATURE                 Location/Qualifiers
source                  1..17
                        mol_type = protein
                        organism = Prevotella intermedia
SEQUENCE: 141
FIVKHRAEKT ARNISKN                                                    17

SEQ ID NO: 142          moltype = AA  length = 16
FEATURE                 Location/Qualifiers
source                  1..16
                        mol_type = protein
                        organism = Porphyromonas gingivalis
SEQUENCE: 142
IVKERAEKTA RNISKQ                                                     16

SEQ ID NO: 143          moltype = AA  length = 16
FEATURE                 Location/Qualifiers
source                  1..16
                        mol_type = protein
                        organism = Mycobacterium tuberculosis
SEQUENCE: 143
EQRRRAARVA RNPRTG                                                     16

SEQ ID NO: 144          moltype = AA  length = 16
FEATURE                 Location/Qualifiers
source                  1..16
                        mol_type = protein
                        organism = Mycobacterium smegmatis
SEQUENCE: 144
EQRRRAARVA RNPRTG                                                     16

SEQ ID NO: 145          moltype = AA  length = 16
FEATURE                 Location/Qualifiers
source                  1..16
                        mol_type = protein
                        organism = Escherichia coli
SEQUENCE: 145
SLHYRAPRTG RNPKTG                                                     16

SEQ ID NO: 146          moltype = AA  length = 16
FEATURE                 Location/Qualifiers
source                  1..16
                        mol_type = protein
                        organism = Salmonella enterica
SEQUENCE: 146
SLHYRAPRTG RNPKTG                                                     16

SEQ ID NO: 147          moltype = AA  length = 16
FEATURE                 Location/Qualifiers
source                  1..16
                        mol_type = protein
                        organism = Vibrio cholerae
SEQUENCE: 147
SLHYREPRVG RNPKTG                                                     16

SEQ ID NO: 148          moltype = AA  length = 16
FEATURE                 Location/Qualifiers
source                  1..16
                        mol_type = protein
                        organism = Escherichia coli
SEQUENCE: 148
AVKERAARTG RNPQTG                                                     16

SEQ ID NO: 149          moltype = AA  length = 16
FEATURE                 Location/Qualifiers
```

```
source                  1..16
                        mol_type = protein
                        organism = Moraxella catarrhalis
SEQUENCE: 149
SVKERAARMG RNPKTG                                                            16

SEQ ID NO: 150          moltype = AA  length = 16
FEATURE                 Location/Qualifiers
source                  1..16
                        mol_type = protein
                        organism = Pseudomonas aeruginosa
SEQUENCE: 150
SLHYRAPRVG RNPKTG                                                            16

SEQ ID NO: 151          moltype = AA  length = 16
FEATURE                 Location/Qualifiers
source                  1..16
                        mol_type = protein
                        organism = Haemophilus influenzae
SEQUENCE: 151
SLHHRQPRLG RNPKTG                                                            16

SEQ ID NO: 152          moltype = AA  length = 16
FEATURE                 Location/Qualifiers
source                  1..16
                        mol_type = protein
                        organism = Aggregatibacter actinomycetemcomitans
SEQUENCE: 152
SLHCRQPRIG RNPKTG                                                            16

SEQ ID NO: 153          moltype = AA  length = 16
FEATURE                 Location/Qualifiers
source                  1..16
                        mol_type = protein
                        organism = Neisseria gonorrhoeae
SEQUENCE: 153
DLNHRPARIG RNPKTG                                                            16

SEQ ID NO: 154          moltype = AA  length = 16
FEATURE                 Location/Qualifiers
source                  1..16
                        mol_type = protein
                        organism = Neisseria meningitidis
SEQUENCE: 154
DLNHRPARIG RNPKTG                                                            16

SEQ ID NO: 155          moltype = AA  length = 16
FEATURE                 Location/Qualifiers
source                  1..16
                        mol_type = protein
                        organism = Burkholderia cenocepacia
SEQUENCE: 155
GLNRRPARVG RNPKSG                                                            16

SEQ ID NO: 156          moltype = AA  length = 16
FEATURE                 Location/Qualifiers
source                  1..16
                        mol_type = protein
                        organism = Burkholderia pseudomallei
SEQUENCE: 156
GLNRRPARVG RNPKSG                                                            16

SEQ ID NO: 157          moltype = AA  length = 16
FEATURE                 Location/Qualifiers
source                  1..16
                        mol_type = protein
                        organism = Bordetella pertussis
SEQUENCE: 157
SLSQRSPRIG RNPKSG                                                            16

SEQ ID NO: 158          moltype = AA  length = 16
FEATURE                 Location/Qualifiers
source                  1..16
                        mol_type = protein
                        organism = Moraxella catarrhalis
SEQUENCE: 158
CLHHRSARIA RNPRTG                                                            16

SEQ ID NO: 159          moltype = AA  length = 17
```

```
FEATURE                 Location/Qualifiers
source                  1..17
                        mol_type = protein
                        organism = Borrelia burgdorferi
SEQUENCE: 159
EVRKRKGRLN ARNPQTG                                                          17

SEQ ID NO: 160          moltype = AA  length = 6
FEATURE                 Location/Qualifiers
source                  1..6
                        mol_type = protein
                        organism = Streptococcus pyogeneses
SEQUENCE: 160
AFKAGK                                                                       6

SEQ ID NO: 161          moltype = AA  length = 7
FEATURE                 Location/Qualifiers
source                  1..7
                        mol_type = protein
                        organism = Streptococcus pyogeneses
SEQUENCE: 161
ALKDAVK                                                                      7

SEQ ID NO: 162          moltype = AA  length = 20
FEATURE                 Location/Qualifiers
source                  1..20
                        mol_type = protein
                        organism = Streptococcus pyogeneses
SEQUENCE: 162
IAASKVPAFK AGKALKDAVK                                                       20

SEQ ID NO: 163          moltype = AA  length = 6
FEATURE                 Location/Qualifiers
source                  1..6
                        mol_type = protein
                        organism = Streptococcus gallolyticus
SEQUENCE: 163
AFKAGK                                                                       6

SEQ ID NO: 164          moltype = AA  length = 7
FEATURE                 Location/Qualifiers
source                  1..7
                        mol_type = protein
                        organism = Streptococcus gallolyticus
SEQUENCE: 164
ALKDAVK                                                                      7

SEQ ID NO: 165          moltype = AA  length = 20
FEATURE                 Location/Qualifiers
source                  1..20
                        mol_type = protein
                        organism = Streptococcus gallolyticus
SEQUENCE: 165
IAASKVPAFK AGKALKDAVK                                                       20

SEQ ID NO: 166          moltype = AA  length = 6
FEATURE                 Location/Qualifiers
source                  1..6
                        mol_type = protein
                        organism = Streptococcus sobrinus
SEQUENCE: 166
AFKAGK                                                                       6

SEQ ID NO: 167          moltype = AA  length = 7
FEATURE                 Location/Qualifiers
source                  1..7
                        mol_type = protein
                        organism = Streptococcus sobrinus
SEQUENCE: 167
ALKDAVK                                                                      7

SEQ ID NO: 168          moltype = AA  length = 20
FEATURE                 Location/Qualifiers
source                  1..20
                        mol_type = protein
                        organism = Streptococcus sobrinus
SEQUENCE: 168
IAASKVPAFK AGKALKDAVK                                                       20
```

-continued

```
SEQ ID NO: 169            moltype = AA   length = 6
FEATURE                   Location/Qualifiers
source                    1..6
                          mol_type = protein
                          organism = Streptococcus agalactiae
SEQUENCE: 169
AFKAGK                                                                    6

SEQ ID NO: 170            moltype = AA   length = 7
FEATURE                   Location/Qualifiers
source                    1..7
                          mol_type = protein
                          organism = Streptococcus agalactiae
SEQUENCE: 170
ALKDAVK                                                                   7

SEQ ID NO: 171            moltype = AA   length = 20
FEATURE                   Location/Qualifiers
source                    1..20
                          mol_type = protein
                          organism = Streptococcus agalactiae
SEQUENCE: 171
IAASKVPAFK AGKALKDAVK                                                    20

SEQ ID NO: 172            moltype = AA   length = 6
FEATURE                   Location/Qualifiers
source                    1..6
                          mol_type = protein
                          organism = Streptococcus pneumoniae
SEQUENCE: 172
AFKAGK                                                                    6

SEQ ID NO: 173            moltype = AA   length = 7
FEATURE                   Location/Qualifiers
source                    1..7
                          mol_type = protein
                          organism = Streptococcus pneumoniae
SEQUENCE: 173
ALKDAVK                                                                   7

SEQ ID NO: 174            moltype = AA   length = 20
FEATURE                   Location/Qualifiers
source                    1..20
                          mol_type = protein
                          organism = Streptococcus pneumoniae
SEQUENCE: 174
IAASKVPAFK AGKALKDAVK                                                    20

SEQ ID NO: 175            moltype = AA   length = 6
FEATURE                   Location/Qualifiers
source                    1..6
                          mol_type = protein
                          organism = Streptococcus gordonii
SEQUENCE: 175
AFKAGK                                                                    6

SEQ ID NO: 176            moltype = AA   length = 7
FEATURE                   Location/Qualifiers
source                    1..7
                          mol_type = protein
                          organism = Streptococcus gordonii
SEQUENCE: 176
ALKDAVK                                                                   7

SEQ ID NO: 177            moltype = AA   length = 20
FEATURE                   Location/Qualifiers
source                    1..20
                          mol_type = protein
                          organism = Streptococcus gordonii
SEQUENCE: 177
IAASKVPAFK AGKALKDAVK                                                    20

SEQ ID NO: 178            moltype = AA   length = 6
FEATURE                   Location/Qualifiers
source                    1..6
                          mol_type = protein
                          organism = Streptococcus mutans
SEQUENCE: 178
AFKAGK                                                                    6
```

```
SEQ ID NO: 179          moltype = AA   length = 7
FEATURE                 Location/Qualifiers
source                  1..7
                        mol_type = protein
                        organism = Streptococcus mutans
SEQUENCE: 179
ALKDAVK                                                                    7

SEQ ID NO: 180          moltype = AA   length = 20
FEATURE                 Location/Qualifiers
source                  1..20
                        mol_type = protein
                        organism = Streptococcus mutans
SEQUENCE: 180
IKASKVPAFK AGKALKDAVK                                                     20

SEQ ID NO: 181          moltype = AA   length = 6
FEATURE                 Location/Qualifiers
source                  1..6
                        mol_type = protein
                        organism = Enterococcus faecalis
SEQUENCE: 181
AFKPGK                                                                     6

SEQ ID NO: 182          moltype = AA   length = 7
FEATURE                 Location/Qualifiers
source                  1..7
                        mol_type = protein
                        organism = Enterococcus faecalis
SEQUENCE: 182
ALKDAVK                                                                    7

SEQ ID NO: 183          moltype = AA   length = 20
FEATURE                 Location/Qualifiers
source                  1..20
                        mol_type = protein
                        organism = Enterococcus faecalis
SEQUENCE: 183
IAASKVPAFK PGKALKDAVK                                                     20

SEQ ID NO: 184          moltype = AA   length = 6
FEATURE                 Location/Qualifiers
source                  1..6
                        mol_type = protein
                        organism = Staphylococcus aureus
SEQUENCE: 184
AFKAGK                                                                     6

SEQ ID NO: 185          moltype = AA   length = 7
FEATURE                 Location/Qualifiers
source                  1..7
                        mol_type = protein
                        organism = Staphylococcus aureus
SEQUENCE: 185
ALKDAVK                                                                    7

SEQ ID NO: 186          moltype = AA   length = 20
FEATURE                 Location/Qualifiers
source                  1..20
                        mol_type = protein
                        organism = Staphylococcus aureus
SEQUENCE: 186
IPASKVPAFK AGKALKDAVK                                                     20

SEQ ID NO: 187          moltype = AA   length = 6
FEATURE                 Location/Qualifiers
source                  1..6
                        mol_type = protein
                        organism = Staphylococcus epidermidis
SEQUENCE: 187
AFKAGK                                                                     6

SEQ ID NO: 188          moltype = AA   length = 7
FEATURE                 Location/Qualifiers
source                  1..7
                        mol_type = protein
                        organism = Staphylococcus epidermidis
SEQUENCE: 188
```

```
ALKDAVK                                                             7

SEQ ID NO: 189          moltype = AA   length = 20
FEATURE                 Location/Qualifiers
source                  1..20
                        mol_type = protein
                        organism = Staphylococcus epidermidis
SEQUENCE: 189
IPASKVPAFK AGKALKDAVK                                               20

SEQ ID NO: 190          moltype = AA   length = 6
FEATURE                 Location/Qualifiers
source                  1..6
                        mol_type = protein
                        organism = Haemophilus influenzae
SEQUENCE: 190
AFVSGK                                                              6

SEQ ID NO: 191          moltype = AA   length = 7
FEATURE                 Location/Qualifiers
source                  1..7
                        mol_type = protein
                        organism = Haemophilus influenzae
SEQUENCE: 191
ALKDAIK                                                             7

SEQ ID NO: 192          moltype = AA   length = 20
FEATURE                 Location/Qualifiers
source                  1..20
                        mol_type = protein
                        organism = Haemophilus influenzae
SEQUENCE: 192
IAASKVPAFV SGKALKDAIK                                               20

SEQ ID NO: 193          moltype = AA   length = 6
FEATURE                 Location/Qualifiers
source                  1..6
                        mol_type = protein
                        organism = Aggregatibacter actinomycetemcomitans
SEQUENCE: 193
AFVSGK                                                              6

SEQ ID NO: 194          moltype = AA   length = 7
FEATURE                 Location/Qualifiers
source                  1..7
                        mol_type = protein
                        organism = Aggregatibacter actinomycetemcomitans
SEQUENCE: 194
ALKDAVK                                                             7

SEQ ID NO: 195          moltype = AA   length = 20
FEATURE                 Location/Qualifiers
source                  1..20
                        mol_type = protein
                        organism = Aggregatibacter actinomycetemcomitans
SEQUENCE: 195
IAASKVPAFV SGKALKDAVK                                               20

SEQ ID NO: 196          moltype = AA   length = 6
FEATURE                 Location/Qualifiers
source                  1..6
                        mol_type = protein
                        organism = Vibrio cholerae
SEQUENCE: 196
AFVAGK                                                              6

SEQ ID NO: 197          moltype = AA   length = 7
FEATURE                 Location/Qualifiers
source                  1..7
                        mol_type = protein
                        organism = Vibrio cholerae
SEQUENCE: 197
ALKDAIK                                                             7

SEQ ID NO: 198          moltype = AA   length = 20
FEATURE                 Location/Qualifiers
source                  1..20
                        mol_type = protein
                        organism = Vibrio cholerae
```

| | | |
|---|---|---|
| SEQUENCE: 198 IAAANVPAFV AGKALKDAIK | | 20 |
| SEQ ID NO: 199 FEATURE source | moltype = AA length = 6 Location/Qualifiers 1..6 mol_type = protein organism = Escherichia coli | |
| SEQUENCE: 199 AFVSGK | | 6 |
| SEQ ID NO: 200 FEATURE source | moltype = AA length = 7 Location/Qualifiers 1..7 mol_type = protein organism = Escherichia coli | |
| SEQUENCE: 200 ALKDAVK | | 7 |
| SEQ ID NO: 201 FEATURE source | moltype = AA length = 20 Location/Qualifiers 1..20 mol_type = protein organism = Escherichia coli | |
| SEQUENCE: 201 IAAANVPAFV SGKALKDAVK | | 20 |
| SEQ ID NO: 202 FEATURE source | moltype = AA length = 6 Location/Qualifiers 1..6 mol_type = protein organism = Pseudomonas aeruginosa | |
| SEQUENCE: 202 GFKAGK | | 6 |
| SEQ ID NO: 203 FEATURE source | moltype = AA length = 7 Location/Qualifiers 1..7 mol_type = protein organism = Pseudomonas aeruginosa | |
| SEQUENCE: 203 ALKDAVN | | 7 |
| SEQ ID NO: 204 FEATURE source | moltype = AA length = 20 Location/Qualifiers 1..20 mol_type = protein organism = Pseudomonas aeruginosa | |
| SEQUENCE: 204 IAAAKIPGFK AGKALKDAVN | | 20 |
| SEQ ID NO: 205 FEATURE source | moltype = AA length = 6 Location/Qualifiers 1..6 mol_type = protein organism = Escherichia coli | |
| SEQUENCE: 205 SFRAGK | | 6 |
| SEQ ID NO: 206 FEATURE source | moltype = AA length = 7 Location/Qualifiers 1..7 mol_type = protein organism = Escherichia coli | |
| SEQUENCE: 206 ALKDAVN | | 7 |
| SEQ ID NO: 207 FEATURE source | moltype = AA length = 20 Location/Qualifiers 1..20 mol_type = protein organism = Escherichia coli | |
| SEQUENCE: 207 IAAAKVPSFR AGKALKDAVN | | 20 |
| SEQ ID NO: 208 FEATURE source | moltype = AA length = 6 Location/Qualifiers 1..6 mol_type = protein | |

```
                         organism = Vibrio cholerae
SEQUENCE: 208
SFKAGK                                                                   6

SEQ ID NO: 209           moltype = AA  length = 7
FEATURE                  Location/Qualifiers
source                   1..7
                         mol_type = protein
                         organism = Vibrio cholerae
SEQUENCE: 209
ALKDACN                                                                  7

SEQ ID NO: 210           moltype = AA  length = 20
FEATURE                  Location/Qualifiers
source                   1..20
                         mol_type = protein
                         organism = Vibrio cholerae
SEQUENCE: 210
IAEAKVPSFK AGKALKDACN                                                   20

SEQ ID NO: 211           moltype = AA  length = 6
FEATURE                  Location/Qualifiers
source                   1..6
                         mol_type = protein
                         organism = Bordetella pertussis
SEQUENCE: 211
KFRPGK                                                                   6

SEQ ID NO: 212           moltype = AA  length = 7
FEATURE                  Location/Qualifiers
source                   1..7
                         mol_type = protein
                         organism = Bordetella pertussis
SEQUENCE: 212
ALKDAVN                                                                  7

SEQ ID NO: 213           moltype = AA  length = 20
FEATURE                  Location/Qualifiers
source                   1..20
                         mol_type = protein
                         organism = Bordetella pertussis
SEQUENCE: 213
IKKAKVPKFR PGKALKDAVN                                                   20

SEQ ID NO: 214           moltype = AA  length = 6
FEATURE                  Location/Qualifiers
source                   1..6
                         mol_type = protein
                         organism = Prevotella melaninogenica
SEQUENCE: 214
KFKAGA                                                                   6

SEQ ID NO: 215           moltype = AA  length = 8
FEATURE                  Location/Qualifiers
source                   1..8
                         mol_type = protein
                         organism = Prevotella melaninogenica
SEQUENCE: 215
ELADAVNK                                                                 8

SEQ ID NO: 216           moltype = AA  length = 20
FEATURE                  Location/Qualifiers
source                   1..20
                         mol_type = protein
                         organism = Prevotella melaninogenica
SEQUENCE: 216
AAKKVAKFKA GAELADAVNK                                                   20

SEQ ID NO: 217           moltype = AA  length = 6
FEATURE                  Location/Qualifiers
source                   1..6
                         mol_type = protein
                         organism = Prevotella intermedia
SEQUENCE: 217
KFKPGA                                                                   6

SEQ ID NO: 218           moltype = AA  length = 8
FEATURE                  Location/Qualifiers
source                   1..8
```

```
                        mol_type = protein
                        organism = Prevotella intermedia
SEQUENCE: 218
ELADAVNA                                                                 8

SEQ ID NO: 219          moltype = AA  length = 20
FEATURE                 Location/Qualifiers
source                  1..20
                        mol_type = protein
                        organism = Prevotella intermedia
SEQUENCE: 219
AAKKVAKFKP GAELADAVNA                                                   20

SEQ ID NO: 220          moltype = AA  length = 6
FEATURE                 Location/Qualifiers
source                  1..6
                        mol_type = protein
                        organism = Moraxella catarrhalis
SEQUENCE: 220
SFKAGK                                                                   6

SEQ ID NO: 221          moltype = AA  length = 7
FEATURE                 Location/Qualifiers
source                  1..7
                        mol_type = protein
                        organism = Moraxella catarrhalis
SEQUENCE: 221
VLKESVN                                                                  7

SEQ ID NO: 222          moltype = AA  length = 20
FEATURE                 Location/Qualifiers
source                  1..20
                        mol_type = protein
                        organism = Moraxella catarrhalis
SEQUENCE: 222
IAASKVPSFK AGKVLKESVN                                                   20

SEQ ID NO: 223          moltype = AA  length = 6
FEATURE                 Location/Qualifiers
source                  1..6
                        mol_type = protein
                        organism = Porphyromonas gingivalis
SEQUENCE: 223
RFKPGS                                                                   6

SEQ ID NO: 224          moltype = AA  length = 5
FEATURE                 Location/Qualifiers
source                  1..5
                        mol_type = protein
                        organism = Porphyromonas gingivalis
SEQUENCE: 224
TLELK                                                                    5

SEQ ID NO: 225          moltype = AA  length = 20
FEATURE                 Location/Qualifiers
source                  1..20
                        mol_type = protein
                        organism = Porphyromonas gingivalis
SEQUENCE: 225
ISIPARKVVR FKPGSTLELK                                                   20

SEQ ID NO: 226          moltype = AA  length = 6
FEATURE                 Location/Qualifiers
source                  1..6
                        mol_type = protein
                        organism = Helicobacter pylori
SEQUENCE: 226
KFKPGK                                                                   6

SEQ ID NO: 227          moltype = AA  length = 10
FEATURE                 Location/Qualifiers
source                  1..10
                        mol_type = protein
                        organism = Helicobacter pylori
SEQUENCE: 227
TLKQKVEEGK                                                              10

SEQ ID NO: 228          moltype = AA  length = 20
FEATURE                 Location/Qualifiers
```

-continued

```
source                  1..20
                        mol_type = protein
                        organism = Helicobacter pylori
SEQUENCE: 228
KRVPKFKPGK TLKQKVEEGK                                                   20

SEQ ID NO: 229          moltype = AA   length = 6
FEATURE                 Location/Qualifiers
source                  1..6
                        mol_type = protein
                        organism = Prevotella melaninogenica
SEQUENCE: 229
SFKPAK                                                                   6

SEQ ID NO: 230          moltype = AA   length = 8
FEATURE                 Location/Qualifiers
source                  1..8
                        mol_type = protein
                        organism = Prevotella melaninogenica
SEQUENCE: 230
TFIEDMKK                                                                 8

SEQ ID NO: 231          moltype = AA   length = 20
FEATURE                 Location/Qualifiers
source                  1..20
                        mol_type = protein
                        organism = Prevotella melaninogenica
SEQUENCE: 231
PAHDFPSFKP AKTFIEDMKK                                                   20

SEQ ID NO: 232          moltype = AA   length = 6
FEATURE                 Location/Qualifiers
source                  1..6
                        mol_type = protein
                        organism = Prevotella intermedia
SEQUENCE: 232
SFKPAK                                                                   6

SEQ ID NO: 233          moltype = AA   length = 8
FEATURE                 Location/Qualifiers
source                  1..8
                        mol_type = protein
                        organism = Prevotella intermedia
SEQUENCE: 233
TFIEDMKK                                                                 8

SEQ ID NO: 234          moltype = AA   length = 20
FEATURE                 Location/Qualifiers
source                  1..20
                        mol_type = protein
                        organism = Prevotella intermedia
SEQUENCE: 234
PAHDFPSFKP AKTFIEDMKK                                                   20

SEQ ID NO: 235          moltype = AA   length = 6
FEATURE                 Location/Qualifiers
source                  1..6
                        mol_type = protein
                        organism = Porphyromonas gingivalis
SEQUENCE: 235
AFKPSK                                                                   6

SEQ ID NO: 236          moltype = AA   length = 9
FEATURE                 Location/Qualifiers
source                  1..9
                        mol_type = protein
                        organism = Porphyromonas gingivalis
SEQUENCE: 236
IFMSQMKQD                                                                9

SEQ ID NO: 237          moltype = AA   length = 20
FEATURE                 Location/Qualifiers
source                  1..20
                        mol_type = protein
                        organism = Porphyromonas gingivalis
SEQUENCE: 237
KRNIPAFKPS KIFMSQMKQD                                                   20

SEQ ID NO: 238          moltype = AA   length = 6
```

```
FEATURE                 Location/Qualifiers
source                  1..6
                        mol_type = protein
                        organism = Mycobacterium tuberculosis
SEQUENCE: 238
AFRPGA                                                                        6

SEQ ID NO: 239          moltype = AA  length = 22
FEATURE                 Location/Qualifiers
source                  1..22
                        mol_type = protein
                        organism = Mycobacterium tuberculosis
SEQUENCE: 239
QFKAVVSGAQ RLPAEGPAVK RG                                                     22

SEQ ID NO: 240          moltype = AA  length = 20
FEATURE                 Location/Qualifiers
source                  1..20
                        mol_type = protein
                        organism = Mycobacterium tuberculosis
SEQUENCE: 240
AKRPATKAPA KKATARRGRK                                                        20

SEQ ID NO: 241          moltype = AA  length = 6
FEATURE                 Location/Qualifiers
source                  1..6
                        mol_type = protein
                        organism = Mycobacterium smegmatis
SEQUENCE: 241
AFRPGA                                                                        6

SEQ ID NO: 242          moltype = AA  length = 22
FEATURE                 Location/Qualifiers
source                  1..22
                        mol_type = protein
                        organism = Mycobacterium smegmatis
SEQUENCE: 242
QFKAVISGAQ KLPADGPAVK RG                                                     22

SEQ ID NO: 243          moltype = AA  length = 20
FEATURE                 Location/Qualifiers
source                  1..20
                        mol_type = protein
                        organism = Mycobacterium smegmatis
SEQUENCE: 243
TKAPAKKAAA KKAPAKKGRR                                                        20

SEQ ID NO: 244          moltype = AA  length = 6
FEATURE                 Location/Qualifiers
source                  1..6
                        mol_type = protein
                        organism = Prevotella melaninogenica
SEQUENCE: 244
NFKPAA                                                                        6

SEQ ID NO: 245          moltype = AA  length = 14
FEATURE                 Location/Qualifiers
source                  1..14
                        mol_type = protein
                        organism = Prevotella melaninogenica
SEQUENCE: 245
TIKGHVRKGG QDNG                                                              14

SEQ ID NO: 246          moltype = AA  length = 20
FEATURE                 Location/Qualifiers
source                  1..20
                        mol_type = protein
                        organism = Prevotella melaninogenica
SEQUENCE: 246
NFKPAATIKG HVRKGGQDNG                                                        20

SEQ ID NO: 247          moltype = AA  length = 6
FEATURE                 Location/Qualifiers
source                  1..6
                        mol_type = protein
                        organism = Prevotella intermedia
SEQUENCE: 247
NFRATA                                                                        6
```

```
SEQ ID NO: 248          moltype = AA   length = 12
FEATURE                 Location/Qualifiers
source                  1..12
                        mol_type = protein
                        organism = Prevotella intermedia
SEQUENCE: 248
SVKEKLKKGG AE                                                           12

SEQ ID NO: 249          moltype = AA   length = 20
FEATURE                 Location/Qualifiers
source                  1..20
                        mol_type = protein
                        organism = Prevotella intermedia
SEQUENCE: 249
VLNFRATASV KEKLKKGGAE                                                   20

SEQ ID NO: 250          moltype = AA   length = 6
FEATURE                 Location/Qualifiers
source                  1..6
                        mol_type = protein
                        organism = Escherichia coli
SEQUENCE: 250
TFRPGQ                                                                   6

SEQ ID NO: 251          moltype = AA   length = 14
FEATURE                 Location/Qualifiers
source                  1..14
                        mol_type = protein
                        organism = Escherichia coli
SEQUENCE: 251
KLKSRVENAS PKDE                                                         14

SEQ ID NO: 252          moltype = AA   length = 20
FEATURE                 Location/Qualifiers
source                  1..20
                        mol_type = protein
                        organism = Escherichia coli
SEQUENCE: 252
TFRPGQKLKS RVENASPKDE                                                   20

SEQ ID NO: 253          moltype = AA   length = 6
FEATURE                 Location/Qualifiers
source                  1..6
                        mol_type = protein
                        organism = Salmonella enterica
SEQUENCE: 253
TFRPGQ                                                                   6

SEQ ID NO: 254          moltype = AA   length = 14
FEATURE                 Location/Qualifiers
source                  1..14
                        mol_type = protein
                        organism = Salmonella enterica
SEQUENCE: 254
KLKSRVENAS PKEE                                                         14

SEQ ID NO: 255          moltype = AA   length = 20
FEATURE                 Location/Qualifiers
source                  1..20
                        mol_type = protein
                        organism = Salmonella enterica
SEQUENCE: 255
TFRPGQKLKS RVENASPKEE                                                   20

SEQ ID NO: 256          moltype = AA   length = 6
FEATURE                 Location/Qualifiers
source                  1..6
                        mol_type = protein
                        organism = Vibrio cholerae
SEQUENCE: 256
TFRPGQ                                                                   6

SEQ ID NO: 257          moltype = AA   length = 13
FEATURE                 Location/Qualifiers
source                  1..13
                        mol_type = protein
                        organism = Vibrio cholerae
SEQUENCE: 257
KLKARVENIK VEK                                                          13
```

```
SEQ ID NO: 258           moltype = AA   length = 20
FEATURE                  Location/Qualifiers
source                   1..20
                         mol_type = protein
                         organism = Vibrio cholerae
SEQUENCE: 258
VTFRPGQKLK ARVENIKVEK                                                        20

SEQ ID NO: 259           moltype = AA   length = 6
FEATURE                  Location/Qualifiers
source                   1..6
                         mol_type = protein
                         organism = Pseudomonas aeruginosa
SEQUENCE: 259
TFRPGQ                                                                        6

SEQ ID NO: 260           moltype = AA   length = 14
FEATURE                  Location/Qualifiers
source                   1..14
                         mol_type = protein
                         organism = Pseudomonas aeruginosa
SEQUENCE: 260
KLKARVEAYA GTKS                                                              14

SEQ ID NO: 261           moltype = AA   length = 20
FEATURE                  Location/Qualifiers
source                   1..20
                         mol_type = protein
                         organism = Pseudomonas aeruginosa
SEQUENCE: 261
TFRPGQKLKA RVEAYAGTKS                                                        20

SEQ ID NO: 262           moltype = AA   length = 6
FEATURE                  Location/Qualifiers
source                   1..6
                         mol_type = protein
                         organism = Burkholderia cenocepacia
SEQUENCE: 262
TFHASQ                                                                        6

SEQ ID NO: 263           moltype = AA   length = 11
FEATURE                  Location/Qualifiers
source                   1..11
                         mol_type = protein
                         organism = Burkholderia cenocepacia
SEQUENCE: 263
KLKALVENGA E                                                                 11

SEQ ID NO: 264           moltype = AA   length = 20
FEATURE                  Location/Qualifiers
source                   1..20
                         mol_type = protein
                         organism = Burkholderia cenocepacia
SEQUENCE: 264
RVVTFHASQK LKALVENGAE                                                        20

SEQ ID NO: 265           moltype = AA   length = 6
FEATURE                  Location/Qualifiers
source                   1..6
                         mol_type = protein
                         organism = Burkholderia pseudomallei
SEQUENCE: 265
TFHASQ                                                                        6

SEQ ID NO: 266           moltype = AA   length = 16
FEATURE                  Location/Qualifiers
source                   1..16
                         mol_type = protein
                         organism = Burkholderia pseudomallei
SEQUENCE: 266
KLKALVENGA EPDLAR                                                            16

SEQ ID NO: 267           moltype = AA   length = 20
FEATURE                  Location/Qualifiers
source                   1..20
                         mol_type = protein
                         organism = Burkholderia pseudomallei
SEQUENCE: 267
```

-continued

HASQKLKALV ENGAEPDLAR                                                           20

SEQ ID NO: 268          moltype = AA   length = 6
FEATURE                 Location/Qualifiers
source                  1..6
                        mol_type = protein
                        organism = Bordetella pertussis
SEQUENCE: 268
TFHASQ                                                                          6

SEQ ID NO: 269          moltype = AA   length = 19
FEATURE                 Location/Qualifiers
source                  1..19
                        mol_type = protein
                        organism = Bordetella pertussis
SEQUENCE: 269
KLKSVVEQPN SPPDPASAE                                                            19

SEQ ID NO: 270          moltype = AA   length = 20
FEATURE                 Location/Qualifiers
source                  1..20
                        mol_type = protein
                        organism = Bordetella pertussis
SEQUENCE: 270
QKLKSVVEQP NSPPDPASAE                                                           20

SEQ ID NO: 271          moltype = AA   length = 6
FEATURE                 Location/Qualifiers
source                  1..6
                        mol_type = protein
                        organism = Neisseria gonorrhoeae
SEQUENCE: 271
TFHASQ                                                                          6

SEQ ID NO: 272          moltype = AA   length = 14
FEATURE                 Location/Qualifiers
source                  1..14
                        mol_type = protein
                        organism = Neisseria gonorrhoeae
SEQUENCE: 272
KLKGMVEHYY DKQR                                                                 14

SEQ ID NO: 273          moltype = AA   length = 20
FEATURE                 Location/Qualifiers
source                  1..20
                        mol_type = protein
                        organism = Neisseria gonorrhoeae
SEQUENCE: 273
TFHASQKLKG MVEHYYDKQR                                                           20

SEQ ID NO: 274          moltype = AA   length = 6
FEATURE                 Location/Qualifiers
source                  1..6
                        mol_type = protein
                        organism = Neisseria meningitidis
SEQUENCE: 274
TFHASQ                                                                          6

SEQ ID NO: 275          moltype = AA   length = 14
FEATURE                 Location/Qualifiers
source                  1..14
                        mol_type = protein
                        organism = Neisseria meningitidis
SEQUENCE: 275
KLKSMVEHYY DKQR                                                                 14

SEQ ID NO: 276          moltype = AA   length = 20
FEATURE                 Location/Qualifiers
source                  1..20
                        mol_type = protein
                        organism = Neisseria meningitidis
SEQUENCE: 276
TFHASQKLKS MVEHYYDKQR                                                           20

SEQ ID NO: 277          moltype = AA   length = 6
FEATURE                 Location/Qualifiers
source                  1..6
                        mol_type = protein
                        organism = Haemophilus influenzae

```
SEQUENCE: 277
TFKPGQ                                                                        6

SEQ ID NO: 278         moltype = AA  length = 10
FEATURE                Location/Qualifiers
source                 1..10
                       mol_type = protein
                       organism = Haemophilus influenzae
SEQUENCE: 278
KLRARVEKTK                                                                   10

SEQ ID NO: 279         moltype = AA  length = 20
FEATURE                Location/Qualifiers
source                 1..20
                       mol_type = protein
                       organism = Haemophilus influenzae
SEQUENCE: 279
RRVVTFKPGQ KLRARVEKTK                                                        20

SEQ ID NO: 280         moltype = AA  length = 6
FEATURE                Location/Qualifiers
source                 1..6
                       mol_type = protein
                       organism = Aggregatibacter actinomycetemcomitans
SEQUENCE: 280
VFKPGQ                                                                        6

SEQ ID NO: 281         moltype = AA  length = 13
FEATURE                Location/Qualifiers
source                 1..13
                       mol_type = protein
                       organism = Aggregatibacter actinomycetemcomitans
SEQUENCE: 281
KLRNRVEKVK PKA                                                               13

SEQ ID NO: 282         moltype = AA  length = 20
FEATURE                Location/Qualifiers
source                 1..20
                       mol_type = protein
                       organism = Aggregatibacter actinomycetemcomitans
SEQUENCE: 282
VVFKPGQKLR NRVEKVKPKA                                                        20

SEQ ID NO: 283         moltype = AA  length = 6
FEATURE                Location/Qualifiers
source                 1..6
                       mol_type = protein
                       organism = Moraxella catarrhalis
SEQUENCE: 283
TFKAGQ                                                                        6

SEQ ID NO: 284         moltype = AA  length = 12
FEATURE                Location/Qualifiers
source                 1..12
                       mol_type = protein
                       organism = Moraxella catarrhalis
SEQUENCE: 284
KLRGWIDSQN EG                                                                12

SEQ ID NO: 285         moltype = AA  length = 20
FEATURE                Location/Qualifiers
source                 1..20
                       mol_type = protein
                       organism = Moraxella catarrhalis
SEQUENCE: 285
VVTFKAGQKL RGWIDSQNEG                                                        20

SEQ ID NO: 286         moltype = AA  length = 6
FEATURE                Location/Qualifiers
source                 1..6
                       mol_type = protein
                       organism = Treponema palladium
SEQUENCE: 286
VFRPSK                                                                        6

SEQ ID NO: 287         moltype = AA  length = 17
FEATURE                Location/Qualifiers
source                 1..17
                       mol_type = protein
```

```
                        organism = Treponema palladium
SEQUENCE: 287
RLKSAVRGYR SGEVGAD                                                  17

SEQ ID NO: 288          moltype = AA  length = 20
FEATURE                 Location/Qualifiers
source                  1..20
                        mol_type = protein
                        organism = Treponema palladium
SEQUENCE: 288
PSKRLKSAVR GYRSGEVGAD                                               20

SEQ ID NO: 289          moltype = AA  length = 6
FEATURE                 Location/Qualifiers
source                  1..6
                        mol_type = protein
                        organism = Prevotella melaninogenica
SEQUENCE: 289
SFTPDT                                                              6

SEQ ID NO: 290          moltype = AA  length = 22
FEATURE                 Location/Qualifiers
source                  1..22
                        mol_type = protein
                        organism = Prevotella melaninogenica
SEQUENCE: 290
VMKELVNKPF SQFETVVIND GV                                            22

SEQ ID NO: 291          moltype = AA  length = 20
FEATURE                 Location/Qualifiers
source                  1..20
                        mol_type = protein
                        organism = Prevotella melaninogenica
SEQUENCE: 291
MQAGDTMKVP KVELRPEYRK                                               20

SEQ ID NO: 292          moltype = AA  length = 6
FEATURE                 Location/Qualifiers
source                  1..6
                        mol_type = protein
                        organism = Prevotella intermedia
SEQUENCE: 292
SFTPDA                                                              6

SEQ ID NO: 293          moltype = AA  length = 22
FEATURE                 Location/Qualifiers
source                  1..22
                        mol_type = protein
                        organism = Prevotella intermedia
SEQUENCE: 293
TMKELVNKPF AQFETVVLND GV                                            22

SEQ ID NO: 294          moltype = AA  length = 20
FEATURE                 Location/Qualifiers
source                  1..20
                        mol_type = protein
                        organism = Prevotella intermedia
SEQUENCE: 294
SAGDTMKVPK VELRPQYRTK                                               20

SEQ ID NO: 295          moltype = AA  length = 6
FEATURE                 Location/Qualifiers
source                  1..6
                        mol_type = protein
                        organism = Escherichia coli
SEQUENCE: 295
HFKPGK                                                              6

SEQ ID NO: 296          moltype = AA  length = 10
FEATURE                 Location/Qualifiers
source                  1..10
                        mol_type = protein
                        organism = Escherichia coli
SEQUENCE: 296
ELRDRANIYG                                                          10

SEQ ID NO: 297          moltype = AA  length = 20
FEATURE                 Location/Qualifiers
source                  1..20
```

```
                                   mol_type = protein
                                   organism = Escherichia coli
SEQUENCE: 297
KYVPHFKPGK ELRDRANIYG                                                    20

SEQ ID NO: 298                     moltype = AA   length = 6
FEATURE                            Location/Qualifiers
source                             1..6
                                   mol_type = protein
                                   organism = Salmonella enterica
SEQUENCE: 298
HFKPGK                                                                    6

SEQ ID NO: 299                     moltype = AA   length = 10
FEATURE                            Location/Qualifiers
source                             1..10
                                   mol_type = protein
                                   organism = Salmonella enterica
SEQUENCE: 299
ELRDRANIYG                                                               10

SEQ ID NO: 300                     moltype = AA   length = 20
FEATURE                            Location/Qualifiers
source                             1..20
                                   mol_type = protein
                                   organism = Salmonella enterica
SEQUENCE: 300
KYVPHFKPGK ELRDRANIYG                                                    20

SEQ ID NO: 301                     moltype = AA   length = 6
FEATURE                            Location/Qualifiers
source                             1..6
                                   mol_type = protein
                                   organism = Vibrio cholerae
SEQUENCE: 301
HFKPGK                                                                    6

SEQ ID NO: 302                     moltype = AA   length = 8
FEATURE                            Location/Qualifiers
source                             1..8
                                   mol_type = protein
                                   organism = Vibrio cholerae
SEQUENCE: 302
ELRERVNL                                                                  8

SEQ ID NO: 303                     moltype = AA   length = 20
FEATURE                            Location/Qualifiers
source                             1..20
                                   mol_type = protein
                                   organism = Vibrio cholerae
SEQUENCE: 303
EGKYVPHFKP GKELRERVNL                                                    20

SEQ ID NO: 304                     moltype = AA   length = 6
FEATURE                            Location/Qualifiers
source                             1..6
                                   mol_type = protein
                                   organism = Pseudomonas aeruginosa
SEQUENCE: 304
HFKPGK                                                                    6

SEQ ID NO: 305                     moltype = AA   length = 10
FEATURE                            Location/Qualifiers
source                             1..10
                                   mol_type = protein
                                   organism = Pseudomonas aeruginosa
SEQUENCE: 305
ELRDRVNEPE                                                               10

SEQ ID NO: 306                     moltype = AA   length = 20
FEATURE                            Location/Qualifiers
source                             1..20
                                   mol_type = protein
                                   organism = Pseudomonas aeruginosa
SEQUENCE: 306
KFVPHFKPGK ELRDRVNEPE                                                    20

SEQ ID NO: 307                     moltype = AA   length = 6
FEATURE                            Location/Qualifiers
```

```
source                 1..6
                       mol_type = protein
                       organism = Haemophilus influenzae
SEQUENCE: 307
YFKAGK                                                                6

SEQ ID NO: 308         moltype = AA  length = 10
FEATURE                Location/Qualifiers
source                 1..10
                       mol_type = protein
                       organism = Haemophilus influenzae
SEQUENCE: 308
ELKARVDVQA                                                           10

SEQ ID NO: 309         moltype = AA  length = 20
FEATURE                Location/Qualifiers
source                 1..20
                       mol_type = protein
                       organism = Haemophilus influenzae
SEQUENCE: 309
KSVPYFKAGK ELKARVDVQA                                                20

SEQ ID NO: 310         moltype = AA  length = 6
FEATURE                Location/Qualifiers
source                 1..6
                       mol_type = protein
                       organism = Aggregatibacter actinomycetemcomitans
SEQUENCE: 310
YFKAGK                                                                6

SEQ ID NO: 311         moltype = AA  length = 11
FEATURE                Location/Qualifiers
source                 1..11
                       mol_type = protein
                       organism = Aggregatibacter actinomycetemcomitans
SEQUENCE: 311
ELRERVDVYA A                                                         11

SEQ ID NO: 312         moltype = AA  length = 20
FEATURE                Location/Qualifiers
source                 1..20
                       mol_type = protein
                       organism = Aggregatibacter actinomycetemcomitans
SEQUENCE: 312
CVPYFKAGKE LRERVDVYAA                                                20

SEQ ID NO: 313         moltype = AA  length = 6
FEATURE                Location/Qualifiers
source                 1..6
                       mol_type = protein
                       organism = Neisseria gonorrhoeae
SEQUENCE: 313
HFKPGK                                                                6

SEQ ID NO: 314         moltype = AA  length = 15
FEATURE                Location/Qualifiers
source                 1..15
                       mol_type = protein
                       organism = Neisseria gonorrhoeae
SEQUENCE: 314
ELRERVDLAL KENAN                                                     15

SEQ ID NO: 315         moltype = AA  length = 20
FEATURE                Location/Qualifiers
source                 1..20
                       mol_type = protein
                       organism = Neisseria gonorrhoeae
SEQUENCE: 315
FKPGKELRER VDLALKENAN                                                20

SEQ ID NO: 316         moltype = AA  length = 6
FEATURE                Location/Qualifiers
source                 1..6
                       mol_type = protein
                       organism = Neisseria meningitidis
SEQUENCE: 316
HFKPGK                                                                6

SEQ ID NO: 317         moltype = AA  length = 15
```

-continued

```
FEATURE                 Location/Qualifiers
source                  1..15
                        mol_type = protein
                        organism = Neisseria meningitidis
SEQUENCE: 317
ELRERVDLAL KENAN                                                       15

SEQ ID NO: 318          moltype = AA  length = 20
FEATURE                 Location/Qualifiers
source                  1..20
                        mol_type = protein
                        organism = Neisseria meningitidis
SEQUENCE: 318
FKPGKELRER VDLALKENAN                                                  20

SEQ ID NO: 319          moltype = AA  length = 6
FEATURE                 Location/Qualifiers
source                  1..6
                        mol_type = protein
                        organism = Burkholderia cenocepacia
SEQUENCE: 319
HFKPGK                                                                  6

SEQ ID NO: 320          moltype = AA  length = 23
FEATURE                 Location/Qualifiers
source                  1..23
                        mol_type = protein
                        organism = Burkholderia cenocepacia
SEQUENCE: 320
ELRERVDGRA GEPLKADDPD DDR                                              23

SEQ ID NO: 321          moltype = AA  length = 20
FEATURE                 Location/Qualifiers
source                  1..20
                        mol_type = protein
                        organism = Burkholderia cenocepacia
SEQUENCE: 321
ERVDGRAGEP LKADDPDDDR                                                  20

SEQ ID NO: 322          moltype = AA  length = 6
FEATURE                 Location/Qualifiers
source                  1..6
                        mol_type = protein
                        organism = Burkholderia pseudomallei
SEQUENCE: 322
HFKPGK                                                                  6

SEQ ID NO: 323          moltype = AA  length = 23
FEATURE                 Location/Qualifiers
source                  1..23
                        mol_type = protein
                        organism = Burkholderia pseudomallei
SEQUENCE: 323
ELRERVDGRA GEPLKNDEPE DAQ                                              23

SEQ ID NO: 324          moltype = AA  length = 20
FEATURE                 Location/Qualifiers
source                  1..20
                        mol_type = protein
                        organism = Burkholderia pseudomallei
SEQUENCE: 324
ERVDGRAGEP LKNDEPEDAQ                                                  20

SEQ ID NO: 325          moltype = AA  length = 6
FEATURE                 Location/Qualifiers
source                  1..6
                        mol_type = protein
                        organism = Bordetella pertussis
SEQUENCE: 325
HFKAGK                                                                  6

SEQ ID NO: 326          moltype = AA  length = 22
FEATURE                 Location/Qualifiers
source                  1..22
                        mol_type = protein
                        organism = Bordetella pertussis
SEQUENCE: 326
ELREWVDLVG NDQGDDSSNG SS                                               22
```

| | | |
|---|---|---|
| SEQ ID NO: 327<br>FEATURE<br>source | moltype = AA   length = 20<br>Location/Qualifiers<br>1..20<br>mol_type = protein<br>organism = Bordetella pertussis | |
| SEQUENCE: 327<br>DSSNGSSDPL QSVMDMHAMH | | 20 |
| SEQ ID NO: 328<br>FEATURE<br>source | moltype = AA   length = 6<br>Location/Qualifiers<br>1..6<br>mol_type = protein<br>organism = Moraxella catarrhalis | |
| SEQUENCE: 328<br>YFKPGK | | 6 |
| SEQ ID NO: 329<br>FEATURE<br>source | moltype = AA   length = 11<br>Location/Qualifiers<br>1..11<br>mol_type = protein<br>organism = Moraxella catarrhalis | |
| SEQUENCE: 329<br>ALRESVNLVN D | | 11 |
| SEQ ID NO: 330<br>FEATURE<br>source | moltype = AA   length = 20<br>Location/Qualifiers<br>1..20<br>mol_type = protein<br>organism = Moraxella catarrhalis | |
| SEQUENCE: 330<br>ATPYFKPGKA LRESVNLVND | | 20 |
| SEQ ID NO: 331<br>FEATURE<br>source | moltype = AA   length = 6<br>Location/Qualifiers<br>1..6<br>mol_type = protein<br>organism = Borrelia burgdorferi | |
| SEQUENCE: 331<br>YFRPGK | | 6 |
| SEQ ID NO: 332<br>FEATURE<br>source | moltype = AA   length = 11<br>Location/Qualifiers<br>1..11<br>mol_type = protein<br>organism = Borrelia burgdorferi | |
| SEQUENCE: 332<br>DLKERVWGIK G | | 11 |
| SEQ ID NO: 333<br>FEATURE<br>source | moltype = AA   length = 20<br>Location/Qualifiers<br>1..20<br>mol_type = protein<br>organism = Borrelia burgdorferi | |
| SEQUENCE: 333<br>HVAYFRPGKD LKERVWGIKG | | 20 |
| SEQ ID NO: 334<br>FEATURE<br>source | moltype = AA   length = 6<br>Location/Qualifiers<br>1..6<br>mol_type = protein<br>organism = Treponema denticola | |
| SEQUENCE: 334<br>RFKPGK | | 6 |
| SEQ ID NO: 335<br>FEATURE<br>source | moltype = AA   length = 17<br>Location/Qualifiers<br>1..17<br>mol_type = protein<br>organism = Treponema denticola | |
| SEQUENCE: 335<br>ELKEALHKID TQELIES | | 17 |
| SEQ ID NO: 336<br>FEATURE<br>source | moltype = AA   length = 20<br>Location/Qualifiers<br>1..20<br>mol_type = protein<br>organism = Treponema denticola | |
| SEQUENCE: 336<br>PGKELKEALH KIDTQELIES | | 20 |

```
SEQ ID NO: 337          moltype = AA   length = 12
FEATURE                 Location/Qualifiers
source                  1..12
                        mol_type = protein
                        organism = Escherichia coli
SEQUENCE: 337
GRNPKTGEDI PI                                                              12

SEQ ID NO: 338          moltype = AA   length = 12
FEATURE                 Location/Qualifiers
source                  1..12
                        mol_type = protein
                        organism = Escherichia coli
SEQUENCE: 338
GRNPKTGDKV EL                                                              12

SEQ ID NO: 339          moltype = AA   length = 12
FEATURE                 Location/Qualifiers
source                  1..12
                        mol_type = protein
                        organism = Escherichia coli
SEQUENCE: 339
GRNPQTGKEI KI                                                              12

SEQ ID NO: 340          moltype = AA   length = 12
FEATURE                 Location/Qualifiers
source                  1..12
                        mol_type = protein
                        organism = Escherichia coli
SEQUENCE: 340
GRNPQTGKEI TI                                                              12

SEQ ID NO: 341          moltype = AA   length = 94
FEATURE                 Location/Qualifiers
source                  1..94
                        mol_type = protein
                        organism = Haemophilus influenzae
SEQUENCE: 341
MTKSELMEKL SAKQPTLSAK EIENMVKDIL EFISQSLENG DRVEVRGFGS FSLHHRQPRL          60
GRNPKTGDSV NLSAKSVPYF KAGKELKARV DVQA                                     94

SEQ ID NO: 342          moltype = AA   length = 20
FEATURE                 Location/Qualifiers
source                  1..20
                        mol_type = protein
                        organism = Haemophilus influenzae
SEQUENCE: 342
MTKSELMEKL SAKQPTLSAK                                                      20

SEQ ID NO: 343          moltype = AA   length = 20
FEATURE                 Location/Qualifiers
source                  1..20
                        mol_type = protein
                        organism = Haemophilus influenzae
SEQUENCE: 343
TLSAKEIENM VKDILEFISQ                                                      20

SEQ ID NO: 344          moltype = AA   length = 20
FEATURE                 Location/Qualifiers
source                  1..20
                        mol_type = protein
                        organism = Haemophilus influenzae
SEQUENCE: 344
EFISQSLENG DRVEVRGFGS                                                      20

SEQ ID NO: 345          moltype = AA   length = 20
FEATURE                 Location/Qualifiers
source                  1..20
                        mol_type = protein
                        organism = Haemophilus influenzae
SEQUENCE: 345
RGFGSFSLHH RQPRLGRNPK                                                      20

SEQ ID NO: 346          moltype = AA   length = 20
FEATURE                 Location/Qualifiers
source                  1..20
                        mol_type = protein
                        organism = Haemophilus influenzae
```

```
SEQUENCE: 346
GRNPKTGDSV NLSAKSVPYF                                                          20

SEQ ID NO: 347          moltype = AA  length = 19
FEATURE                 Location/Qualifiers
source                  1..19
                        mol_type = protein
                        organism = Haemophilus influenzae
SEQUENCE: 347
SVPYFKAGKE LKARVDVQA                                                           19

SEQ ID NO: 348          moltype = AA  length = 20
FEATURE                 Location/Qualifiers
source                  1..20
                        mol_type = protein
                        organism = Haemophilus influenzae
SEQUENCE: 348
MATITKLDII EYLSDKYHLS                                                          20

SEQ ID NO: 349          moltype = AA  length = 20
FEATURE                 Location/Qualifiers
source                  1..20
                        mol_type = protein
                        organism = Haemophilus influenzae
SEQUENCE: 349
KYHLSKQDTK NVVENFLEEI                                                          20

SEQ ID NO: 350          moltype = AA  length = 20
FEATURE                 Location/Qualifiers
source                  1..20
                        mol_type = protein
                        organism = Haemophilus influenzae
SEQUENCE: 350
FLEEIRLSLE SGQDVKLSGF                                                          20

SEQ ID NO: 351          moltype = AA  length = 20
FEATURE                 Location/Qualifiers
source                  1..20
                        mol_type = protein
                        organism = Haemophilus influenzae
SEQUENCE: 351
KLSGFGNFEL RDKSSRPGRN                                                          20

SEQ ID NO: 352          moltype = AA  length = 20
FEATURE                 Location/Qualifiers
source                  1..20
                        mol_type = protein
                        organism = Haemophilus influenzae
SEQUENCE: 352
RPGRNPKTGD VVPVSARRVV                                                          20

SEQ ID NO: 353          moltype = AA  length = 21
FEATURE                 Location/Qualifiers
source                  1..21
                        mol_type = protein
                        organism = Haemophilus influenzae
SEQUENCE: 353
ARRVVTFKPG QKLRARVEKT K                                                        21

SEQ ID NO: 354          moltype = AA  length = 16
FEATURE                 Location/Qualifiers
source                  1..16
                        mol_type = protein
                        organism = Haemophilus influenzae
SEQUENCE: 354
IEYLSDKYHL SKQDTK                                                              16

SEQ ID NO: 355          moltype = AA  length = 22
FEATURE                 Location/Qualifiers
source                  1..22
                        mol_type = protein
                        organism = Haemophilus influenzae
SEQUENCE: 355
DKSSRPGRNP KTGDVVAASA RR                                                       22

SEQ ID NO: 356          moltype = AA  length = 21
FEATURE                 Location/Qualifiers
source                  1..21
                        mol_type = protein
```

```
                            organism = Haemophilus influenzae
SEQUENCE: 356
NFELRDKSSR PGRNPKTGDV V                                              21

SEQ ID NO: 357          moltype = AA   length = 21
FEATURE                 Location/Qualifiers
source                  1..21
                        mol_type = protein
                        organism = Haemophilus influenzae
SEQUENCE: 357
SLHHRQPRLG RNPKTGDSVN L                                              21

SEQ ID NO: 358          moltype = DNA  length = 333
FEATURE                 Location/Qualifiers
misc_feature            1..333
                        note = Description of Artificial Sequence: Synthetic
                         polynucleotide
source                  1..333
                        mol_type = other DNA
                        organism = synthetic construct
SEQUENCE: 358
gaggtgcagc tgcaggagtc tggacctggc ctggtgacgc cctcacagag cctgtccatg   60
acttgcactg tctctgggtt ttcattaacc agctatagtg tacactgggt tcgccagcct  120
ccaggaaaga gtctggagtg gctgggagta atatgggctg gtggaagcac aaattataat  180
tcggctctca tgtccagact gagcatcagc aaagacaact ccaagagcca agttttctta  240
aaaatggaca gtctgcaaac tgatgacaca gccatatact actgtgccag agaggactcc  300
tggggtcaag gaacctcagt caccgtctcc tca                                333

SEQ ID NO: 359          moltype = AA   length = 111
FEATURE                 Location/Qualifiers
REGION                  1..111
                        note = Description of Artificial Sequence: Synthetic
                         polypeptide
source                  1..111
                        mol_type = protein
                        organism = synthetic construct
SEQUENCE: 359
EVQLQESGPG LVTPSQSLSM TCTVSGFSLT SYSVHWVRQP PGKSLEWLGV IWAGGSTNYN   60
SALMSRLSIS KDNSKSQVFL KMDSLQTDDT AIYYCAREDS WGQGTSVTVS S            111

SEQ ID NO: 360          moltype = DNA  length = 318
FEATURE                 Location/Qualifiers
misc_feature            1..318
                        note = Description of Artificial Sequence: Synthetic
                         polynucleotide
source                  1..318
                        mol_type = other DNA
                        organism = synthetic construct
SEQUENCE: 360
gacattgtga tgacccagtc tcaaaaattc atgtccacat cagtaggaga cagggtcagc   60
gtcacctgca aggccagtca gaatgtgggt actaatgtag cctggtatca acagaaacca  120
gggcaatctc ctaaagcact gatttactcg gcatcctacc ggtacagtgg agtccctgat  180
cgcttcacag gcagtggatc tgggacagat ttcactctca ccatcagcaa tgtgcagtct  240
gaagacttgg cagagtattt ctgtcagcaa tataacagct atcccacgtt cggagggggg  300
accaagttgg aaataaaa                                                 318

SEQ ID NO: 361          moltype = AA   length = 106
FEATURE                 Location/Qualifiers
REGION                  1..106
                        note = Description of Artificial Sequence: Synthetic
                         polypeptide
source                  1..106
                        mol_type = protein
                        organism = synthetic construct
SEQUENCE: 361
DIVMTQSQKF MSTSVGDRVS VTCKASQNVG TNVAWYQQKP GQSPKALIYS ASYRYSGVPD   60
RFTGSGSGTD FTLTISNVQS EDLAEYFCQQ YNSYPTFGGG TKLEIK                  106

SEQ ID NO: 362          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 362
FSLTSYS                                                              7

SEQ ID NO: 363          moltype = AA   length = 8
```

```
                        -continued

FEATURE                 Location/Qualifiers
REGION                  1..8
                        note = Description of Artificial Sequence: Synthetic peptide
source                  1..8
                        mol_type = protein
                        organism = synthetic construct
SEQUENCE: 363
FSLTSYSV                                                                       8

SEQ ID NO: 364          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 364
FSLTSYSVH                                                                      9

SEQ ID NO: 365          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 365
GFSLTSYS                                                                       8

SEQ ID NO: 366          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 366
IWAGGST                                                                        7

SEQ ID NO: 367          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 367
VIWAGGST                                                                       8

SEQ ID NO: 368          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 368
GVIWAGGST                                                                      9

SEQ ID NO: 369          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 369
LGVIWAGGST                                                                    10

SEQ ID NO: 370          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 370
WLGVIWAGGS T                                                                  11
```

```
SEQ ID NO: 371           moltype = AA  length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 371
IWAGGSTN                                                                        8

SEQ ID NO: 372           moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 372
VIWAGGSTN                                                                       9

SEQ ID NO: 373           moltype = AA  length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 373
GVIWAGGSTN                                                                      10

SEQ ID NO: 374           moltype = AA  length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 374
LGVIWAGGST N                                                                    11

SEQ ID NO: 375           moltype = AA  length = 12
FEATURE                  Location/Qualifiers
REGION                   1..12
                         note = Description of Artificial Sequence: Synthetic peptide
source                   1..12
                         mol_type = protein
                         organism = synthetic construct
SEQUENCE: 375
WLGVIWAGGS TN                                                                   12

SEQ ID NO: 376           moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 376
IWAGGSTNY                                                                       9

SEQ ID NO: 377           moltype = AA  length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 377
VIWAGGSTNY                                                                      10

SEQ ID NO: 378           moltype = AA  length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 378
GVIWAGGSTN Y                                                                    11
```

| SEQ ID NO: 379 | moltype = AA  length = 12 |
| --- | --- |
| FEATURE | Location/Qualifiers |
| REGION | 1..12 |
| | note = Description of Artificial Sequence: Synthetic peptide |
| source | 1..12 |
| | mol_type = protein |
| | organism = synthetic construct |

SEQUENCE: 379
LGVIWAGGST NY                                                            12

| SEQ ID NO: 380 | moltype = AA  length = 13 |
| --- | --- |
| FEATURE | Location/Qualifiers |
| REGION | 1..13 |
| | note = Description of Artificial Sequence: Synthetic peptide |
| source | 1..13 |
| | mol_type = protein |
| | organism = synthetic construct |

SEQUENCE: 380
WLGVIWAGGS TNY                                                           13

| SEQ ID NO: 381 | moltype = AA  length = 4 |
| --- | --- |
| FEATURE | Location/Qualifiers |
| REGION | 1..4 |
| | note = Description of Artificial Sequence: Synthetic peptide |
| source | 1..4 |
| | mol_type = protein |
| | organism = synthetic construct |

SEQUENCE: 381
REDS                                                                      4

| SEQ ID NO: 382 | moltype = AA  length = 5 |
| --- | --- |
| FEATURE | Location/Qualifiers |
| REGION | 1..5 |
| | note = Description of Artificial Sequence: Synthetic peptide |
| source | 1..5 |
| | mol_type = protein |
| | organism = synthetic construct |

SEQUENCE: 382
AREDS                                                                     5

| SEQ ID NO: 383 | moltype = AA  length = 6 |
| --- | --- |
| FEATURE | Location/Qualifiers |
| REGION | 1..6 |
| | note = Description of Artificial Sequence: Synthetic peptide |
| source | 1..6 |
| | mol_type = protein |
| | organism = synthetic construct |

SEQUENCE: 383
QNVGTN                                                                    6

| SEQ ID NO: 384 | moltype = AA  length = 7 |
| --- | --- |
| FEATURE | Location/Qualifiers |
| REGION | 1..7 |
| | note = Description of Artificial Sequence: Synthetic peptide |
| source | 1..7 |
| | mol_type = protein |
| | organism = synthetic construct |

SEQUENCE: 384
QNVGTNV                                                                   7

| SEQ ID NO: 385 | moltype = AA  length = 8 |
| --- | --- |
| FEATURE | Location/Qualifiers |
| REGION | 1..8 |
| | note = Description of Artificial Sequence: Synthetic peptide |
| source | 1..8 |
| | mol_type = protein |
| | organism = synthetic construct |

SEQUENCE: 385
QNVGTNVA                                                                  8

| SEQ ID NO: 386 | moltype =    length = |
| --- | --- |

SEQUENCE: 386
000

| SEQ ID NO: 387 | moltype = AA  length = 4 |
| --- | --- |
| FEATURE | Location/Qualifiers |
| REGION | 1..4 |
| | note = Description of Artificial Sequence: Synthetic peptide |

```
                                        -continued source                  1..4
                        mol_type = protein
                        organism = synthetic construct
SEQUENCE: 387
YSAS                                                                        4

SEQ ID NO: 388          moltype = AA   length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 388
IYSAS                                                                       5

SEQ ID NO: 389          moltype = AA   length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 389
LIYSAS                                                                      6

SEQ ID NO: 390          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 390
ALIYSAS                                                                     7

SEQ ID NO: 391          moltype = AA   length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 391
SASY                                                                        4

SEQ ID NO: 392          moltype = AA   length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 392
YSASY                                                                       5

SEQ ID NO: 393          moltype = AA   length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 393
IYSASY                                                                      6

SEQ ID NO: 394          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 394
LIYSASY                                                                     7

SEQ ID NO: 395          moltype = AA   length = 8
FEATURE                 Location/Qualifiers
REGION                  1..8
```

```
                        note = Description of Artificial Sequence: Synthetic peptide
source                  1..8
                        mol_type = protein
                        organism = synthetic construct
SEQUENCE: 395
ALIYSASY                                                                        8

SEQ ID NO: 396          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 396
SASYR                                                                           5

SEQ ID NO: 397          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 397
YSASYR                                                                          6

SEQ ID NO: 398          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 398
IYSASYR                                                                         7

SEQ ID NO: 399          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 399
LIYSASYR                                                                        8

SEQ ID NO: 400          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 400
ALIYSASYR                                                                       9

SEQ ID NO: 401          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 401
SASYRY                                                                          6

SEQ ID NO: 402          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 402
YSASYRY                                                                         7

SEQ ID NO: 403          moltype = AA  length = 8
FEATURE                 Location/Qualifiers
```

```
REGION                  1..8
                        note = Description of Artificial Sequence: Synthetic peptide
source                  1..8
                        mol_type = protein
                        organism = synthetic construct
SEQUENCE: 403
IYSASYRY                                                                        8

SEQ ID NO: 404          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 404
LIYSASYRY                                                                       9

SEQ ID NO: 405          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 405
ALIYSASYRY                                                                     10

SEQ ID NO: 406          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 406
SASYRYS                                                                         7

SEQ ID NO: 407          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 407
YSASYRYS                                                                        8

SEQ ID NO: 408          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 408
IYSASYRYS                                                                       9

SEQ ID NO: 409          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 409
LIYSASYRYS                                                                     10

SEQ ID NO: 410          moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 410
ALIYSASYRY S                                                                   11

SEQ ID NO: 411          moltype = AA   length = 7
```

```
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 411
QQYNSYP                                                                         7

SEQ ID NO: 412          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 412
QQYNSYPT                                                                        8

SEQ ID NO: 413          moltype = AA  length = 123
FEATURE                 Location/Qualifiers
REGION                  1..123
                        note = Description of Artificial Sequence: Synthetic
                        polypeptide
source                  1..123
                        mol_type = protein
                        organism = synthetic construct
SEQUENCE: 413
QVQLVESGGG LVQPGGSLRL SCAASGFPFS SYAMSWVRQA PGKGLEWVSA ISGNGADSYY   60
ADSVKGRFTT SRDKSKNTVY LQMNRLRAED TAVYYCAKDM RRYHYDSSGL HFWGQGTLVT  120
VSS                                                              123

SEQ ID NO: 414          moltype = AA  length = 109
FEATURE                 Location/Qualifiers
REGION                  1..109
                        note = Description of Artificial Sequence: Synthetic
                        polypeptide
source                  1..109
                        mol_type = protein
                        organism = synthetic construct
SEQUENCE: 414
DIELTQAPSV SVYPGQTARI TCSGDALPKQ YAYWYQQKPG QAPVVVIYKD SERPSGISER   60
FSGSSSGTTV TLTISGVQAG DEADYYCQSV DTSVSYYVVF GGGTKLTVL             109

SEQ ID NO: 415          moltype = AA  length = 118
FEATURE                 Location/Qualifiers
REGION                  1..118
                        note = Description of Artificial Sequence: Synthetic
                        polypeptide
source                  1..118
                        mol_type = protein
                        organism = synthetic construct
SEQUENCE: 415
QVQLVQSGGG LVQPGGSLRL SCAASGFTFS HYNMNWVRQA PGKGPEWVSY ISSGSDIIYY   60
ADSVKGRFTI SRDNAKNSLY LQMNSLRDED TAVYYCARAL DRDGFDIWGQ GTMVTVSS   118

SEQ ID NO: 416          moltype = AA  length = 106
FEATURE                 Location/Qualifiers
REGION                  1..106
                        note = Description of Artificial Sequence: Synthetic
                        polypeptide
source                  1..106
                        mol_type = protein
                        organism = synthetic construct
SEQUENCE: 416
DIVLTQSPSS LSASVGDKVT ITCRASQSIS TFLNWYQHKP GKAPKLLIYG ASSLQSGVPS   60
RFSGSGSGTD FTLTISSLQP EDFATYYCQQ SYSTPTFGQG TKVEIK               106

SEQ ID NO: 417          moltype = AA  length = 123
FEATURE                 Location/Qualifiers
REGION                  1..123
                        note = Description of Artificial Sequence: Synthetic
                        polypeptide
source                  1..123
                        mol_type = protein
                        organism = synthetic construct
SEQUENCE: 417
QVQLVESGGG LVQPGGSLRL SCAASGFPFS SYAMSWVRQA PGKGLEWVSA ISGNGADSYY   60
ADSVKGRFTT SRDKSKNTVY LQMNRLRAED TAVYYCAKDM RRYHYDSSGL HFWGQGTLVT  120
```

```
VSS                                                                      123

SEQ ID NO: 418         moltype = AA  length = 110
FEATURE                Location/Qualifiers
REGION                 1..110
                       note = Description of Artificial Sequence: Synthetic
                        polypeptide
source                 1..110
                       mol_type = protein
                       organism = synthetic construct
SEQUENCE: 418
DIMLTQPPSV SAAPGQKVTI SCSGSSSNIG TNYVSWFQQV PGTAPKFLIY DNYKRPSETP         60
DRFSGSKSGT SATLDITGLQ TGDEANYYCA TWDSSLSAWV FGGGTKVTVL                   110

SEQ ID NO: 419         moltype = AA  length = 119
FEATURE                Location/Qualifiers
REGION                 1..119
                       note = Description of Artificial Sequence: Synthetic
                        polypeptide
source                 1..119
                       mol_type = protein
                       organism = synthetic construct
SEQUENCE: 419
QVQLVESGPG LVKPSETLSL TCRVSGDSNR PSYWSWIRQA PGKAMEWIGY VYDSGVTIYN         60
PSLKGRVTIS LDTSKTRFSL KLTSVIAADT AVYYCARERF DRTSYKSWWG QGTQVTVSS         119

SEQ ID NO: 420         moltype = AA  length = 108
FEATURE                Location/Qualifiers
REGION                 1..108
                       note = Description of Artificial Sequence: Synthetic
                        polypeptide
source                 1..108
                       mol_type = protein
                       organism = synthetic construct
SEQUENCE: 420
DIVLTQAPGT LSLSPGDRAT LSCRASQRLG GTSLAWYQHR SGQAPRLILY GTSNRATDTP         60
DRFSGSGSGT DFVLTISSLE PEDFAVYYCQ QYGSPPYTFG QGTTLDIK                     108

SEQ ID NO: 421         moltype = AA  length = 122
FEATURE                Location/Qualifiers
REGION                 1..122
                       note = Description of Artificial Sequence: Synthetic
                        polypeptide
source                 1..122
                       mol_type = protein
                       organism = synthetic construct
SEQUENCE: 421
QVQLVQSGGT LVQPGGSLRL SCAASGFTFS YYSMSWVRQA PGKGLEWVAN IKHDGTERNY         60
VDSVKGRFTI SRDNSEKSLY LQMNSLRAED TAVYYCAKYY YGAGTNYPLK YWGQGTRVTV        120
SS                                                                       122

SEQ ID NO: 422         moltype = AA  length = 108
FEATURE                Location/Qualifiers
REGION                 1..108
                       note = Description of Artificial Sequence: Synthetic
                        polypeptide
source                 1..108
                       mol_type = protein
                       organism = synthetic construct
SEQUENCE: 422
DILMTQSPSS LSASVGDRVT ITCRASQGIR NDLGWYQQKP GKAPKLLIYA ASSLQSGVPS         60
RFSGSGSGTD FTLTISSLQP EDFATYYCLQ DYNYPLTFGG GTKVEIKR                     108

SEQ ID NO: 423         moltype = AA  length = 116
FEATURE                Location/Qualifiers
REGION                 1..116
                       note = Description of Artificial Sequence: Synthetic
                        polypeptide
source                 1..116
                       mol_type = protein
                       organism = synthetic construct
SEQUENCE: 423
QVQLLESGPG LVRPSDTLSL TCTFSADLST NAYWTWIRQP PGKGLEWIGY MSHSGGRDYN         60
PSFNRRVTIS VDTSKNQVFL RLTSVTSADT AVYFCVREVG SYYDYWGQGI LVTVSS            116

SEQ ID NO: 424         moltype = AA  length = 108
FEATURE                Location/Qualifiers
REGION                 1..108
                       note = Description of Artificial Sequence: Synthetic
```

```
                              polypeptide
source                        1..108
                              mol_type = protein
                              organism = synthetic construct
SEQUENCE: 424
DIEMTQSPSS LSASVGDRIT ITCRASQGIS TWLAWYQQKP GKAPKSLIFS TSSLHSGVPS    60
KFSGSGSGTD FTLTITNLQP EDFATYYCQQ KWETPYSFGQ GTKLDMIR               108

SEQ ID NO: 425                moltype = AA  length = 116
FEATURE                       Location/Qualifiers
REGION                        1..116
                              note = Description of Artificial Sequence: Synthetic
                              polypeptide
source                        1..116
                              mol_type = protein
                              organism = synthetic construct
SEQUENCE: 425
QVQLVESGTE VKNPGASVKV SCTASGYKFD EYGVSWVRQS PGQGLEWMGW ISVYNGKTNY    60
SQNFQGRLTL TTETSTDTAY MELTSLRPDD TAVYYCATDK NWFDPWGPGT LVTVSS       116

SEQ ID NO: 426                moltype = AA  length = 107
FEATURE                       Location/Qualifiers
REGION                        1..107
                              note = Description of Artificial Sequence: Synthetic
                              polypeptide
source                        1..107
                              mol_type = protein
                              organism = synthetic construct
SEQUENCE: 426
DIVMTQSPSA SGSPGQSITI SCTGTNTDYN YVSWYQHHPG KAPKVIIYDV KKRPSGVPSR    60
FSGSRSGNTA TLTVSGLQTE DEADYYCVSY ADNNHYVFGS GTKVTVL                 107

SEQ ID NO: 427                moltype = AA  length = 128
FEATURE                       Location/Qualifiers
REGION                        1..128
                              note = Description of Artificial Sequence: Synthetic
                              polypeptide
source                        1..128
                              mol_type = protein
                              organism = synthetic construct
SEQUENCE: 427
QVQLVESGGG VVQPGGSLRV SCAASAFSFR DYGIHWVRQA PGKGLQWVAV ISHDGGKKFY    60
ADSVRGRFTI SRDNSENTLY LQMNSLRSDD TAVYYCARLV ASCSGSTCTT QPAAFDIWGP   120
GTLVTVSS                                                            128

SEQ ID NO: 428                moltype = AA  length = 108
FEATURE                       Location/Qualifiers
REGION                        1..108
                              note = Description of Artificial Sequence: Synthetic
                              polypeptide
source                        1..108
                              mol_type = protein
                              organism = synthetic construct
SEQUENCE: 428
DIMLTQPPSV SVSPGQTARI TCSGDALPKK YTYWYQQKSG QAPVLLIYED RKRPSEIPER    60
FSAFTSWTTA TLTITGAQVR DEADYYCYST DISGDIGVFG GGTKLTVL                108

SEQ ID NO: 429                moltype = AA  length = 120
FEATURE                       Location/Qualifiers
REGION                        1..120
                              note = Description of Artificial Sequence: Synthetic
                              polypeptide
source                        1..120
                              mol_type = protein
                              organism = synthetic construct
SEQUENCE: 429
QVQLLESGAD MVQPGRSLRL SCAASGFNFR TYAMHWVRQA PGKGLEWVAV MSHDGYTKYY    60
SDSVRGQFTI SRDNSKNTLY LQMNNLRPDD TAIYYCARGL TGLSVGFDYW GQGTLVTVSS   120

SEQ ID NO: 430                moltype = AA  length = 111
FEATURE                       Location/Qualifiers
REGION                        1..111
                              note = Description of Artificial Sequence: Synthetic
                              polypeptide
source                        1..111
                              mol_type = protein
                              organism = synthetic construct
SEQUENCE: 430
DIVLTQSASV SGSPGQSITI SCTGTSSDVG GYNYVSWYQQ HPGKAPKLMI YDVTTRPSGV    60
```

```
SDRFSGSKSG NTASLTISGL QAEDEADYYC SSYSSGSTPA LFGGGTQLTV L            111

SEQ ID NO: 431            moltype = AA   length = 122
FEATURE                   Location/Qualifiers
REGION                    1..122
                          note = Description of Artificial Sequence: Synthetic
                          polypeptide
source                    1..122
                          mol_type = protein
                          organism = synthetic construct
SEQUENCE: 431
QVQLVQSGGG LVKPGGSLRL SCGASGFNLS SYSMNWVRQA PGKGLEWVSS ISSRSSYIYY    60
ADSVQGRFTI SRDNAKNSLY LQMNSLRAED TAIYYCARVS PSTYYYYGMD VWGQGTTVTV   120
SS                                                                  122

SEQ ID NO: 432            moltype = AA   length = 108
FEATURE                   Location/Qualifiers
REGION                    1..108
                          note = Description of Artificial Sequence: Synthetic
                          polypeptide
source                    1..108
                          mol_type = protein
                          organism = synthetic construct
SEQUENCE: 432
DIVLTQPSSV SVSPGQTARI TCSGDELPKQ YAYWYQQKPG QAPVLVIYKD NERPSGIPER    60
FSGSSSGTTV TLTISGVQAE DEADYYCQSA DSSGTYVVFG GGTKLTVL                108

SEQ ID NO: 433            moltype = AA   length = 136
FEATURE                   Location/Qualifiers
REGION                    1..136
                          note = Description of Artificial Sequence: Synthetic
                          polypeptide
source                    1..136
                          mol_type = protein
                          organism = synthetic construct
SEQUENCE: 433
QVQLVESGAE VKKPGALVKV SCKASGYTFS GYYMHWVRQA PGQGLEWMGW INPKSGGTKY    60
AQKFQGRVTM TRDTSISTAY MELSRLRSDD TAVYFCARGG PSNLERFLER LQPRYSYDDK   120
YAMDVWGQGT TVTVSS                                                   136

SEQ ID NO: 434            moltype = AA   length = 109
FEATURE                   Location/Qualifiers
REGION                    1..109
                          note = Description of Artificial Sequence: Synthetic
                          polypeptide
source                    1..109
                          mol_type = protein
                          organism = synthetic construct
SEQUENCE: 434
DIVMTQSPGT LSLSPGARAT LSCRASQSVS SIYLAWYQQK PGQAPRLLIF GASSRATGIP    60
DRFSGSGSGT DFTLTISRLE PEDFAVYYCQ QYGSSPYTFG QGTKLEIKR               109

SEQ ID NO: 435            moltype = AA   length = 124
FEATURE                   Location/Qualifiers
REGION                    1..124
                          note = Description of Artificial Sequence: Synthetic
                          polypeptide
source                    1..124
                          mol_type = protein
                          organism = synthetic construct
SEQUENCE: 435
QVQLVQSGTE VKKPGESLKI SCEGSRYNFA RYWIGWVRQM PGKGLDWMGI IYPGDSDTRY    60
SPSFQGQVSI SADKSISTAY LQWNSLKASD TAMYYCARLG SELGVVSDYY FDSWGQGTLV   120
TVSS                                                                124

SEQ ID NO: 436            moltype = AA   length = 114
FEATURE                   Location/Qualifiers
REGION                    1..114
                          note = Description of Artificial Sequence: Synthetic
                          polypeptide
source                    1..114
                          mol_type = protein
                          organism = synthetic construct
SEQUENCE: 436
DIVLTQSPDS LAVSLGERAT INCKSSQSVL DRSNNKNCVA WYQQKPGQPP KLLIYRAATR    60
ESGVPDRFSG SGSGTDFSLT ISSLQAEDVA VYFCQQYYSI PNTFGQGTKL EIKR         114

SEQ ID NO: 437            moltype = AA   length = 120
FEATURE                   Location/Qualifiers
```

```
REGION                  1..120
                        note = Description of Artificial Sequence: Synthetic
                         polypeptide
source                  1..120
                        mol_type = protein
                        organism = synthetic construct
SEQUENCE: 437
QVQLVESGGG LVKAGGSLRL SCVASGFTFS DYYMSWIRQA PGKGLEWISF ISSSGDTIFY    60
ADSVKGRFTV SRDSAKNSLY LQMNSLKVED TAVYYCARKG VSDEELLRFW GQGTLVTVSS   120

SEQ ID NO: 438          moltype = AA   length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 438
DIVLTQDPSV SVSPGQTARI TCSGDALPKK YAYWYQQKSG QAPVLVIYED TKRPSGIPER    60
FSGSSSGTVA TLTISGAQVE DEADYYCYST DSSGNQRVFG GGTKLTVL                108

SEQ ID NO: 439          moltype = AA   length = 116
FEATURE                 Location/Qualifiers
REGION                  1..116
                        note = Description of Artificial Sequence: Synthetic
                         polypeptide
source                  1..116
                        mol_type = protein
                        organism = synthetic construct
SEQUENCE: 439
QVQLVESGTE VKNPGASVKV SCTASGYKFD EYGVSWVRQS PGQGLEWMGW ISVYNGKTNY    60
SQNFQGRLTL TTETSTDTAY MELTSLRPDD TAVYYCATDK NWFDPWGPGT LVTVSS       116

SEQ ID NO: 440          moltype = AA   length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 440
DIVLTQSPSA SGSPGQSITI SCTGTNTDYN YVSWYQHHPG KAPKVIIYDV KKRPSGVPSR    60
FSGSRSGNTA TLTVSGLQTE DEADYYCVSY ADNNHYVFGS GTKVTVL                 107

SEQ ID NO: 441          moltype = AA   length = 113
FEATURE                 Location/Qualifiers
REGION                  1..113
                        note = Description of Artificial Sequence: Synthetic
                         polypeptide
source                  1..113
                        mol_type = protein
                        organism = synthetic construct
SEQUENCE: 441
QVQLVESGAE VKKPGESLKI SCKGSGYNFT SYWIGWVRQM PGKGLEWMGV IYPDDSDTRY    60
SPSFKGQVTI SADKSISTAF LQWSSLKASD TAVYHCARPP DSWGQGTLVT VSS          113

SEQ ID NO: 442          moltype = AA   length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 442
DIVMTQSPAT LSVSPGERAT LSCRASQSVS SNLAWYQQKP GLAPRLLIVG ASNRATGIPA    60
RFSGSGSGTE FTLTISSLQS EDFAFYYCQQ YNNWPFTFGP GTKVDVKR                108

SEQ ID NO: 443          moltype = AA   length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 443
```

```
QVQLLESGPG LVKPSETPSL TCTVSGGSIR SYYWSWIRQP PGKGLEWIGY IYYSGSTNYN    60
PSLKSRVTIS VDMSKNQFSL KLSSVTAADT AMYYCARVYG GSGSYDFDYW GQGTLVTVSS   120

SEQ ID NO: 444          moltype = AA  length = 111
FEATURE                 Location/Qualifiers
REGION                  1..111
                        note = Description of Artificial Sequence: Synthetic
                         polypeptide
source                  1..111
                        mol_type = protein
                        organism = synthetic construct
SEQUENCE: 444
DIVLTQSPSA SGSPGQSVTI SCTGTSSDVG GYNYVSWYQQ LPGKAPKLMI YEVTKRPSGV    60
PDRFSGSKSG NTASLTVSGL QAEDEADYYC SSFAGSNNHV VFGGGTKLTV L            111

SEQ ID NO: 445          moltype = AA  length = 130
FEATURE                 Location/Qualifiers
REGION                  1..130
                        note = Description of Artificial Sequence: Synthetic
                         polypeptide
source                  1..130
                        mol_type = protein
                        organism = synthetic construct
SEQUENCE: 445
QVQLTLRESG PTLVKPTQTL TLTCTFSGFS LSTNGVGVGW IRQPPGKALE WLAIIYWDDD    60
KRYSPSLKSR LTITKDTSKN QVVLTLTNMD PVDTGTYYCA HILGASNYWT GYLRYYFDYW   120
GQGTLVTVST                                                          130

SEQ ID NO: 446          moltype = AA  length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 446
DIEMTQSPSV SVSPGQTARI TCSGEPLAKQ YAYWYQQKSG QAPVVVIYKD TERPSGIPER    60
FSGSSSGTTV TLTISGVQAE DEADYHCESG DSSGTYPVFG GGTKLTVL                108

SEQ ID NO: 447          moltype = AA  length = 117
FEATURE                 Location/Qualifiers
REGION                  1..117
                        note = Description of Artificial Sequence: Synthetic
                         polypeptide
source                  1..117
                        mol_type = protein
                        organism = synthetic construct
SEQUENCE: 447
QVQLQESGGG LVQPGGSLKL SCAASGFIFS GSTMHWVRQA SGKGLEWVGR IRSKTNNYAT    60
AYAASVKGRF TISRDDSKNT AYLQMNSLKT EDTAVYYCIS LPGGYSSGQG TLVTVSS      117

SEQ ID NO: 448          moltype = AA  length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 448
DIMLTQPPSV SVSPGQTARI TCSGDALPKK YTYWYQQKSG QAPVLVIYED SKRPSEIPER    60
FSAFTSWTTA TLTITGAQVG DEADYYCYST DITGDIGVFG GGTKLTVL                108

SEQ ID NO: 449          moltype = AA  length = 124
FEATURE                 Location/Qualifiers
REGION                  1..124
                        note = Description of Artificial Sequence: Synthetic
                         polypeptide
source                  1..124
                        mol_type = protein
                        organism = synthetic construct
SEQUENCE: 449
QVQLVQSGGG LVQPGGSLKV SCVGSGFTFS ASTIHWVRQA SGKGLEWVGR IRSKANNYAT    60
VSAASLKGRF TISRDDSKNT AYLQVNSLKI EDTAIYYCTR PTACGDRVCW HGAWGQGTQV   120
TVSP                                                                124

SEQ ID NO: 450          moltype = AA  length = 110
FEATURE                 Location/Qualifiers
```

```
REGION                    1..110
                          note = Description of Artificial Sequence: Synthetic
                           polypeptide
source                    1..110
                          mol_type = protein
                          organism = synthetic construct
SEQUENCE: 450
DIVLTQSPSA SGTPGQRVTI SCSGSRSNLG NNNVNWYQQL PGTAPKLLIF DNNERPSGVP    60
GRFSGSKSGT SASLAISGLR SEDEADYYCA SWDDSLNGWV FGGGTKVTVL              110

SEQ ID NO: 451            moltype = AA  length = 124
FEATURE                   Location/Qualifiers
REGION                    1..124
                          note = Description of Artificial Sequence: Synthetic
                           polypeptide
source                    1..124
                          mol_type = protein
                          organism = synthetic construct
SEQUENCE: 451
QVQLVESGGG LAQPGGSLRL SCAASGFIFN TYAMGWVRQA PGKGLEWVST VSAPGAGTYY    60
TDSVKGRFII SRDNSKNILY LQMNRLRVED TAVYYCARDQ GGPAVAGARI FDYWGQGALV   120
TVSS                                                                124

SEQ ID NO: 452            moltype = AA  length = 112
FEATURE                   Location/Qualifiers
REGION                    1..112
                          note = Description of Artificial Sequence: Synthetic
                           polypeptide
source                    1..112
                          mol_type = protein
                          organism = synthetic construct
SEQUENCE: 452
DIVLTQSPLS LSVTPGQPAS ISCKSSQSLL RSDGKTYLCW YLQKPGQPPQ LLIYEVSNRV    60
SGVPDRFSGS GSGTDFTLKI SRVEAEDVGV YYCMQSIQLR TFGQGTKVEI KR           112

SEQ ID NO: 453            moltype = AA  length = 15
FEATURE                   Location/Qualifiers
source                    1..15
                          mol_type = protein
                          organism = Staphylococcus aureus
SEQUENCE: 453
AARKGRNPQT GKEID                                                     15

SEQ ID NO: 454            moltype = AA  length = 15
FEATURE                   Location/Qualifiers
source                    1..15
                          mol_type = protein
                          organism = Staphylococcus aureus
SEQUENCE: 454
KGRNPQTGKE IDIPA                                                     15

SEQ ID NO: 455            moltype = AA  length = 13
FEATURE                   Location/Qualifiers
source                    1..13
                          mol_type = protein
                          organism = Staphylococcus aureus
SEQUENCE: 455
KGRNPQTGKE IDI                                                       13

SEQ ID NO: 456            moltype = AA  length = 15
FEATURE                   Location/Qualifiers
source                    1..15
                          mol_type = protein
                          organism = Staphylococcus aureus
SEQUENCE: 456
VPAFKAGKAL KDAVK                                                     15

SEQ ID NO: 457            moltype = AA  length = 15
FEATURE                   Location/Qualifiers
source                    1..15
                          mol_type = protein
                          organism = Staphylococcus aureus
SEQUENCE: 457
SLAKGEKVQL IGFGN                                                     15
```

```
SEQ ID NO: 458         moltype = AA  length = 15
FEATURE                Location/Qualifiers
source                 1..15
                       mol_type = protein
                       organism = Staphylococcus aureus
SEQUENCE: 458
KGEKVQLIGF GNFEV                                                     15
```

COMPOSITIONS AND METHODS FOR THE REMOVAL OF BIOFILMS

CROSS-REFERENCE TO RELATED APPLICATIONS

This application is a divisional under 35 U.S.C. § 120 of U.S. application Ser. No. 17/552,986, filed Dec. 16, 2021, now U.S. Pat. No. 11,629,182, issued on Apr. 18, 2023, which is a continuation under 35 U.S.C. § 120 of U.S. application Ser. No. 15/999,215, filed Aug. 16, 2018, now U.S. Pat. No. 11,274,144, issued on Mar. 15, 2022, which is a divisional under 35 U.S.C. § 120 of U.S. application Ser. No. 15/078,987, filed Mar. 23, 2016, now abandoned, which claims priority under 35 U.S.C. § 119 (e) to U.S. Application No. 62/199,952, filed Jul. 31, 2015, and U.S. application Ser. No. 15/078,987 is a continuation-in-part under 35 U.S.C. § 120 of U.S. application Ser. No. 14/967,228, filed Dec. 11, 2015, now abandoned, which in turn is a continuation under 35 U.S.C. § 120 of International Application No. PCT/US2014/042201, filed Jun. 12, 2014, which claims priority under 35 U.S.C. § 119 (e) to U.S. Application No. 61/834,846, filed Jun. 13, 2013, the content of each of which is hereby incorporated by reference in its entirety.

STATEMENT OF GOVERNMENT SUPPORT

This invention was made with government support under Contract No. R01DC011818 awarded by the National Institute of Deafness and Communication Disorders (NIDCD) at the National Institutes of Health. The government has certain rights in the invention.

SEQUENCE LISTING

The instant application contains a Sequence Listing which has been submitted electronically in XML format and is hereby incorporated by reference in its entirety. Said XML copy, created on Feb. 9, 2023, is named 106887-3896.xml and is 441 kilobytes in size.

FIELD

The present disclosure generally relates to the methods and compositions to lessen and/or cure bacterial biofilms.

BACKGROUND

The DNABII family of proteins are naturally found outside of the bacterial cell and contribute to biofilm formation. At least one protein from the DNABII family is found in all known eubacteria. While these proteins elicit a strong innate immune response, host subjects fail to naturally produce immunoprotective antibodies to family members as a result of infection. The major problem with bacterial biofilms is the inability of the host immune system and/or antibiotics and other antimicrobials to gain access to the bacteria protected within the biofilm.

Biofilms are present in an industrial setting as well. For example, biofilms are implicated in a wide range of petroleum process problems, from the production field to the gas station storage tank. In the field, sulfate reducing biofilm bacteria produce hydrogen sulfide (soured oil). In the process pipelines, biofilm activity develops slimes which impede filters and orifices. Biofilm and biofilm organisms also cause corrosion of pipeline and petroleum process equipment. These problems can be manifested throughout an oil or gas production facility, to the point where fouling and corrosive biofilm organisms have even been found on the surfaces of final product storage tanks.

Biofilms are implicated in a wide range of water processes, both domestic and industrial. They can grow on the surface of process equipment and impede the performance of the equipment, such as degradation of heat transfer or plugging of filters and membranes. Biofilms growing on a cooling tower fill can add enough weight to cause collapse of the fill. Biofilms cause corrosion of even highly specialized stainless steels. Biofilms in a water process can degrade the value of a final product such as biofilm contamination in a paper process or the attachment of even a single cell on a silicon chip. Biofilms growing in drinking water distribution systems can harbor potential pathogenic organisms, corrosive organisms or bacteria that degrade the aesthetic quality of the water. In the home, biofilms are found in or on any surface that supports microbial growth, e.g., in drains, on food preparation surfaces, in toilets, and in swimming pools and spas.

Thus, a need exists to break through the protective barrier of biofilms to treat or kill the associated bacterial infections and clear them from surfaces and in water systems.

DESCRIPTION OF TABLES

Tables 1-5 are the results of an in vitro bioassay of the reversal of the biofilm in the indicated organism.

Table 6 is the scoring scheme of the relative amount of biomass within the middle ear in the Chinchilla model of otitis media (OM).

Table 7 is the results of an in vitro bioassay of the reversal of the biofilm upon treatment with DNase.

Table 8 is a non-limited summary of DNA binding proteins produced by gram (+) and gram (−) bacteria that can be used in the methods provided herein.

Table 9 is a listing of α, β, and C-terminal portions of DNABII proteins from the indicated organism.

Table 10 is a listing of non-limiting exemplary hybridoma cell lines that produce non-limiting exemplary monoclonal antibodies.

SUMMARY

Within bacterial cells, the DNABII proteins are DNA binding proteins that necessarily bend DNA substrates upon binding. Similarly, DNA that is already in a bent conformation is an exemplary substrate as the energy required for bending is rendered unnecessary.

The DNABII family is a member of a class of proteins referred to as nucleoid associated proteins (NAPs), bacterial proteins that, in part, shape the intracellular bacterial nucleoid (Browning et al. (2010) Curr. Opin. Microbiol. 13:773-780). In addition, this family is ubiquitous, expressed by virtually all eubacteria. All characterized family members to date function as either a homodimer or heterodimer of subunits. The family is divided into two types, HU (histone-like protein) and IHF (integration host factor) with *B. cenocepacia* capable of expressing both (strain J2315 genes: BCAL3530, hupA; BCAL1585, hupB; BCAL1487, ihfA and BCAL2949, ihfb). The primary distinction between these family members is that HU binds DNA in a sequence independent manner, while IHF binds a consensus sequence (WATCAANNNNTTR (SEQ ID NO: 36) where W is A or T and R is a purine) conserved across genera (Swinger et al. (2004) Curr. Opin. Struct. Biol. 14:28-35)]. All DNABII proteins bind to and bend DNA considerably e.g. *E. coli* IHF can bend DNA into a virtual U-turn (Rice et al. (1996) Cell 87: 1295-1306). In addition, all family members have a preference for pre-bent or curved DNA structures e.g. Holliday junctions, a cruciform-like structure central to DNA recombination. In fact, DNABII proteins function as accessory factors facilitating all intracellular DNA functions, including gene expression, recombination, repair and replication (Swinger et al. (2004) Curr. Opin. Struct. Biol. 14:28-35).

The DNABII family of proteins is found outside of bacterial cells in the biofilm state. Applicants have shown that these proteins are in fact bound to the extracellular DNA at critical branched junctions. In one aspect, Applicants have shown that by immunizing the host with polypeptides and proteins that produce specific antibodies as well as administrating antibodies and other interfering agents, the DNA-based lattice is sufficiently altered to now permit the host immune system to clear the biofilm.

Applicants also have demonstrated the removal of preformed non-typeable *Haemophilus influenzae* biofilms in the middle ear of the chinchilla host by various modes of immunization with a DNABII family member (*E. coli* integration host factor, IHF). This chinchilla middle ear biofilm animal system has been well documented as an excellent model for human otitis media (or middle ear infections).

The method for using this technology is straightforward. In one embodiment, the polypeptides disclosed herein are used to vaccinate individuals as a prophylactic to chronic/recurrent biofilm disease or as a therapeutic for those with an existing infection. The individual's immune system will then clear the organism by use of the host's innate or acquired immune response, e.g., by binding of antibody and complement, phagocytosis, destruction by binding of effectors of innate immunity etc. Alternatively, antibodies as well as fragments, derivatives, variants and interfering polynucleotides that bind to the polypeptides or microbial DNA can be administered to treat or prevent infection. Bacteria that cannot form functional biofilms are more readily cleared by the remainder of the host's immune system. In this way, antibiotic and drug resistance of the bacteria can be reversed by allowing the therapeutic agents to reach the bacteria.

Thus, in one aspect a method for inhibiting, competing or titrating the binding of a DNABII polypeptide or protein to a microbial DNA is provided, the method comprising, or alternatively consisting essentially of, or yet further consisting of contacting the DNABII polypeptide or protein or the microbial DNA with an interfering agent, thereby inhibiting, competing or titrating the binding of the DNABII protein or polypeptide to the microbial DNA. The contacting can be performed in vitro or in vivo.

In another aspect, provided is a method for inhibiting, preventing or breaking down a microbial biofilm, comprising, or alternatively consisting essentially of, or yet further consisting of contacting the biofilm with an interfering agent, thereby inhibiting, preventing or breaking down the microbial biofilm. The contacting can be performed in vitro or in vivo and therefore can break down, prevent, or inhibit a biofilm on surface or in an industrial or therapeutic setting.

In a further aspect, provided is a method of inhibiting, preventing or breaking down a biofilm in a subject, comprising, or alternatively consisting essentially of, or yet further consisting of administering to the subject an effective amount of an interfering agent, thereby inhibiting, preventing or breaking down the microbial biofilm.

In a yet further aspect, a method for inhibiting, preventing or treating a microbial infection that produces a biofilm in a subject is provided. The method comprises, or alternatively consists essentially of or yet further consists of administering to the subject an effective amount of an interfering agent, thereby inhibiting, preventing or treating the microbial infection that produces the biofilm in the subject.

In one aspect, provided herein is an isolated antibody, an antigen binding fragment, or an interfering agent that specifically recognizes or binds an isolated or recombinant DNABII polypeptide or a fragment or an equivalent each thereof. In one aspect, the isolated antibody, antigen binding fragment, or an interfering agent has affinity for at least one DNABII protein that exceeds the affinity of the DNABII protein for components of a biofilm that includes the DNABII protein. In another aspect, the isolated antibody, antigen binding fragment, or an interfering agent is selected from the group of: a monoclonal antibody, a bispecific antibody, a chimeric antibody, an antigen binding fragment, e.g., an Fv antibody, or a complete antibody that comprises constant regions heterologous to variable regions. In a further aspect, the antigen binding fragment comprises an isolated polypeptide or a polynucleotide. In one aspect, the biofilm component comprises branched DNA. In another aspect the DNABII protein of the biofilm is selected from the group of an IHF or a subunit thereof, HU protein, DPS, Hfq, CbpA or CbpB or a fragment or subunit thereof, e.g., a tip fragment of the protein. In a further aspect, the antibody, interfering agent or antigen binding fragment binds an epitope on the DNABII protein that is conserved across bacterial species. In another aspect, the antibody, antigen binding fragment or interfering agent dissolves a biofilm derived from at least two bacterial species, including both Gram positive and Gram negative species. In one aspect, the DNABII protein is *Staphylococcus aureus* HU or a fragment thereof; and optionally wherein the fragment of *Staphylococcus aureus* HU comprises a tip fragment or a beta hairpin fragment or a biological equivalent thereof. In another aspect the antibody, antigen binding fragment or interfering agent dissolves a biofilm that is produced by *S. aureus, P. aeruginosa* and *K. pneumonia*. In another aspect, the affinity of the isolated antibody, an antigen binding fragment, or an interfering agent for the DNABII protein is at least as strong as 100 pM or optionally 40 pM. In a further aspect, the antibody, the antigen binding fragment, or an interfering agent, produces an immune response that is immunodominant and immunoprotective. In a further aspect, the antibody, the antigen binding fragment, or the interfering agent specifically binds the tip fragment of a DNABII polypeptide, e.g., the tip fragment of IHF or HU polypeptide. In another aspect, the antibody, the antigen binding fragment, or the interfering agent is a protein or a nucleic acid, these are prepared for use in a method to a dissolve, interfere, prevent, treat or titrate a biofilm in a subject or to confer passively on a subject a capability to dissolve biofilms.

In a further aspect, a method is provided to prevent formation of or to disperse a biofilm associated with an industrial process by treating a surface or industrial environment (e.g., within a pipe) susceptible to or containing a biofilm with the antibody, antigen binding fragment, or an interfering agent as disclosed herein.

In another aspect, also provided is a polynucleotide encoding the antibody, antigen binding fragment, or the interfering agent as described herein, wherein in one aspect, the polynucleotide is operably linked to a regulatory element, that optionally is contained within an expression vector or a host cell. When the polynucleotide encodes the antibody, antigen binding fragment, or the interfering agent, the polynucleotide can be used to recombinantly produce the antibody, antigen binding fragment or interfering agent by culturing the cells under conditions to produce the antibody, antigen binding fragment or interfering agent and isolating or purifying the product from the cell or cell culture. In one aspect the host cell is a mammalian cell.

Also provided herein is a method to identify a binding moiety, e.g., an antibody, antigen binding fragment or an interfering agent, that has affinity with at least one DNABII protein greater than the affinity of a biofilm component for the DNABII protein, by contacting a candidate binding moiety with a biofilm component and with the at least one DNABII protein, and determining the ratio of the DNABII protein bound to said binding moiety as compared to DNABII bound with the biofilm component, whereby a ratio greater than one identifies a binding moiety that has affinity with respect to at least one DNABII protein greater than the affinity of a biofilm component for the DNABII protein.

In another aspect, also provided is a method to identify an agent, e.g., an antibody, an antigen binding agent or an interfering agent, that reverses drug resistance in multiple species of bacteria by evaluating an agent for activity in disrupting biofilms produced by multiple species, wherein an agent which disrupts said biofilms is identified as an agent that reverses drug resistance, and optionally wherein evaluating an agent for binding to DNABII proteins characteristic of a multiplicity of microbial species and wherein an agent that binds a multiplicity of said proteins is identified as an agent that reverses drug resistance. In one aspect, the agent is effective against biofilms derived from at least two bacterial species, including gram positive and gram negative species, non-limiting examples of such include *S. aureus, P. aeruginosa*, and *K. pneumoniae*.

Also provided herein is an isolated polypeptide comprising the amino acid sequence of the *Haemophilus influenzae* IHFa or a fragment or equivalent thereof; and optionally wherein the polypeptide comprises: the tip portion of the DNABII polypeptide; the A5 fragment of IHFa chain; or a polypeptide consisting of an amino acid sequence selected from the group consisting of an amino acid sequence corresponding to positions 10-25 of the *Haemophilus influenzae* IHFa chain; an amino acid sequence corresponding to positions 56-78 of the *Haemophilus influenzae* IHFa; or an amino acid sequence corresponding to positions 86-96 of the *Haemophilus influenzae* IHFa; or a polypeptide comprises the amino acid sequence selected from the group consisting of TFRPGQKLKSRVENASPKDE (SEQ ID NO: 252), MATITKLDIIEYLSDKYHLS (SEQ ID NO: 348), KYHLSKQDTKNVVENFLEEI (SEQ ID NO: 349), FLEEIRLSLESGQDVKLSGF (SEQ ID NO: 350), KLSGFGNFELRDKSSRPGRN (SEQ ID NO: 351), RPGRNPKTGDVVPVSARRVV (SEQ ID NO: 352), ARRVVTFKPGQKLRARVEKTK (SEQ ID NO: 353), or a biological equivalent each thereof; and optionally wherein the isolated polypeptide further comprises a heterologous amino acid sequence or is coupled to a heterologous non-peptide domain.

In a further aspect, also provided is a non-physiological surface coated with the antibody, an antigen binding fragment, or an interfering agent as described herein. In one aspect the surface is in an industrial setting. In a further aspect, the antibody, antigen binding fragment, further comprises, consists essentially of, or yet further consists of a carrier, such as a pharmaceutically acceptable carrier. In a further aspect, the composition further comprises, consisting essentially of, or yet further consists of an additional agent such as an antibiotic.

In a further aspect, also provided is a method to obtain antibodies immunoreactive with a DNABII protein, e.g., an IHF protein or to generate B cells that secrete antibodies immunoreactive with the DNABII protein, e.g., an IHF protein, by administering the polypeptides identified herein to a subject and then recovering antibodies from the subject; or recovering B cells that produce the antibodies from the subject. In a further aspect, the method further comprises screening the B cells for secretion of an antibody with high affinity for a DNABII, e.g., IHF protein, thus identifying B cells that secrete antibodies immunoreactive with DNABII, e.g., IHF protein; and optionally isolating DNA or mRNA encoding the antibodies from the cells.

Also provided is a method to treat or prevent a condition in a subject or detect the formation of a biofilm in the subject characterized by the formation of a biofilm, by treating the subject with the antibody, the antigen binding fragment or interfering agent as described herein. In one aspect, when the biofilm is to be detected, the method further comprises observing complexation of the antibody, the antigen binding fragment, or the interfering agent with any biofilm present. In one aspect, the antibody, the antigen binding fragment, or the interfering agent dissolves biofilm derived from at least three bacterial species, wherein the three bacteria species comprises a gram negative or a gram positive bacteria. Non-limiting examples of such include *S. aureus, P. aeruginosa*, and *K. Pneumoniae*. Non-limiting examples of conditions include chronic non-healing wounds, including venous ulcers and diabetic foot ulcers, ear infections, sinus infections, urinary tract infections, pulmonary infections, cystic fibrosis, chronic obstructive pulmonary disease, catheter-associated infections, infections associated with implanted prostheses, and periodontal disease.

In a yet further aspect, a method is provided to identify an immunogen useful to elicit the formation of antibodies for treating, preventing, inhibiting or titrating a biofilm, by screening a library of candidate immunogens for high affinity binding to an antibody, antigen binding fragment or interfering agent as described herein, where a candidate member of the library that binds with high affinity to the antibody, antigen binding fragment or interfering agent, is identified as an immunogen. In a further aspect, an antibody, antigen binding fragment and interfering agent can be prepared by administering to a subject the immunogen.

Yet further provided is a pharmaceutical composition for treating a biofilm in a subject or a condition characterized by formation of biofilms which comprises as active ingredient the antibody, an antigen binding fragment, or an interfering agent as disclosed herein, in an amount effective to prevent or inhibit, disperse or dissolve a biofilm characteristic of the condition. In one aspect, the composition further includes a pharmaceutically acceptable excipient, and optionally at least one antibiotic.

Yet further provided is a method to prepare an interfering nucleic acid by preparing a nucleic acid consisting of 10-20 nucleotides that specifically binds a specific binding partner to antibody, an antigen binding fragment, or an interfering agent as described herein. In a further aspect, the specific binding partner is an epitope of a DNABII protein; and optionally wherein the epitope is conserved across at least three bacterial species. In a further aspect, this disclosure further provides the interfering nucleic acid prepared by this method.

In a further aspect, also provided is a method to identify an antibody, antigen binding fragment or an interfering agent, e.g., a binding moiety that has affinity with respect to at least one DNABII protein greater than the affinity of a biofilm component for the DNABII protein, by contacting a candidate antibody, antigen binding fragment, an interfering agent, or binding moiety with a biofilm component and with the at least one DNABII protein, and determining the ratio of said DNABII protein bound to the antibody, antigen binding fragment, an interfering agent or binding moiety as compared to DNABII bound with the biofilm component, whereby a ratio greater than one identifies the antibody, antigen binding fragment, the interfering agent or the binding moiety that has affinity with respect to at least one DNABII protein greater than the affinity of a biofilm component for the DNABII protein. In one aspect, the antibody, the antigen binding fragment, the interfering agent or the binding moiety binds the DNABII protein in low acid environments or over a range of pH.

Yet further provided is a small molecule that an antibody, an antigen binding fragment, or an interfering agent that mimics the epitope to which the antibody, antigen binding fragment or interfering agent as described herein binds. In one aspect the epitope is a *Staphylococcus aureus* DNABII or a fragment thereof or a biological equivalent thereof; and optionally, wherein the fragment of *Staphylococcus aureus* DNABII comprises a beta hairpin fragment or a biological equivalent thereof. Yet further provided is a method to obtain antisera effective to dissolve biofilm, by immunizing a subject with the small molecule that mimics the epitope to which an antibody, an antigen binding fragment, or an interfering agent as described herein binds, and recovering antiserum from the subject, and optionally isolating polyclonal antiserum or monoclonal antibodies derived therefrom. In a further aspect, the antisera is used to treat biofilm-related conditions in a subject, by administering to the subject this antiserum or monoclonal antibodies.

Also provided is a method to image a biofilm by treating a biofilm with an antibody, an antigen binding fragment, or an interfering agent, e.g., a monoclonal antibody or antigen binding fragment thereof. In one aspect, the antibody or fragment is conjugated to an observable label, and an image is obtained using the label.

For the methods as described herein, any agent that interferes or impedes the binding of the microbial DNA to the DNABII protein or polypeptide is intended within the scope of this disclosure. Non-limiting examples of interfering agents include:

(a) an isolated or recombinant DNABII or an integration host factor (IHF) polypeptide or a fragment or an equivalent of each thereof;

(b) an isolated or recombinant histone-like protein from *E. coli*, e.g., *E. coli* strain U93 (HU) polypeptide or a fragment or an equivalent of each thereof;

(c) an isolated or recombinant protein or polypeptide identified in Table 8, FIG. 19, FIG. 20, Table 9 or a DNA binding peptide identified in FIGS. 6A-6B, or a fragment or an equivalent of each thereof, wherein in one aspect the fragment comprises, or consists essentially of, or yet consists of, the polypeptides identified as A1 through A6 or B1 through B6 as disclosed in FIG. 18; or comprising, or alternatively consisting essentially of, or yet further consisting of the "tip" portion of the DNABII protein or polypeptide, non-limiting examples of such include polypeptides comprising, or alternatively consisting essentially of, or yet further consisting of

KLSGFGNFELRDKSSRPGRN
(also referred to herein as hIFA4; (SEQ ID NO. 351));

RGFGSFSLHHRQPRLGRNPK
(also referred to as B4 (SEQ ID NO. 345));

RPGRNPKTGDVVPVSARRVV
(also referred to herein as hIFA5; (SEQ ID NO. 352));

ARRVVTFKPGQKLRARVEKTK
(also referred to herein as hIFA6; (SEQ ID NO. 353)), or an equivalent of each thereof, or an equivalent of each thereof or a polypeptide having at least 60%, or alternatively at least 65%, or alternatively at least 70%, or alternatively at least 75%, or alternatively 80%, or alternatively at least 85%, or alternatively at least 90%, or alternatively at least 95% identity thereto or for polypeptide sequences, which is encoded by a polynucleotide or its complement that hybridizes under conditions of high stringency to a polynucleotide encoding such polypeptide sequences. Conditions of high stringency are described herein and incorporated herein by reference. Applicants have determined that the bolded and underlined amino acids are heavily conserved and therefore in one aspect, are not modified or altered in designing an equivalent polypeptide. Additional examples of equivalent polypeptides include, for example, IEYLSDKYHL-SKQDTK (SEQ ID NO. 354), DKSSRPGRNPKTGDVVAASARR (SEQ ID NO.: 355), and KLRARVEKTK (SEQ ID NO. 17), described in U.S. Ser. Nos. 14/497,147 and 14/668,767 now abandoned). Equivalent polypeptides also include a polypeptide consisting of or comprising the above noted polypeptides with the addition of up to 25, or alternatively 20, or alternatively 15, or alternatively up to 10, or alternatively up to 5 random amino acids on either the amine or carboxy termini (or on both);

(d) an isolated or recombinant polypeptide of SEQ ID NO: 1 through 353, or a fragment or an equivalent of each thereof;

(e) an isolated or recombinant C-terminal polypeptide of SEQ ID NO: 6 through 11, 28, 29, 42 through 100, Table 8 or those C-terminal polypeptides identified in Table 9 or a fragment or an equivalent of each thereof;

(f) a polypeptide or polynucleotide that competes with a DNABII protein on binding to a microbial DNA, e.g., DNABII or an integration host factor IHF and/or HU polypeptide or protein;

(g) a four-way junction polynucleotide resembling a Holliday junction, a 3 way junction polynucleotide resembling a replication fork, a polynucleotide that has inherent flexibility or bent polynucleotide;

(h) an isolated or recombinant polynucleotide encoding any one of (a) through (f) or an isolated or recombinant polynucleotide of SEQ ID NO: 36 or an equivalent of each thereof, or a polynucleotide that hybridizes under stringent conditions to the polynucleotide its equivalent or its complement;

(i) an antibody or antigen binding fragment that specifically recognizes or binds any one of (a) through (g), or an equivalent or fragment of each antibody or antigen binding fragment thereof;

(j) an isolated or recombinant polynucleotide encoding the antibody or antigen binding fragment of (i) or its complement;

(k) a small molecule that competes with the binding of a DNABII protein or polypeptide to a microbial DNA;
(l) an antibody or antigen binding fragment that specifically recognizes or binds any one of an isolated or recombinant polypeptide of SEQ ID NO: 342 through 353 or a fragment or an equivalent of each thereof; and/or
(m) polypeptide that comprises, or alternatively consists essentially of, or yet further consists of polypeptides A1 through A6 or B1 through B6 as disclosed in FIG. 18; or

KLSGFGNFELRDKSSRPGRN
(also referred to herein as hIFA4; (SEQ ID NO. 351));

RPGRNPKTGDVVPVSARRVV
(also referred to herein as hIFA5; (SEQ ID NO. 352));

ARRVVTFKPGQKLRARVEKTK
(also referred to herein as hIFA6; (SEQ ID NO. 353)), or an equivalent of each thereof or a polypeptide having at least 60%, or alternatively at least 65%, or alternatively at least 70%, or alternatively at least 75%, or alternatively 80%, or alternatively at least 85%, or alternatively at least 90%, or alternatively at least 95% identity thereto or for polypeptide sequences, which is encoded by a polynucleotide or its complement that hybridizes under conditions of high stringency to a polynucleotide encoding such polypeptide sequences. Conditions of high stringency are described herein and incorporated herein by reference. Applicants have determined that the bolded and underlined amino acids are heavily conserved and therefore in one aspect, are not modified or altered in designing an equivalent polypeptide. Additional examples of equivalent polypeptides include, for example IEYLSDKYHLSKQDTK (SEQ ID NO. 354), DKSSRPGRNPKTGDVVAASARR (SEQ ID NO.: 355), AND KLRARVEKTK (SEQ ID NO. 17) described in U.S. Ser. Nos. 14/497,147 and 14/668,767 now abandoned), a polypeptide consisting of or comprising the above noted polypeptides with the addition of up to 25, or alternatively 20, or alternatively 15, or alternatively up to 10, or alternatively up to 5 random amino acids on either the amine or carboxy termini (or on both).

Also provided herein is a method for inducing an immune response in or conferring passive immunity in a subject in need thereof, comprising, or alternatively consisting essentially of or yet further consisting of, administering to the subject an effective amount of one or more agents of the group:
(a) an isolated or recombinant DNABII or an integration host factor (IHF) polypeptide, or a fragment or an equivalent of each thereof;
(b) an isolated or recombinant histone-like protein from *E. coli*, e.g., *E. coli* strain U93 (HU) polypeptide or a fragment or an equivalent of each thereof;
(c) an isolated or recombinant protein polypeptide identified in Table 8, FIG. 19, FIG. 20, Table 9 or an DNA binding peptide identified in FIGS. 6A-6B, or a fragment or an equivalent of each thereof, a polypeptide A1 to A6, or B1 to B6 as shown in FIG. 18, or a fragment that comprises, or consists essentially of, or yet further consists of, the "tip" portion of the DNABII protein or polypeptide, non-limiting examples of such include without limitation a polypeptide that comprises, or alternatively consists essentially of, or yet further consists of

KLSGFGNFELRDKSSRPGRN
(also referred to herein as hIFA4; (SEQ ID NO. 351));

RGFGSFSLHHRQPRLGRNPK
(also referred to B4 (SEQ ID NO. 345));

RPGRNPKTGDVVPVSARRVV
(also referred to herein as hIFA5; (SEQ ID NO. 352));

ARRVVTFKPGQKLRARVEKTK
(also referred to herein as hIFA6; (SEQ ID NO. 353)), or an equivalent of each thereof. Additional examples of equivalent polypeptides include, for example IEYLSDKYHLSKQDTK (SEQ ID NO. 354), DKSSRPGRNPKTGDVVAASARR (SEQ ID NO.: 355), AND KLRARVEKTK (SEQ ID NO. 17) described in U.S. Ser. Nos. 14/497,147 and 14/668,767 now abandoned), a polypeptide consisting of or comprising the above noted polypeptides with the addition of up to 25, or alternatively 20, or alternatively 15, or alternatively up to 10, or alternatively up to 5 random or naturally occurring amino acids on either the amine or carboxy termini (or on both);
(d) an isolated or recombinant polypeptide of SEQ ID NO: 1 through 353 or a fragment or an equivalent thereof;
(e) an isolated or recombinant C-terminal polypeptide of SEQ ID NO: 6 through 11, 28, 29, 42 through 100, Table 8 or those C-terminal polypeptides identified in Table 9 or a fragment or an equivalent of each thereof;
(f) an isolated or recombinant polynucleotide encoding any one of (a) through (e) or an isolated or recombinant polynucleotide SEQ ID NO: 36 or an equivalent of each thereof, or a polynucleotide that hybridizes under stringent conditions to the polynucleotide, its equivalent or its complement;
(g) an antibody or antigen binding fragment that specifically recognizes or binds any one of (a) through (e), or an equivalent or fragment of each thereof;
(h) an isolated or recombinant polynucleotide encoding the antibody or antigen binding fragment of (g);
(i) an antigen presenting cell pulsed with any one of (a) through (e);
(j) an antigen presenting cell transfected with one or more polynucleotides encoding any one of (a) through (e); and/or
(k) an antibody or antigen binding fragment that specifically recognizes or binds any one of an isolated or recombinant polypeptide noted herein as A1, A2, A3, A4, A5, A6, B1, B2, B3, B4, B5, B6 or an isolated or recombinant polypeptide of SEQ ID NO: 342 through 353 or a fragment or an equivalent of each thereof.

Subjects in need of such immune response include those at risk of or suffering from an infection that produces a microbial biofilm.

Also provided herein are compositions for use in the above methods, non-limiting examples of which are discussed below.

In one aspect, provided is an isolated or recombinant polypeptide comprising, or alternatively consisting essentially of an amino acid sequence selected from A1, A2, A3, A4, A5, A6, B1, B2, B3, B4, B5, B6 (see FIG. 18) or SEQ ID NO: 1 to 5 or 12 to 27, 30 to 35, 101-340, or 341-353, or a DNA binding peptide identified in FIGS. 6A-6B, or a DNABII fragment that comprises, or consists essentially of, or yet consists of, the "tip" portion of the DNABII protein or polypeptide, non-limiting examples of such include without limitation a polypeptide that comprises, or alternatively consist essentially of, or yet further consists of

```
KLSGFGNFELRDKSSRPGRN
(also referred to herein as hIFA4; (SEQ ID NO.
351));

RPGRNPKTGDVVPVSARRVV
(also referred to herein as hIFA5; (SEQ ID NO.
352));

ARRVVTFKPGQKLRARVEKTK
(also referred to herein as hIFA6; (SEQ ID NO.
353));

RGFGSFSLHHRQPRLGRNPK
(also referred to B4 (SEQ ID NO. 345));
``` or an equivalent of each thereof. An example of equivalent polypeptides include, for example IEYLSDKYHLSKQDTK (SEQ ID NO. 354), DKSSRPGRNPKTGDVVAASARR (SEQ ID NO.: 355), and KLRARVEKTK (SEQ ID NO. 17) described in U.S. Ser. Nos. 14/497,147 and 14/668,767 now abandoned), antibody sequences as provided herein, a polypeptide consisting of or comprising the above noted polypeptides with the addition of up to 25, or alternatively 20, or alternatively 15, or alternatively up to 10, or alternatively up to 5 random or naturally occurring amino acids on either the amine or carboxy termini (or on both), or an equivalent of each thereof, or an equivalent of each thereof or a polypeptide having at least 60%, or alternatively at least 65%, or alternatively at least 70%, or alternatively at least 75%, or alternatively 80%, or alternatively at least 85%, or alternatively at least 90%, or alternatively at least 95% identity thereto or for polypeptide sequences, which is encoded by a polynucleotide or its complement that hybridizes under conditions of high stringency to a polynucleotide encoding such polypeptide sequences. Conditions of high stringency are described herein and incorporated herein by reference. Applicants have determined that the bolded and underlined amino acids are heavily conserved and therefore in one aspect, are not modified or altered in designing an equivalent polypeptide. Additional examples of equivalent polypeptides include, for example IEYLSDKYHLSKQDTK (SEQ ID NO. 354), DKSSRPGRNPKTGDVVAASARR (SEQ ID NO.: 355), and KLRARVEKTK (SEQ ID NO. 17) described in U.S. Ser. Nos. 14/497,147 and 14/668,767 now abandoned). Equivalent polypeptides also include a polypeptide consisting of or comprising the above noted polypeptides with the addition of up to 25, or alternatively 20, or alternatively 15, or alternatively up to 10, or alternatively up to 5 random amino acids on either the amine or carboxy termini (or on both).

In another aspect, provided is an isolated or recombinant polypeptide comprising, or alternatively consisting essentially of, or yet further consisting of SEQ ID NO: 1 or 2, with the proviso that the polypeptide is none of SEQ ID NO: 6 to 11, 28, 29, or 42 through 100.

In one aspect, provided is an isolated or recombinant polypeptide comprising, or alternatively consisting essentially of, or yet further consisting of SEQ ID NO: 3, 4 or 5, with the proviso that the polypeptide is none of SEQ ID NO: 6 to 11, 28, 29, or 42 through 100.

In one aspect, provided is an isolated or recombinant polypeptide comprising, or alternatively consisting essentially of, or yet further consisting of, SEQ ID NO: 12, 14, 16, 18, 20, 22, 24, 26, 30 or 32, with the proviso that the polypeptide is none of SEQ ID NO: 6 to 11, 28, 29, or 42 through 100.

In one aspect, provided is an isolated or recombinant polypeptide comprising, or alternatively consisting essentially of, or yet further consisting of SEQ ID NO: 13, 15, 17, 19, 21, 23, 25, 27, 31 or 33, with the proviso that the polypeptide is none of SEQ ID NO: 6 to 11, 28, 29, or 42 through 100.

In one aspect, provided is an isolated or recombinant polypeptide comprising, or alternatively consisting essentially of, or yet further consisting of SEQ ID NO: 337, 338, 339, or 340, with the proviso that the polypeptide is none of SEQ ID NO: 6 to 11, 28, 29, or 42 through 100.

In one aspect, provided is an isolated or recombinant polypeptide comprising, or alternatively consisting essentially of, or yet further consisting of, SEQ ID NO: 12 and 13 or 14 and 15 or 16 and 17 or 18 and 19 or 20 and 21 or 22 and 23 or 24 and 25, or 26 and 27 or 30 and 31 or 32 and 33, with the proviso that the polypeptide is none of SEQ ID NO: 6 to 11, 28, 29, or 42 through 100.

In one aspect, provided is an isolated or recombinant polypeptide comprising, or alternatively consisting essentially of, or yet further consisting of, one or more of the polypeptides noted above, none limiting examples of such include polypeptides containing the "tip" portion, the "tail portion" or the C-terminal region containing at least 10, or alternatively at least 15, or alternatively at least 20, or alternatively at least 25, or alternatively at least 30, C-terminal amino acids of a polypeptide of the group of a DNABII polypeptide, an IHF polypeptide, a DPS polypeptide, an Hfq polypeptide, a CbpA polypeptide, a CbpB polypeptide, an HU polypeptide, SEQ ID NO: 6 through 11, 28, 29 or those identified in Table 8, Table 9 or a fragment or an equivalent of each thereof.

Also provided are the polynucleotides encoding the polypeptides, recombinant expression systems and host cells comprising the polynucleotides and use of same for the recombinant expression of the polypeptides as well as the recombinant polypeptides encoding by the system and host cells. In one aspect, the host cell is a mammalian cell. The isolated polynucleotides can be operatively linked to regulatory elements necessary for the expression and/or replication of the polynucleotide. The polynucleotide can be contained within a vector. In one aspect, the polynucleotides further comprise an artificial or non-naturally occurring label (e.g., excluding naturally fluorescent polynucleotides) bound to the polynucleotide for use as probes for use in detection of biofilms and monitoring of biofilm treatment.

In one aspect, provided is an isolated or recombinant polypeptide of the group of:
  a polypeptide comprising SEQ ID NO: 12 and 13;
  a polypeptide comprising SEQ ID NO: 14 and 15;
  a polypeptide comprising SEQ ID NO: 16 and 17;
  a polypeptide comprising SEQ ID NO: 18 and 19;
  a polypeptide comprising SEQ ID NO: 20 and 21;
  a polypeptide comprising SEQ ID NO: 23 and 24;
  a polypeptide comprising SEQ ID NO: 25 and 26;
  a polypeptide comprising SEQ ID NO: 30 and 31;
  a polypeptide comprising SEQ ID NO: 32 and 33;
  a polypeptide comprising SEQ ID NO: 34 and 35;
  a polypeptide comprising SEQ ID NO: 337 and 338; or
  a polypeptide comprising SEQ ID NO: 339 and 340;

a polypeptide consisting essentially of any one or more of SEQ ID NO: 342 to 453;

with the proviso that the polypeptide is none of wild-type of any one of IHF alpha, IHF beta or SEQ ID NO: 6 to 11, 28, 29, or 42 through 100.

In one aspect, provided is an isolated or recombinant polypeptide of the group of:

a polypeptide consisting essentially of SEQ ID NO: 12 and 13;

a polypeptide consisting essentially of SEQ ID NO: 14 and 15;

a polypeptide consisting essentially of SEQ ID NO: 16 and 17;

a polypeptide consisting essentially of SEQ ID NO: 18 and 19;

a polypeptide consisting essentially of SEQ ID NO: 20 and 21;

a polypeptide consisting essentially of SEQ ID NO: 23 and 24;

a polypeptide consisting essentially of SEQ ID NO: 25 and 26;

a polypeptide consisting essentially of SEQ ID NO: 30 and 31;

a polypeptide consisting essentially of SEQ ID NO: 32 and 33;

a polypeptide consisting essentially of SEQ ID NO: 34 and 35;

a polypeptide consisting essentially of SEQ ID NO: 337 and 338; or a polypeptide consisting essentially of SEQ ID NO: 339 and 340;

a polypeptide consisting essentially of any one or more of SEQ ID NO: 342 to 453;

with the proviso that the polypeptide is none of wild-type of any one of IHF alpha, IHF beta or SEQ ID NO: 6 to 11, 28, 29, or 42 through 100.

Also provided are isolated or recombinant polypeptides comprising, or alternatively consisting essentially of or yet further consisting of, two or more, or three or more or four or more, or multiples of the above-identified isolated polypeptides, including fragments and equivalents thereof. Examples of such include isolated polypeptides comprising SEQ ID NO: 1 through 4 and/or 12 through 29, and/or 30 through 33, and/or 30 through 35 e.g., SEQ ID NO: 1 and 2, or alternatively 1 and 3 or alternatively 1 and 4, or alternatively 2 and 3, or alternatively SEQ ID NO: 1, 2 and 3 or alternatively, 2, 3 and 4, or alternatively 1, 3 and 4 or equivalent polypeptides, examples of which are shown in Table 9. The polypeptides can be in any orientation, e.g., SEQ ID NO: 1, 2, and 3 or SEQ ID NO: 3, 2 and 1 or alternatively SEQ ID NO: 2, 1 and 3, or alternatively, 3, 1 and 2, or alternatively 11 and 12, or alternatively 1 and 12, or alternatively 2 and 12, or alternatively, 1 and 12, or alternatively 2 and 13, or alternatively 12, 16 and 1, or alternatively 1, 16 and 12.

In another aspect, this disclosure provides an isolated or recombinant polypeptide comprising SEQ ID NO: 1 or 2 and 3 or 4 or a polypeptide or recombinant polypeptide comprising, or alternatively consisting essentially of, or yet further consisting of an amino acid corresponding to fragments of a DNABII protein such as the tail fragment or the tip fragment, non-limiting examples of such include without limitation a polypeptide that comprises one or more of the sequences identified as A1 through A6; or identified as B1 through B6 (see FIG. 18);

MATITKLDHIEYLSDKYHLS
(also referred to herein as hIFA1; (SEQ ID NO. 348));

KYHLSKQDTKNVVENFLEEI
(also referred to herein as hIFA2; (SEQ ID NO. 349));

FLEEIRLSLESGQDVKLSGF
(also referred to herein as MFA3; (SEQ ID NO. 350));

KLSGFGNFELRDKSSRPGRN
(also referred to herein as hIFA4; (SEQ ID NO. 351));

RPGRNPKTGDVVPVSARRVV
(also referred to herein as hIFA5; (SEQ ID NO. 352));

ARRVVTFKPGQKLRARVEKTK
(also referred to herein as hIFA6; (SEQ ID NO. 353));

RGFGSFSLHHRQPRLGRNPK
(also referred to B4 (SEQ ID NO. 345));

Applicants have determined that the bolded and underlined amino acids are heavily conserved and therefore in one aspect, are not modified or altered in designing an equivalent polypeptide, or an equivalent thereof, (examples of equivalent polypeptides include, for example IEYLSDKYHL-SKQDTK (SEQ ID NO. 354), DKSSRPGRNPKTGDVVAASARR (SEQ ID NO.: 355), and KLRARVEKTK (SEQ ID NO. 17) described in U.S. Ser. Nos. 14/497,147 and 14/668,767 now abandoned), a polypeptide consisting of or comprising the above noted polypeptides with the addition of up to 25, or alternatively 20, or alternatively 15, or alternatively up to 10, or alternatively up to 5 random or naturally occurring amino acids on either the amine or carboxy termini (or on both). the tail fragment, the β-3 and/or α-3 fragments of a DPS polypeptide, an Hfq polypeptide, a CbpA polypeptide, a CbpB polypeptide, an HU polypeptide, a *Haemophilus influenzae* IHFα or IHFβ, non-limiting examples of which include SEQ ID NO: 12 through 27, or a fragment or an equivalent of each of the polypeptides, examples of which are shown in Table 9. In one aspect, isolated wildtype polypeptides are specifically excluded, e.g., that the polypeptide is none of SEQ ID NO: 6 through 11 or a wildtype sequence identified in Table 8. In this embodiment, SEQ ID NO: 1 or 2 or a polypeptide comprising, or alternatively consisting essentially of, or yet further consisting of an amino acid corresponding to the β-3 and/or α-3 fragments of an IHFα or IHFβ microorganism, non-limiting examples of which include SEQ ID NO: 12 through 27 and 30 through 33 or an equivalent of each thereof is located upstream or amino terminus from SEQ ID NO: 3 or 4 or a fragment or an equivalent thereof. In another aspect, the isolated polypeptide comprises SEQ ID NO: 3 or 4 or a polypeptide comprising, or alternatively consisting essentially of, or yet further consisting of an amino acid corresponding to the β-3 and/or α-3 fragments of an IHFα or IHFβ microorganism, non-limiting examples of which include SEQ ID NO: 12 through 27, or an equivalent thereof located upstream or amino terminus to SEQ ID NO: 1 or 2 or an equivalent thereof.

In any of the above embodiments, a peptide linker can be added to the tip fragment (non-limiting examples of such include without limitation a polynucleotide that comprises one or more of the sequences:

RPGRNPKTGDVVPVSARRVV
(also referred to herein as hIFA5; (SEQ ID NO. 352));
and

RGFGSFSLHHRQPRLGRNPK
(also referred to B4 (SEQ ID NO 345));

or an equivalent of each thereof, the tail fragment, the N-terminus or the C-terminus of the polypeptide, fragment or equivalent thereof. In one aspect, the linker joins the polypeptides disclosed herein, e.g., SEQ ID NO: 1 to 4, 28, 29, 34, or 35 or 30 to 33, 34, or 35 or a polypeptide comprising, or alternatively consisting essentially of, or yet further consisting of an amino acid corresponding to the β-3 and/or α-3 fragments of a *Haemophilus influenzae* IHFα or IHFβ protein (non-limiting examples of full length *Haemophilus influenzae* IHFα and IHFβ are disclosed as SEQ ID NO: 6 and SEQ ID NO: 341, respectively); non-limiting examples of the polypeptides disclosed herein above include SEQ ID NO: 12 through 27 or an equivalent of each thereof. The a polypeptides can further consists of or comprise the above noted polypeptides with the addition of up to 25, or alternatively 20, or alternatively 15, or alternatively up to 10, or alternatively up to 5 random or naturally occurring amino acids on either the amine or carboxy termini (or on both).

A "linker" or "peptide linker" refers to a peptide sequence linked to either the N-terminus or the C-terminus of a polypeptide sequence. In one aspect, the linker is from about 1 to about 20 amino acid residues long or alternatively 2 to about 10, about 3 to about 5 amino acid residues long. An example of a peptide linker is Gly-Pro-Ser-Leu-Lys-Leu (SEQ ID NO: 37).

Further provided is a fragment or an equivalent of the isolated or recombinant polypeptide of any one of polypeptides identified above as well as an isolated or recombinant polypeptide comprising, or alternatively consisting essentially of, or yet further consisting of, two or more of the isolated or recombinant polypeptides identified above.

Yet further provided is a polynucleotide that interferes with the binding between the microbial DNA and a polypeptide or fragment or equivalent thereof, e.g., SEQ ID 36, or a four-way junction polynucleotide resembling a Holliday junction, a 3 way junction polynucleotide resembling a replication fork, a polynucleotide that has inherent flexibility or bent polynucleotide; an isolated or recombinant polynucleotide encoding a polypeptide described above or an antibody or fragment thereof, which can be operatively linked to regulatory elements necessary for the expression and/or replication of the polynucleotide. The polynucleotide can be contained within a vector.

Also provided is an isolated host cell comprising, or alternatively consisting essentially of, or yet further consisting of an isolated or recombinant polypeptide described above, a four-way junction polynucleotide resembling a Holliday junction, a 3 way junction polynucleotide resembling a replication fork, a polynucleotide that has inherent flexibility or bent polynucleotide; an isolated or recombinant polynucleotide as described above, or a vector as described above.

In one aspect the cell is an isolated antigen presenting cell comprising the isolated or recombinant polypeptide. In a further aspect, the polypeptide is present on the surface of the cell, such as a dendritic cell. In a further aspect, the antigen presenting cell is transfected with one or more polynucleotides encoding the polypeptide.

Yet further provided is an antibody or antigen binding fragment that specifically recognizes and binds the isolated or recombinant polypeptide as describe above, including a fragment or an equivalent of the polypeptide. Non-limiting examples of antibodies include a polyclonal antibody, a monoclonal antibody, a humanized antibody, a human antibody, an antibody derivative, a veneered antibody, a diabody, a chimeric antibody, an antibody derivative, a recombinant human antibody, or an antibody fragment. In a particular aspect, the antibody is a monoclonal antibody. Yet further provided is a hybridoma cell line that produces the monoclonal antibody.

In certain aspects, the disclosure relates to an antibody or antigen binding fragment that specifically recognizes or binds an isolated or recombinant polypeptide comprising, consisting essentially of, or consisting of one or more amino acid sequence selected from A1 to A6 or B1 to B6 (See FIG. 18);

SEQ ID NO: 342-353,
MATITKLDIIEYLSDKYHLS (also referred to herein as hIFA1; (SEQ ID NO. 348));

KYHLSKQDTKNVVENFLEEI
(also referred to herein as MFA2; (SEQ ID NO. 349));

FLEEIRLSLESGQDVKLSGF
(also referred to herein as MFA3; (SEQ ID NO. 350));

KLSGFGNFELRDKSSRPGRN
(also referred to herein as MFA4; (SEQ ID NO. 351));

RPGRNPKTGDVVPVSARRVV
(also referred to herein as MFA5; (SEQ ID NO. 352));

ARRVVTFKPGQKLRARVEKTK
(also referred to herein as MFA6; (SEQ ID NO. 353));

RGFGSFSLHHRQPRLGRNPK
(also referred to herein as B4 (SEQ ID NO. 345));

or the tip or the tail portion of the DNABII protein or polypeptide, a polypeptide that comprises one or more of the sequences MATITKLDIIEYLSDKYHLS (also referred to herein as hIFA1; (SEQ ID NO. 348)); KYHLSKQDT-KNVVENFLEEI (also referred to herein as hIFA2; (SEQ ID NO. 349)); or FLEEIRLSLESGQDVKLSGF (also referred to herein as hIFA3; (SEQ ID NO. 350)). The polypeptides may consist of or comprise the above noted polypeptides with the addition of up to 25, or alternatively 20, or alternatively 15, or alternatively up to 10, or alternatively up to 5 random or naturally occurring amino acids on either the amine or carboxy termini (or on both). In some embodiments, such antibodies or antigen binding fragments are administered alone or in combination with each other, or an agent other than the antibody, or yet a further pharmaceutically effective agent, alone or in combination with a pharmaceutically acceptable carrier.

This disclosure also provides isolated or recombinant polynucleotides encoding one or more of the above-identified isolated or recombinant polypeptides or antibodies or a fragment thereof. Vectors comprising the isolated polynucleotides are further provided. In one aspect where more than one isolated polypeptide disclosed herein, the isolated polynucleotides can be contained within a polycistronic vector.

Isolated host cells comprising one or more of isolated or recombinant polypeptides or isolated or recombinant polynucleotides or the vectors, described herein are further provided. In one aspect the isolated host cell is a prokaryotic cell or eukaryotic cell such as antigen presenting cell, e.g., a dendritic cell.

The polynucleotides, polypeptides, antibodies, antigen binding fragment, vectors or host cells can father comprise a detectable label.

Compositions comprising a carrier and one or more of an isolated or recombinant polypeptide disclosed herein, an isolated or recombinant polynucleotide disclosed herein, a vector disclosed herein, an isolated host cell disclosed herein, or an antibody of the embodiments are also provided. The carriers can be one or more of a solid support, a medical device like a stent or dental implant, or a liquid such as a pharmaceutically acceptable carrier. The compositions can further comprise an adjuvant, an antimicrobial or an antigenic peptide.

The compositions can further comprise additional biologically active agents. A non-limiting example of such is a antimicrobial agent such as other vaccine components (i.e., antigenic proteins or peptides) such as surface antigens, e.g., an OMP P5, rsPilA, OMP 26, OMP P2, or Type IV Pilin protein (see Jurcisek and Bakaletz (2007) J. Bacteriology 189(10):3868-3875 and Murphy, T. F. et al. (2009) The Pediatric Infectious Disease Journal 28:S121-S126) and antimicrobial agents.

This disclosure also provides a method for producing an antigenic peptide by growing or culturing a host cell comprising an isolated polynucleotide encoding an antigenic peptide as described above under conditions that favor the expression of the polynucleotide. The polypeptide produced by this method can be isolating for further in vitro or in vivo use.

Also provided are hybridoma cell lines that produce exemplary monoclonal antibodies for use in the methods disclosed herein. The hybridoma cell lines that produce monoclonal antibodies that specifically recognize and bind *Haemophilus influenzae* IhfA fragment A5 (SEQ ID NO. 352)), IhfB4 (RGFGSFSLHHRQPRLGRNPK (also referred to B4 (SEQ ID NO. 345)); were deposited with American Type Culture Collection (ATCC) under Accession Numbers (IhfA5 (Accession No. PTA-122334)) and (IhfB4 (Accession No. PTA-122336)), pursuant to the provisions of the Budapest Treaty on Jul. 30, 2015. Further non-limiting exemplary antibodies include those that specifically recognize and bind *Haemophilus influenzae* IhfA fragment A3 (SEQ ID NO. 350), IhfB fragment B2 (SEQ ID NO. 343) produced by hybridoma cell lines IhfA3 NTHI 9B10.F2.H3 and IhfB2 NTHI 7A4.E4.G4.

A kit is also provided for diagnostic or therapeutic use comprising a composition as described above and instructions for use. A kit is also provided to perform screens for new drugs and/or combination therapies as provided herein.

BRIEF DESCRIPTION OF THE DRAWINGS

FIGS. 3A-3E shows that antibodies directed against IHF reversed an established NTHI formed in a chamber slide. FIG. 3A shows a biofilm treated with nonspecific antibody. FIG. 3B shows a biofilm treated with naïve rabbit serum. Note the robust NTHI biofilm with abundant towers (appear as white to light gray clustered areas) and water channels (black spaces). FIG. 3C is a biofilm treated with anti-IHF. Note the eradication of biofilm structure after treatment with an anti-IHF. Individual NTHI (appear as small punctuate white to light gray spots) and sparse, short towers (appear as denser white to light gray clustered areas) remain. FIGS. 3D and 3E further depict that antibodies directed against IHF reverse an established NTHI biofilm. As shown in FIG. 3E, the biofilm showed a dramatic loss of 3-dimensional structure when compared to a biofilm incubated with naive serum (FIG. 3D), Via COMSTAT analysis of multiple replicate assays, the measured parameters of biofilm height, biomass and biofilm thickness were all diminished by a mean of greater than 80% upon incubation with anti-IHF.

FIGS. 8A & 8B—parental strain MG1655; FIGS. 8C & 8D—HU-deficient hupA, hupB double mutant; FIGS. 8E & 8F—IHF-deficient himD, himA double mutant. Note the ability of anti-IHF serum to reduce biomass induced by either the parental isolate or the HU-deficient mutant, but not the IHF-deficient strain, as expected.

FIG. 9A demonstrates that immunization with IHF via a transcutaneous delivery route induced the formation of antibodies that significantly reduced the biomass of an NTHI-induced biofilm resident within the middle ears of chinchillas ($p<0.001$). FIG. 9B depicts representative images of biomasses that remained in the ears of animals immunized with adjuvant alone versus those immunized with IHF+adjuvant. Last column in FIG. 9B shows images of biomasses at the extremes of the scoring system used here. Top image is that of a middle ear that contains a biomass that would receive a score of 4+, whereas lower image is a healthy middle ear that would receive a score of 0, indicating no biomass.

FIGS. 14A-14C show a demonstration of synergism between a sub-optimal concentration of anti-IHF serum (1:200) and DNAseI individually, then mixed (FIG. 14A); a sub-optimal concentration of anti-IHF (1:100) and anti-outer membrane protein P5 serum (OMP P5) individually, then mixed (FIG. 14B); or that of an effective dilution of anti-IHF (in terms of debulking a biofilm but not inducing bacterial cell death) and amoxicillin individually, then mixed (FIG. 14C). In each of these situations, when any agent was combined with anti-IHF, the biofilm debulking and/or killing effect observed was greater than that noted when any single agent was used alone. Note: biofilm height (in microns) is indicated under each image.

FIG. 19 is a sequence alignment of relevant portions of the DNA binding proteins of various embodiments disclosed herein. Bold letters indicate an exact match to consensus, light gray lettering indicates a conservative amino acid change, and lightly or darkly shaded sequences are highly conserved across species. Gray shaded undefined sequences at the amino and/or carboxy-terminal are undefined amino acids that do not share consensus sequences. FIG. 19 is based on information previously published Oberto et al. (1994) Biochimie 76:901-908.

FIG. 20 is a comparison of the 16 amino acid peptide motif to Liu et al. (2008) Cell Microbiol. 10(1):262-276.

DETAILED DESCRIPTION

Figure 1A:
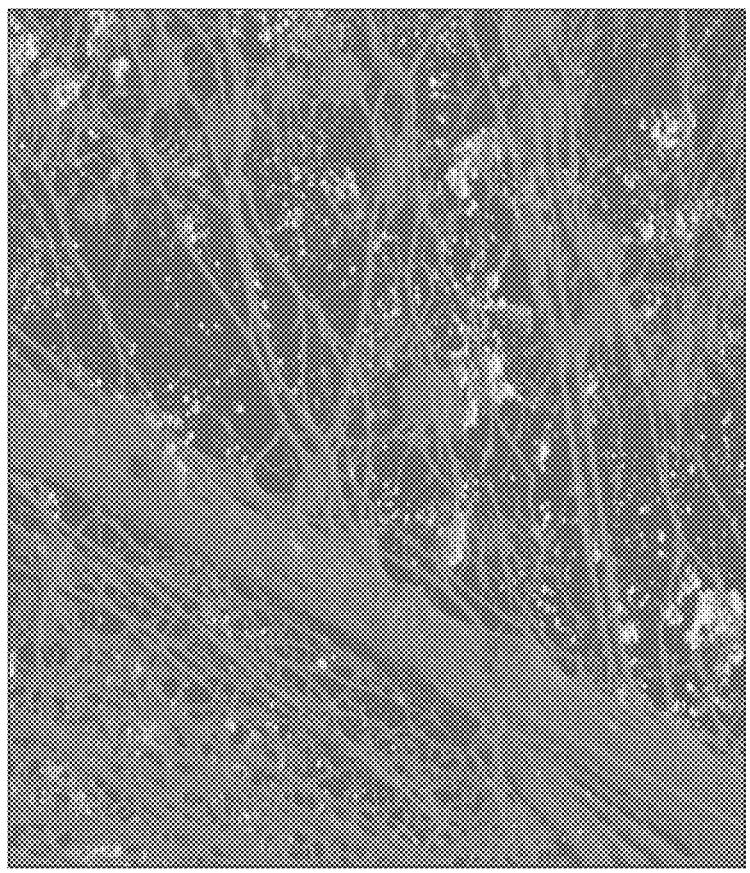
FIG. 1A is a biofilm formed in the chinchilla middle ear by NTHI strain 86-028NP and labeled for NTHI Tfp pilin protein (appears as white or light gray speckles and small clusters in the background of this image), as well as with DAPI for labeling of the double stranded DNA (dsDNA) (appears as dark gray overlapping strands and bundles of material with intermittent clumps in the foreground of this image). This figure has been reproduced from Jurcisek and Bakaletz (2007) J. Bacteriology 189(10):3868-3875.

Unless defined otherwise, all technical and scientific terms used herein have the same meanings as commonly understood by one of ordinary skill in the art to which this disclosure belongs. All nucleotide sequences provided herein are presented in the 5' to 3' direction. Although any methods and materials similar or equivalent to those described herein can be used in the practice or testing of the present disclosure, particular, non-limiting exemplary methods, devices, and materials are now described. All technical and patent publications cited herein are incorporated herein by reference in their entirety. Nothing herein is to be construed as an admission that the disclosure is not entitled to antedate such disclosure by virtue of prior invention.

The practice of the present disclosure will employ, unless otherwise indicated, conventional techniques of tissue culture, immunology, molecular biology, microbiology, cell biology and recombinant DNA, which are within the skill of the art. See, e.g., Sambrook and Russell eds, (2001) Molecular Cloning: A Laboratory Manual, 3$^{rd}$ edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, 5$^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds, (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); and Herzenberg et al. eds (1996) Weir's Handbook of Experimental Immunology.

All numerical designations, e.g., pH, temperature, time, concentration, and molecular weight, including ranges, are approximations which are varied (+) or (−) by increments of 1.0 or 0.1, as appropriate or alternatively by a variation of +/− 15%, or alternatively 10% or alternatively 5% or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

As used in the specification and claims, the singular form "a", "an" and "the" include plural references unless the context clearly dictates otherwise. For example, the term "a polypeptide" includes a plurality of polypeptides, including mixtures thereof.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions disclosed herein. Embodiments defined by each of these transition terms are within the scope of this disclosure.

A "biofilm" intends an organized community of microorganisms that at times adhere to the surface of a structure, that may be organic or inorganic, together with the polymers such as DNA that they secrete and/or release. The biofilms are very resistant to microbiotics and antimicrobial agents. They live on gingival tissues, teeth and restorations, causing caries and periodontal disease, also known as periodontal plaque disease. They also cause chronic middle ear infections. Biofilms can also form on the surface of dental implants, stents, catheter lines and contact lenses. They grow on pacemakers, heart valve replacements, artificial joints and other surgical implants. The Centers for Disease Control) estimate that over 65% of nosocomial (hospital-acquired) infections are caused by biofilms. They cause chronic vaginal infections and lead to life-threatening systemic infections in people with hobbled immune systems. Biofilms also are involved in numerous diseases. For instance, cystic fibrosis patients have *Pseudomonas* infections that often result in antibiotic resistant biofilms.

Figure 1B:
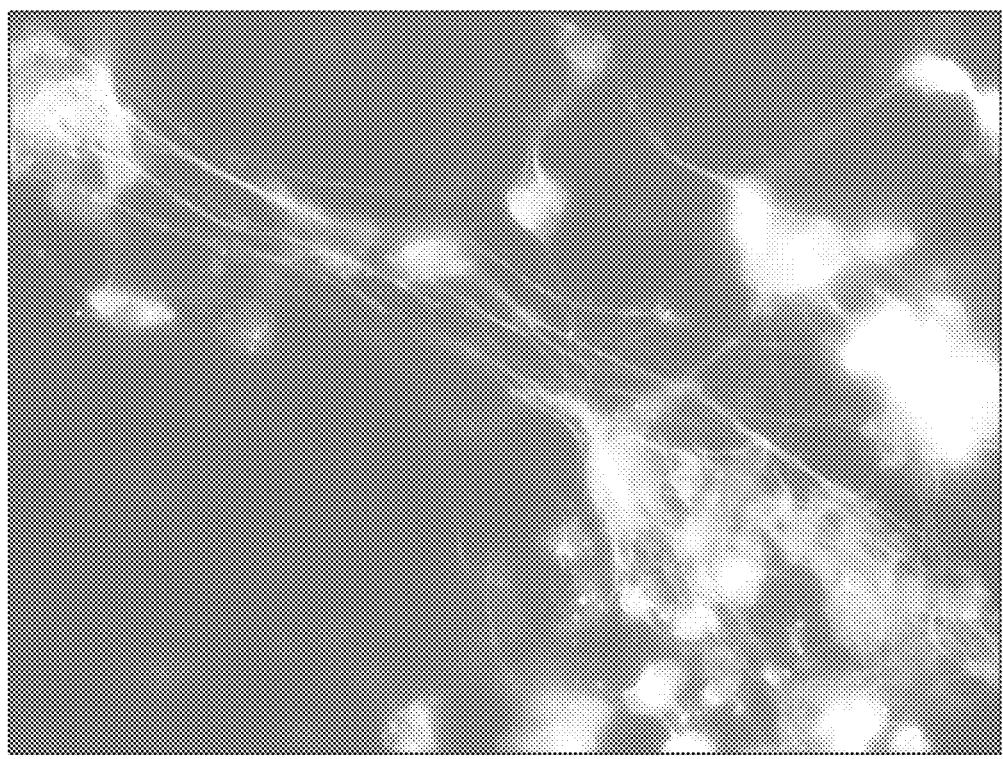
FIG. 1B shows immunolabeling bronchoalveolar lavage (BAL) from the lung of a child with cystic fibrosis. The lung of a child with cystic fibrosis was washed out via BAL and the particulate matter from the wash was frozen and affixed to slides for immunolabeling. The frozen particulate matter was immunolabeled with the anti-IHF antibody. The presence of DNABII positive foci in the biofilm of human cystic fibrosis patients exemplifies that the etiology of human cystic fibrosis includes a biofilm with IHF at the vertices of the dsDNA.
Figure 1C:
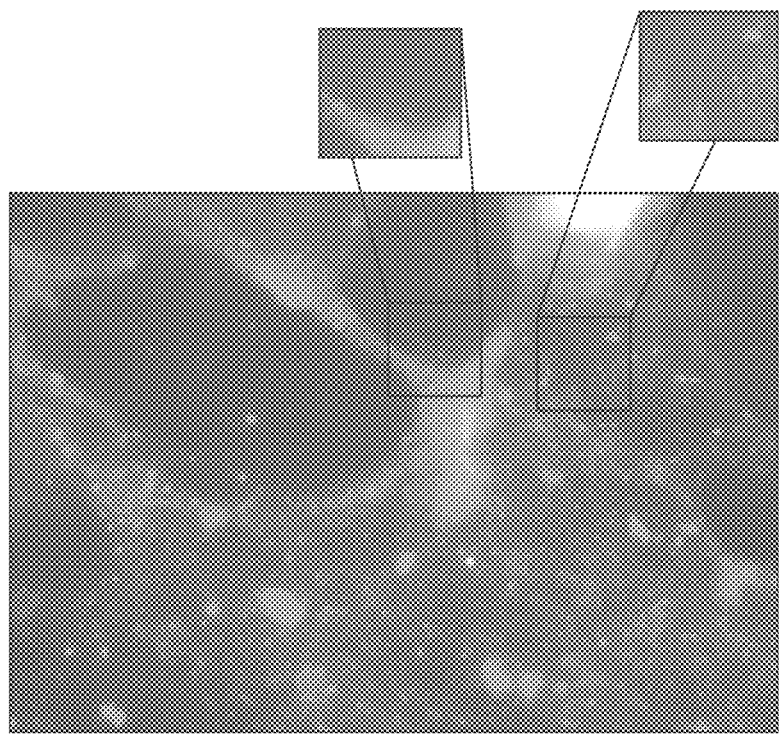
FIG. 1C shows secretions from human sinus collected at the time of sinus surgery and embedded in OCT freezing medium (Optimal Cutting Temperature medium, available commercially from Fisher Scientific Cat. No. 14-373-65). 10 μm frozen sections were cut and labeled with anti-IHF (appearing as gray clusters). dsDNA within the sample was stained with a fluorescent stain, DAPI (4',6-diamidino-2-phenylindole, available commercially from Invitrogen). The presence of IHF positive foci in the biofilm of sinusitis patients exemplifies that the etiology of human sinusitis includes a biofilm with IHF at the vertices of the dsDNA.
Figure 2:
FIG. 2 is an immunohistochemical labeling of double stranded DNA (appears as white strands in this image) within an NTHI biofilm formed in the middle ear of chinchilla. Positive labeling for IHF (as indicated by arrows pointing to punctuate foci in the middle panel of this 3-panel image) was observed at nearly 100% of vertices formed by dsDNA. Mean distance between vertices was approximately 6 μm, or approximately 18 kb between each vertex if one assumes 0.34 nm per base of DNA for B-form DNA. To the best of our knowledge, the only proteins that possess epitopes that cross-react with anti-IHF are HU and IHF. Therefore, based on these observations, it appeared that not only were there extracellular DNABII proteins within the NTHI biofilm matrix, but more importantly that these proteins appeared to be exclusively positioned on eDNA strands that resembled cruciform structures in conformation (see FIG. 6B, bottom section), thus strongly suggesting their role in mediating the resulting bent conformation of the eDNA.
Figures 3D, 3E:
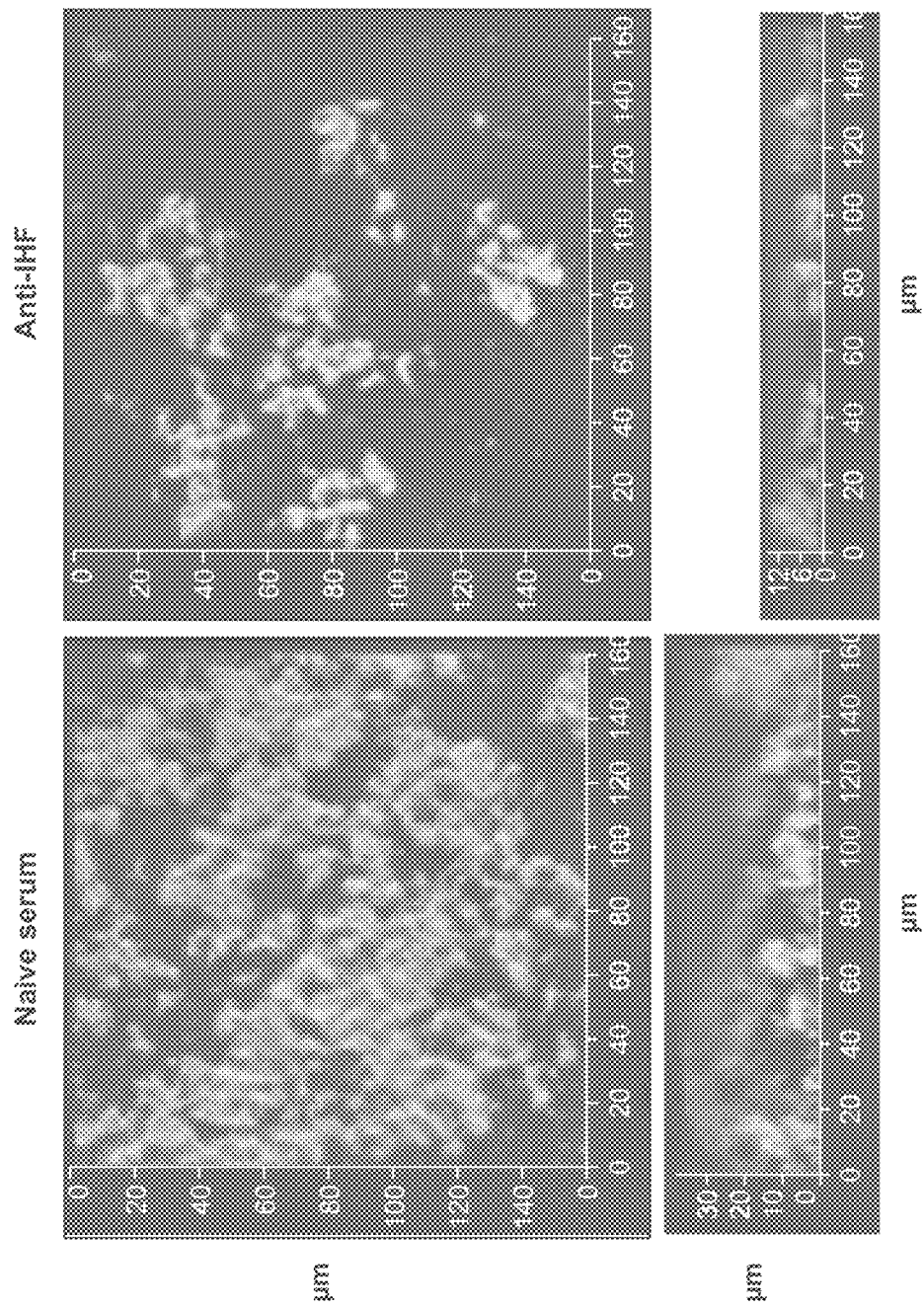

The term "inhibiting, competing or titrating" intends a reduction in the formation of the DNA/protein matrix (for example as shown in FIGS. 1A-1C) that is a component of a microbial biofilm.

A "DNABII polypeptide or protein" intends a DNA binding protein or polypeptide that is composed of DNA-binding domains and thus have a specific or general affinity for microbial DNA. In one aspect, they bind DNA in the minor grove. Non-limiting examples of DNABII proteins are an integration host factor (IHF) protein and a histone-like protein from *E. coli* strain U93 (HU). Other DNA binding proteins that may be associated with the biofilm include DPS (Genbank Accession No.: CAA49169), H-NS (Genbank Accession No.: CAA47740), Hfq (Genbank Accession No.: ACE63256), CbpA (Genbank Accession No.: BAA03950) and CbpB (Genbank Accession No.: NP_418813).

An "integration host factor" of "IHF" protein is a bacterial protein that is used by bacteriophages to incorporate their DNA into the host bacteria. They also bind extracellular microbial DNA. The genes that encode the IHF protein subunits in *E. coli* are himA (Genbank Accession No.: POA6X7.1) and himD (POA6Y1.1) genes. Homologs for these genes are found in other organisms, and peptides corresponding to these genes from other organisms can be found in Table 9.

"HMGB1" is a high mobility group box (HMGB) 1 protein that is reported to bind to and distort the minor groove of DNA and is an example of an interfering agent. Recombinant or isolated protein and polypeptide are commercially available from Atgenglobal, ProSpecBio, Protein1 and Abnova.

"HU" or "histone-like protein from *E. coli* strain U93" refers to a class of heterodimeric proteins typically associate with *E. coli*. HU proteins are known to bind DNA junctions.

Related proteins have been isolated from other microorganisms. The complete amino acid sequence of *E. coli* HU was reported by Laine et al. (1980) Eur. J. Biochem 103(3)447-481. Antibodies to the HU protein are commercially available from Abcam. The genes that encode the HU protein subunits in *E. coli* are hupA and hupB corresponding to SEQ ID Nos: 28 and 29, respectively. Homologs for these genes are found in other organisms, and peptides corresponding to these genes from other organisms can be found in Table 9.

The term "surface antigens" or "surface proteins" refers to proteins or peptides on the surface of cells such as bacterial cells. Examples of surface antigens are Outer membrane proteins such as OMP P5 (Genbank Accession No.: YP_004139079.1), OMP P2 (Genbank Accession No.: ZZX87199.1), OMP P26 (Genbank Accession No.: YP_665091.1), rsPilA or recombinant soluble PilA (Genbank Accession No.: EFU96734.1) and Type IV Pilin (Genbank Accession No.: Yp_003864351.1).

The term "*Haemophilus influenzae*" refers to pathogenic bacteria that can cause many different infections such as, for example, ear infections, eye infections, and sinusitis. Many different strains of *Haemophilus influenzae* have been isolated and have an IhfA gene or protein. Some non-limiting examples of different strains of *Haemophilus influenzae* include Rd KW20, 86-028NP, R2866, PittGG, PittEE, R2846, and 2019.

"Microbial DNA" intends single or double stranded DNA from a microorganism that produces a biofilm.

Figure 5:
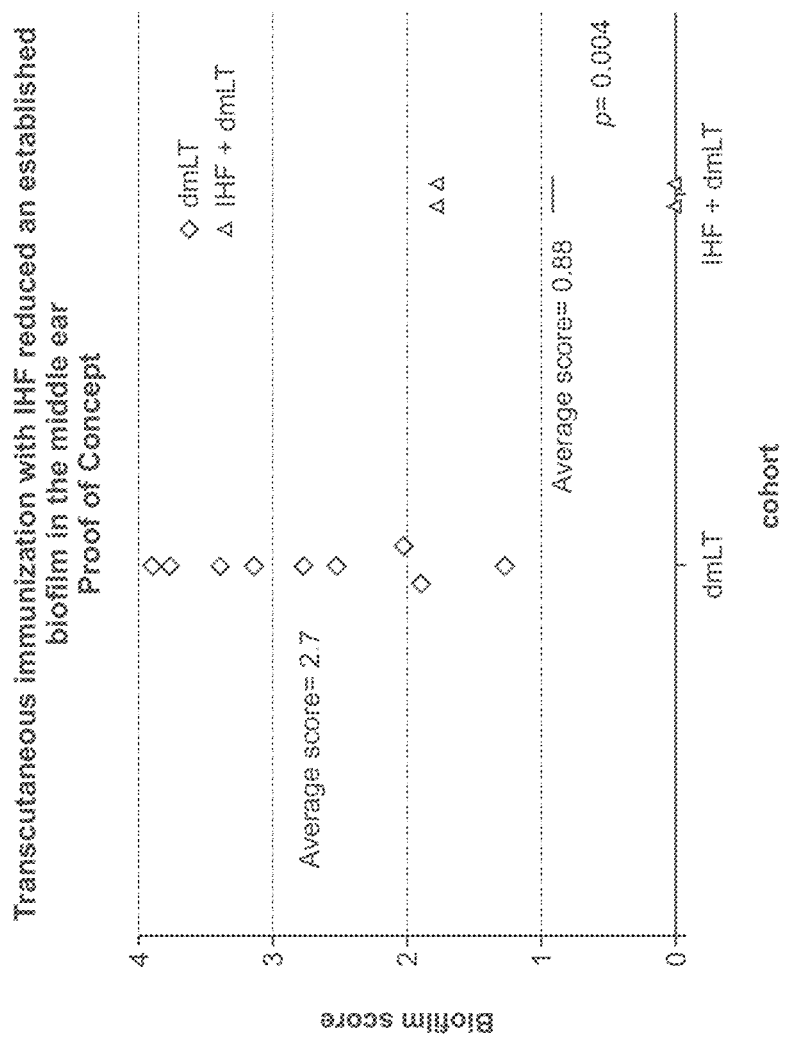
FIG. 5 shows the results of a transcutaneous immunization with IHF reduced an established biofilm in the middle ear. Note that bullae were blindly ranked onto a 0 to 4+ scale of relative remaining biofilm mass.

"Inhibiting, preventing or breaking down" a biofilm intends the prophylactic or therapeutic reduction in the structure of a biofilm. An example of breaking down or reducing a biofilm is shown in FIG. 5.

An "interfering agent" intends an agent that any one or more of competes, inhibits, prevents, titrates a DNABII polypeptide such as IHF to a microbial DNA or also breaks down a microbial biofilm. It can be any one or more of a chemical or biological molecule. For example, DNABII such as IHF can specifically bind, bend or distorted DNA structures such as DNA containing four-way junctions, cis-platinum adducts, DNA loop or base bulges. Examples of such agents, without limitation, include (1) small molecules that inhibit the DNA-binding activity of IHF, (2) small molecules such as polyamines and spermine that compete with IHF in DNA binding, (3) polypeptides such as peptide fragments of IHF that compete with IHF in DNA binding, (4) antibodies or fragments thereof directed to IHF, (5) a short polynucleotide that binds the polypeptide or biofilm forming DNA, or (6) a four-way or bent polynucleotides or other types of polynucleotides containing bent or distorted DNA structures that compete in IHF-binding. A "small molecule that inhibits the binding of an IHF to a nucleic acid" refers to (1) or (2) above and includes those that bind DNA in the minor grove, i.e., minor groove binding molecules. A "four-way polynucleotide" intends a polynucleotide that contains a four-way junction, also known as the Holliday junction, between four strands of DNA.

A "bent polynucleotide" intends a double strand polynucleotide that contains a small loop on one strand which does not pair with the other strand. In some embodiments, the loop is from 1 base to about 20 bases long, or alternatively from 2 bases to about 15 bases long, or alternatively from about 3 bases to about 12 bases long, or alternatively from about 4 bases to about 10 bases long, or alternatively has about 4, 5, or 6, or 7, or 8, or 9, or 10 bases.

Figure 6A:
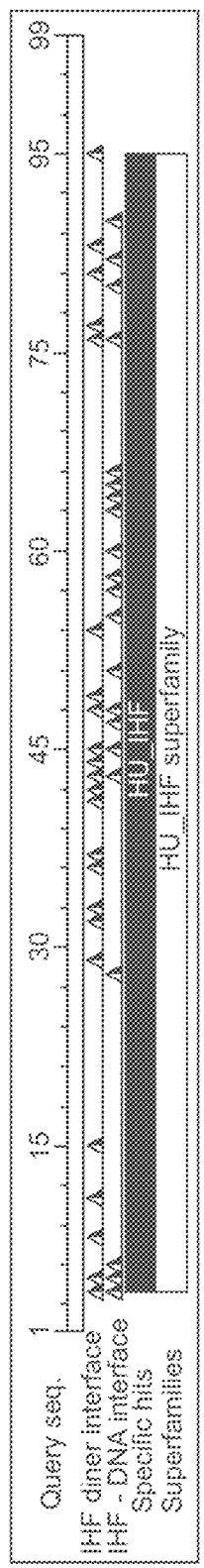
FIG. 6A is a map indicating the amino acid residues of IHF that interact with or bind to another IHF in an IHF-IHF dimer (indicated by triangles at the upper level) or interact with or bind DNA (indicated by triangles at the lower level). The peptide is divided by the short vertical bars into regions containing 3 amino acids.
Figure 6B:
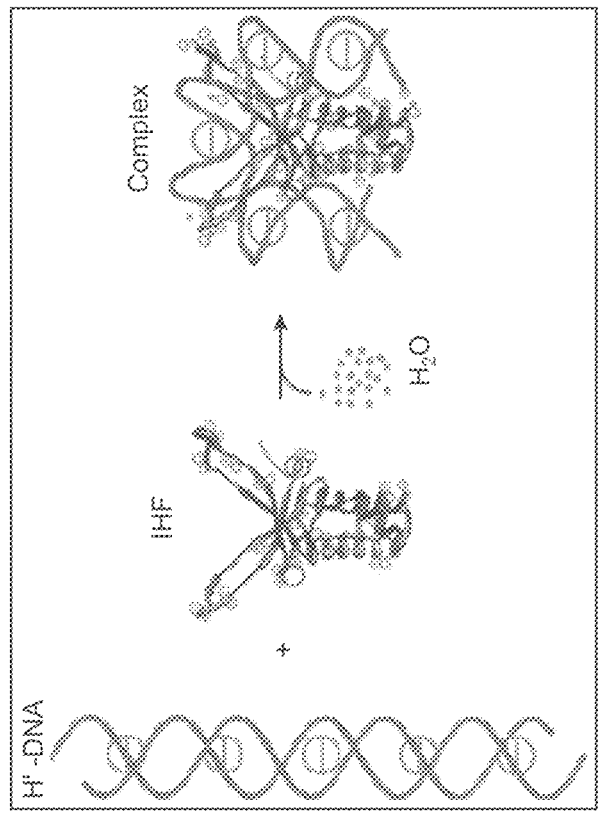
FIG. 6B graphically depicts the interaction of microbial DNA with an IHF.

"Polypeptides that compete with DNABII binding, such as IHF in DNA binding" intend proteins or peptides that compete with DNABII (e.g., IHF) in binding bent or distorted DNA structures but do not form a biofilm with the DNA. Examples, without limitation, include fragments of IHF that include one or more DNA binding domains of the IHF, or the biological equivalents thereof. DNA binding domains are shown in FIGS. 6A-6B.

A "subject" of diagnosis or treatment is a cell or an animal such as a mammal, or a human. Non-human animals subject to diagnosis or treatment and are those subject to infections or animal models, for example, simians, murines, such as, rats, mice, chinchilla, canine, such as dogs, leporids, such as rabbits, livestock, sport animals, and pets.

The term "protein", "peptide" and "polypeptide" are used interchangeably and in their broadest sense to refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

A "C-terminal polypeptide" intends at least the 10, or alternatively at least the 15, or alternatively at least 20, or at least the 25 C-terminal amino acids or alternatively half of a polypeptide. In another aspect, for polypeptides containing 90 amino acids, the C-terminal polypeptide would comprise amino acids 46 through 90. In one aspect, the term intends the C-terminal 20 amino acids from the carboxy terminus.

A "tip fragment" of a DNABII polypeptide intends a DNA polypeptide that, using IHFalpha as an example, forms the two arms of the proteins (see FIG. 6B). Non-limiting examples of such include IhfA, A tip fragment: NFELRDKSSRPGRNPKTGDVV (SEQ ID NO: 356) and IhfB, B tip fragment: SLHHRQPRLGRNPKTGDSVNL (SEQ ID NO: 357).

A "tail fragment" of a DNABII polypeptide intends a region of the protein that is both exposed to the bulk medium and not occluded by DNA or other polypeptides.

An immunodominant antigen intends a region of the protein that is recognized and binds with high affinity to an antibody.

An immunoprotective antigen intends a region of the protein that is recognized and binds with high affinity to an antibody to interfere with protein function; the antibodies generated against an immuonprotective antigen are characterized by enhanced or optimal effect against a target indication as a result to the interference with protein function—in this case, an improve capability to clear biofilms.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, RNAi, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment disclosed herein that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

The term "isolated" or "recombinant" as used herein with respect to nucleic acids, such as DNA or RNA, refers to molecules separated from other DNAs or RNAs, respectively that are present in the natural source of the macromolecule as well as polypeptides. The term "isolated or recombinant nucleic acid" is meant to include nucleic acid fragments which are not naturally occurring as fragments and would not be found in the natural state. The term "isolated" is also used herein to refer to polynucleotides, polypeptides and proteins that are isolated from other cellular proteins and is meant to encompass both purified and recombinant polypeptides. In other embodiments, the term "isolated or recombinant" means separated from constituents, cellular and otherwise, in which the cell, tissue, polynucleotide, peptide, polypeptide, protein, antibody or fragment(s) thereof, which are normally associated in nature. For example, an isolated cell is a cell that is separated from tissue or cells of dissimilar phenotype or genotype. An isolated polynucleotide is separated from the 3' and 5' contiguous nucleotides with which it is normally associated in its native or natural environment, e.g., on the chromosome. As is apparent to those of skill in the art, a non-naturally occurring polynucleotide, peptide, polypeptide, protein, antibody or fragment(s) thereof, does not require "isolation" to distinguish it from its naturally occurring counterpart.

It is to be inferred without explicit recitation and unless otherwise intended, that when the present disclosure relates to a polypeptide, protein, polynucleotide or antibody, an equivalent or a biologically equivalent of such is intended within the scope of this disclosure. As used herein, the term "biological equivalent thereof" is intended to be synonymous with "equivalent thereof" when referring to a reference protein, antibody, fragment, polypeptide or nucleic acid, intends those having minimal homology while still maintaining desired structure or functionality. Unless specifically recited herein, it is contemplated that any polynucleotide, polypeptide or protein mentioned herein also includes equivalents thereof. In one aspect, an equivalent polynucleotide is one that hybridizes under stringent conditions to the polynucleotide or complement of the polynucleotide as described herein for use in the described methods. In another aspect, an equivalent antibody or antigen binding polypeptide intends one that binds with at least 70%, or alternatively at least 75%, or alternatively at least 80%, or alternatively at least 85%, or alternatively at least 90%, or alternatively at least 95% affinity or higher affinity to a reference antibody or antigen binding fragment. In another aspect, the equivalent thereof competes with the binding of the antibody or antigen binding fragment to its antigen tinder a competitive ELISA assay. In another aspect, an equivalent intends at least about 80% homology or identity and alternatively, at least about 85%, or alternatively at least about 90%, or alternatively at least about 95%, or alternatively 98% percent homology or identity and exhibits substantially equivalent biological activity to the reference protein, polypeptide or nucleic acid. Examples of biologically equivalent polypeptides are provided in Table 9 which identifies conservative amino acid substitutions to the disclosed amino acid sequences.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. In certain embodiments, default parameters are used for alignment. A non-limiting exemplary alignment program is BLAST, using default parameters. In particular, exemplary programs include BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST. Sequence identity and percent identity were determined by incorporating them into clustalW (available at the web address:align.genome.jp, last accessed on Mar. 7, 2011.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present disclosure.

"Homology" or "identity" or "similarity" can also refer to two nucleic acid molecules that hybridize under stringent conditions.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

As used herein, the terms "treating," "treatment" and the like are used herein to mean obtaining a desired pharmacologic and/or physiologic effect. The effect may be prophylactic in terms of completely or partially preventing a disorder or sign or symptom thereof, and/or may be therapeutic in terms of a partial or complete cure for a disorder and/or adverse effect attributable to the disorder.

To prevent intends to prevent a disorder or effect in vitro or in vivo in a system or subject that is predisposed to the disorder or effect. An example of such is preventing the formation of a biofilm in a system that is infected with a microorganism known to produce one.

A "composition" is intended to mean a combination of active agent and another compound or composition, inert (for example, a detectable agent or label) or active, such as an adjuvant.

A "pharmaceutical composition" is intended to include the combination of an active agent with a carrier, inert or active, making the composition suitable for diagnostic or therapeutic use in vitro, in vivo or ex vivo.

"Pharmaceutically acceptable carriers" refers to any diluents, excipients, or carriers that may be used in the compositions disclosed herein. Pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Suitable pharmaceutical carriers are described in Remington's Pharmaceutical Sciences, Mack Publishing Company, a standard reference text in this field. They may be selected with respect to the intended form of administration, that is, oral tablets, capsules, elixirs, syrups and the like, and consistent with conventional pharmaceutical practices.

A "biologically active agent" or an active agent disclosed herein intends one or more of an isolated or recombinant polypeptide, an isolated or recombinant polynucleotide, a vector, an isolated host cell, or an antibody, as well as compositions comprising one or more of same.

"Administration" can be effected in one dose, continuously or intermittently throughout the course of treatment. Methods of determining the most effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and target cell or tissue. Non-limiting examples of route of administration include oral administration, nasal administration, injection, and topical application.

An agent of the present disclosure can be administered for therapy by any suitable route of administration. It will also be appreciated that the optimal route will vary with the condition and age of the recipient, and the disease being treated.

The term "effective amount" refers to a quantity sufficient to achieve a desired effect. In the context of therapeutic or prophylactic applications, the effective amount will depend on the type and severity of the condition at issue and the characteristics of the individual subject, such as general health, age, sex, body weight, and tolerance to pharmaceutical compositions. In the context of an immunogenic composition, in some embodiments the effective amount is the amount sufficient to result in a protective response against a pathogen. In other embodiments, the effective amount of an immunogenic composition is the amount sufficient to result in antibody generation against the antigen. In some embodiments, the effective amount is the amount required to confer passive immunity on a subject in need thereof. With respect to immunogenic compositions, in some embodiments the effective amount will depend on the intended use, the degree of immunogenicity of a particular antigenic compound, and the health/responsiveness of the subject's immune system, in addition to the factors described above. The skilled artisan will be able to determine appropriate amounts depending on these and other factors.

In the case of an in vitro application, in some embodiments the effective amount will depend on the size and nature of the application in question. It will also depend on the nature and sensitivity of the in vitro target and the methods in use. The skilled artisan will be able to determine the effective amount based on these and other considerations. The effective amount may comprise one or more administrations of a composition depending on the embodiment.

The term "conjugated moiety" refers to a moiety that can be added to an isolated chimeric polypeptide by forming a covalent bond with a residue of chimeric polypeptide. The moiety may bond directly to a residue of the chimeric polypeptide or may form a covalent bond with a linker which in turn forms a covalent bond with a residue of the chimeric polypeptide.

A "peptide conjugate" refers to the association by covalent or non-covalent bonding of one or more polypeptides and another chemical or biological compound. In a non-limiting example, the "conjugation" of a polypeptide with a chemical compound results in improved stability or efficacy of the polypeptide for its intended purpose. In one embodiment, a peptide is conjugated to a carrier, wherein the carrier is a liposome, a micelle, or a pharmaceutically acceptable polymer.

"Liposomes" are microscopic vesicles consisting of concentric lipid bilayers. Structurally, liposomes range in size and shape from long tubes to spheres, with dimensions from a few hundred Angstroms to fractions of a millimeter. Vesicle-forming lipids are selected to achieve a specified degree of fluidity or rigidity of the final complex providing the lipid composition of the outer layer. These are neutral (cholesterol) or bipolar and include phospholipids, such as phosphatidylcholine (PC), phosphatidylethanolamine (PE), phosphatidylinositol (PI), and sphingomyelin (SM) and other types of bipolar lipids including but not limited to dioleoylphosphatidylethanolamine (DOPE), with a hydrocarbon chain length in the range of 14-22, and saturated or with one or more double C=C bonds. Examples of lipids capable of producing a stable liposome, alone, or in combination with other lipid components are phospholipids, such as hydrogenated soy phosphatidylcholine (HSPC), lecithin, phosphatidylethanolamine, lysolecithin, lysophosphatidylethanol-amine, phosphatidylserine, phosphatidylinositol, sphingomyelin, cephalin, cardiolipin, phosphatidic acid, cerebrosides, di stearoylphosphatidylethanolamine (DSPE), dioleoylphosphatidylcholine (DOPC), dipalmitoylphosphatidylcholine (DPPC), palmitoyloteoylphosphatidylcholine (POPC), palmitoyloleoylphosphatidylethanolamine (POPE) and dioleoylphosphatidylethanolamine 4-(N-maleimido-triethyl)cyclohexane-1-carboxylate (DOPE-mal). Additional non-phosphorous containing lipids that can become incorporated into liposomes include stearylamine, dodecylamine, hexadecylamine, isopropyl myristate, triethanolamine-lauryl sulfate, alkyl-aryl sulfate, acetyl palmitate, glycerol ricinoleate, hexadecyl stereate, amphoteric acrylic polymers, polyethyloxylated fatty acid amides, and the cationic lipids mentioned above (DDAB, DODAC, DMRIE, DMTAP, DOGS, DOTAP (DOTMA), DOSPA, DPTAP, DSTAP, DC-Chol). Negatively charged lipids include phosphatidic acid (PA), dipalmitoylphosphatidylglycerol (DPPG), dioteoylphosphatidylglycerol and (DOPG), dicetylphosphate that are able to form vesicles. Typically, liposomes can be divided into three categories based on their overall size and the nature of the lamellar structure. The three classifications, as developed by the New York Academy Sciences Meeting, "Liposomes and Their Use in Biology and Medicine," December 1977, are multi-lamellar vesicles (MLVs), small uni-lamellar vesicles (SUVs) and large uni-lamellar vesicles (LUVs). The biological active agents can be encapsulated in such for administration in accordance with the methods described herein.

A "micelle" is an aggregate of surfactant molecules dispersed in a liquid colloid. A typical micelle in aqueous solution forms an aggregate with the hydrophilic "head" regions in contact with surrounding solvent, sequestering the hydrophobic tail regions in the micelle center. This type of micelle is known as a normal phase micelle (oil-in-water micelle). Inverse micelles have the head groups at the center with the tails extending out (water-in-oil micelle). Micelles can be used to attach a polynucleotide, polypeptide, antibody or composition described herein to facilitate efficient delivery to the target cell or tissue.

The phrase "pharmaceutically acceptable polymer" refers to the group of compounds which can be conjugated to one or more polypeptides described here. It is contemplated that the conjugation of a polymer to the polypeptide is capable of extending the half-life of the polypeptide in vivo and in vitro. Non-limiting examples include polyethylene glycols, polyvinylpyrrolidones, polyvinylalcohols, cellulose derivatives, polyacrylates, polymethacrylates, sugars, polyols and mixtures thereof. The biological active agents can be conjugated to a pharmaceutically acceptable polymer for administration in accordance with the methods described herein.

A "gene delivery vehicle" is defined as any molecule that can carry inserted polynucleotides into a host cell. Examples of gene delivery vehicles are liposomes, micelles biocompatible polymers, including natural polymers and synthetic polymers; lipoproteins; polypeptides; polysaccharides; lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

A polynucleotide disclosed herein can be delivered to a cell or tissue using a gene delivery vehicle. "Gene delivery," "gene transfer," "transducing," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extra-chromosomal replicon (e.g., a plasmid) or a nuclear or mitochondrial chromosome. A number of vectors are known to be capable of mediating transfer of genes to mammalian cells, as is known in the art and described herein.

As used herein the term "eDNA" refers to extracellular DNA found as a component to pathogenic biofilms.

A "plasmid" is an extra-chromosomal DNA molecule separate from the chromosomal DNA which is capable of replicating independently of the chromosomal DNA. In many cases, it is circular and double-stranded. Plasmids provide a mechanism for horizontal gene transfer within a population of microbes and typically provide a selective advantage under a given environmental state. Plasmids may carry genes that provide resistance to naturally occurring antibiotics in a competitive environmental niche, or alternatively the proteins produced may act as toxins under similar circumstances.

"Plasmids" used in genetic engineering are called "plasmid vectors". Many plasmids are commercially available for such uses. The gene to be replicated is inserted into copies of a plasmid containing genes that make cells resistant to particular antibiotics and a multiple cloning site (MCS, or polylinker), which is a short region containing several commonly used restriction sites allowing the easy insertion of DNA fragments at this location. Another major use of plasmids is to make large amounts of proteins. In this case, researchers grow bacteria containing a plasmid harboring the gene of interest. Just as the bacterium produces proteins to confer its antibiotic resistance, it can also be induced to produce large amounts of proteins from the inserted gene. This is a cheap and easy way of mass-producing a gene or the protein it then codes for.

A "yeast artificial chromosome" or "YAC" refers to a vector used to clone large DNA fragments (larger than 100 kb and up to 3000 kb). It is an artificially constructed chromosome and contains the telomeric, centromeric, and replication origin sequences needed for replication and preservation in yeast cells. Built using an initial circular plasmid, they are linearized by using restriction enzymes, and then DNA ligase can add a sequence or gene of interest within the linear molecule by the use of cohesive ends. Yeast expression vectors, such as YACs, YIps (yeast integrating plasmid), and YEps (yeast episomal plasmid), are extremely useful as one can get eukaryotic protein products with posttranslational modifications as yeasts are themselves eukaryotic cells, however YACs have been found to be more unstable than BACs, producing chimeric effects.

A "viral vector" is defined as a recombinantly produced virus or viral particle that comprises a polynucleotide to be delivered into a host cell, either in vivo, ex vivo or in vitro. Examples of viral vectors include retroviral vectors, adenovirus vectors, adeno-associated virus vectors, alphavirus vectors and the like. Infectious tobacco mosaic virus (TMV)-based vectors can be used to manufacturer proteins and have been reported to express Griffithsin in tobacco leaves (O'Keefe et al. (2009) Proc. Nat. Acad. Sci. USA 106(15):6099-6104). Alphavirus vectors, such as Semliki Forest virus-based vectors and Sindbis virus-based vectors, have also been developed for use in gene therapy and immunotherapy. See, Schlesinger & Dubensky (1999) Curr. Opin. Biotechnol. 5:434-439 and Ying et al. (1999) Nat. Med. 5(7):823-827. In aspects where gene transfer is mediated by a retroviral vector, a vector construct refers to the polynucleotide comprising the retroviral genome or part thereof, and a therapeutic gene.

As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. As used herein, retroviral vector refers to a viral particle capable of introducing exogenous nucleic acid into a cell through a viral or viral-like entry mechanism.

Retroviruses carry their genetic information in the form of RNA; however, once the virus infects a cell, the RNA is reverse-transcribed into the DNA form which integrates into the genomic DNA of the infected cell. The integrated DNA form is called a provirus.

In aspects where gene transfer is mediated by a DNA viral vector, such as an adenovirus (Ad) or adeno-associated virus (AAV), a vector construct refers to the polynucleotide comprising the viral genome or part thereof, and a transgene. Adenoviruses (Ads) are a relatively well characterized, homogenous group of viruses, including over 50 serotypes. See, e.g., PCT International Application Publication No. WO 95/27071. Ads do not require integration into the host cell genome. Recombinant Ad derived vectors, particularly those that reduce the potential for recombination and generation of wild-type virus, have also been constructed. See, PCT International Application Publication Nos. WO 95/00655 and WO 95/11984, Wild-type AAV has high infectivity and specificity integrating into the host cell's genome. See, Hermonat & Muzyczka (1984) Proc. Natl. Acad. Sci. USA 81:6466-6470 and Lebkowski et al. (1988) Mol. Cell. Biol. 8:3988-3996.

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Gene delivery vehicles also include DNA/liposome complexes, micelles and targeted viral protein-DNA complexes. Liposomes that also comprise a targeting antibody or fragment thereof can be used in the methods disclosed herein. In addition to the delivery of polynucleotides to a cell or cell population, direct introduction of the proteins described herein to the cell or cell population can be done by the non-limiting technique of protein transfection, alternatively culturing conditions that can enhance the expression and/or promote the activity of the proteins disclosed herein are other non-limiting techniques.

As used herein, the terms "antibody," "antibodies" and "immunoglobulin" includes whole antibodies and any antigen binding fragment or a single chain thereof. Thus the term "antibody" includes any protein or peptide containing molecule that comprises at least a portion of an immunoglobulin molecule. The terms "antibody," "antibodies" and "immunoglobulin" also include immunoglobulins of any isotype, fragments of antibodies which retain specific binding to antigen, including, but not limited to, Fab, Fab', F(ab)$_2$, Fv, scFv, dsFv, Fd fragments, dAb, VH, VL, VhH, and V-NAR domains; minibodies, diabodies, triabodies, tetrabodies and kappa bodies; multispecific antibody fragments formed from antibody fragments and one or more isolated. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, at least one portion of a binding protein, chimeric antibodies, humanized antibodies, single-chain antibodies, and fusion proteins comprising an antigen-binding portion of an antibody and a non-antibody protein. The variable regions of the heavy and light chains of the immunoglobulin molecule contain a binding domain that interacts with an antigen. The constant regions of the antibodies (Abs) may mediate the binding of the immunoglobulin to host tissues. The term "anti-" when used before a protein name, anti-DNABII, anti-IHF, anti-HU, anti-OMP P5, for example, refers to a monoclonal or polyclonal antibody that binds and/or has an affinity to a particular protein. For example, "anti-IHF" refers to an antibody that binds to the IHF protein. The specific antibody may have affinity or bind to proteins other than the protein it was raised against. For example, anti-IHF, while specifically raised against the IHF protein, may also bind other proteins that are related either through sequence homology or through structure homology.

The antibodies can be polyclonal, monoclonal, multispecific (e.g., bispecific antibodies), and antibody fragments, so long as they exhibit the desired biological activity. Antibodies can be isolated from any suitable biological source, e.g., murine, rat, sheep and canine.

As used herein, "monoclonal antibody" refers to an antibody obtained from a substantially homogeneous antibody population. Monoclonal antibodies are highly specific, as each monoclonal antibody is directed against a single determinant on the antigen. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like.

Monoclonal antibodies may be generated using hybridoma techniques or recombinant DNA methods known in the art. A hybridoma is a cell that is produced in the laboratory from the fusion of an antibody-producing lymphocyte and a non-antibody producing cancer cell, usually a myeloma or lymphoma. A hybridoma proliferates and produces a continuous sample of a specific monoclonal antibody. Alternative techniques for generating or selecting antibodies include in vitro exposure of lymphocytes to antigens of interest, and screening of antibody display libraries in cells, phage, or similar systems.

The term "human antibody" as used herein, is intended to include antibodies having variable and constant regions derived from human germline immunoglobulin sequences. The human antibodies disclosed herein may include amino acid residues not encoded by human germline immunoglobulin sequences (e.g., mutations introduced by random or site-specific mutagenesis in vitro or by somatic mutation in vivo). However, the term "human antibody" as used herein, is not intended to include antibodies in which CDR sequences derived from the germline of another mammalian species, such as a mouse, have been grafted onto human framework sequences. Thus, as used herein, the term "human antibody" refers to an antibody in which substantially every part of the protein (e.g., CDR, framework, $C_L$, $C_H$ domains (e.g., $C_{H1}$, $C_{H2}$, $C_{H3}$), hinge, (VL, VH)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

As used herein, a human antibody is "derived from" a particular germline sequence if the antibody is obtained from a system using human immunoglobulin sequences, e.g., by immunizing a transgenic mouse carrying human immunoglobulin genes or by screening a human immunoglobulin gene library. A human antibody that is "derived from" a human germline immunoglobulin sequence can be identified as such by comparing the amino acid sequence of the human antibody to the amino acid sequence of human germline immunoglobulins. A selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

A "human monoclonal antibody" refers to antibodies displaying a single binding specificity which have variable and constant regions derived from human germline immunoglobulin sequences. The term also intends recombinant human antibodies. Methods to making these antibodies are described herein.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the antibody, e.g., from a transfectoma, antibodies isolated from a recombinant, combinatorial human antibody library, and antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. Methods to making these antibodies are described herein.

As used herein, chimeric antibodies are antibodies whose light and heavy chain genes have been constructed, typically by genetic engineering, from antibody variable and constant region genes belonging to different species.

As used herein, the term "humanized antibody" or "humanized immunoglobulin" refers to a human/non-human chimeric antibody that contains a minimal sequence derived from non-human immunoglobulin. For the most part, humanized antibodies are human immunoglobulins (recipient antibody) in which residues from a variable region of the recipient are replaced by residues from a variable region of a non-human species (donor antibody) such as mouse, rat, rabbit, or non-human primate having the desired specificity, affinity and capacity. Humanized antibodies may comprise residues that are not found in the recipient antibody or in the donor antibody. The humanized antibody can optionally also comprise at least a portion of an immunoglobulin constant region (Fc), typically that of a human immunoglobulin, a non-human antibody containing one or more amino acids in a framework region, a constant region or a CDR, that have been substituted with a correspondingly positioned amino acid from a human antibody. In general, humanized antibodies are expected to produce a reduced immune response in a human host, as compared to a non-humanized version of the same antibody. The humanized antibodies may have conservative amino acid substitutions which have substantially no effect on antigen binding or other antibody functions. Conservative substitutions groupings include: glycine-alanine, valine-leucine-isoleucine, phenylalanine-tyrosine, lysine-arginine, alanine-valine, serine-threonine and asparagine-glutamine.

The terms "polyclonal antibody" or "polyclonal antibody composition" as used herein refer to a preparation of antibodies that are derived from different B-cell lines. They are a mixture of immunoglobulin molecules secreted against a specific antigen, each recognizing a different epitope.

As used herein, the term "antibody derivative", comprises a full-length antibody or a fragment of an antibody, wherein one or more of the amino acids are chemically modified by alkylation, pegylation, acylation, ester formation or amide formation or the like, e.g., for linking the antibody to a second molecule. This includes, but is not limited to, pegylated antibodies, cysteine-pegylated antibodies, and variants thereof.

As used herein, the term "label" intends a directly or indirectly detectable compound or composition that is conjugated directly or indirectly to the composition to be detected, e.g., N-terminal histidine tags (N-His), magnetically active isotopes, e.g., $^{115}$Sn, $^{117}$Sn and $^{119}$Sn, a non-radioactive isotopes such as $^{13}$C and $^{15}$N, polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g., radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to magnetically active isotopes, non-radioactive isotopes, radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component. Examples of luminescent labels that produce signals include, but are not limited to bioluminescence and chemiluminescence. Detectable luminescence response generally comprises a change in, or an occurrence of a luminescence signal. Suitable methods and luminophores for luminescently labeling assay components are known in the art and described for example in Haugland, Richard P. (1996) Handbook of Fluorescent Probes and Research Chemicals ($6^{th}$ ed). Examples of luminescent probes include, but are not limited to, aequorin and luciferases.

As used herein, the term "immunoconjugate" comprises an antibody or an antibody derivative associated with or linked to a second agent, such as a cytotoxic agent, a detectable agent, a radioactive agent, a targeting agent, a human antibody, a humanized antibody, a chimeric antibody, a synthetic antibody, a semisynthetic antibody, or a multi-specific antibody.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals ($6^{th}$ ed.).

In another aspect, the fluorescent label is functionalized to facilitate covalent attachment to a cellular component present in or on the surface of the cell or tissue such as a cell surface marker. Suitable functional groups, include, but are not limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

"Eukaryotic cells" comprise all of the life kingdoms except monera. They can be easily distinguished through a membrane-bound nucleus. Animals, plants, fungi, and protists are eukaryotes or organisms whose cells are organized into complex structures by internal membranes and a cytoskeleton. The most characteristic membrane-bound structure is the nucleus. Unless specifically recited, the term "host" includes a eukaryotic host, including, for example, yeast, higher plant, insect and mammalian cells. Non-limiting examples of eukaryotic cells or hosts include simian, bovine, porcine, murine, rat, avian, reptilian and human.

"Prokaryotic cells" that usually lack a nucleus or any other membrane-bound organelles and are divided into two domains, bacteria and archaea. In addition to chromosomal DNA, these cells can also contain genetic information in a circular loop called on episome. Bacterial cells are very small, roughly the size of an animal mitochondrion (about 1-2 μm in diameter and 10 μm long). Prokaryotic cells feature three major shapes: rod shaped, spherical, and spiral. Instead of going through elaborate replication processes like eukaryotes, bacterial cells divide by binary fission. Examples include but are not limited to *Bacillus* bacteria, *E. coli* bacterium, and *Salmonella* bacterium.

A "native" or "natural" antigen is a polypeptide, protein or a fragment which contains an epitope, which has been isolated from a natural biological source, and which can specifically bind to an antigen receptor, in particular a T cell antigen receptor (TCR), in a subject.

The terms "antigen" and "antigenic" refer to molecules with the capacity to be recognized by an antibody or otherwise act as a member of an antibody-ligand pair. "Specific binding" refers to the interaction of an antigen with the variable regions of immunoglobulin heavy and light chains. Antibody-antigen binding may occur in vivo or in vitro. The skilled artisan will understand that macromolecules, including proteins, nucleic acids, fatty acids, lipids, lipopolysaccharides and polysaccharides have the potential to act as an antigen. The skilled artisan will further understand that nucleic acids encoding a protein with the potential to act as an antibody ligand necessarily encode an antigen. The artisan will further understand that antigens are not limited to full-length molecules, but can also include partial molecules. The term "antigenic" is an adjectival reference to molecules having the properties of an antigen. The term encompasses substances which are immunogenic, i.e., immunogens, as well as substances which induce immunological unresponsiveness, or anergy, i.e., anergens.

An "altered antigen" is one having a primary sequence that is different from that of the corresponding wild-type antigen. Altered antigens can be made by synthetic or recombinant methods and include, but are not limited to, antigenic peptides that are differentially modified during or after translation, e.g., by phosphorylation, glycosylation, cross-linking, acylation, proteolytic cleavage, linkage to an antibody molecule, membrane molecule or other ligand. (Ferguson et al. (1988) Ann. Rev. Biochem. 57:285-320). A synthetic or altered antigen disclosed herein is intended to bind to the same TCR as the natural epitope.

A "self-antigen" also referred to herein as a native or wild-type antigen is an antigenic peptide that induces little or no immune response in the subject due to self-tolerance to the antigen. An example of a self-antigen is the melanoma specific antigen gp100.

The terms "major histocompatibility complex" or "MHC" refers to a complex of genes encoding cell-surface molecules that are required for antigen presentation to T cells and for rapid graft rejection. In humans, the MHC is also known as the "human leukocyte antigen" or "HLA" complex. The proteins encoded by the MHC are known as "MHC molecules" and are classified into class I and class II MHC molecules. Class I MHC includes membrane heterodimeric proteins made up of a chain encoded in the MEW noncovalently linked with the β 2-microglobulin. Class I MHC molecules are expressed by nearly all nucleated cells and have been shown to function in antigen presentation to $CD8^+$ T cells. Class I molecules include HLA-A, B, and C in humans. Class II MHC molecules also include membrane heterodimeric proteins consisting of noncovalently associated α and β chains. Class II MEW molecules are known to function in $CD4^-$ T cells and, in humans, include HLA-DP, -DQ, and DR. In a particular embodiment, compositions and ligands can complex with MEW molecules of any HLA type. Those of skill in the art are familiar with the serotypes and genotypes of the HLA. See: bimas.dcrt.nih.gov/cgi-bin/molbio/hla coefficient viewing page. Rammensee H. G., Bachmann J., and Stevanovic S. MHC Ligands and Peptide Motifs (1997) Chapman & Hall Publishers; Schreuder G. M. Th. et al. The HLA dictionary (1999) Tissue Antigens 54:409-437.

The term "antigen-presenting matrix", as used herein, intends a molecule or molecules which can present antigen in such a way that the antigen can be bound by a T-cell antigen receptor on the surface of a T cell. An antigen-presenting matrix can be on the surface of an antigen-presenting cell (APC), on a vesicle preparation of an APC, or can be in the form of a synthetic matrix on a solid support such as a bead or a plate. An example of a synthetic antigen-presenting matrix is purified MHC class I molecules complexed to P2-microglobulin, multimers of such purified MHC class I molecules, purified MHC Class II molecules, or functional portions thereof, attached to a solid support.

The term "antigen presenting cells (APC)" refers to a class of cells capable of presenting one or more antigens in the form of antigen-MHC complex recognizable by specific effector cells of the immune system, and thereby inducing an effective cellular immune response against the antigen or antigens being presented. While many types of cells may be capable of presenting antigens on their cell surface for T-cell recognition, only professional APCs have the capacity to present antigens in an efficient amount and further to activate T-cells for cytotoxic T-lymphocyte (CTL) responses. APCs can be intact whole cells such as macrophages, B-cells and dendritic cells; or other molecules, naturally occurring or synthetic, such as purified MHC class molecules complexed to β2-microglobulin.

The term "dendritic cells (DCs)" refers to a diverse population of morphologically similar cell types found in a variety of lymphoid and non-lymphoid tissues (Steinman (1991) Ann. Rev. Immunol. 9:271-296). Dendritic cells constitute the most potent mammalian APCs. A subset, if not all, of DCs are derived from bone marrow progenitor cells, circulate in small numbers in the peripheral blood and appear either as immature Langerhans' cells or terminally differentiated mature cells. While DCs can be derived from monocytes, they possess distinct phenotypes. For example, a particular differentiating marker, CD14 antigen, is not found in dendritic cells but is expressed at very high levels in monocytes by monocytes. See for example Jersmann et al. (2005) Immunol. Cell Biol. 83:462.

Also, mature dendritic cells are not phagocytic, whereas the monocytes are strongly phagocytosing cells. Mature monocytes and DCs endocytose material through different mechanisms. Monocytes engulf by means of phagocytosis, whereas DCs utilize macropinocytosis. Thus, DCs generally engulf cargo of a smaller size than monocytes (See for example Conner and Schmid (2003) Nature 433:37-44. It has been shown that DCs are as endocytically active as other antigen presenting cells, and provide all the signals necessary for T cell activation and proliferation (See, e.g., Levine and Chain (1992) PNAS 89(17):8342.

The term "antigen presenting cell recruitment factors" or "APC recruitment factors" include both intact, whole cells as well as other molecules that are capable of recruiting antigen presenting cells. Examples of suitable APC recruitment factors include molecules such as interleukin 4 (IL4), granulocyte macrophage colony stimulating factor (GM-CSF), Sepragel and macrophage inflammatory protein 3 alpha (MIP3α). These are available from Immunex, Schering-Plough and R&D Systems (Minneapolis, Minn.). They also can be recombinantly produced using the methods disclosed in Current Protocols In Molecular Biology (F. M. Ausubel et al., eds. (1987)). Peptides, proteins and compounds having the same biological activity as the above-noted factors are included within the scope of this disclosure.

The term "immune effector cells" refers to cells capable of binding an antigen and which mediate an immune response. These cells include, but are not limited to, T cells, B cells, monocytes, macrophages, NK cells and cytotoxic T lymphocytes (CTLs), for example CTL lines, CTL clones, and CTLs from tumor, inflammatory, or other infiltrates. Certain diseased tissue expresses specific antigens and CTLs specific for these antigens have been identified.

The term "immune effector molecule" as used herein, refers to molecules capable of antigen-specific binding, and includes antibodies, T cell antigen receptors, B cell antigen receptors, and MEW Class I and Class II molecules.

A "naive" immune effector cell is an immune effector cell that has never been exposed to an antigen capable of activating that cell. Activation of naive immune effector T cells requires both recognition of the antigen:WIC complex and the simultaneous delivery of a costimulatory signal by a professional APC in order to proliferate and differentiate into antigen-specific armed effector T cells. Activated T cells can then activate specific B cells through immunological synapses by providing a co-stimulation signal. Activated B cells subsequently produce antibodies directed to a specific antigen. Naïve B cells can also be activated by T cell-independent mechanisms. This occurs when antigens are capable of binding to the B cell receptor and producing a co-stimulation signal.

"Immune response" broadly refers to the antigen-specific responses of lymphocytes to foreign substances. The terms "immunogen" and "immunogenic" refer to molecules with the capacity to elicit an immune response. All immunogens are antigens, however, not all antigens are immunogenic. An immune response disclosed herein can be humoral (via antibody activity) or cell-mediated (via T cell activation). The response may occur in vivo or in vitro. The skilled artisan will understand that a variety of macromolecules, including proteins, nucleic acids, fatty acids, lipids, lipopolysaccharides and polysaccharides have the potential to be immunogenic. The skilled artisan will further understand that nucleic acids encoding a molecule capable of eliciting an immune response necessarily encode an immunogen. The artisan will further understand that immunogens are not limited to full-length molecules, but may include partial molecules.

The term "passive immunity" refers to the transfer of immunity from one subject to another through the transfer of antibodies. Passive immunity may occur naturally, as when maternal antibodies are transferred to a fetus. Passive immunity may also occur artificially as when antibody compositions are administered to non-immune subjects. Antibody donors and recipients may be human or non-human subjects. Antibodies may be polyclonal or monoclonal, may be generated in vitro or in vivo, and may be purified, partially purified, or unpurified depending on the embodiment. In some embodiments described herein, passive immunity is conferred on a subject in need thereof through the administration of antibodies or antigen binding fragments that specifically recognize or bind to a particular antigen. In some embodiments, passive immunity is conferred through the administration of an isolated or recombinant polynucleotide encoding an antibody or antigen binding fragment that specifically recognizes or binds to a particular antigen.

In the context of this disclosure, a "ligand" is a polypeptide. In one aspect, the term "ligand" as used herein refers to any molecule that binds to a specific site on another molecule. In other words, the ligand confers the specificity of the protein in a reaction with an immune effector cell or an antibody to a protein or DNA to a protein. In one aspect it is the ligand site within the protein that combines directly with the complementary binding site on the immune effector cell.

In one aspect, a peptide or ligand disclosed herein binds to an antigenic determinant or epitope on an immune effector cell, such as an antibody or a T cell receptor (TCR). A ligand may be an antigen, peptide, protein or epitope disclosed herein.

In another aspect, ligands may bind to a receptor on an antibody. In one embodiment, the ligand disclosed herein is about 4 to about 8 amino acids in length.

In a further aspect, ligands may bind to a receptor on an MEW class I molecule. In one embodiment, the ligand disclosed herein is about 7 to about 11 amino acids in length.

In a yet further aspect, ligands may bind to a receptor on an MEW class II molecule. In one embodiment, the ligand disclosed herein is about 10 to about 20 amino acids long.

As used herein, the term "educated, antigen-specific immune effector cell", is an immune effector cell as defined above, which has previously encountered an antigen. In contrast with its naive counterpart, activation of an educated, antigen-specific immune effector cell does not require a costimulatory signal. Recognition of the peptide:MHC complex is sufficient.

"Activated", when used in reference to a T cell, implies that the cell is no longer in Go phase, and begins to produce one or more of cytotoxins, cytokines, and other related membrane-associated proteins characteristic of the cell type (e.g., $CD8^+$ or $CD4^+$), is capable of recognizing and binding any target cell that displays the particular antigen on its surface, and releasing its effector molecules.

The term "cross-reactive" is used to describe compounds disclosed herein which are functionally overlapping. More particularly, the immunogenic properties of a native ligand and/or immune effector cells activated thereby are shared to a certain extent by the altered ligand such that the altered ligand is "cross-reactive" with the native ligand and/or the immune effector cells activated thereby. For purposes of this disclosure, cross-reactivity is manifested at multiple levels: (i) at the ligand level, e.g., the altered ligands can bind the TCR of and activate native ligand CTLs; (ii) at the T cell level, i.e., altered ligands disclosed herein bind the TCR of and activate a population of T cells (distinct from the population of native ligand CTLs) which can effectively target and lyse cells displaying the native ligand; and (iii) at the antibody level, e.g., "anti"-altered ligand antibodies can detect, recognize and bind the native ligand and initiate effector mechanisms in an immune response which ultimately result in elimination of the native ligand from the host.

As used herein, the term "inducing an immune response in a subject" is a term well understood in the art and intends that an increase of at least about 2-fold, at least about 5-fold, at least about 10-fold, at least about 100-fold, at least about 500-fold, or at least about 1000-fold or more in an immune response to an antigen (or epitope) can be detected or measured, after introducing the antigen (or epitope) into the subject, relative to the immune response (if any) before introduction of the antigen (or epitope) into the subject. An immune response to an antigen (or epitope), includes, but is not limited to, production of an antigen-specific (or epitope-specific) antibody, and production of an immune cell expressing on its surface a molecule which specifically binds to an antigen (or epitope). Methods of determining whether an immune response to a given antigen (or epitope) has been induced are well known in the art. For example, antigen-specific antibody can be detected using any of a variety of immunoassays known in the art, including, but not limited to, ELISA, wherein, for example, binding of an antibody in a sample to an immobilized antigen (or epitope) is detected with a detectably-labeled second antibody (e.g., enzyme-labeled mouse anti-human Ig antibody).

"Co-stimulatory molecules" are involved in the interaction between receptor-ligand pairs expressed on the surface of antigen presenting cells and T cells. Research accumulated over the past several years has demonstrated convincingly that resting T cells require at least two signals for induction of cytokine gene expression and proliferation (Schwartz (1990) Science 248:1349-1356 and Jenkins (1992) Immunol. Today 13:69-73). One signal, the one that confers specificity, can be produced by interaction of the TCR/CD3 complex with an appropriate MHC/peptide complex. The second signal is not antigen specific and is termed the "co-stimulatory" signal. This signal was originally defined as an activity provided by bone-marrow-derived accessory cells such as macrophages and dendritic cells, the so called "professional" APCs. Several molecules have been shown to enhance co-stimulatory activity. These are heat stable antigen (HSA) (Liu et al. (1992) J. Exp. Med. 175: 437-445), chondroitin sulfate-modified MHC invariant chain (Ii-CS) (Naujokas et al. (1993) Cell 74:257-268), intracellular adhesion molecule 1 (ICAM-1) (Van (1992) Cell 71:1065-1068). These molecules each appear to assist co-stimulation by interacting with their cognate ligands on the T cells. Co-stimulatory molecules mediate co-stimulatory signal(s), which are necessary, under normal physiological conditions, to achieve full activation of naive T cells. One exemplary receptor-ligand pair is the B7 co-stimulatory molecule on the surface of APCs and its counter-receptor CD28 or CTLA-4 cells (Freeman et al. (1993) Science 262:909-911; Young et al. (1992) J. Clin. Invest. 90:229 and Nabavi et al. (1992) Nature 360:266-268). Other important co-stimulatory molecules are CD40, CD54, CD80, and CD86. The term "co-stimulatory molecule" encompasses any single molecule or combination of molecules which, when acting together with a peptide/MHC complex bound by a TCR on the surface of a T cell, provides a co-stimulatory effect which achieves activation of the T cell that binds the peptide. The term thus encompasses B7 or other co-stimulatory molecule(s) on an antigen-presenting matrix such as an APC, fragments thereof (alone, complexed with another molecule(s), or as part of a fusion protein) which, together with peptide/MHC complex, binds to a cognate ligand and results in activation of the T cell when the TCR on the surface of the T cell specifically binds the peptide. Co-stimulatory molecules are commercially available from a variety of sources, including, for example, Beckman Coulter, Inc. (Fullerton, Calif.). It is intended, although not always explicitly stated, that molecules having similar biological activity as wild-type or purified co-stimulatory molecules (e.g., recombinantly produced or muteins thereof) are intended to be used within the spirit and scope of the disclosure.

As used herein, "solid phase support" or "solid support", used interchangeably, is not limited to a specific type of support. Rather a large number of supports are available and are known to one of ordinary skill in the art. Solid phase supports include silica gels, resins, derivatized plastic films, glass beads, cotton, plastic beads, alumina gels. As used herein, "solid support" also includes synthetic antigen-presenting matrices, cells, and liposomes. A suitable solid phase support may be selected on the basis of desired end use and suitability for various protocols. For example, for peptide synthesis, solid phase support may refer to resins such as polystyrene (e.g., PAM-resin obtained from Bachem Inc., Peninsula Laboratories, etc.), POLYHIPE® resin (obtained from Aminotech, Canada), polyamide resin (obtained from Peninsula Laboratories), polystyrene resin grafted with polyethylene glycol (TentaGel®, Rapp Polymere, Tubingen, Germany) or polydimethylacrylamide resin (obtained from Milligen/Biosearch, Calif.).

An example of a solid phase support include glass, polystyrene, polypropylene, polyethylene, dextran, nylon, amylases, natural and modified celluloses, polyacrylamides, gabbros, and magnetite. The nature of the carrier can be either soluble to some extent or insoluble. The support material may have virtually any possible structural configuration so long as the coupled molecule is capable of binding to a polynucleotide, polypeptide or antibody. Thus, the support configuration may be spherical, as in a bead, or cylindrical, as in the inside surface of a test tube, or the external surface of a rod. Alternatively, the surface may be flat such as a sheet, test strip, etc. or alternatively polystyrene beads. Those skilled in the art will know many other suitable carriers for binding antibody or antigen, or will be able to ascertain the same by use of routine experimentation.

The term "immunomodulatory agent", as used herein, is a molecule, a macromolecular complex, or a cell that modulates an immune response and encompasses a synthetic antigenic peptide disclosed herein alone or in any of a variety of formulations described herein; a polypeptide comprising a synthetic antigenic peptide disclosed herein; a polynucleotide encoding a peptide or polypeptide disclosed herein; a synthetic antigenic peptide disclosed herein bound to a Class I or a Class II MHC molecule on an antigen-presenting matrix, including an APC and a synthetic antigen-presenting matrix (in the presence or absence of co-stimulatory molecule(s)); a synthetic antigenic peptide disclosed herein covalently or non-covalently complexed to another molecule(s) or macromolecular structure; and an educated, antigen-specific immune effector cell which is specific for a peptide disclosed herein.

The term "modulate an immune response" includes inducing (increasing, eliciting) an immune response; and reducing (suppressing) an immune response. An immunomodulatory method (or protocol) is one that modulates an immune response in a subject.

As used herein, the term "cytokine" refers to any one of the numerous factors that exert a variety of effects on cells, for example, inducing growth or proliferation. Non-limiting examples of cytokines which may be used alone or in combination in the practice of the present disclosure include, interleukin-2 (IL-2), stem cell factor (SCF), interleukin 3 (IL-3), interleukin 6 (IL-6), interleukin 12 (IL-12), G-CSF, granulocyte macrophage-colony stimulating factor (GM-CSF), interleukin-1 alpha (IL-1α), interleukin-11 (IL-11), MIP-11, leukemia inhibitory factor (LIF), c-kit ligand, thrombopoietin (TPO) and flt3 ligand. The present disclosure also includes culture conditions in which one or more cytokine is specifically excluded from the medium. Cytokines are commercially available from several vendors such as, for example, Genzyme (Framingham, Mass.), Genentech (South San Francisco, Calif.), Amgen (Thousand Oaks, Calif.), R&D Systems (Minneapolis, Minn.) and Immunex (Seattle, Wash.). It is intended, although not always explicitly stated, that molecules having similar biological activity as wild-type or purified cytokines (e.g., recombinantly produced or muteins thereof) are intended to be used within the spirit and scope of the disclosure.

Diagnostic and Therapeutic Methods

A method is provided for inhibiting, competing or titrating the binding of a DNABII polypeptide or protein to a microbial DNA, by contacting the DNABII polypeptide or protein or the microbial DNA with an interfering agent, thereby inhibiting, competing or titrating the binding of the DNABII protein or polypeptide to the microbial DNA. In a further aspect, the DNABII polypeptide and the microbial DNA are detectably labeled, for example with luminescent molecules that will emit a signal when brought into close contact with each other. The contacting can be performed in vitro or in vivo.

In another aspect, a method for inhibiting, preventing or breaking down a microbial biofilm is provided by contacting the biofilm with an interfering agent, thereby inhibiting, preventing or breaking down the microbial biofilm. In a further aspect, the DNABII polypeptide and the microbial DNA are detectably labeled, for example with luminescent molecules that will emit a signal when brought into close contact with each other. The contacting can be performed in vitro or in vivo.

When practiced in vitro, the methods are useful to screen for or confirm interfering agents having the same, similar or opposite ability as the polypeptides, polynucleotides, antibodies, host cells, small molecules and compositions disclosed herein. Alternatively, they can be used to identify which interfering agent is best suited to treat a microbial infection or if the treatment has been effective. For example, one can screen for new agents or combination therapies by having two samples containing for example, the DNABII polypeptide and microbial DNA and the agent to be tested. The second sample contains the DNABII polypeptide and microbial DNA and an agent known to active, e.g., an anti-IHF antibody or a small molecule to serve as a positive control. In a further aspect, several samples are provided and the interfering agents are added to the system in increasing dilutions to determine the optimal dose that would likely be effective in treating a subject in the clinical setting. As is apparent to those of skill in the art, a negative control containing the DNABII polypeptide and the microbial DNA can be provided. In a further aspect, the DNABII polypeptide and the microbial DNA are detectably labeled, for example with luminescent molecules that will emit a signal when brought into close contact with each other. The samples are contained under similar conditions for an effective amount of time for the agent to inhibit, compete or titrate the interaction between the DNABII polypeptide and microbial DNA and then the sample is assayed for emission of signal from the luminescent molecules. If the sample emits a signal, then the agent is not effective to inhibit binding.

In another aspect, the in vitro method is practiced in a miniaturized chamber slide system wherein the microbial (such as a bacterial) isolate causing an infection could be isolated from the human/animal then cultured to allow it to grow as a biofilm in vitro, see for example Experiment No. 1 below. The interfering agent (such as anti-DNABII or IHF antibody) or potential interfering agent biofilm is added alone or in combination with another agent to the culture with or without increasing dilutions of the potential interfering agent or interfering agent such as an anti-DNABII or IHF (or other antibody, small molecule, agent, etc.) to find the optimal dose that would likely be effective at treating that patient when delivered to the subject where the infection existed. As apparent to those of skill in the art, a positive and negative control can be performed simultaneously.

In a further aspect, the method is practiced in a high throughput platform with the interfering agent (such as anti-DNABII or IHF antibody) and/or potential interfering agent (alone or in combination with another agent) in a flow cell. The interfering agent (such as anti-DNABII or IHF antibody) or potential interfering agent biofilm is added alone or in combination with another agent to the culture with or without increasing dilutions of the potential interfering agent or interfering agent such as an anti-DNABII or IHF (or other antibody, small molecule, agent, etc.) to find the optimal dose that would likely be effective at treating that patient when delivered to the subject where the infection existed. Biofilm isolates are sonicated to separate biofilm bacteria from DNABII polypeptide such as IHF bound to microbial DNA. The DNABII polypeptide—DNA complexes are isolated by virtue of the anti-DNABII or IHF antibody on the platform. The microbial DNA is then be released with e.g., a salt wash, and used to identify the biofilm bacteria added. The freed DNA is then identified, e.g., by PCR sequenced. If DNA is not freed, then the interfering agent(s) successfully performed or bound the microbial DNA. If DNA is found in the sample, then the agent did not interfere with DNABII polypeptide-microbial DNA binding. As is apparent to those of skill in the art, a positive and/or negative control can be simultaneously performed.

The above methods also can be used as a diagnostic test since it is possible that a given bacterial species will respond better to reversal of its biofilm by one agent more than another, this rapid high throughput assay system could allow one skilled the art to assay a panel of possible anti-DNABII or IHF-like agents to identify the most efficacious of the group.

The advantage of these methods is that most clinical microbiology labs in hospitals are already equipped to perform these sorts of assays (i.e., determination of MIC, MBC values) using bacteria that are growing in liquid culture (or planktonically). As is apparent to those of skill in the art, bacteria generally do not grow planktonic ally when they are causing diseases. Instead they are growing as a stable biofilm and these biofilms are significantly more resistant to treatment by antibiotics, antibodies or other therapeutics. This resistance is why most MIC/MBC values fail to accurately predict efficacy in vivo. Thus, by determining what "dose" of agent could reverse a bacterial biofilm in vitro (as described above) Applicants' pre-clinical assay would be a more reliable predictor of clinical efficacy, even as an application of personalized medicine.

In addition to the clinical setting, the methods can be used to identify the microbe causing the infection and/or confirm effective interfering agents in an industrial setting. Thus, the interfering agents can be used to treat, inhibit or titrate a biofilm in an industrial setting.

In a further aspect of the above methods, an antibiotic or antimicrobial known to inhibit growth of the underlying infection is added sequentially or concurrently, to determine if the infection can be inhibited. It is also possible to add the interfering agent to the microbial DNA or DNABII polypeptide before adding the missing complex to assay for biofilm inhibition.

When practiced in vivo in non-human animal such as a chinchilla, the method provides a pre-clinical screen to identify interfering agents that can be used alone or in combination with other agents to break down biofilms. Examples of this method are shown in Experiment Nos. 2 through 7, below.

In another aspect, provided herein is a method of inhibiting, preventing or breaking down a biofilm in a subject by administering to the subject an effective amount of an interfering agent, thereby inhibiting, preventing or breaking down the microbial biofilm. Examples of this method are shown in Experiment Nos. 2 through 7, below. Non-limiting examples of such subjects include mammals, e.g., pets, and human patients.

Figure 18:
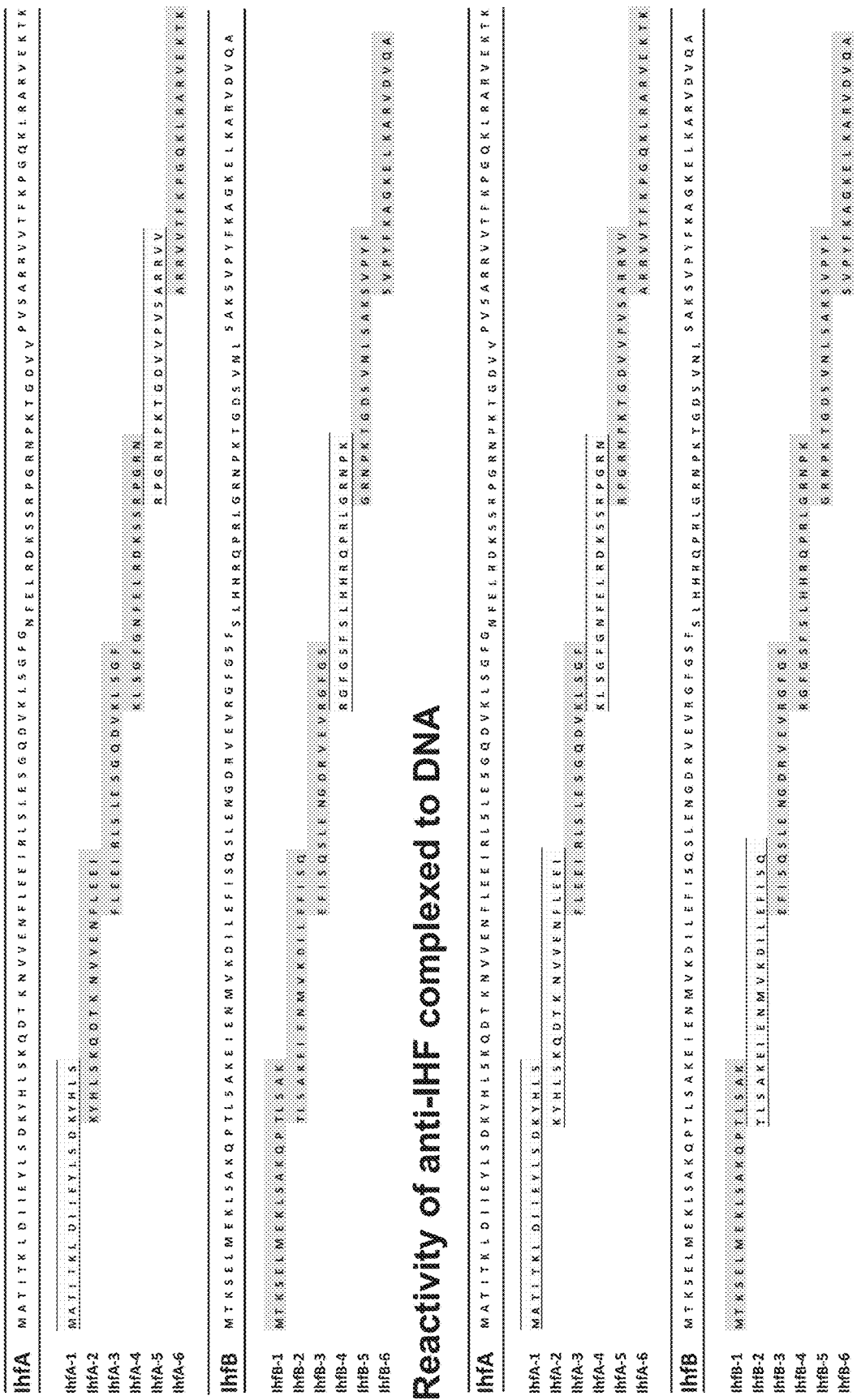
FIG. 18 depicts the peptide sequences generated in the fine mapping process and highlights the peptides of interest based on epitope mapping using chinchilla polyclonal antisera against either IHF from E. coli plus an adjuvant or IHF that has been complexed to an excess of DNA plus the same adjuvant. Figure discloses SEQ ID NOS 6, 348-353, 341-347, 6, 348-353 and 341-347, respectively, in order of appearance.

For the purpose of the above noted in vitro and in vivo methods, the interfering agent is of the group of:

(a) an isolated or recombinant DNABII or an integration host factor (IHF) polypeptide or a fragment or an equivalent of each thereof;

(b) an isolated or recombinant histone-like protein from *E. coli*, e.g., *E. coli* strain U93 (HU) polypeptide or a fragment or an equivalent of each thereof;

(c) an isolated or recombinant protein or polypeptide identified in Table 8, FIG. 19, FIG. 20, Table 9 or a DNA binding peptide identified in FIGS. 6A-6B, or a fragment or an equivalent of each thereof, wherein in one aspect the fragment comprises, or consists essentially of, or yet consists of, the polypeptides identified as A1 through A6 or B1 through B6 as disclosed in FIG. 18; or comprising, or alternatively consisting essentially of, or yet further consisting of the "tip" portion of the DNABII protein or polypeptide, comprising, or alternatively consisting essentially of, or yet further consisting of

```
KLSGFGNFELRDKSSRPGRN
(also referred to herein as hIFA4; (SEQ ID NO.
351);

RPGRNPKTGDVVPVSARRVV
(also referred to herein as hIFA5; (SEQ ID NO.
352);

ARRVVTFKPGQKLRARVEKTK
(also referred to herein as hIFA6; (SEQ ID NO.
353),
``` or an equivalent of each thereof, or an equivalent of each thereof or a polypeptide having at least 60%, or alternatively at least 65%, or alternatively at least 70%, or alternatively at least 75%, or alternatively 80%, or alternatively at least 85%, or alternatively at least 90%, or alternatively at least 95% identity thereto or for polypeptide sequences, which is encoded by a polynucleotide or its complement that hybridizes under conditions of high stringency to a polynucleotide encoding such polypeptide sequences. Conditions of high stringency are described herein and incorporated herein by reference. Applicants have determined that the bolded and underlined amino acids are heavily conserved and therefore in one aspect, are not modified or altered in designing an equivalent polypeptide. Additional examples of equivalent polypeptides include, for example IEYLSDKYHLSKQDTK (SEQ ID NO. 354), DKSSRPGRNPKTGDVVAASARR (SEQ ID NO.: 355), and KLRARVEKTK (SEQ ID NO. 17), described in U.S. Ser. Nos. 14/497,147 and 14/668,767 now abandoned). Equivalent polypeptides also include a polypeptide consisting of or comprising the above noted polypeptides with the addition of up to 25, or alternatively 20, or alternatively 15, or alternatively up to 10, or alternatively up to 5 random amino acids on either the amine or carboxy termini (or on both);

(d) an isolated or recombinant polypeptide of SEQ ID NO: 1 through 353, or a fragment or an equivalent of each thereof;

(e) an isolated or recombinant C-terminal polypeptide of SEQ ID NO: 6 through 11, 28, 29, 42 through 100, Table 8 or those C-terminal polypeptides identified in Table 9 or a fragment or an equivalent of each thereof;

(f) a polypeptide or polynucleotide that competes with a DNABII protein on binding to a microbial DNA, e.g., DNABII or an integration host factor IHF and/or HU polypeptide or protein;

(g) a four-way junction polynucleotide resembling a Holliday junction, a 3 way junction polynucleotide resembling a replication fork, a polynucleotide that has inherent flexibility or bent polynucleotide;

(h) an isolated or recombinant polynucleotide encoding any one of (a) through (f) or an isolated or recombinant polynucleotide of SEQ ID NO: 36 or an equivalent of each thereof, or a polynucleotide that hybridizes under stringent conditions to the polynucleotide its equivalent or its complement;

(i) an antibody or antigen binding fragment that specifically recognizes or binds any one of (a) through (g), or an equivalent or fragment of each antibody or antigen binding fragment thereof;

(j) an isolated or recombinant polynucleotide encoding the antibody or antigen binding fragment of (i) or its complement;

(k) a small molecule that competes with the binding of a DNABII protein or polypeptide to a microbial DNA;

(l) an antibody or antigen binding fragment that specifically recognizes or binds any one of an isolated or recombinant polypeptide of SEQ ID NO: 342 through 353 or a fragment or an equivalent of each thereof; and/or (m) polypeptide that comprises, or alternatively consists essentially of, or yet further consists of polypeptides A1 through A6 or B1 through B6 as disclosed in FIG. 18; or

```
KLSGFGNFELRDKSSRPGRN
(also referred to herein as hIFA4; (SEQ ID NO.
351);

RPGRNPKTGDVVPVSARRVV
(also referred to herein as hIFA5; (SEQ ID NO.
352);

ARRVVTFKPGQKLRARVEKTK
(also referred to herein as hIFA6; (SEQ ID NO.
353),
``` or an equivalent of each thereof or a polypeptide having at least 60%, or alternatively at least 65%, or alternatively at least 70%, or alternatively at least 75%, or alternatively 80%, or alternatively at least 85%, or alternatively at least 90%, or alternatively at least 95% identity thereto or for polypeptide sequences, which is encoded by a polynucleotide or its complement that hybridizes under conditions of high stringency to a polynucleotide encoding such polypeptide sequences. Conditions of high stringency are described herein and incorporated herein by reference. Applicants have determined that the bolded and underlined amino acids are heavily conserved and therefore in one aspect, are not modified or altered in designing an equivalent polypeptide. Additional examples of equivalent polypeptides include, for example IEYLSDKYHLSKQDTK (SEQ ID NO. 354), DKSSRPGRNPKTGDVVAASARR (SEQ ID NO.: 355), and KLRARVEKTK (SEQ ID NO. 17) described in U.S. Ser. Nos. 14/497,147 and 14/668,767 now abandoned), a polypeptide consisting of or comprising the above noted polypeptides with the addition of up to 25, or alternatively 20, or alternatively 15, or alternatively up to 10, or alternatively up to 5 random amino acids on either the amine or carboxy termini (or on both).

Also provided herein is a method for inducing an immune response in or conferring passive immunity in a subject in need thereof, comprising, or alternatively consisting essentially of or yet further consisting of, administering to the subject an effective amount of one or more agents of the group:

(a) an isolated or recombinant DNABII or an integration host factor (IHF) polypeptide, or a fragment or an equivalent of each thereof;

(b) an isolated or recombinant histone-like protein from *E. coli*, e.g., *E. coli* strain U93 (HU) polypeptide or a fragment or an equivalent of each thereof;

(c) an isolated or recombinant protein polypeptide identified in Table 8, FIG. 19, FIG. 20, Table 9 or an DNA binding peptide identified in FIGS. 6A-6B, or a fragment or an equivalent of each thereof, a polypeptide A1 to A5, or B1 to B5 as shown in FIG. 18, or a fragment that comprises, or consists essentially of, or yet consists of, the "tip" portion of the DNABII protein or polypeptide, non-limiting examples of such include without limitation a polypeptide that comprises, or alternatively consists essentially of, or yet further consists of

```
KLSGFGNFELRDKSSRPGRN
(also referred to herein as hIFA4; (SEQ ID NO.
351);

RPGRNPKTGDVVPVSARRVV
(also referred to herein as hIFA5; (SEQ ID NO.
352);

ARRVVTFKPGQKLRARVEKTK
(also referred to herein as hIFA6; (SEQ ID NO.
353),
``` or an equivalent of each thereof. Additional examples of equivalent polypeptides include, for example IEYLSDKYHLSKQDTK (SEQ ID NO. 354), DKSSRPGRNPKTGDVVAASARR (SEQ ID NO.: 355), AND KLRARVEKTK (SEQ ID NO. 17) described in U.S. Ser. Nos. 14/497,147 and 14/668,767 now abandoned), a polypeptide consisting of or comprising the above noted polypeptides with the addition of up to 25, or alternatively 20, or alternatively 15, or alternatively up to 10, or alternatively up to 5 random or naturally occurring amino acids on either the amine or carboxy termini (or on both);

(d) an isolated or recombinant polypeptide of SEQ ID NO: 1 through 353 or a fragment or an equivalent thereof;

(e) an isolated or recombinant C-terminal polypeptide of SEQ ID NO: 6 through 11, 28, 29, 42 through 100, Table 8 or those C-terminal polypeptides identified in Table 9 or a fragment or an equivalent of each thereof;

(f) an isolated or recombinant polynucleotide encoding any one of (a) through (e) or an isolated or recombinant polynucleotide SEQ ID NO: 36 or an equivalent of each thereof, or a polynucleotide that hybridizes under stringent conditions to the polynucleotide, its equivalent or its complement;

(g) an antibody or antigen binding fragment that specifically recognizes or binds any one of (a) through (e), or an equivalent or fragment of each thereof;

(h) an isolated or recombinant polynucleotide encoding the antibody or antigen binding fragment of (g);

(i) an antigen presenting cell pulsed with any one of (a) through (e);

(j) an antigen presenting cell transfected with one or more polynucleotides encoding any one of (a) through (e); and/or (k) an antibody or antigen binding fragment that specifically recognizes or binds any one of an isolated or recombinant polypeptide noted herein as A1, A2, A3, A4, A5, A6, B1, B2, B3, B4, B5, B6 (se FIG. 18) or an isolated or recombinant polypeptide of SEQ ID NO: 342 through 353 or a fragment or an equivalent of each thereof.

In one particular aspect, the interfering agent is an isolated or recombinant DNABII protein, e.g., an integration host factor (IHF) polypeptide or a fragment thereof, a C-terminal fragment of an IHF polypeptide, a tip fragment, of an equivalent of each thereof. In another particular aspect, the interfering agent is an isolated or recombinant HU polypeptide or a fragment thereof, a tip fragment, a C-terminal fragment of HU polypeptide, or an equivalent of each thereof. Non-limiting examples of such are an IHF or HU alpha or beta polypeptide; an IHF polypeptide; *Moraxella catarrhalis* HU; *E. coli* HupA, HupB, himA, himD; *E. faecalis* HU (such as V583), HMGB1 (High Mobility Group Box 1, a protein with similar DNA binding and DNA substrate specificities but not in primary amino acid sequence to the DNABII family of proteins; a functional orthologue) and those identified in Table 8 or Table 9.

In a further aspect, the methods further comprise, or alternatively consist essentially of, or yet further consist of administering to the subject an effective amount of one or more of an antimicrobial, an antigenic peptide or an adjuvant.

A non-limiting example of an antimicrobial agent is another vaccine component such as a surface antigen, e.g., an OMP P5, rsPilA, OMP 26, OMP P2, or Type IV Pilin protein (see Jurcisek and Bakaletz (2007) J. Bacteriology 189(10):3868-3875; Murphy, T. F. et al. (2009) The Pediatric Infectious Disease Journal 28: S121-S126).

The agents and compositions disclosed herein can be concurrently or sequentially administered with other antimicrobial agents and/or surface antigens. In one particular aspect, administration is locally to the site of the infection by direct injection or by inhalation for example. Other non-limiting examples of administration include by one or more method comprising transdermally, urethrally, sublingually, rectally, vaginally, ocularly, subcutaneous, intramuscularly, intraperitoneally, intranasally, by inhalation or orally.

Microbial infections and disease that can be treated by the methods disclosed herein include infection by the organisms identified in Experiment No. 1 and Table 8, e.g., *Streptococcus agalactiae, Neisseria meningitidis, Treponemes, denticola, pallidum, Burkholderia cepacia*, or *Burkholderia pseudomallei*. In one aspect, the microbial infection is one or more of *Haemophilus influenzae* (nontypeable), *Moraxella catarrhalis, Streptococcus pneumoniae, Streptococcus pyogenes, Pseudomonas aeruginosa, Mycobacterium tuberculosis*. These microbial infections may be present in the upper, mid and lower airway (otitis, sinusitis, bronchitis but also exacerbations of chronic obstructive pulmonary disease (COPD), chronic cough, complications of and/or primary cause of cystic fibrosis (CF) and community acquired pneumonia (CAP). Thus, by practicing the in vivo methods disclosed herein, these diseases and complications from these infections can also be prevented or treated.

Infections might also occur in the oral cavity (caries, periodontitis) and caused by *Streptococcus mutans, Porphyromonas gingivalis, Aggregatibacter actinomvctemcomitans*. Infections might also be localized to the skin (abscesses, 'staph' infections, impetigo, secondary infection of burns, Lyme disease) and caused by *Staphylococcus aureus, Staphylococcus epidermidis, Pseudomonas aeruginosa* and *Borrelia burdorferi*. Infections of the urinary tract (UTI) can also be treated and are typically caused by *Escherichia coli*.

Infections of the gastrointestinal tract (GI) (diarrhea, cholera, gall stones, gastric ulcers) are typically caused by *Salmonella enterica* serovar, *Vibrio cholerae* and *Helicobacter pylori*. Infections of the genital tract include and are typically caused by *Neisseria gonorrhoeae*. Infections can be of the bladder or of an indwelling device caused by *Enterococcus faecalis*. Infections associated with implanted prosthetic devices, such as artificial hip or knee replacements, or dental implants, or medical devices such as pumps, catheters, stents, or monitoring systems, typically caused by a variety of bacteria, can be treated by the methods disclosed herein. These devices can be coated or conjugated to an agent as described herein. Thus, by practicing the in vivo methods disclosed herein, these diseases and complications from these infections can also be prevented or treated.

Infections caused by *Streptococcus agalactiae* can also be treated by the methods disclosed herein and it is the major cause of bacterial septicemia in newborns. Infections caused by *Neisseria meningitidis* which can cause meningitis can also be treated.

Thus, routes of administration applicable to the methods disclosed herein include intranasal, intramuscular, urethrally, intratracheal, subcutaneous, intradermal, transdermal, topical application, intravenous, rectal, nasal, oral, inhalation, and other enteral and parenteral routes of administration. Routes of administration may be combined, if desired, or adjusted depending upon the agent and/or the desired effect. An active agent can be administered in a single dose or in multiple doses. Embodiments of these methods and routes suitable for delivery include systemic or localized routes. In general, routes of administration suitable for the methods disclosed herein include, but are not limited to, direct injection, enteral, parenteral, or inhalational routes.

Parenteral routes of administration other than inhalation administration include, but are not limited to, topical, transdermal, subcutaneous, intramuscular, intraorbital, intracapsular, intraspinal, intrasternal, and intravenous routes, i.e., any route of administration other than through the alimentary canal. Parenteral administration can be conducted to effect systemic or local delivery of the inhibiting agent. Where systemic delivery is desired, administration typically involves invasive or systemically absorbed topical or mucosal administration of pharmaceutical preparations.

The interfering agents disclosed herein can also be delivered to the subject by enteral administration. Enteral routes of administration include, but are not limited to, oral and rectal (e.g., using a suppository) delivery.

Methods of administration of the active through the skin or mucosa include, but are not limited to, topical application of a suitable pharmaceutical preparation, transcutaneous transmission, transdermal transmission, injection and epidermal administration. For transdermal transmission, absorption promoters or iontophoresis are suitable methods. Iontophoretic transmission may be accomplished using commercially available "patches" that deliver their product continuously via electric pulses through unbroken skin for periods of several days or more.

In various embodiments of the methods disclosed herein, the interfering agent will be administered by inhalation, injection or orally on a continuous, daily basis, at least once per day (QD), and in various embodiments two (BID), three (TID), or even four times a day. Typically, the therapeutically effective daily dose will be at least about 1 mg, or at least about 10 mg, or at least about 100 mg, or about 200 to about 500 mg, and sometimes, depending on the compound, up to as much as about 1 g to about 2.5 g.

Dosing of can be accomplished in accordance with the methods disclosed herein using capsules, tablets, oral suspension, suspension for intra-muscular injection, suspension for intravenous infusion, get or cream for topical application, or suspension for intra-articular injection.

Dosage, toxicity and therapeutic efficacy of compositions described herein can be determined by standard pharmaceutical procedures in cell cultures or experimental animals, for example, to determine the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. In certain embodiments, compositions exhibit high therapeutic indices. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies (in certain embodiments, within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In some embodiments, an effective amount of a composition sufficient for achieving a therapeutic or prophylactic effect, ranges from about 0.000001 mg per kilogram body weight per administration to about 10,000 mg per kilogram body weight per administration. Suitably, the dosage ranges are from about 0.0001 mg per kilogram body weight per administration to about 100 mg per kilogram body weight per administration. Administration can be provided as an initial dose, followed by one or more "booster" doses. Booster doses can be provided a day, two days, three days, a week, two weeks, three weeks, one, two, three, six or twelve months after an initial dose. In some embodiments, a booster dose is administered after an evaluation of the subject's response to prior administrations.

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

Polypeptides

Also provided herein are interfering agents and compositions for use in the methods described herein, wherein the interfering agent is of the group:

(a) an isolated or recombinant DNABII or an integration host factor (IHF) polypeptide or a fragment or an equivalent of each thereof;

(b) an isolated or recombinant histone-like protein from *E. coli*, e.g., *E. coli* strain U93 (HU) polypeptide or a fragment or an equivalent of each thereof;

(c) an isolated or recombinant protein or polypeptide identified in Table 8, FIG. 19, FIG. 20, Table 9 or a DNA binding peptide identified in FIGS. 6A-6B, or a fragment or an equivalent of each thereof, wherein in one aspect the fragment comprises, or consists essentially of, or yet consists of, the polypeptides identified as A1 through A6 or B1 through B6 as disclosed in FIG. 18; or comprising, or alternatively consisting essentially of, or yet further consisting of the "tip" portion of the DNABII protein or polypeptide, comprising, or alternatively consisting essentially of, or yet further consisting of

KLSGFGNFELRDKSSRPGRN
(also referred to herein as hIFA4; (SEQ ID NO. 351);

RPGRNPKTGDVVPVSARRVV
(also referred to herein as hIFA5; (SEQ ID NO. 352);

ARRVVTFKPGQKLRARVEKTK
(also referred to herein as hIFA6; (SEQ ID NO. 353);

or an equivalent of each thereof, or an equivalent of each thereof or a polypeptide having at least 60%, or alternatively at least 65%, or alternatively at least 70%, or alternatively at least 75%, or alternatively 80%, or alternatively at least 85%, or alternatively at least 90%, or alternatively at least 95% identity thereto or for polypeptide sequences, which is encoded by a polynucleotide or its complement that hybridizes under conditions of high stringency to a polynucleotide encoding such polypeptide sequences. Conditions of high stringency are described herein and incorporated herein by reference. Applicants have determined that the bolded and underlined amino acids are heavily conserved and therefore in one aspect, are not modified or altered in designing an equivalent polypeptide. Additional examples of equivalent polypeptides include, for example IEYLSDKYHLSKQDTK (SEQ ID NO. 354), DKSSRPGRNPKTGDVVAASARR (SEQ ID NO.: 355), and KLRARVEKTK (SEQ ID NO. 17), described in U.S. Ser. Nos. 14/497,147 and 14/668,767 now abandoned). Equivalent polypeptides also include a polypeptide consisting of or comprising the above noted polypeptides with the addition of up to 25, or alternatively 20, or alternatively 15, or alternatively up to 10, or alternatively up to 5 random amino acids on either the amine or carboxy termini (or on both);

(d) an isolated or recombinant polypeptide of SEQ ID NO: 1 through 353, or a fragment or an equivalent of each thereof;

(e) an isolated or recombinant C-terminal polypeptide of SEQ ID NO: 6 through 11, 28, 29, 42 through 100, Table 8 or those C-terminal polypeptides identified in Table 9 or a fragment or an equivalent of each thereof;

(f) a polypeptide or polynucleotide that competes with a DNABII protein on binding to a microbial DNA, e.g., DNABII or an integration host factor IHF and/or HU polypeptide or protein;

(g) a four-way junction polynucleotide resembling a Holliday junction, a 3 way junction polynucleotide resembling a replication fork, a polynucleotide that has inherent flexibility or bent polynucleotide;

(h) an isolated or recombinant polynucleotide encoding any one of (a) through (f) or an isolated or recombinant polynucleotide of SEQ ID NO: 36 or an equivalent of each thereof, or a polynucleotide that hybridizes under stringent conditions to the polynucleotide its equivalent or its complement;

(i) an antibody or antigen binding fragment that specifically recognizes or binds any one of (a) through (g), or an equivalent or fragment of each antibody or antigen binding fragment thereof;

(j) an isolated or recombinant polynucleotide encoding the antibody or antigen binding fragment of (i) or its complement;

(k) a small molecule that competes with the binding of a DNABII protein or polypeptide to a microbial DNA;

(l) an antibody or antigen binding fragment that specifically recognizes or binds any one of an isolated or recombinant polypeptide of SEQ ID NO: 342 through 353 or a fragment or an equivalent of each thereof; and/or (m) polypeptide that comprises, or alternatively consists essentially of, or yet further consists of polypeptides A1 through A6 or B1 through B6, as disclosed in FIG. 18; or

KLSGFGNFELRDKSSRPGRN
(also referred to herein as hIFA4; (SEQ ID NO. 351);

RPGRNPKTGDVVPVSARRVV
(also referred to herein as hIFA5; (SEQ ID NO. 352);

ARRVVTFKPGQKLRARVEKTK
(also referred to herein as hIFA6; (SEQ ID NO. 353), or an equivalent of each thereof or a polypeptide having at least 60%, or alternatively at least 65%, or alternatively at least 70%, or alternatively at least 75%, or alternatively 80%, or alternatively at least 85%, or alternatively at least 90%, or alternatively at least 95% identity thereto or for polypeptide sequences, which is encoded by a polynucleotide or its complement that hybridizes under conditions of high stringency to a polynucleotide encoding such polypeptide sequences. Conditions of high stringency are described herein and incorporated herein by reference. Applicants have determined that the bolded and underlined amino acids are heavily conserved and therefore in one aspect, are not modified or altered in designing an equivalent polypeptide. Additional examples of equivalent polypeptides include, for example IEYLSDKYHLSKQDTK (SEQ ID NO. 354), DKSSRPGRNPKTGDVVAASARR (SEQ ID NO.: 355), and KLRARVEKTK (SEQ ID NO. 17) described in U.S. Ser. Nos. 14/497,147 and 14/668,767 now abandoned), a polypeptide consisting of or comprising the above noted polypeptides with the addition of up to 25, or alternatively 20, or alternatively 15, or alternatively up to 10, or alternatively up to 5 random amino acids on either the amine or carboxy termini (or on both).

In one particular aspect, the interfering agent is an isolated or recombinant DNABII polypeptide or a fragment or an equivalent of each thereof. Non-limiting examples of such are an IHF or HU alpha or beta polypeptide; an IHF a polypeptide; *Moraxella catarrhalis* HU; *E. coli* HupA, HupB, himA, himD; *E. faecalis* HU (such as V583), HMGB1 and those identified in Table 8.

In another aspect, the interfering agent is an isolated or recombinant polypeptide consisting essentially of an amino acid sequence selected from SEQ ID NO: 1 to 5 or 12 to 27, 30 to 35, 101-353 or a DNA binding peptide identified in FIGS. 6A-6B.

In another aspect, the isolated or recombinant polypeptide comprises, or alternatively consists essentially of or yet further consists of SEQ ID NO: 1 or 2, with the proviso that the polypeptide is none of SEQ ID NO: 6 to 11, 28, 29, or 42 through 100.

In another aspect, the isolated or recombinant polypeptide comprises, or alternatively consists essentially of, or yet further consists of SEQ ID NO: 3, 4 or 5, with the proviso that the polypeptide is none of SEQ ID NO: 6 to 11, 28, 29, or 42 through 100.

In another aspect, the isolated or recombinant polypeptide comprises, or alternatively consists essentially of, or yet further consists of SEQ ID NO: 12, 14, 16, 18, 20, 22, 24, 26, 30 or 32, with the proviso that the polypeptide is none of SEQ ID NO: 6 to 11, 28, 29, or 42 through 100.

In another aspect, the isolated or recombinant polypeptide comprises, or alternatively consists essentially of, or yet further consists of SEQ ID NO: 13, 15, 17, 19, 21, 23, 25, 27, 31 33, 34, or 35 with the proviso that the polypeptide is none of SEQ ID NO: 6 to 11, 28, 29, or 42 through 100.

In another aspect, the isolated or recombinant polypeptide comprises, or alternatively consists essentially of, or yet further consists of an isolated or recombinant polypeptide of the group of:
a polypeptide comprising SEQ ID NO: 12 and 13;
a polypeptide comprising SEQ ID NO: 14 and 15;
a polypeptide comprising SEQ ID NO: 16 and 17;
a polypeptide comprising SEQ ID NO: 18 and 19;
a polypeptide comprising SEQ ID NO: 20 and 21;
a polypeptide comprising SEQ ID NO: 23 and 24;
a polypeptide comprising SEQ ID NO: 25 and 26;
a polypeptide comprising SEQ ID NO: 30 and 31;
a polypeptide comprising SEQ ID NO: 32 and 33;
a polypeptide comprising SEQ ID NO: 34 and 35;
a polypeptide comprising SEQ ID NO: 337 and 338; or
a polypeptide comprising SEQ ID NO: 339 and 340;
a polypeptide consisting essentially of any one or more of SEQ ID NO: 342 to 353;
with the proviso that the polypeptide is none of wild-type of any one of IHF alpha, IHF beta or SEQ ID NO: 6 to 11, 28, 29, or 42 through 100.

In another aspect, the isolated or recombinant polypeptide is of the group:
a polypeptide consisting essentially of SEQ ID NO: 12 and 13;
a polypeptide consisting essentially of SEQ ID NO: 14 and 15;
a polypeptide consisting essentially of SEQ ID NO: 16 and 17;
a polypeptide consisting essentially of SEQ ID NO: 18 and 19;
a polypeptide consisting essentially of SEQ ID NO: 20 and 21;
a polypeptide consisting essentially of SEQ ID NO: 23 and 24;
a polypeptide consisting essentially of SEQ ID NO: 25 and 26;
a polypeptide consisting essentially of SEQ ID NO: 30 and 31;
a polypeptide consisting essentially of SEQ ID NO: 32 and 33;
a polypeptide consisting essentially of SEQ ID NO: 34 and 35;
a polypeptide consisting essentially of SEQ ID NO: 337 and 338; or
a polypeptide consisting essentially of SEQ ID NO: 339 and 340;
a polypeptide consisting essentially of any one or more of SEQ ID NO: 342 to 353;
with the proviso that the polypeptide is none of wild-type of any one of IHF alpha, IHF beta or SEQ ID NO: 6 to 11, 28, 29, or 42 through 100.

Further provided as agents for use in the methods disclosed herein are fragments or an equivalent of the isolated or recombinant polypeptides described above. Examples of fragments are A1 through A6; B1 through B6 (see FIG. 18); or a C-terminal polypeptide. In another aspect, the fragment is a tip portion of the DNABII, non-limiting examples of such includes without limitation a polypeptide that comprises KLSGFGNFELRDKSSRPGRN
(also referred to herein as hIFA4; (SEQ ID NO. 351));

RPGRNPKTGDVVPVSARRVV
(also referred to herein as hIFA5; (SEQ ID NO. 352));

ARRVVTFKPGQKLRARVEKTK
(also referred to herein as hIFA6; (SEQ ID NO. 353));

or an equivalent of each thereof. In a further aspect, the isolated or recombinant polypeptide comprises, or alternatively consists essentially of, or yet further consists of two or more of the isolated or recombinant polypeptides described above.

Additionally, the isolated or recombinant polypeptide comprises, or alternatively consists essentially of, or yet further consists of any one of SEQ ID NO: 1 to 6, 12 to 27 or 30 to 33, or a fragment or an equivalent polypeptide, examples of which are identified in Table 8 or shown in FIG. 19, FIG. 20 or Table 9. In one aspect, isolated wild-type polypeptides are excluded, i.e., that the polypeptide is none of SEQ ID NO: 6 through 11, 28, 29, or a wildtype sequence identified in Table 8 or shown in FIG. 19.

In one aspect, this disclosure provides an isolated or recombinant polypeptide consisting essentially of an amino acid sequence of the group SEQ ID NO: 1 to 6, 12 to 27 or 30 to 35, 1 to 6 and 13 to 35, or a polypeptide comprising, or alternatively consisting essentially of, or yet further consisting of an amino acid corresponding to the β-3 and/or α-3 fragments of a *Haemophilus influenzae* IHFα or IHFβ, non-limiting examples of which include SEQ ID NO: 12 through 27, or a fragment or equivalent thereof of each thereof. In another aspect, the disclosure provides an isolated or recombinant polypeptide comprising, or alternatively consisting essentially of, or yet further consisting of an amino acid sequence of the group SEQ ID NO: 1 to 4, or a fragment or an equivalent of each thereof, or a polypeptide comprising, or alternatively consisting essentially of, or yet further consisting of an amino acid corresponding to the β-3 and/or α-3 fragments of a *Haemophilus influenzae* IHFα or IHFβ, non-limiting examples of which include SEQ ID NO: 12 through 27 or a fragment or a biological equivalent thereof which further comprises independently at least 2, or alternatively at least 3, or alternatively at least 4, or alternatively at least 5, or at least 6, or alternatively at least 7, or alternatively at least 8, or alternatively at least 9 or alternatively at least 10 amino acids at the amino and/or carboxyl terminus of the polypeptide. In one aspect, isolated wildtype DNA binding polypeptides are excluded, i.e., that the polypeptide is none of SEQ ID NO: 6 through 11, 28, 29, or 42 through 100 or an isolated wildtype polypeptide sequence listed in Table 8 or shown in FIG. 19.

In another aspect, this disclosure provides an isolated or recombinant polypeptide comprising, or alternatively consisting essentially of, or yet further consisting of, SEQ ID. NO 1 or 2 alone or in combination with a polypeptide comprising, or alternatively consisting essentially of, or yet further consisting of an amino acid corresponding to the β-3 and/or α-3 fragments of a *Haemophilus influenzae* IHFα or IHFβ, on-limiting examples of which include SEQ ID NO: 12 through 27 or a fragment or a biological equivalent of each thereof. In one aspect, isolated wildtype DNA binding polypeptides are excluded, i.e., that the polypeptide is none of SEQ ID NO: 6 through 11, 28, 29, or 42 through 100 or an isolated polypeptide sequence listed in Table 8 or shown in FIG. 19.

In a yet further aspect, this disclosure provides an isolated or recombinant polypeptide comprising or alternatively consisting essentially of, or yet further consisting of, SEQ ID NO: 3 or 4 or a fragment or an equivalent of each thereof alone or in combination with a polypeptide comprising, or alternatively consisting essentially of, or yet further consisting of an amino acid corresponding to the β-3 and/or α-3 fragments of a *Haemophilus influenzae* IHFα or IHFβ, non-limiting examples of which include SEQ ID NO: 12 through 27, and 34-35 or a biological equivalent of each thereof. In one aspect, isolated wildtype DNA binding polypeptides are excluded, i.e., that the polypeptide is none of SEQ ID NO: 6 through 11, 28, 29, or 42 through 100 or an isolated wildtype polypeptide sequence listed in Table 8 or shown in FIG. 19, or a polypeptide that comprises

KLSGFGNFELRDKSSRPGRN (also referred to herein as hIFA4; (SEQ ID NO. 351));

RPGRNPKTGDVVPVSARRVV (also referred to herein as hIFA5; (SEQ ID NO. 352));

ARRVVTFKPGQKLRARVEKTK (also referred to herein as hIFA6; (SEQ ID NO. 353)), or an equivalent of each thereof.

This disclosure also provides isolated or recombinant polypeptides comprising or alternatively consisting essentially of, or yet further consisting of, two or more, or three or more, four or more, five or more, six or more, seven or more, eight or more, nine or more, ten or more, eleven or more, twelve or more, thirteen or more of all fourteen of the isolated polypeptides or a fragment or an equivalent of each thereof. Non-limiting examples of such include isolated or recombinant polypeptides comprising SEQ ID NO: 1 through 4, e.g., SEQ ID NO: 1 and 2, or alternatively 1 and 3 or alternatively 1 and 4, or alternatively 2 and 3, or alternatively SEQ ID NO: 1, 2 and 3 or alternatively, 2, 3 and 4, or alternatively 1, 3 and 4. The polypeptides can be in any orientation, e.g., SEQ ID NO: 1, 2, and 3 or SEQ ID NO: 3, 2 and 1 or alternatively 2, 1 and 3, or alternatively, 3, 1 and 2. Biological equivalents of these polypeptides are further included in this disclosure with the proviso that the sequences do not include isolated wildtype sequences such as those identified in Tables 8 and 9.

In another aspect, this disclosure provides an isolated or recombinant polypeptide comprising or alternatively consisting essentially of, or yet further consisting of, SEQ ID NO: 1 or 2 and 3 or 4, or a fragment or an equivalent of each thereof, with the proviso that the polypeptide is none of SEQ ID NO: 5 through 10, and they may further comprise any one or more of SEQ ID NO: 11 through 26, e.g., 11 and 12, or alternatively 1 and 11, or alternatively 2 and 11, or alternatively, 1 and 12, or alternatively 2 and 12, or alternatively 11, 12 and 1, or alternatively 2, 11 and 12. In this embodiment, SEQ ID NO: 1 or 2 is located upstream or amino terminus from SEQ ID NO: 3 or 4, with the proviso that the amino acid sequence is not an isolated wildtype polypeptide, e.g., none of SEQ ID NO: 6 through 11, 28 and 29. In another aspect, the isolated polypeptide comprises SEQ ID NO: 3 or 4 located upstream or amino terminus to SEQ ID NO: 1 or 2. Biological equivalents of these polypeptides are further included in this disclosure with the proviso that the sequence do not include isolated wildtype polypeptides.

In one embodiment, any polypeptide or protein having sequence identity to the wildtype polypeptides or those disclosed in Pedulla et al. (1996) PNAS 93:15411-15416 is excluded from this disclosure.

In any of the above embodiments, a peptide linker can be added to the N-terminus or C-terminus of the polypeptide. A "linker" or "peptide linker" refers to a peptide sequence linked to either the N-terminus or the C-terminus of a polypeptide sequence. In one aspect, the linker is from about 1 to about 20 amino acid residues long or alternatively 2 to about 10, about 3 to about 5 amino acid residues long. An example of a peptide linker is Gly-Pro-Ser-Leu-Lys-Leu (SEQ ID NO: 37). Other examples include Gly-Gly-Gly; Gly-Pro-Ser-Leu (SEQ ID NO: 38); Gly-Pro-Ser; Pro-Ser-Leu-Lys (SEQ ID NO: 39); Gly-Pro-Ser-Leu-Lys (SEQ ID NO: 40) and Ser-Leu-Lys-Leu (SEQ ID NO: 41).

The isolated polypeptides disclosed herein are intended to include isolated wildtype and recombinantly produced polypeptides and proteins from prokaryotic and eukaryotic host cells, as well as muteins, analogs and fragments thereof, examples of such cells are described above. In some embodiments, the term also includes antibodies and anti-idiotypic antibodies as described herein. Such polypeptides can be isolated or produced using the methods known in the art and briefly described herein.

It is understood that functional equivalents or variants of the wild type polypeptide or protein also are within the scope of this disclosure, for example, those having conservative amino acid substitutions of the amino acids, see for example, Table 9. Other analogs include fusion proteins comprising a protein or polypeptide disclosed herein which can include a polypeptide joined to an antigen presenting matrix.

In a further aspect, the polypeptides are conjugated or linked to a detectable label. Suitable labels are known in the art and described herein.

In a yet further aspect, the polypeptides with or without a detectable label can be contained or expressed on the surface of a host prokaryotic or eukaryotic host cell, such as a dendritic cell.

The proteins and polypeptides are obtainable by a number of processes known to those of skill in the art, which include purification, chemical synthesis and recombinant methods. Polypeptides can be isolated from preparations such as host cell systems by methods such as immunoprecipitation with antibody, and standard techniques such as gel filtration, ion-exchange, reversed-phase, and affinity chromatography. For such methodology, see for example Deutscher et al. (1999) Guide To Protein Purification: Methods In Enzymology (Vol. 182, Academic Press). Accordingly, this disclosure also provides the processes for obtaining these polypeptides as well as the products obtainable and obtained by these processes.

The polypeptides also can be obtained by chemical synthesis using a commercially available automated peptide synthesizer such as those manufactured by Perkin/Elmer/Applied Biosystems, Inc., Model 430A or 431A, Foster City, Calif., USA. The synthesized polypeptide can be precipitated and further purified, for example by high performance liquid chromatography (HPLC). Accordingly, this disclosure also provides a process for chemically synthesizing the proteins disclosed herein by providing the sequence of the protein and reagents, such as amino acids and enzymes and linking together the amino acids in the proper orientation and linear sequence.

Alternatively, the proteins and polypeptides can be obtained by well-known recombinant methods as described, for example, in Sambrook et al. (1989) supra, using a host cell and vector systems described herein.

Also provided by this application are the polypeptides described herein conjugated to a detectable agent for use in the diagnostic methods. For example, detectably labeled polypeptides can be bound to a column and used for the detection and purification of antibodies. They also are useful as immunogens for the production of antibodies as described below. The polypeptides disclosed herein are useful in an in vitro assay system to screen for agents or drugs, which modulate cellular processes.

It is well known to those skilled in the art that modifications can be made to the peptides disclosed herein to provide them with altered properties. As used herein the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

Peptides disclosed herein can be modified to include unnatural amino acids. Thus, the peptides may comprise D-amino acids, a combination of and L-amino acids, and various "designer" amino acids (e.g., .beta.-methyl amino acids, C-alpha-methyl amino acids, and N-alpha-methyl amino acids, etc.) to convey special properties to peptides. Additionally, by assigning specific amino acids at specific coupling steps, peptides with alpha-helices, beta. turns, beta. sheets, gamma-turns, and cyclic peptides can be generated. Generally, it is believed that .alpha.-helical secondary structure or random secondary structure may be of particular use.

The polypeptides disclosed herein also can be combined with various solid phase carriers, such as an implant, a stent, a paste, a gel, a dental implant, or a medical implant or liquid phase carriers, such as beads, sterile or aqueous solutions, pharmaceutically acceptable carriers, pharmaceutically acceptable polymers, liposomes, micelles, suspensions and emulsions. Examples of non-aqueous solvents include propyl ethylene glycol, polyethylene glycol and vegetable oils. When used to prepare antibodies or induce an immune response in vivo, the carriers also can include an adjuvant that is useful to non-specifically augment a specific immune response. A skilled artisan can easily determine whether an adjuvant is required and select one. However, for the purpose of illustration only, suitable adjuvants include, but are not limited to Freund's Complete and Incomplete, mineral salts and polynucleotides. Other suitable adjuvants include monophosphoryl lipid A (MPL), mutant derivatives of the heat labile enterotoxin of *E. coli*, mutant derivatives of cholera toxin, CPG oligonucleotides, and adjuvants derived from squalene.

This disclosure also provides a pharmaceutical composition comprising or alternatively consisting essentially of, or yet further consisting of, any of a polypeptide, analog, mutein, or fragment disclosed herein, alone or in combination with each other or other agents, such an antibiotic and an acceptable carrier or solid support. These compositions are useful for various diagnostic and therapeutic methods as described herein.

Polynucleotides

This disclosure also provides isolated or recombinant polynucleotides encoding one or more of the above-identified isolated or recombinant polypeptides and their respective complementary strands. Vectors comprising the isolated or recombinant polynucleotides are further provided examples of which are known in the art and briefly described herein. In one aspect where more than one isolated or recombinant polynucleotide is to be expressed as a single unit, the isolated or recombinant polynucleotides can be contained within a polycistronic vector. The polynucleotides can be DNA, RNA, mRNA or interfering RNA, such as siRNA, miRNA or dsRNA.

In another aspect, this disclosure provides an interfering agent that is a polynucleotide that interferes with the binding of the DNA to a polypeptide or protein in a microbial biofilm, or a four-way junction polynucleotide resembling a Holliday junction, a 3 way junction polynucleotide resembling a replication fork, a polynucleotide that has inherent flexibility or bent polynucleotide which can treat or inhibit DNABII polynucleotide from binding to microbial DNA as well treat, prevent or inhibit biofilm formation and associated infections and disorders. One of skill in the art can make such polynucleotides using the information provided herein and knowledge of those of skill in the art. See Goodman and Kay (1999) J. Biological Chem. 274(52):37004-37011 and Kamashev and Rouviere-Yaniv (2000) EMBO J. 19(23): 6527-6535.

The disclosure further provides the isolated or recombinant polynucleotide operatively linked to a promoter of RNA transcription, as well as other regulatory sequences for replication and/or transient or stable expression of the DNA or RNA. As used herein, the term "operatively linked" means positioned in such a manner that the promoter will direct transcription of RNA off the DNA molecule. Examples of such promoters are SP6, T4 and T7. In certain embodiments, cell-specific promoters are used for cell-specific expression of the inserted polynucleotide. Vectors which contain a promoter or a promoter/enhancer, with termination codons and selectable marker sequences, as well as a cloning site into which an inserted piece of DNA can be operatively linked to that promoter are known in the art and commercially available. For general methodology and cloning strategies, see Gene Expression Technology (Goeddel ed., Academic Press, Inc. (1991)) and references cited therein and Vectors: Essential Data Series (Gacesa and Ramji, eds., John Wiley & Sons, N.Y. (1994)) which contains maps, functional properties, commercial suppliers and a reference to GenEMBL accession numbers for various suitable vectors.

In one embodiment, polynucleotides derived from the polynucleotides disclosed herein encode polypeptides or proteins having diagnostic and therapeutic utilities as described herein as well as probes to identify transcripts of the protein that may or may not be present. These nucleic acid fragments can by prepared, for example, by restriction enzyme digestion of larger polynucleotides and then labeled with a detectable marker. Alternatively, random fragments can be generated using nick translation of the molecule. For methodology for the preparation and labeling of such fragments, see, Sambrook et al. (1989) supra.

Expression vectors containing these nucleic acids are useful to obtain host vector systems to produce proteins and polypeptides. It is implied that these expression vectors must be replicable in the host organisms either as episomes or as an integral part of the chromosomal DNA. Non-limiting examples of suitable expression vectors include plasmids, yeast vectors, viral vectors and liposomes. Adenoviral vectors are particularly useful for introducing genes into tissues in vivo because of their high levels of expression and efficient transformation of cells both in vitro and in vivo. When a nucleic acid is inserted into a suitable host cell, e.g., a prokaryotic or a eukaryotic cell and the host cell replicates, the protein can be recombinantly produced. Suitable host cells will depend on the vector and can include mammalian cells, animal cells, human cells, simian cells, insect cells, yeast cells, and bacterial cells constructed using known methods. See, Sambrook et al. (1989) supra. In addition to the use of viral vector for insertion of exogenous nucleic acid into cells, the nucleic acid can be inserted into the host cell by methods known in the art such as transformation for bacterial cells; transfection using calcium phosphate precipitation for mammalian cells; or DEAE-dextran; electroporation; or microinjection. See, Sambrook et al. (1989) supra, for methodology. Thus, this disclosure also provides a host cell, e.g., a mammalian cell, an animal cell (rat or mouse), a human cell, or a prokaryotic cell such as a bacterial cell, containing a polynucleotide encoding a protein or polypeptide or antibody.

A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment disclosed herein that is a polynucleotide encompasses both the double-stranded form and each of two complementary single-stranded forms known or predicted to make up the double-stranded form.

When the vectors are used for gene therapy in vivo or ex vivo, a pharmaceutically acceptable vector, such as a replication-incompetent retroviral or adenoviral vector, are exemplary (but non-limiting) and may be of particular use. Pharmaceutically acceptable vectors containing the nucleic acids disclosed herein can be further modified for transient or stable expression of the inserted polynucleotide. As used herein, the term "pharmaceutically acceptable vector" includes, but is not limited to, a vector or delivery vehicle having the ability to selectively target and introduce the nucleic acid into dividing cells. An example of such a vector is a "replication-incompetent" vector defined by its inability to produce viral proteins, precluding spread of the vector in the infected host cell. An example of a replication-incompetent retroviral vector is LNL6 (Miller et al. (1989) Bio-Techniques 7:980-990). The methodology of using replication-incompetent retroviruses for retroviral-mediated gene transfer of gene markers has been established. (Bordignon (1989) PNAS USA 86:8912-8952; Culver (1991) PNAS USA 88:3155; and Rill (1991) Blood 79(10):2694-2700).

This disclosure also provides genetically modified cells that contain and/or express the polynucleotides disclosed herein. The genetically modified cells can be produced by insertion of upstream regulatory sequences such as promoters or gene activators (see, U.S. Pat. No. 5,733,761).

The polynucleotides can be conjugated to a detectable marker, e.g., an enzymatic label or a radioisotope for detection of nucleic acid and/or expression of the gene in a cell. A wide variety of appropriate detectable markers are known in the art, including fluorescent, radioactive, enzymatic or other ligands, such as avidin/biotin, which are capable of giving a detectable signal. In one aspect, one will likely desire to employ a fluorescent label or an enzyme tag, such as urease, alkaline phosphatase or peroxidase, instead of radioactive or other environmentally undesirable reagents. In the case of enzyme tags, calorimetric indicator substrates can be employed to provide a means visible to the human eye or spectrophotometrically, to identify specific hybridization with complementary nucleic acid-containing samples. Thus, this disclosure further provides a method for detecting a single-stranded polynucleotide or its complement, by contacting target single-stranded polynucleotide with a labeled, single-stranded polynucleotide (a probe) which is a portion of the polynucleotide disclosed herein under conditions permitting hybridization (optionally moderately stringent hybridization conditions) of complementary single-stranded polynucleotides, or optionally, under highly stringent hybridization conditions. Hybridized polynucleotide pairs are separated from un-hybridized, single-stranded polynucleotides. The hybridized polynucleotide pairs are detected using methods known to those of skill in the art and set forth, for example, in Sambrook et al. (1989) supra.

The polynucleotide embodied in this disclosure can be obtained using chemical synthesis, recombinant cloning methods, PCR, or any combination thereof. Methods of chemical polynucleotide synthesis are known in the art and need not be described in detail herein. One of skill in the art can use the sequence data provided herein to obtain a desired polynucleotide by employing a DNA synthesizer or ordering from a commercial service.

The polynucleotides disclosed herein can be isolated or replicated using PCR. The PCR technology is the subject matter of U.S. Pat. Nos. 4,683,195; 4,800,159; 4,754,065; and 4,683,202 and described in PCR: The Polymerase Chain Reaction (Mullis et al. eds., Birkhauser Press, Boston (199.4)) or MacPherson et al. (1991) and (1995) supra, and references cited therein. Alternatively, one of skill in the art can use the sequences provided herein and a commercial DNA synthesizer to replicate the DNA. Accordingly, this disclosure also provides a process for obtaining the polynucleotides disclosed herein by providing the linear sequence of the polynucleotide, nucleotides, appropriate primer molecules, chemicals such as enzymes and instructions for their replication and chemically replicating or linking the nucleotides in the proper orientation to obtain the polynucleotides. In a separate embodiment, these polynucleotides are further isolated. Still further, one of skill in the art can insert the poly-nucleotide into a suitable replication vector and insert the vector into a suitable host cell (prokaryotic or eukaryotic) for replication and amplification. The DNA so amplified can be isolated from the cell by methods known to those of skill in the art. A process for obtaining polynucleotides by this method is further provided herein as well as the polynucleotides so obtained.

RNA can be obtained by first inserting a DNA polynucleotide into a suitable host cell. The DNA can be delivered by any appropriate method, e.g., by the use of an appropriate gene delivery vehicle (e.g., liposome, plasmid or vector) or by electroporation. When the cell replicates and the DNA is transcribed into RNA; the RNA can then be isolated using methods known to those of skill in the art, for example, as set forth in Sambrook et al. (1989) supra. For instance, mRNA can be isolated using various lytic enzymes or chemical solutions according to the procedures set forth in Sambrook et al. (1989) supra, or extracted by nucleic-acid-binding resins following the accompanying instructions provided by manufactures.

Polynucleotides exhibiting sequence complementarity or homology to a polynucleotide disclosed herein are useful as hybridization probes or as an equivalent of the specific polynucleotides identified herein. Since the full coding sequence of the transcript is known, any portion of this sequence or homologous sequences can be used in the methods disclosed herein.

It is known in the art that a "perfectly matched" probe is not needed for a specific hybridization. Minor changes in probe sequence achieved by substitution, deletion or insertion of a small number of bases do not affect the hybridization specificity. In general, as much as 20% base-pair mismatch (when optimally aligned) can be tolerated. In some embodiments, a probe useful for detecting the aforementioned mRNA is at least about 80% identical to the homologous region. In some embodiments, the probe is 85% identical to the corresponding gene sequence after alignment of the homologous region; in some embodiments, it exhibits 90% identity.

These probes can be used in radioassays (e.g., Southern and Northern blot analysis) to detect, prognose, diagnose or monitor various cells or tissues containing these cells. The probes also can be attached to a solid support or an array such as a chip for use in high throughput screening assays for the detection of expression of the gene corresponding a polynucleotide disclosed herein. Accordingly, this disclosure also provides a probe comprising or corresponding to a polynucleotide disclosed herein, or its equivalent, or its complement, or a fragment thereof, attached to a solid support for use in high throughput screens.

The total size of fragment, as well as the size of the complementary stretches, will depend on the intended use or application of the particular nucleic acid segment. Smaller fragments will generally find use in hybridization embodiments, wherein the length of the complementary region may be varied, such as between at least 5 to 10 to about 100 nucleotides, or even full length according to the complementary sequences one wishes to detect.

Nucleotide probes having complementary sequences over stretches greater than 5 to 10 nucleotides in length are generally well suited, so as to increase stability and selectivity of the hybrid, and thereby improving the specificity of particular hybrid molecules obtained. In certain embodiments, one can design polynucleotides having gene-complementary stretches of 10 or more or more than 50 nucleotides in length, or even longer where desired. Such fragments may be readily prepared by, for example, directly synthesizing the fragment by chemical means, by application of nucleic acid reproduction technology, such as the PCR technology with two priming oligonucleotides as described in U.S. Pat. No. 4,603,102 or by introducing selected sequences into recombinant vectors for recombinant production. In one aspect, a probe is about 50-75 or more alternatively, 50-100, nucleotides in length.

The polynucleotides of the present disclosure can serve as primers for the detection of genes or gene transcripts that are expressed in cells described herein. In this context, amplification means any method employing a primer-dependent polymerase capable of replicating a target sequence with reasonable fidelity. Amplification may be carried out by natural or recombinant DNA-polymerases such as T7 DNA polymerase, Klenow fragment of E. coli DNA polymerase, and reverse transcriptase. For illustration purposes only, a primer is the same length as that identified for probes.

One method to amplify polynucleotides is PCR and kits for PCR amplification are commercially available. After amplification, the resulting DNA fragments can be detected by any appropriate method known in the art, e.g., by agarose gel electrophoresis followed by visualization with ethidium bromide staining and ultraviolet illumination.

Methods for administering an effective amount of a gene delivery vector or vehicle to a cell have been developed and are known to those skilled in the art and described herein. Methods for detecting gene expression in a cell are known in the art and include techniques such as in hybridization to DNA microarrays, in situ hybridization, PCR, RNase protection assays and Northern blot analysis. Such methods are useful to detect and quantify expression of the gene in a cell. Alternatively expression of the encoded polypeptide can be detected by various methods.

In particular it is useful to prepare polyclonal or monoclonal antibodies that are specifically reactive with the target polypeptide. Such antibodies are useful for visualizing cells that express the polypeptide using techniques such as immunohistology, ELISA, and Western blotting. These techniques can be used to determine expression level of the expressed polynucleotide.

Antibodies and Derivatives Thereof

This disclosure also provides an antibody that binds and/or specifically recognizes and binds an isolated polypeptide for use in the methods disclosed herein. The antibody can be any of the various antibodies described herein, non-limiting, examples of such include a polyclonal antibody, a monoclonal antibody, a chimeric antibody, a human antibody, a veneered antibody, a diabody, a humanized antibody, an antibody derivative, a recombinant humanized antibody, or a derivative or fragment of each thereof. In one aspect, the fragment comprises, or alternatively consists essentially of, or yet further consists of the CDR of the antibody. In one aspect, the antibody is detectably labeled or further comprises a detectable label conjugated to it. Also provided is a hybridoma cell line that produces a monoclonal antibody disclosed herein. Compositions comprising or alternatively consisting essentially of or yet further, consisting of one or more of the above embodiments are further provided herein. Further provided are polynucleotides that encode the amino acid sequence of the antibodies and fragments as well as methods to produce recombinantly or chemically synthesize the antibody polypeptides and fragments thereof. The antibody polypeptides can be produced in a eukaryotic or prokaryotic cell, or by other methods known in the art and described herein.

Examples of CDR sequences include without limitation comprise, consist essentially of, or yet further consist of, the following: the heavy chain variable region of the antibody or a fragment thereof comprises, or alternatively consists essentially of, or yet further consists of, the polypeptide encoded by the below polynucleotide sequence:

SEQ ID NO. (358): Non-limiting exemplary heavy
chain variable region nucleotide sequence, IhfA5
fragment
GAGGTGCAGCTGCAGGAGTCTGGACCTGGCCTGGTGACGCCCTCACAGAG

CCTGTCCATGACTTGCACTGTCTCTGGGTTTTCATTAACCAGCTATAGTG

TACACTGGGTTCGCCAGCCTCCAGGAAAGAGTCTGGAGTGGCTGGGAGTA

ATATGGGCTGGTGGAAGCACAAATTATAATTCGGCTCTCATGTCCAGACT

GAGCATCAGCAAAGACAACTCCAAGAGCCAAGTTTTCTTAAAAATGGACA

GTCTGCAAACTGATGACACAGCCATATACTACTGTGCCAGAGAGGACTCC

TGGGGTCAAGGAACCTCAGTCACCGTCTCCTCA

In some embodiments, the heavy chain variable region of the antibody or a fragment thereof comprises, or alternatively consists essentially of, or yet further consists of, the amino acid sequence:

SEQ ID NO. (359): Non-limiting exemplary heavy
chain variable region amino acid sequence, IhfA5
fragment
EVQLQESGPGLVTPSQSLSMTCTVSGFSLTSYSVHWVRQPPGKSLEWLGV

IWAGGSTNYNSALMSRLSISKDNSKSQVFLKMDSLQTDDTAIYYCAREDS

WGQGTSVTVSS

In some embodiments, the light chain variable region of the antibody or a fragment thereof comprises, or alternatively consists essentially of, or yet further consists of, the polypeptide encoded by the below polynucleotide sequence:

SEQ ID NO. (360): Non-limiting exemplary light
chain variable region nucleotide sequence, IhfA5
fragment
GACATTGTGATGACCCAGTCTCAAAAATTCATGTCCACATCAGTAGGAGA

CAGGGTCAGCGTCACCTGCAAGGCCAGTCAGAATGTGGGTACTAATGTAG

CCTGGTATCAACAGAAACCAGGGCAATCTCCTAAAGCACTGATTTACTCG

GCATCCTACCGGTACAGTGGAGTCCCTGATCGCTTCACAGGCAGTGGATC

TGGGACAGATTTCACTCTCACCATCAGCAATGTGCAGTCTGAAGACTTGG

CAGAGTATTTCTGTCAGCAATATAACAGCTATCCCACGTTCGGAGGGGGG

ACCAAGTTGGAAATAAAA

In some embodiments, the light chain variable region of the antibody or a fragment thereof comprises, or alternatively consists essentially of, or yet further consists of, the amino acid sequence:

SEQ ID NO. (361): Non-limiting exemplary light
chain variable region amino acid sequence, IhfA5
fragment
DIVMTQSQKFMSTSVGDRVSVTCKASQNVGTNVAWYQQKPGQSPKALIYS

ASYRYSGVPDRFTGSGSGTDFTLTISNVQSEDLAEYFCQQYNSYPTFGGG

TKLEIK

In some embodiments the antibodies disclosed herein comprise, or alternatively consists essentially of, or yet further consists of, the polypeptide encoded by the polynucleotide sequence comprising one or more of the CDR sequences listed herein below:

SEQ ID NO. (362) Partial non-limiting exemplary
CDRH1 sequence, IhfA5 fragment
FSLTSYS SEQ ID NO. (363) Partial non-limiting exemplary
CDRH1 sequence, IhfA5 fragment
FSLTSYSV SEQ ID NO. (364): Partial non-limiting exemplary
CDRH1 sequence, IhfA5 fragment
FSLTSYSVH SEQ ID NO. (365): Partial non-limiting exemplary
CDRH1 sequence, IhfA5 fragment
GFSLTSYS SEQ ID NO. (366): Partial non-limiting exemplary
CDRH2 sequence, IhfA5 fragment
IWAGGST SEQ ID NO. (367): Partial non-limiting exemplary
CDRH2 sequence, IhfA5 fragment
VIWAGGST SEQ ID NO. (368): Partial non-limiting exemplary
CDRH2 sequence, IhfA5 fragment
GVIWAGGST SEQ ID NO. (369): Partial non-limiting exemplary
CDRH2 sequence, IhfA5 fragment
LGVIWAGGST SEQ ID NO. (370): Partial non-limiting exemplary
CDRH2 sequence, IhfA5 fragment
WLGVIWAGGST SEQ ID NO. (371): Partial non-limiting exemplary
CDRH2 sequence, IhfA5 fragment
IWAGGSTN SEQ ID NO. (372): Partial non-limiting exemplary
CDRH2 sequence, IhfA5 fragment
VIWAGGSTN SEQ ID NO. (373): Partial non-limiting exemplary
CDRH2 sequence, IhfA5 fragment
GVIWAGGSTN SEQ ID NO. (374): Partial non-limiting exemplary
CDRH2 sequence, IhfA5 fragment
LGVIWAGGSTN SEQ ID NO. (375): Partial non-limiting exemplary
CDRH2 sequence, IhfA5 fragment
WLGVIWAGGSTN SEQ ID NO. (376): Partial non-limiting exemplary
CDRH2 sequence, IhfA5 fragment
IWAGGSTNY SEQ ID NO. (377): Partial non-limiting exemplary
CDRH2 sequence, IhfA5 fragment
VIWAGGSTNY SEQ ID NO. (378): Partial non-limiting exemplary
CDRH2 sequence, IhfA5 fragment
GVIWAGGSTNY SEQ ID NO. (379): Partial non-limiting exemplary
CDRH2 sequence, IhfA5 fragment
LGVIWAGGSTNY SEQ ID NO. (380): Partial non-limiting exemplary
CDRH2 sequence, IhfA5 fragment
WLGVIWAGGSTNY SEQ ID NO. (381): Partial non-limiting exemplary
CDRH3 sequence, IhfA5 fragment
REDS

```
SEQ ID NO. (382): Partial non-limiting exemplary
CDRH3 sequence, IhfA5 fragment
AREDS SEQ ID NO. (383): Partial non-limiting exemplary
CDRL1 sequence, IhfA5 fragment
QNVGTN SEQ ID NO. (384): Partial non-limiting exemplary
CDRL1 sequence, IhfA5 fragment
QNVGTNV SEQ ID NO. (385): Partial non-limiting exemplary
CDRL1 sequence, IhfA5 fragment
QNVGTNVA SEQ ID NO. (386): Partial non-limiting exemplary
CDRL2 sequence, IhfA5 fragment
SAS SEQ ID NO. (387): Partial non-limiting exemplary
CDRL2 sequence, IhfA5 fragment
YSAS SEQ ID NO. (388): Partial non-limiting exemplary
CDRL2 sequence, IhfA5 fragment
IYSAS SEQ ID NO. (389) Partial non-limiting exemplary
CDRL2 sequence, IhfA5 fragment
LIYSAS SEQ ID NO. (390): Partial non-limiting exemplary
CDRL2 sequence, IhfA5 fragment
ALIYSAS SEQ ID NO. (391) Partial non-limiting exemplary
CDRL2 sequence, IhfA5 fragment
SASY SEQ ID NO. (392): Partial non-limiting exemplary
CDRL2 sequence, IhfA5 fragment
YSASY SEQ ID NO. (393): Partial non-limiting exemplary
CDRL2 sequence, IhfA5 fragment
IYSASY SEQ ID NO. (394): Partial non-limiting exemplary
CDRL2 sequence, IhfA5 fragment
LIYSASY SEQ ID NO. (395): Partial non-limiting exemplary
CDRL2 sequence, IhfA5 fragment
ALIYSASY SEQ ID NO (396): Partial non-limiting exemplary
CDRL2 sequence, IhfA5 fragment
SASYR SEQ ID NO. (397): Partial non-limiting exemplary
CDRL2 sequence, IhfA5 fragment
YSASYR SEQ ID NO. (398) Partial non-limiting exemplary
CDRL2 sequence, IhfA5 fragment
IYSASYR SEQ ID NO. (399): Partial non-limiting exemplary
CDRL2 sequence, IhfA5 fragment
LIYSASYR SEQ ID NO. (400): Partial non-limiting exemplary
CDRL2 sequence, IhfA5 fragment
ALIYSASYR SEQ ID NO. (401): Partial non-limiting exemplary
CDRL2 sequence, IhfA5 fragment
SASYRY SEQ ID NO. (402): Partial non-limiting exemplary
CDRL2 sequence, IhfA5 fragment
YSASYRY SEQ ID NO. (403): Partial non-limiting exemplary
CDRL2 sequence, IhfA5 fragment
IYSASYRY SEQ ID NO. (404): Partial non-limiting exemplary
CDRL2 sequence, IhfA5 fragment
LIYSASYRY SEQ ID NO. (405): Partial non-limiting exemplary
CDRL2 sequence, IhfA5 fragment
ALIYSASYRY SEQ ID NO. (406): Partial non-limiting exemplary
CDRL2 sequence, IhfA5 fragment
SASYRYS SEQ ID NO. (407): Partial non-limiting exemplary
CDRL2 sequence, IhfA5 fragment
YSASYRYS SEQ ID NO. (408): Partial non-limiting exemplary
CDRL2 sequence, IhfA5 fragment
IYSASYRYS SEQ ID NO. (409): Partial non-limiting exemplary
CDRL2 sequence, IhfA5 fragment
LIYSASYRYS SEQ ID NO. (410): Partial non-limiting exemplary
CDRL2 sequence, IhfA5 fragment
ALIYSASYRYS SEQ ID NO. (411): Partial non-limiting exemplary
CDRL3 sequence, IhfA5 fragment
QQYNSYP SEQ ID NO. (412): Partial non-limiting exemplary
CDRL3 sequence, IhfA5 fragment
QQYNSYPT
```

Antibodies can be generated using conventional techniques known in the art and are well-described in the literature. Several methodologies exist for production of polyclonal antibodies. For example, polyclonal antibodies are typically produced by immunization of a suitable mammal such as, but not limited to, chickens, goats, guinea pigs, hamsters, horses, mice, rats, and rabbits. An antigen is injected into the mammal, induces the B-lymphocytes to produce immunoglobulins specific for the antigen. Immunoglobulins may be purified from the mammal's serum. Antibodies specific to DNABII polypeptides, e.g., IHFα and IHFβ can be generated by injection of polypeptides corresponding to different epitopes of IHFα and IHFβ. For example, antibodies can be generated using the 20 amino acids of each subunit such as TFRPGQKLKSRVENASPKDE (SEQ ID NO:34) for IHFα and KYVPHFKPGKELRDRANIYG (SEQ ID NO:35) for IHFβ or A1 to A6 or B1 to B6 (See FIG. 18). Antibodies specific to the "tip" or "tail" portion of the DNABII protein or polypeptide can be generated. Additional non-limiting examples include without limitation a polypeptide fragment that comprises one or more of

```
MATITKLDIIEYISDKYHLS (also referred to herein as
hIFA1; (SEQ ID NO. 348));

KYHLSKQDTKNVVENFLEEI (also referred to herein as
hIFA2; (SEQ ID NO. 349));
```

```
FLEEIRLSLESGQDVKLSGF (also referred to herein as
hIFA3; (SEQ ID NO. 350));

KLSGFGNFELRDKSSRPGRN (also referred to herein as
hIFA4; (SEQ ID NO. 351));

RPGRNPKTGDVVPVSARRVV (also referred to herein as
hIFA5; (SEQ ID NO. 352));

ARRVVTFKPGQKLRARVEKTK (also referred to herein as
hIFA6; (SEQ ID NO. 353));
``` or an equivalent thereof. Other exemplary antibodies include monoclonal antibodies that specifically recognize and bind *Haemophilus influenzae* IhfA fragment A5 (SEQ ID NO. 352)). The hybridoma cell lines that produce monoclonal antibodies that specifically recognize and bind *Haemophilus influenzae* IhfA fragment A5 (SEQ ID NO. 352)) and IhfB4 (RGFGSFSLHHRQPRLGRNPK (also referred to B4 (SEQ ID NO. 345)); were deposited with American Type Culture Collection (ATCC) under Accession Numbers (IhfA5 (Accession No. PTA-122334)) and (IhfB4 (Accession No. PTA-122336)), pursuant to the provisions of the Budapest Treaty on Jul. 30, 2015; the respective hybridoma cell lines designated: IhfA5-NTHI 14 GB.F5.G6; and IhfB4-NTHI 4EII.E5.G2. Further non-limiting exemplary antibodies include those that specifically recognize and bind *Haemophilus influenzae* IhfA fragment A3 (SEQ ID NO. 350), IhfB fragment B2 (SEQ ID NO. 343) produced by hybridoma cell lines IhfA3 NTHI 9B10.F2.H3 and IhfB2 NTHI 7A4.E4.G4, respectively.

Further, non-limiting exemplary antibodies that fall within the scope of this disclosure include but are not limited to those disclosed in now abandoned U.S. Ser. No. 14/497,147, filed Sep. 25, 2014; U.S. Ser. No. 14/668,767, filed Mar. 25, 2015; and U.S. Ser. No. 14/789,842, filed Jul. 1, 2015, and provided under the following designations: TRL295, TRL299, TRL1012, TRL1068, TRL1070, TRL1087, TRL1215, TRL1216, TRL1218, TRL1230, TRL1232, TRL1242, TRL1245, TRL1330, TRL1335, TRL1337, TRL1338, TRL1341, TRL1347, and TRL1361, the heavy chain and light chain sequences of which are provided herein below.

```
TRL295 HC,
                                            SEQ ID NO: 413
QVQLVESGGGLVQPGGSLRLSCAASGFPFSSYAMSWVRQAPGKGLEWVSAISGNGADS
YYADSVKGRFTTSRDKSKNTVYLQMNRLRAEDTAVYYCAKDMRRYHDSSGLHFWG
QGTLVTVSS

TRL295 LC,
                                            SEQ ID NO: 414
DIELTQAPSVSVYPGQTARITCSGDALPKQYAYWYQQKPGQAPVVVIYKDSERPSGISER
FSGSSSGTTVTLTISGVQAGDEADYYCQSVDTSVSYYVVFGGGTKLTVL

TRL299 HC,
                                            SEQ ID NO: 415
QVQLVQSGGGLVQPGGSLRLSCAASGFTFSHYNMNWVRQAPGKGPEWVSYISSGSDIIY
YADSVKGRFTISRDNAKNSLYLQMNSLRDEDTAVYYCARALDRDGFDIWGQGTMVTV
SS

TRL299 LC,
                                            SEQ ID NO: 416
DIVLTQSPSSLSASVGDKVTITCRASQSISTFLNWYQHKPGKAPKLLIYGASSLQSGVPSR
FSGSGSGTDFTLTISSLQPEDFATYYCQQSYSTPTFGQGTKVEIK

TRL1012 HC,
                                            SEQ ID NO: 417
QVQLVESGGGLVQPGGSLRLSCAASGFPFSSYAMSWVRQAPGKGLEWVSAISGNGADS
YYADSVKGRFTTSRDKSKNTVYLQMNRLRAEDTAVYYCAKDMRRYHDSSGLHFWG
QGTLVTVSS

TRL1012 LC,
                                            SEQ ID NO: 418
DIMLTQPPSVSAAPGQKVTISCSGSSSNIGTNYVSWFQQVPGTAPKFLIYDNYKRPSETPD
RFSGSKSGTSATLDITGLQTGDEANYYCATWDSSLSAWVFGGGTKVTVL

TRL1068 HC,
                                            SEQ ID NO: 419
QVQLVESGPGLVKPSETLSLTCRVSGDSNRPSYWSWIRQAPGKAMEWIGYVYDSGVTIY
NPSLKGRVTISLDTSKTRFSLKLTSVIAADTAVYYCARERFDRTSYKSWWGQGTQVTVS
S

TRL1068 LC,
                                            SEQ ID NO: 420
DIVLTQAPGTLSLSPGDRATLSCRASQRLGGTSLAWYQHRSGQAPRLILYGTSNRATDTP
DRFSGSGSGTDFVLTISSLEPEDFAVYYCQQYGSPPYTFGQGTTLDIK

TRL1070 HC,
                                            SEQ ID NO: 421
QVQLVQSGGTLVQPGGSLRLSCAASGFTFSYYSMSWVRQAPGKGLEWVANIKHDGTER
NYVDSVKGRFTISRDNSEKSLYLQMNSLRAEDTAVYYCAKYYYGAGTNYPLKYWGQG
TRVTVSS
```

-continued

TRL1070 LC,
SEQ ID NO: 422
DILMTQSPSSLSASVGDRVTITCRASQGIRNDLGWYQQKPGKAPKLLIYAASSLQSGVPS
RFSGSGSGTDFTLTISSLQPEDFATYYCLQDYNYPLTFGGGTKVEIKR

TRL1087 HC,
SEQ ID NO: 423
QVQLLESGPGLVRPSDTLSLTCTFSADLSTNAYWTWIRQPPGKGLEWIGYMSHSGGRDY
NPSFNRRVTISVDTSKNQVFLRLTSVTSADTAVYFCVREVGSYYDYWGQGILVTVSS

TRL1087 LC,
SEQ ID NO: 424
DIEMTQSPSSLSASVGDRITITCRASQGISTWLAWYQQKPGKAPKSLIFSTSSLHSGVPSK
FSGSGSGTDFTLTITNLQPEDFATYYCQQKWETPYSFGQGTKLDMIR

TRL1215 HC,
SEQ ID NO: 425
QVQLVESGTEVKNPGASVKVSCTASGYKFDEYGVSWVRQSPGQGLEWMGWISVYNGK
TNYSQNFQGRLTLTTETSTDTAYMELTSLRPDDTAVYYCATDKNWFDPWGPGTLVTVS
S

TRL1215 LC,
SEQ ID NO: 426
DIVMTQSPSASGSPGQSITISCTGTNTDYNYVSWYQHHPGKAPKVIIYDVKKRPSGVPSR
FSGSRSGNTATLTVSGLQTEDEADYYCVSYADNNHYVFGSGTKVTVL

TRL1216 HC,
SEQ ID NO: 427
QVQLVESGGGVVQPGGSLRVSCAASAFSFRDYGIHWVRQAPGKGLQWVAVISHDGGK
KFYADSVRGRFTISRDNSENTLYLQMNSLRSDDTAVYYCARLVASCSGSTCTTQPAAFD
IWGPGTLVTVSS

TRL1216 LC,
SEQ ID NO: 428
DIMLTQPPSVSVSPGQTARITCSGDALPKKYTYWYQQKSGQAPVLLIYEDRKRPSEIPER
FSAFTSWTTATLTITGAQVRDEADYYCYSTDISGDIGVFGGGTKLTVL

TRL1218 HC,
SEQ ID NO: 429
QVQLLESGADMVQPGRSLRLSCAASGFNFRTYAMHWVRQAPGKGLEWVAVMSHDGY
TKYYSDSVRGQFTISRDNSKNTLYLQMNNLRPDDTAIYYCARGLTGLSVGFDYWGQGT
LVTVSS

TRL1218 LC,
SEQ ID NO: 430
DIVLTQSASVSGSPGQSITISCTGTSSDVGGYNYVSWYQQHPGKAPKLMIYDVTTRPSGV
SDRFSGSKSGNTASLTISGLQAEDEADYYCSSYSSGSTPALFGGGTQLTVL

TRL1230 HC,
SEQ ID NO: 431
QVQLVQSGGGLVKPGGSLRLSCGASGFNLSSYSMNWVRQAPGKGLEWVSSISSRSSYIY
YADSVQGRFTISRDNAKNSLYLQMNSLRAEDTAIYYCARVSPSTYYYYGMDVWGQGT
TVTVSS

TRL1230 LC,
SEQ ID NO: 432
DIVLTQPSSVSVSPGQTARITCSGDELPKQYAYWYQQKPGQAPVLVIYKDNERPSGIPER
FSGSSSGTTVTLTISGVQAEDEADYYCQSADSSGTYVVFGGGTKLTVL

TRL1232 HC,
SEQ ID NO: 433
QVQLVESGAEVKKPGALVKVSCKASGYTFSGYYMHWVRQAPGQGLEWMGWINPKSG
GTKYAQKFQGRVTMTRDTSISTAYMELSRLRSDDTAVYFCARGGPSNLERFLERLQPRY
SYDDKYAMDVWGQGTTVTVSS

TRL1232 LC,
SEQ ID NO: 434
DIVMTQSPGTLSLSPGARATLSCRASQSVSSIYLAWYQQKPGQAPRLLIFGASSRATGIPD
RFSGSGSGTDFTLTISRLEPEDFAVYYCQQYGSSPYTFGQGTKLEIKR

TRL1242 HC,
SEQ ID NO: 435
QVQLVQSGTEVKKPGESLKISCEGSRYNFARYWIGWVRQMPGKGLDWMGIIYPGDSDT
RYSPSFQGQVSISADKSISTAYLQWNSLKASDTAMYYCARLGSELGVVSDYYFDSWGQ
GTLVTVSS

TRL1242 LC, SEQ ID NO: 436
DIVLTQSPDSLAVSLGERATINCKSSQSVLDRSNNKNCVAWYQQKPGQPPKLLIYRAAT
RESGVPDRFSGSGSGTDFSLTISSLQAEDVAVYFCQQYYSIPNTFGQGTKLEIKR

TRL1245 HC, SEQ ID NO: 437
QVQLVESGGGLVKAGGSLRLSCVASGFTFSDYYMSWIRQAPGKGLEWISFISSSGDTIFY
ADSVKGRFTVSRDSAKNSLYLQMNSLKVEDTAVYYCARKGVSDEELLRFWGQGTLVT
VSS

TRL1245 LC, SEQ ID NO: 438
DIVLTQDPSVSVSPGQTARITCSGDALPKKYAYWYQQKSGQAPVLVIYEDTKRPSGIPER
FSGSSSGTVATLTISGAQVEDEADYYCYSTDSSGNQRVFGGGTKLTVL

TRL1330 HC, SEQ ID NO: 439
QVQLVESGTEVKNPGASVKVSCTASGYKFDEYGVSWVRQSPGQGLEWMGWISVYNGK
TNYSQNFQGRLTLTTETSTDTAYMELTSLRPDDTAVYYCATDKNWFDPWGPGTLVTVS
S

TRL1330 LC, SEQ ID NO: 440
DIVLTQSPSASGSPGQSITISCTGTNTDYNYVSWYQHHPGKAPKVIIYDVKKRPSGVPSRF
SGSRSGNTATLTVSGLQTEDEADYYCVSYADNNHYVFGSGTKVTVL

TRL1335 HC, SEQ ID NO: 441
QVQLVESGAEVKKPGESLKISCKGSGYNFTSYWIGWVRQMPGKGLEWMGVIYPDDSDT
RYSPSFKGQVTISADKSISTAFLQWSSLKASDTAVYHCARPPDSWGQGTLVTVSS

TRL1335 LC, SEQ ID NO: 442
DIVMTQSPATLSVSPGERATLSCRASQSVSSNLAWYQQKPGLAPRLLIVGASNRATGIPA
RFSGSGSGTEFTLTISSLQSEDFAFYYCQQYNNWPFTFGPGTKVDVKR

TRL1337 HC, SEQ ID NO: 443
QVQLLESGPGLVKPSETPSLTCTVSGGSIRSYYWSWIRQPPGKGLEWIGYIYYSGSTNYN
PSLKSRVTISVDMSKNQFSLKLSSVTAADTAMYYCARVYGGSGSYDFDYWGQGTLVTV
SS

TRL1337 LC, SEQ ID NO: 444
DIVLTQSPSASGSPGQSVTISCTGTSSDVGGYNYVSWYQQLPGKAPKLMIYEVTKRPSGV
PDRFSGSKSGNTASLTVSGLQAEDEADYYCSSFAGSNNHVVFGGGTKLTVL

TRL1338 HC, SEQ ID NO: 445
QVQLTLRESGPTLVKPTQTLTLTCTFSGFSLSTNGVGVGWIRQPPGKALEWLAIIYWDDD
KRYSPSLKSRLTITKDTSKNQVVLTLTNMDPVDTGTYYCAHILGASNYWTGYLRYYFD
YWGQGTLVTVST

TRL1338 LC, SEQ ID NO: 446
DIEMTQSPSVSVSPGQTARITCSGEPLAKQYAYWYQQKSGQAPVVVIYKDTERPSGIPER
FSGSSSGTTVTLTISGVQAEDEADYHCESGDSSGTYPVFGGGTKLTVL

TRL1341 HC, SEQ ID NO: 447
QVQLQESGGGLVQPGGSLKLSCAASGFIFSGSTMHWVRQASGKGLEWVGRIRSKTNNY
ATAYAASVKGRFTISRDDSKNTAYLQMNSLKTEDTAVYYCISLPGGYSSGQGTLVTVSS

TRL1341 LC, SEQ ID NO: 448
DIMLTQPPSVSVSPGQTARITCSGDALPKKYTYWYQQKSGQAPVLVIYEDSKRPSEIPER
FSAFTSWTTATLTITGAQVGDEADYYCYSTDITGDIGVFGGGTKLTVL

TRL1347 HC, SEQ ID NO: 449
QVQLVQSGGGLVQPGGSLKVSCVGSGFTFSASTIHWVRQASGKGLEWVGRIRSKANNY
ATVSAASLKGRFTISRDDSKNTAYLQVNSLKIEDTAIYYCTRPTACGDRVCWHGAWGQ
GTQVTVSP

TRL1347 LC, SEQ ID NO: 450
DIVLTQSPSASGTPGQRVTISCSGSRSNLGNNNVNWYQQLPGTAPKLLIFDNNERPSGVP
GRFSGSKSGTSASLAISGLRSEDEADYYCASWDDSLNGWVFGGGTKVTVL

-continued

TRL1361 HC,
SEQ ID NO: 451
QVQLVESGGGLAQPGGSLRLSCAASGFIFNTYAMGWVRQAPGKGLEWVSTVSAPGAG
TYYTDSVKGRFIISRDNSKNILYLQMNRLRVEDTAVYYCARDQGGPAVAGARIFDYWG
QGALVTVSS

TRL1361 LC,
SEQ ID NO: 452
DIVLTQSPLSLSVTPGQPASISCKSSQSLLRSDGKTYLCWYLQKPGQPPQLLIYEVSNRVS
GVPDRFSGSGSGTDFTLKISRVEAEDVGVYYCMQSIQLRTFGQGTKVEIKR

Further non-limiting exemplary antibodies contemplated are antibodies having the CDR regions of the above-noted TRL295, TRL299, TRL1012, TRL1068, TRL1070, TRL1087, TRL1215, TRL1216, TRL1218, TRL1230, TRL1232, TRL1242, TRL1245, TRL1330, TRL1335, TRL1337, TRL1338, TRL1341, TRL1347, and TRL1361. Methods of identifying CDR regions are known in the art. For example, CDR predictions may be made based on the heavy and/or light chain sequences—e.g. based on the Kabat, Clothia, AbM, or contact definitions of CDR specificity; details of these CDR prediction methods are known in the art (see, e.g., bioinf.org.uk/abs/#cdrid), utilizing the CDR prediction algorithms provided by the Ofran Lab (Paratome available at ofranservices.biu.ac.il/site/services/paratome/index.html) and Green Mountain Antibodies' CDR prediction program, and/or other commercially available resources.

The disclosed antibodies are known to bind to DNABII proteins. For example. TRL295 is reported to bind to residues 61-80 of *Haemophilus influenzae* IHF—also known as IhfA5. TRL1068 and TRL1337 are reported to exhibit high affinity binding for the amino acid fragments AARKGRNPQTGKEID (SEQ ID NO: 453) and KGRNPQTGKEIDIPA (SEQ ID NO: 454) of *Staphylococcus aureus* HU (SEQ ID NO: 59). TRL1330 is reported to exhibit high affinity binding for the amino acid fragment KGRNPQTGKEIDI (SEQ ID NO: 455) of *Staphylococcus aureus* HU (SEQ ID NO: 59). TRL1338 is reported to exhibit high affinity binding for the amino acid fragment VPAFKAGKALKDAVK (SEQ ID NO: 456) of *Staphylococcus aureus* HU (SEQ ID NO: 59). TRL1361 is reported to exhibit high affinity binding for the amino acid fragments SLAKGEKVQLIGFGN (SEQ ID NO: 457) and KGEKVQLIGFGNFEV (SEQ ID NO: 458) of *Staphylococcus aureus* HU (SEQ ID NO: 59).

Variations of this methodology include modification of adjuvants, routes and site of administration, injection volumes per site and the number of sites per animal for optimal production and humane treatment of the animal. For example, adjuvants typically are used to improve or enhance an immune response to antigens. Most adjuvants provide for an injection site antigen depot, which allows for a stow release of antigen into draining lymph nodes. Other adjuvants include surfactants which promote concentration of protein antigen molecules over a large surface area and immunostimulatory molecules. Non-limiting examples of adjuvants for polyclonal antibody generation include Freund's adjuvants, Ribi adjuvant system, and Titermax. Polyclonal antibodies can be generated using methods known in the art some of which are described in U.S. Pat. Nos. 7,279,559; 7,119,179; 7,060,800; 6,709,659; 6,656,746; 6,322,788; 5,686,073; and 5,670,153.

Monoclonal antibodies can be generated using conventional hybridoma techniques known in the art and well-described in the literature. For example, a hybridoma is produced by fusing a suitable immortal cell line (e.g., a myeloma cell line such as, but not limited to, Sp2/0, Sp2/0-AG14, NSO, NS1, NS2, AE-1, L.5, P3X63Ag8,653, Sp2 SA3, Sp2 MAI, Sp2 SS1, Sp2 SA5, U397, MIA 144, ACT IV, MOLT4, DA-1, JURKAT, WEHI, K-562, COS, RAJI, NIH 313, HL-60, MLA 144, NAMAIWA, NEURO 2A, CHO, PerC.6, YB2/O) or the like, or heteromyelomas, fusion products thereof, or any cell or fusion cell derived there from, or any other suitable cell line as known in the art (see, those at the following web addresses, e.g., atcc.org, lifetech.com, last accessed on Nov. 26, 2007), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. Antibody producing cells can also be obtained from the peripheral blood or, in particular embodiments, the spleen or lymph nodes, of humans or other suitable animals that have been immunized with the antigen of interest and then screened for the activity of interest. Any other suitable host cell can also be used for expressing-heterologous or endogenous nucleic acid encoding an antibody, specified fragment or variant thereof, of the present disclosure. The fused cells (hybridomas) or recombinant cells can be isolated using selective culture conditions or other suitable known methods, and cloned by limiting dilution or cell sorting, or other known methods.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, cDNA, or the like, display library; e.g., as available from various commercial vendors such as MorphoSys (Martinsreid/Planegg, Del.), Biolnvent (Lund, Sweden), Affitech (Oslo, Norway) using methods known in the art. Art known methods are described in the patent literature some of which include U.S. Pat. Nos. 4,704,692; 5,723,323; 5,763,192; 5,814,476; 5,817,483; 5,824,514; and 5,976,862. Alternative methods rely upon immunization of transgenic animals (e.g., SCID mice, Nguyen et al. (1977) Microbiol. Immunol. 41:901-907 (1997); Sandhu et al. (1996) Crit, Rev. Biotechnol. 16:95-118; Eren et al. (1998) Mumma 93:154-161 that are capable of producing a repertoire of human antibodies, as known in the art and/or as described herein. Such techniques, include, but are not limited to, ribosome display Wanes et al. (1997) Proc. Natl. Acad. Sci. USA 94:4937-4942; Hanes et al. (1998) Proc. Natl. Acad. Sci. USA 95:14130-14135); single cell antibody producing technologies (e.g., selected lymphocyte antibody method ("SLAM") (U.S. Pat. No. 5,627,052;

Wen et al. (1987) J. Immunol 17:887-892; Babcook et al. (1996) Proc. Natl. Acad. Sci. USA 93:7843-7848); gel microdroplet and flow cytometry (Powell et al. (1990) Biotechnol. 8:333-337; One Cell Systems, (Cambridge, Mass.); Gray et al. (1995) J. Imm. Meth. 182:155-163; and Kenny et al. (1995) Bio. Technol. 13:787-790); B-cell selection (Steenbakkers et al. (1994) Molec. Biol. Reports 19:125-134).

Antibody derivatives of the present disclosure can also be prepared by delivering a polynucleotide encoding an antibody disclosed herein to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873,316; 5,849,992; 5,994,616; 5,565,362; and 5,304,489.

The term "antibody derivative" includes post-translational modification to linear polypeptide sequence of the antibody or fragment. For example, U.S. Pat. No. 6,602,684 B1 describes a method for the generation of modified glycol-forms of antibodies, including whole antibody molecules, antibody fragments, or fusion proteins that include a region equivalent to the Fc region of an immunoglobulin, having enhanced Fe-mediated cellular toxicity, and glycoproteins so generated.

The antibodies disclosed herein also include derivatives that are modified by the covalent attachment of any type of molecule to the antibody such that covalent attachment does not prevent the antibody from generating an anti-idiotypic response. Antibody derivatives include, but are not limited to, antibodies that have been modified by glycosylation, acetylation, pegylation, phosphorylation, amidation, derivatization by known protecting/blocking groups, proteolytic cleavage, linkage to a cellular ligand or other protein, etc. Additionally, the derivatives may contain one or more non-classical amino acids.

Antibody derivatives also can be prepared by delivering a polynucleotide disclosed herein to provide transgenic plants and cultured plant cells (e.g., but not limited to tobacco, maize, and duckweed) that produce such antibodies, specified portions or variants in the plant parts or in cells cultured therefrom. For example, Cramer et al. (1999) Curr. Top. Microbol. Immunol. 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al. (1999) Adv. Exp. Med. Biol. 464:127-147 and references cited therein. Antibody derivatives have also been produced in large amounts from transgenic plant seeds including antibody fragments, such as single chain antibodies (scFv's), including tobacco seeds and potato tubers. See, e.g., Conrad et al. (1998) Plant Mol. Biol. 38:101-109 and references cited therein. Thus, antibodies can also be produced using transgenic plants, according to know methods.

Antibody derivatives also can be produced, for example, by adding exogenous sequences to modify immunogenicity or reduce, enhance or modify binding, affinity, on-rate, off-rate, avidity, specificity, half-life, or any other suitable characteristic. Generally part or all of the non-human or human CDR sequences are maintained while the non-human sequences of the variable and constant regions are replaced with human or other amino acids or variable or constant regions from other isotypes.

In general, the CDR residues are directly and most substantially involved in influencing antigen binding. Humanization or engineering of antibodies can be performed using any known method such as, but not limited to, those described in U.S. Pat. Nos. 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567.

Chimeric, humanized or primatized antibodies of the present disclosure can be prepared based on the sequence of a reference monoclonal antibody prepared using standard molecular biology techniques. DNA encoding the heavy and light chain immunoglobulins can be obtained from the hybridoma of interest and engineered to contain non-reference (e.g., human) immunoglobulin sequences using standard molecular biology techniques. For example, to create a chimeric antibody, the murine variable regions can be linked to human constant regions using methods known in the art (U.S. Pat. No. 4,816,567). To create a humanized antibody, the murine CDR regions can be inserted into a human framework using methods known in the art (U.S. Pat. Nos. 5,225,539 and 5,530,101; 5,585,089; 5,693,762; and 6,180,370). Similarly, to create a primatized antibody the murine CDR regions can be inserted into a primate framework using methods known in the art (WO 93/02108 and WO 99/55369).

Techniques for making partially to fully human antibodies are known in the art and any such techniques can be used. According to one embodiment, fully human antibody sequences are made in a transgenic mouse which has been engineered to express human heavy and light chain antibody genes. Multiple strains of such transgenic mice have been made which can produce different classes of antibodies. B cells from transgenic mice which are producing a desirable antibody can be fused to make hybridoma cell lines for continuous production of the desired antibody. (See for example, Russel et al. (2000) Infection and Immunity April 2000:1820-1826; Gallo et al. (2000) European J. of Immun. 30:534-540; Green (1999) J. of Immun. Methods 231:11-23; Yang et al. (1999A) J. of Leukocyte Biology 66:401-410; Yang (1999B) Cancer Research 59(6):1236-1243; Jakobovits (1998) Advanced Drug Reviews 31:33-42; Green and Jakobovits (1998) J. Exp. Med. 188(3):483-495; Jakobovits (1998) Exp. Opin. Invest. Drugs 7(4):607-614; Tsuda et al. (1997) Genomics 42:413-421; Sherman-Gold (1997) Genetic Engineering News 17(14); Mendez et al. (1997) Nature Genetics 15:146-156; Jakobovits (1996) Weir's Handbook of Experimental Immunology, The Integrated Immune System Vol. IV, 194.1-194.7; Jakobovits (1995) Current Opinion in Biotechnology 6:561-566; Mendez et al. (1995) Genomics 26:294-307; Jakobovits (1994) Current Biology 4(8):761-763; Arbones et al. (1994) Immunity 1(4):247-260; Jakobovits (1993) Nature 362(6417):255-258; Jakobovits et al. (1993) Proc. Natl. Acad. Sci. USA 90(6):2551-2555; and U.S. Pat. No. 6,075,181.)

The antibodies disclosed herein also can be modified to create chimeric antibodies. Chimeric antibodies are those in which the various domains of the antibodies' heavy and light chains are coded for by DNA from more than one species. See, e.g., U.S. Pat. No. 4,816,567.

Alternatively, the antibodies disclosed herein can also be modified to create veneered antibodies. Veneered antibodies are those in which the exterior amino acid residues of the antibody of one species are judiciously replaced or "veneered" with those of a second species so that the antibodies of the first species will not be immunogenic in the second species thereby reducing the immunogenicity of the antibody. Since the antigenicity of a protein is primarily dependent on the nature of its surface, the immunogenicity of an antibody could be reduced by replacing the exposed residues which differ from those usually found in another mammalian species antibodies. This judicious replacement of exterior residues should have little, or no, effect on the interior domains, or on the interdomain contacts. Thus, ligand binding properties should be unaffected as a consequence of alterations which are limited to the variable region framework residues. The process is referred to as "veneering" since only the outer surface or skin of the antibody is altered, the supporting residues remain undisturbed.

The procedure for "veneering" makes use of the available sequence data for human antibody variable domains compiled by Kabat et al. (1987) Sequences of Proteins of Immunological interest, 4th ed., Bethesda, Md., National Institutes of Health, updates to this database, and other accessible U.S. and foreign databases (both nucleic acid and protein). Non-limiting examples of the methods used to generate veneered antibodies include EP 519596; U.S. Pat. No. 6,797,492; and described in Padlan et al. (1991) Mol. Immunol. 28(4-5):489-498.

The term "antibody derivative" also includes "diabodies" which are small antibody fragments with two antigen-binding sites, wherein fragments comprise a heavy chain variable domain (VH) connected to a light chain variable domain (VL) in the same polypeptide chain. (See for example, EP 404,097; WO 93/11161; and Hollinger et al. (1993) Proc. Natl. Acad. Sci. USA 90:6444-6448.) By using a linker that is too short to allow pairing between the two domains on the same chain, the domains are forced to pair with the complementary domains of another chain and create two antigen-binding sites. (See also, U.S. Pat. No. 6,632,926 to Chen et al., which discloses antibody variants that have one or more amino acids inserted into a hypervariable region of the parent antibody and a binding affinity for a target antigen which is at least about two fold stronger than the binding affinity of the parent antibody for the antigen).

The term "antibody derivative" further includes engineered antibody molecules, fragments and single domains such as scFv, dAbs, nanobodies, minibodies, Unibodies, and Affibodies & Hudson (2005) Nature Biotech 23(9):1126-36; U.S. Pat. Application Publication No. 2006/0211088; PCT International Application Publication No. WO 2007/059782; U.S. Pat. No. 5,831,012).

The term "antibody derivative" further includes "linear antibodies". The procedure for making linear antibodies is known in the art and described in Zapata et al. (1995) Protein Eng. 8(10):1057-1062. Briefly, these antibodies comprise a pair of tandem Ed segments ($V_H$-$C_H$1-VH-$C_H$1) which form a pair of antigen binding regions. Linear antibodies can be bispecific or monospecific.

The antibodies disclosed herein can be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

Antibodies of the present disclosure include naturally purified products, products of chemical synthetic procedures, and products produced by recombinant techniques from a eukaryotic host, including, for example, yeast, higher plant, insect and mammalian cells, or alternatively from a prokaryotic host as described above. A number of antibody production systems are described in Birch & Radner (2006) Adv. Drug Delivery Rev. 58: 671-685.

If an antibody being tested binds with protein or polypeptide, then the antibody being tested and the antibodies provided by this disclosure are equivalent. It also is possible to determine without undue experimentation, whether an antibody has the same specificity as the antibody disclosed herein by determining whether the antibody being tested prevents an antibody disclosed herein from binding the protein or polypeptide with which the antibody is normally reactive. If the antibody being tested competes with the antibody disclosed herein as shown by a decrease in binding by the monoclonal antibody disclosed herein, then it is likely that the two antibodies bind to the same or a closely related epitope. Alternatively, one can pre-incubate the antibody disclosed herein with a protein with which it is normally reactive, and determine if the antibody being tested is inhibited in its ability to bind the antigen. If the antibody being tested is inhibited then, in all likelihood, it has the same, or a closely related, epitopic specificity as the antibody disclosed herein.

The term "antibody" also is intended to include antibodies of all immunoglobulin isotypes and subclasses. Particular isotypes of a monoclonal antibody can be prepared either directly by selecting from an initial fusion, or prepared secondarily, from a parental hybridoma secreting a monoclonal antibody of different isotype by using the sib selection technique to isolate class switch variants using the procedure described in Steplewski et al. (1985) Proc. Natl. Acad. Sci. USA 82:8653 or Spira et al. (1984) J. Immunol. Methods 74:307. Alternatively, recombinant DNA techniques may be used.

The isolation of other monoclonal antibodies with the specificity of the monoclonal antibodies described herein can also be accomplished by one of ordinary skill in the art by producing anti-idiotypic antibodies. Herlyn et al. (1986) Science 232:100. An anti-idiotypic antibody is an antibody which recognizes unique determinants present on the monoclonal antibody of interest.

In some aspects disclosed herein, it will be useful to detectably or therapeutically label the antibody. Suitable labels are described supra. Methods for conjugating antibodies to these agents are known in the art. For the purpose of illustration only, antibodies can be labeled with a detectable moiety such as a radioactive atom, a chromophore, a fluorophore, or the like. Such labeled antibodies can be used for diagnostic techniques, either in vivo, or in an isolated test sample.

The coupling of antibodies to low molecular weight haptens can increase the sensitivity of the antibody in an assay. The haptens can then be specifically detected by means of a second reaction. For example, it is common to use haptens such as biotin, which reacts avidin, or dinitrophenol, pyridoxal, and fluorescein, which can react with specific anti-hapten antibodies. See, Harlow and Lane (1988) supra.

The variable region of the antibodies of the present disclosure can be modified by mutating amino acid residues within the VH and/or VL CDR 1, CDR 2 and/or CDR 3 regions to improve one or more binding properties (e.g., affinity) of the antibody. Mutations may be introduced by site-directed mutagenesis or PCR-mediated mutagenesis and the effect on antibody binding, or other functional property of interest, can be evaluated in appropriate in vitro or in vivo assays. In certain embodiments, conservative modifications are introduced and typically no more than one, two, three, four or five residues within a CDR region are altered. The mutations may be amino acid substitutions, additions or deletions.

Framework modifications can be made to the antibodies to decrease immunogenicity, for example, by "backmutating" one or more framework residues to the corresponding germline sequence.

In addition, the antibodies disclosed herein may be engineered to include modifications within the Fc region to alter one or more functional properties of the antibody, such as serum half-fife, complement fixation, Fc receptor binding, and/or antigen-dependent cellular cytotoxicity. Such modifications include, but are not limited to, alterations of the number of cysteine residues in the hinge region to facilitate assembly of the light and heavy chains or to increase or decrease the stability of the antibody (U.S. Pat. No. 5,677, 425) and amino acid mutations in the Fc hinge region to decrease the biological half-life of the antibody (U.S. Pat. No. 6,165,745).

Additionally, the antibodies disclosed herein may be chemically modified. Glycosylation of an antibody can be altered, for example, by modifying one or more sites of glycosylation within the antibody sequence to increase the affinity of the antibody for antigen (U.S. Pat. Nos. 5,714,350 and 6,350,861). Alternatively, to increase antibody-dependent cell-mediated cytotoxicity, a hypofucosylated antibody having reduced amounts of fucosyl residues or an antibody having increased bisecting GlcNac structures can be obtained by expressing the antibody in a host cell with altered glycosylation mechanism (Shields, R. L. et al. (2002) J. Biol. Chem. 277:26733-26740; Umana et al. (1999) Nat. Biotech. 17:176-180).

The antibodies disclosed herein can be pegylated to increase biological half-life by reacting the antibody or fragment thereof with polyethylene glycol (PEG) or a reactive ester or aldehyde derivative of PEG, under conditions in which one or more PEG groups become attached to the antibody or antibody fragment. Antibody pegylation may be carried out by an acylation reaction or an alkylation reaction with a reactive PEG molecule (or an analogous reactive water soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. The antibody to be pegylated can be an aglycosylated antibody. Methods for pegylating proteins are known in the art and can be applied to the antibodies disclosed herein (EP 0154316 and EP 0401384).

Additionally, antibodies may be chemically modified by conjugating or fusing the antigen-binding region of the antibody to serum protein, such as human serum albumin, to increase half-life of the resulting molecule. Such approach is for example described in EP 0322094 and EP 0486525.

The antibodies or fragments thereof of the present disclosure may be conjugated to a diagnostic agent and used diagnostically, for example, to monitor the development or progression of a disease and determine the efficacy of a given treatment regimen. Examples of diagnostic agents include enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody or fragment thereof, or indirectly, through a linker using techniques known in the art. Examples of suitable enzymes include horseradish peroxidase, alkaline phosphatase, beta-galactosidase, or acetylcholinesterase. Examples of suitable prosthetic group complexes include streptavidin/biotin and avidin/biotin.

Examples of suitable fluorescent materials include umbelliferone, fluorescein, fluorescein isothiocyanate, rhodamine, dichlorotriazinylamine fluorescein, dansyl chloride or phycoerythrin. An example of a luminescent material includes luminol. Examples of bioluminescent materials include luciferase, luciferin, and aequorin. Examples of suitable radioactive material include $^{125}$I, $^{131}$I, Indium-111, Lutetium-171, Bismuth-212, Bismuth-213, Astatine-211, Copper-62, Copper-64, Copper-67, Yttrium-90, Iodine-125, Iodine-131, Phosphorus-32, Phosphorus-33, Scandium-47, Silver-111, Gallium-67, Praseodymium-142, Samarium-153, Terbium-161, Dysprosium-166, Holmium-166, Rhenium-186, Rhenium-188, Rhenium-189, Lead-212, Radium-223, Actinium-225, Iron-59, Selenium-75, Arsenic-77, Strontium-89, Molybdenum-99, Rhodium-1105, Palladium-109, Praseodymium-143, Promethium-149, Erbium-169, Iridium-194, Gold-198, Gold-199, and Lead-211. Monoclonal antibodies may be indirectly conjugated with radiometal ions through the use of bifunctional chelating agents that are covalently linked to the antibodies. Chelating agents may be attached through amities (Meares et al. (1984) Anal. Biochem. 142:68-78); sulfhydral groups (Koyama (1994) Chem. Abstr. 120:217-262) of amino acid residues and carbohydrate groups (Rodwell et al. (1986) PNAS USA 83:2632-2636; Quadri et al. (1993) Nucl. Med. Biol. 20:559-570).

Further, the antibodies or fragments thereof of the present disclosure may be conjugated to a therapeutic agent. Suitable therapeutic agents include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin, antimetabolites (such as methotrexate, 6-mercaptopurine, 6-thioguanine, cytarabine, fludarabin, 5-fluorouracil, decarbazine, hydroxyurea, asparaginase, gemcitabinc, cladribine), alkylating agents (such as mechlorethamine, thioepa, chloramhucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin), antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)), diphtheria toxin and related molecules (such as diphtheria A chain and active fragments thereof and hybrid molecules), ricin toxin (such as ricin A or a deglycosylated ricin A chain toxin), cholera toxin, a Shiga-like toxin (SLT-I, SLT-II, SLT-IIV), LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alphasarcin, *Aleurites fordii* proteins, dianthin proteins, *Phytolacca americana* proteins (PAPI, PAPII, and PAP-S), *Momordica charantia* inhibitor, curcin, crotin, *Sapaonaria officinalis* inhibitor, gelonin, mitogellin, restrietocin, phenomycin, enomycin toxins and mixed toxins.

Additional suitable conjugated molecules include ribonuclease (RNase), DNase I, an antisense nucleic acid, an inhibitory RNA molecule such as a siRNA molecule, an immunostimulatory nucleic acid, aptamers, ribozymes, triplex forming molecules, and external guide sequences.

Aptamers are small nucleic acids ranging from 15-50 bases in length that fold into defined secondary and tertiary structures, such as stem-loops or G-quartets, and can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Ribozymes are nucleic acid molecules that are capable of catalyzing a chemical reaction, either intramolecularly or intermolecularly. Ribozymes typically cleave nucleic acid substrates through recognition and binding of the target substrate with subsequent cleavage. Triplex forming function nucleic acid molecules can interact with double-stranded or single-stranded nucleic acid by forming a triplex, in which three strands of DNA form a complex dependent on both Watson-Crick and Hoogsteen base-pairing. Triplex molecules can bind target regions with high affinity and specificity.

The functional nucleic acid molecules may act as effectors, inhibitors, modulators, and stimulators of a specific activity possessed by a target molecule, or the functional nucleic acid molecules may possess a de novo activity independent of any other molecules.

The therapeutic agents can be linked to the antibody directly or indirectly, using any of a large number of available methods. For example, an agent can be attached at the hinge region of the reduced antibody component via disulfide bond formation, using cross-linkers such as N-succinyl 3-(2-pyridyldithio)proprionate (SPDP), or via a carbohydrate moiety in the Fc region of the antibody (Yu et al. 1994 Int. J. Cancer 56: 244; Upeslacis et al., "Modification of Antibodies by Chemical Methods," in Monoclonal antibodies: principles and applications, Birch et al. (eds.), pages 187-230 (Wiley-Liss, Inc. 1995); Price, "Production and Characterization of Synthetic Peptide-Derived Antibodies," in Monoclonal antibodies: Production, engineering and clinical application, Ritter et al. (eds.), pages 60-84 (Cambridge University Press 1995)).

Techniques for conjugating therapeutic agents to antibodies are well known (Amon et al. "Monoclonal Antibodies For Immunotargeting Of Drugs In Cancer Therapy," in Monoclonal Antibodies And Cancer Therapy; Reisfeld et al. (eds.), pp. 243-56 (Alan R. Liss, Inc. 1985); Hellstrom et al. "Antibodies For Drug Delivery," in Controlled Drug Delivery (2nd Ed.); Robinson et al. (eds.), pp. 623-53 (Marcel Dekker, Inc. 1987); Thorpe "Antibody Carriers Of Cytotoxic Agents In Cancer Therapy: A Review," in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody in Cancer Therapy," in Monoclonal Antibodies For Cancer Detection And Therapy, Baldwin et al. (eds.), pp. 303-16 (Academic Press 1985), and Thorpe et al. "The Preparation And Cytotoxic Properties Of Antibody-Toxin Conjugates," (1982) Immunol. Rev. 62:119-58).

The antibodies disclosed herein or antigen-binding regions thereof can be linked to another functional molecule such as another antibody or ligand for a receptor to generate a bi-specific or multi-specific molecule that binds to at least two or more different binding sites or target molecules. Linking of the antibody to one or more other binding molecules, such as another antibody, antibody fragment, peptide or binding mimetic, can be done, for example, by chemical coupling, genetic fusion, or noncovalent association. Multi-specific molecules can further include a third binding specificity, in addition to the first and second target epitope.

Bi-specific and multi-specific molecules can be prepared using methods known in the art. For example, each binding unit of the hi-specific molecule can be generated separately and then conjugated to one another. When the binding molecules are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitroberizoic acid) (DTNB), o-phenylenedima-leimide (oPDM), N-succinimidyl-3-(2-pyridyldithio) propionate (SPDP), and sulfosuccinimidyl 4-(N-maleimidomethyl)cyclohaxane-I-carboxylate (sulfo-SMCC) (Karpovsky et al. (1984) J. Exp. Med. 160:1686; Liu et al. (1985) Proc. Natl. Acad. Sci. USA 82:8648). When the binding molecules are antibodies, they can be conjugated by sulfhydryl bonding of the C-terminus hinge regions of the two heavy chains.

The antibodies or fragments thereof of the present disclosure may be linked to a moiety that is toxic to a cell to which the antibody is bound to form "depleting" antibodies. These antibodies are particularly useful in applications where it is desired to deplete an NK cell.

The antibodies disclosed herein may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

The antibodies also can be bound to many different carriers. Thus, this disclosure also provides compositions containing the antibodies and another substance, active or inert. Examples of well-known carriers include glass, polystyrene, polypropylene, polyethylene, dextran, nylon, amylase, natural and modified cellulose, polyacrylamide, agarose, and magnetite. The nature of the carrier can be either soluble or insoluble for purposes disclosed herein. Those skilled in the art will know of other suitable carriers for binding monoclonal antibodies, or will be able to ascertain such, using routine experimentation.

In certain aspects, the disclosure relates to an antibody or antigen binding fragment that specifically recognizes or binds an isolated or recombinant polypeptide consisting essentially of an amino acid sequence of a DNABII protein or fragment thereof, the tail fragment or tip fragment. Non-limiting examples of such fragments include without limitation a polypeptide that comprises one or more of the sequences: polypeptides designated as B1 through B6 (see FIG. 18);

```
MATITKLDIIEYISDKYHLS (also referred to herein as
hIFA1; (SEQ ID NO. 348));

KYHLSKQDTKNVVENFLEEI (also referred to herein as
hIFA2; (SEQ ID NO. 349));

FLEEIRLSLESGQDVKLSGF (also referred to herein as
hIFA3; (SEQ ID NO. 350));

KLSGFGNFELRDKSSRPGRN (also referred to herein as
hIFA4; (SEQ ID NO. 351));

RPGRNPKTGDVVPVSARRVV (also referred to herein as
hIFA5; (SEQ ID NO. 352));

ARRVVTFKPGQKLRARVEKTK (also referred to herein as
hIFA6; (SEQ ID NO. 353));
``` or an equivalent of each thereof, that may include additional amino acids as described above;

Non-limiting exemplary antibodies produced by the disclosed hybridomas disclosed in Table 10. The hybridoma cell lines that produce monoclonal antibodies that specifically recognize and bind *Haemophilus influenzae* IHfA fragment A5 (SEQ ID NO: 352) and Ihf fragment B4 (SEQ ID NO: 345), were deposited with American Type Culture Collection (ATCC) pursuant to the provisions of the Budapest Treaty on Jul. 30, 2015 and the CDRs of the antibodies can be identified by sequence using conventional techniques. Further non-limiting exemplary antibodies include those that specifically recognize and bind *Haemophilus influenzae* IHfA fragment A3 (SEQ ID NO: 350), IhfB fragment B2 (SEQ ID NO: 343) produced by hybridoma cell lines IhfA3 NTHI 9B10.F2.H3 and IhfB2 NTHI 7A4.E4.G4.

TABLE 10

| Specificity | SEQ ID NO: | ATCC Accession No. | Hybridoma Cell Line |
|---|---|---|---|
| IhfA frag. A5 | SEQ ID NO: 352 | PTA-122334 | IhfA5 NTHI 14G8.F5.G6 |
| IhfB frag. B4 | SEQ ID NO: 345 | PTA-122335 | IhfB4 NTHI 4E11.E5.G2 |

In one aspect, the present disclosure provides an isolated antibody, derivative or fragment thereof that is at least 85% identical to an antibody selected from the group consisting of (i) the antibody produced by hybridoma cell line IhfA5 NTHI 14G8.F5.G6 or (ii) the antibody produced by hybridoma cell line IhfB4 NTHI 4E11.E5.G2.

In one aspect, the present disclosure provides an isolated antibody, derivative or fragment thereof comprising the CDRs of (i) the antibody produced by hybridoma cell line IhfA5 NTHI 14G8.F5.G6; or (ii) the antibody produced by hybridoma cell line IhfB4 NTHI 4E11.E5.G2. In one aspect, the present disclosure provides an isolated antibody, derivative or fragment thereof that has CDR that is at least 85% identical to (i) the antibody produced by hybridoma cell line IhfA5 NTHI 14G8.F5.G6 or (ii) the antibody produced by hybridoma cell line IhfB4 NTHI 4E11.E5.G2.

In some aspects of the antibodies provided herein, the HC variable domain sequence comprises the HC variable domain sequence of (i) the antibody produced by hybridoma cell line IhfA5 NTHI 14G8.F5.G6 or (ii) the antibody produced by hybridoma cell line IhfB4 NTHI 4E11.E5.G2, and/or the LC variable domain sequence comprises the LC variable domain sequence of (i) the antibody produced by hybridoma cell line IhfA5 NTHI 14G8.F5.G6 or (ii) the antibody produced by hybridoma cell line IhfB4 NTHI 4E11.E5.G2.

In some aspects of the antibodies provided herein, the HC variable domain sequence comprises a HC variable domain sequence at least 85% identical to a HC variable domain sequence of (i) the antibody produced by hybridoma cell line IhfA5 NTHI 14G8.F5.G6; or (ii) the antibody produced by hybridoma cell line IhfB4 NTHI 4E11.E5.G2; and/or the LC variable domain sequence comprises a LC variable domain sequence at least 85% identical to the of LC variable domain sequence of (i) the antibody produced by hybridoma cell line IhfA5 NTHI 14G8.F5.G6; or (ii) the antibody produced by hybridoma cell line IhfB4 NTHI 4E11.E5.G2.

In one aspect, the present disclosure provides an isolated antibody comprising a heavy chain (HC) variable domain sequence and a light chain (LC) variable domain sequence, wherein the heavy chain and light chain immunoglobulin variable domain sequences form an antigen binding site that binds to an epitope of a DNABII protein.

In some embodiments, the heavy chain variable region comprises a CDRH1 sequence comprising, or alternatively consisting essentially of, or yet further consisting of, an amino acid sequence comprising the CDRH1 of any one of the following antibodies: (i) the antibody produced by hybridoma cell line IhfA5 NTHI 14G8.F5.G6; or (ii) the antibody produced by hybridoma cell line IhfB4 NTHI 4E11.E5.G2.

In some embodiments, the heavy chain variable region comprises a CDRH2 sequence comprising, or alternatively consisting essentially of, or yet further consisting of, an amino acid sequence comprising the CDRH2 of any one of the following antibodies: (i) the antibody produced by hybridoma cell line IhfA5 NTHI 14G8.F5.G6; or (ii) the antibody produced by hybridoma cell line IhfB4 NTHI 4E11.E5.G2.

In some embodiments, the heavy chain variable region comprises a CDRH3 sequence comprising, or alternatively consisting essentially of, or yet further consisting of, an amino acid sequence comprising the CDRH3 of any one of the following antibodies: (i) the antibody produced by hybridoma cell line IhfA5 NTHI 14G8.F5.G6; or (ii) the antibody produced by hybridoma cell line IhfB4 NTHI 4E11.E5.G2.

In some embodiments, the heavy chain variable region comprises, or alternatively consists essentially of, or yet further consists of, the amino acid sequence comprising the heavy chain variable region sequence of any one of the following antibodies: (i) the antibody produced by hybridoma cell line IhfA5 NTHI 14G8.F5.G6; or (ii) the antibody produced by hybridoma cell line IhfB4 NTHI 4E11.E5.G2.

In some embodiments, the light chain variable region comprises a CDRL1 sequence comprising, or alternatively consisting essentially of, or yet further consisting of, an amino acid sequence comprising the CDRL1 of any one of the following antibodies: (i) the antibody produced by hybridoma cell line IhfA5 NTHI 14G8.F5.G6; or (ii) the antibody produced by hybridoma cell line IhfB4 NTHI 4E11.E5.G2.

In some embodiments, the light chain variable region comprises a CDRL2 sequence comprising, or alternatively consisting essentially of, or yet further consisting of, an amino acid sequence comprising the CDRL2 of any one of the following antibodies: (i) the antibody produced by hybridoma cell line IhfA5 NTHI 14G8.F5.G6; or (ii) the antibody produced by hybridoma cell line IhfB4 NTHI 4E11.E5.G2.

In some embodiments, the light chain variable region comprises a CDRL3 sequence comprising, or alternatively consisting essentially of, or yet further consisting of, an amino acid sequence comprising the CDRL3 of any one of the following antibodies: (i) the antibody produced by hybridoma cell line IhfA5 NTHI 14G8.F5.G6; or (ii) the antibody produced by hybridoma cell line IhfB4 NTHI 4E11.E5.G2.

In some embodiments, the light chain variable region comprises, or alternatively consists essentially of, or yet further consists of, the polypeptide encoded by the polynucleotide sequence comprising the light chain variable region sequence of any one of the following antibodies: (i) the antibody produced by hybridoma cell line IhfA5 NTHI 14G8.F5.G6; or (ii) the antibody produced by hybridoma cell line IhfB4 NTHI 4E11.E5.G2.

In another aspect of the present technology, the isolated antibody includes one or more of the following characteristics:

(a) the light chain immunoglobulin variable domain sequence comprises one or more CDRs that are at least 85% identical to a CDR of a light chain variable domain of any of the disclosed light chain sequences;
(b) the heavy chain immunoglobulin variable domain sequence comprises one or more CDRs that are at least 85% identical to a CDR of a heavy chain variable domain of any of the disclosed heavy chain sequences;
(c) the light chain immunoglobulin variable domain sequence is at least 85% identical to a light chain variable domain of any of the disclosed light chain sequences;
(d) the HC immunoglobulin variable domain sequence is at least 85% identical to a heavy chain variable domain of any of the disclosed light chain sequences; and/or
(e) the antibody binds an epitope that overlaps with an epitope bound by any of the disclosed sequences.

In some of the aspects of the antibodies provided herein, the antibody binds a DNABII protein with a dissociation constant ($K_D$) of less than $10^{-4}$M, $10^{-5}$M, $10^{-6}$M, $10^{-7}$ M, $10^{-8}$M, $10^{-9}$M, $10^{-10}$ M, $10^{-11}$ M, or $10^{-12}$M. In some of the aspects of the antibodies provided herein, the antigen binding site specifically binds to a DNABII protein.

In some of the aspects of the antibodies provided herein, the antibody is soluble Fab.

In some of the aspects of the antibodies provided herein, the HC and LC variable domain sequences are components of the same polypeptide chain. In some of the aspects of the antibodies provided herein, the HC and LC variable domain sequences are components of different polypeptide chains.

In some of the aspects of the antibodies provided herein, the antibody is a full-length antibody.

In some of the aspects of the antibodies provided herein, the antibody is a monoclonal antibody.

In some of the aspects of the antibodies provided herein, the antibody is chimeric or humanized.

In some of the aspects of the antibodies provided herein, the antibody is selected from the group consisting of Fab, F(ab)'2, Fab', scF$_v$, and F$_v$.

In some of the aspects of the antibodies provided herein, the antibody comprises an Fc domain. In some of the aspects of the antibodies provided herein, the antibody is a non-human animal such as a rat, sheep, bovine, canine, feline or rabbit antibody. In some of the aspects of the antibodies provided herein, the antibody is a human or humanized antibody or is non-immunogenic in a human.

In some of the aspects of the antibodies provided herein, the antibody comprises a human antibody framework region.

In other aspects, one or more amino acid residues in a CDR of the antibodies provided herein are substituted with another amino acid. The substitution may be "conservative" in the sense of being a substitution within the same family of amino acids. The naturally occurring amino acids may be divided into the following four families and conservative substitutions will take place within those families.
1) Amino acids with basic side chains: lysine, arginine, histidine.
2) Amino acids with acidic side chains: aspartic acid, glutamic acid
3) Amino acids with uncharged polar side chains: asparagine, glutamine, serine, threonine, tyrosine.
4) Amino acids with nonpolar side chains: glycine, alanine, valine, leucine, isoleucine, proline, phenylalanine, methionine, tryptophan, cysteine.

In another aspect, one or more amino acid residues are added to or deleted from one or more CDRs of an antibody. Such additions or deletions occur at the N or C termini of the CDR or at a position within the CDR.

By varying the amino acid sequence of the CDRs of an antibody by addition, deletion or substitution of amino acids, various effects such as increased binding affinity for the target antigen may be obtained.

It is to be appreciated that antibodies of the present disclosure comprising such varied CDR sequences still bind a DNABII protein with similar specificity and sensitivity profiles as the disclosed antibodies. This may be tested by way of the binding assays.

In a further aspect, the antibodies are characterized by being both immunodominant and immunoprotective, as determined using appropriate assays and screens.

Isolation, Culturing and Expansion of APCs, Including Dendritic Cells

This disclosure also provides isolated host cells comprising one or more of an isolated polypeptides or isolated polynucleotides or the vectors disclosed herein. In one aspect the isolated host cell is a eukaryotic cell such as antigen presenting cell (APC), e.g., a dendritic cell. In another aspect, the isolated host cell is a prokaryotic cell. In one aspect, the disclosure is an isolated host cell that is cultured under conditions that promote expression of the polynucleotide. This disclosure also provides the host cell, expression system and polypeptide produced by the expression system.

The following is a brief description of two fundamental approaches for the isolation of APC. These approaches involve (1) isolating bone marrow precursor cells (CD34$^+$) from blood and stimulating them to differentiate into APC; or (2) collecting the precommitted APCs from peripheral blood. In the first approach, the patient must be treated with cytokines such as GM-CSF to boost the number of circulating CD34$^+$ stem cells in the peripheral blood.

The second approach for isolating APCs is to collect the relatively large numbers of precommitted APCs already circulating in the blood. Previous techniques for isolating committed APCs from human peripheral blood have involved combinations of physical procedures such as metrizamide gradients and adherence/nonadherence steps (Freudenthal et al. (1990) PNAS 87:7698-7702); Percoll gradient separations (Mehta-Damani et al. (1994) J. Immunol. 153:996-1003); and fluorescence activated cell sorting techniques (Thomas et al. (1993) J. Immunol. 151:6840-6852).

One technique for separating large numbers of cells from one another is known as countercurrent centrifugal elutriation (CCE). Cell samples are placed in a special elutriation rotor. The rotor is then spun at a constant speed of, for example, 3000 rpm. Once the rotor has reached the desired speed, pressurized air is used to control the flow rate of cells. Cells in the elutriator are subjected to simultaneous centrifugation and a washout stream of buffer which is constantly increasing in flow rate. This results in fractional cell separations based largely but not exclusively on differences in cell size.

In one aspect disclosed herein, the APC are precommitted or mature dendritic cells which can be isolated from the white blood cell fraction of a mammal, such as a murine, simian or a human (See, e.g., WO 96/23060). The white blood cell fraction can be from the peripheral blood of the mammal. This method includes the following steps: (a) providing a white blood cell fraction obtained from a mammalian source by methods known in the art such as leukapheresis; (b) separating the white blood cell fraction of step (a) into four or more subfractions by countercurrent centrifugal elutriation, (c) stimulating conversion of monocytes in one or more fractions from step (b) to dendritic cells by contacting the cells with calcium ionophore, GM-CSF and IL-13 or GM-CSF and IL-4, (d) identifying the dendritic cell-enriched fraction from step (c), and (e) collecting the enriched fraction of step (d), optionally at about 4° C. One way to identify the dendritic cell-enriched fraction is by fluorescence-activated cell sorting. The white blood cell fraction can be treated with calcium ionophore in the presence of other cytokines, such as recombinant (rh) rhIL-12, rhGM-CSF, or rhIL-4. The cells of the white blood cell fraction can be washed in buffer and suspended in $Ca^{++}/Mg^{++}$ free media prior to the separating step. The white blood cell fraction can be obtained by leukapheresis. The dendritic cells can be identified by the presence of at least one of the following markers: HLA-DR, HLA-DQ, or B7.2, and the simultaneous absence of the following markers: CD3, CD16, CD56, CD57, and CD19, CD20. Monoclonal antibodies specific to these cell surface markers are commercially available.

More specifically, the method requires collecting an enriched collection of white cells and platelets from leukapheresis that is then further fractionated by countercurrent centrifugal elutriation (CCE) (Abrahamsen et al. (1991) J. Clin. Apheresis. 6:48-53). In this technique, cells are subject to simultaneous centrifugation and a washout stream of buffer which is constantly increasing flow rate. The constantly increasing countercurrent flow of buffer leads to fractional cell separations that are largely based on cell size.

Quality control of APC and more specifically DC collection and confirmation of their successful activation in culture is dependent upon a simultaneous multi-color FACS analysis technique which monitors both monocytes and the dendritic cell subpopulation as well as possible contaminant T lymphocytes. Cell sorting is based on differential expression of cell surface markers including CD3 (T cells), CD16/CD56/CD57 (NK/LAK cells), and CD19/CD20 (B cells). DCs are distinguishable from monocytes based in part on levels of CD14, which is expressed at very high levels in monocytes compared to DCs. DCs show high levels of expression of HLA-DR, significant HLA-DQ and B7.2 (but little or no B7.1) at the time they are circulating in the blood (in addition they express Leu M7 and M9, myeloid markers which are also expressed by monocytes and neutrophils).

When combined with a third color reagent for analysis of dead cells, propidium iodide (PI), it is possible to make positive identification of all cell subpopulations The goal of FACS analysis at the time of collection is to confirm that the DCs are enriched in the expected fractions, to monitor neutrophil contamination, and to make sure that appropriate markers are expressed. This rapid bulk collection of enriched DCs from human peripheral blood, suitable for clinical applications, is absolutely dependent on the analytic FACS technique described above for quality control. If need be, mature DCs can be immediately separated from monocytes at this point by fluorescent sorting for "cocktail negative" cells. It may not be necessary to routinely separate DCs from monocytes because, the monocytes themselves are still capable of differentiating into DCs or functional DC-like cells in culture.

Once collected, the DC rich/monocyte APC fractions (usually 150 through 190) can be pooled and cryopreserved for future use, or immediately placed in short term culture.

Alternatively, others have reported that a method for upregulating (activating) dendritic cells and converting monocytes to an activated dendritic phenotype. This method involves the addition of calcium ionophore to the culture media convert monocytes into activated dendritic cells. Adding the calcium ionophore A23187, for example, at the beginning of a 24-48 hour culture period resulted in uniform activation and dendritic cell phenotypic conversion of the pooled "monocyte plus DC" fractions: characteristically, the activated population becomes uniformly CD14 (Leu M3) negative, and upregulates HLA-DR, HLA-DQ, ICAM-1, B7.1, and B7.2. Furthermore this activated bulk population functions as well on a small numbers basis as a further purified.

Specific combination(s) of cytokines have been used successfully to amplify (or partially substitute) for the activation/conversion achieved with calcium ionophore: these cytokines include but are not limited to purified or recombinant ("rh") rhGM-CSF, rhIL-2, and rhIL-4. Each cytokine when given alone is inadequate for optimal upregulation.

Presentation of Antigen to the APC

For purposes of immunization, the polypeptides (e.g., SEQ ID NO: 1 through 33) can be delivered to antigen-presenting cells as protein/peptide or in the form of cDNA encoding the protein/peptide. Antigen-presenting cells (APCs) can consist of dendritic cells (DCs), monocytes/macrophages, B lymphocytes or other cell type(s) expressing the necessary MHC/co-stimulatory molecules. The methods described below focus primarily on DCs which are the most potent APCs.

Pulsing is accomplished in vitro/ex vivo by exposing APCs to the antigenic protein or polypeptide(s) disclosed herein. The protein or peptide(s) are added to APCs at a concentration of 1-10 µm for approximately 3 hours. Transfection of APCs with polynucleotides encoding antigens or antigenic polypeptides is accomplished by exposing APCs to the nucleic acids in the presence of transfection agents known in the art, including but not limited to cationic lipids. Transfected or pulsed APCs can subsequently be administered to the host via an intravenous, subcutaneous, intranasal, intramuscular or intraperitoneal route of delivery.

Protein/peptide antigen can also be delivered in vivo with adjuvant via the intravenous, subcutaneous, intranasal, intramuscular or intraperitoneal route of delivery.

Foster Antigen Presenting Cells

Foster antigen presenting cells are particularly useful as a target cell. Foster APCs are derived from the human cell line 174X CEM.T2, referred to as T2, which contains a mutation in its antigen processing pathway that restricts the association of endogenous peptides with cell surface MHC class I molecules (Zweerink et al. (1993) J. Immunol. 150:1763-1771). This is due to a large homozygous deletion in the MHC class II region encompassing the genes TAP 1, TAP2, LMP 1, and LMP2, which are required for antigen presentation to MHC class 1-restricted $CD8^+$ CTLs. In effect, only "empty" MHC class I molecules are presented on the surface of these cells. Exogenous peptide added to the culture medium binds to these MHC molecules provided that the peptide contains the allele-specific binding motif. These T2 cells are referred to herein as "foster" APCs. They can be used in conjunction with this disclosure to present antigen(s).

Transduction of T2 cells with specific recombinant MHC allows for redirection of the MHC restriction profile. Libraries tailored to the recombinant allele will be preferentially presented by them because the anchor residues will prevent efficient binding to the endogenous allele.

High level expression of MHC molecules makes the APC more visible to the CTLs. Expressing the MHC allele of interest in T2 cells using a powerful transcriptional promoter (e.g., the CMV promoter) results in a more reactive APC (most likely due to a higher concentration of reactive MHC-peptide complexes on the cell surface).

Expansion of Immune Effector Cells

The present disclosure makes use of these APCs to stimulate production of an enriched population of antigen-specific immune effector cells. The antigen-specific immune effector cells are expanded at the expense of the APCs, which die in the culture. The process by which naive immune effector cells become educated by other cells is described essentially in Coulie (1997) Molec. Med. Today 3:261-268.

The APCs prepared as described above are mixed with naive immune effector cells. In specific embodiments, the cells may be cultured in the presence of a cytokine, for example IL2. Because dendritic cells secrete potent immunostimulatory cytokines, such as IL12, it may not be necessary to add supplemental cytokines during the first and successive rounds of expansion. In any event, the culture conditions are such that the antigen-specific immune effector cells expand (i.e., proliferate) at a much higher rate than the APCs. Multiple infusions of APCs and optional cytokines can be performed to further expand the population of antigen-specific cells.

In one embodiment, the immune effector cells are T cells. In a separate embodiment, the immune effector cells can be genetically modified by transduction with a transgene coding for example, IL-2, IL-11 or IL-13. Methods for introducing transgenes in vitro, ex vivo and in vivo are known in the art.

Functional Analysis with Antibodies

Antibodies disclosed herein can be used to purify the polypeptides disclosed herein and to identify biological equivalent polypeptide and/or polynucleotides. They also can be used to identify agents that modify the function of the polypeptides disclosed herein. These antibodies include polyclonal antisera, monoclonal antibodies, and various reagents derived from these preparations that are familiar to those practiced in the art and described above.

Antibodies that neutralize the activities of proteins encoded by identified genes can also be used in vivo and in vitro to demonstrate function by adding such neutralizing antibodies into in vivo and in vitro test systems. They also are useful as pharmaceutical agents to modulate the activity of polypeptides disclosed herein.

Various antibody preparations can also be used in analytical methods such as ELISA assays or Western blots to demonstrate the expression of proteins encoded by the identified genes by test cells in vitro or in vivo. Fragments of such proteins generated by protease degradation during metabolism can also be identified by using appropriate polyclonal antisera with samples derived from experimental samples.

The antibodies disclosed herein may be used for vaccination or to boost vaccination, alone or in combination with peptides or protein-based vaccines or dendritic-cell based vaccines.

Compositions

Compositions are further provided. The compositions comprise a carrier and one or more of an isolated polypeptide disclosed herein, an isolated polynucleotide disclosed herein, a vector disclosed herein, an isolated host cell disclosed herein, a small molecule or an antibody disclosed herein. The carriers can be one or more of a solid support or a pharmaceutically acceptable carrier. The compositions can further comprise an adjuvant or other components suitable for administrations as vaccines. In one aspect, the compositions are formulated with one or more pharmaceutically acceptable excipients, diluents, carriers and/or adjuvants. In addition, embodiments of the compositions of the present disclosure include one or more of an isolated polypeptide disclosed herein, an isolated polynucleotide disclosed herein, a vector disclosed herein, a small molecule, an isolated host cell disclosed herein, or an antibody of the disclosure, formulated with one or more pharmaceutically acceptable substances.

For oral preparations, any one or more of an isolated or recombinant polypeptide as described herein, an isolated or recombinant polynucleotide as described herein, a vector as described herein, an isolated host cell as described herein, a small molecule or an antibody as described herein can be used alone or in pharmaceutical formulations disclosed herein comprising, or consisting essentially of, the compound in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Pharmaceutical formulations and unit dose forms suitable for oral administration are particularly useful in the treatment of chronic conditions, infections, and therapies in which the patient self-administers the drug. In one aspect, the formulation is specific for pediatric administration.

The disclosure provides pharmaceutical formulations in which the one or more of an isolated polypeptide disclosed herein, an isolated polynucleotide disclosed herein, a vector disclosed herein, an isolated host cell disclosed herein, or an antibody disclosed herein can be formulated into preparations for injection in accordance with the disclosure by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives or other antimicrobial agents. A non-limiting example of such is a antimicrobial agent such as other vaccine components such as surface antigens, e.g., an OMP P5, OMP 26, OMP P2, or Type IV Pilin protein (see Jurcisek and Bakaletz (2007) J. of Bacteriology 189(10):3868-3875 and Murphy, T F, Bakaletz, L O and Smeesters, P R (2009) The Pediatric Infectious Disease Journal, 28:S121-S126) and antibacterial agents. For intravenous administration, suitable carriers include physiological bacteriostatic water, Cremophor EL™ (BASF, Parsippany, N.J.), or phosphate buffered saline (PBS). In all cases, a composition for parenteral administration must be sterile and should be fluid to the extent that easy syringability exists.

Aerosol formulations provided by the disclosure can be administered via inhalation and can be propellant or non-propellant based. For example, embodiments of the pharmaceutical formulations disclosed herein comprise a compound disclosed herein formulated into pressurized acceptable propellants such as dichlorodifluoromethane, propane, nitrogen and the like. For administration by inhalation, the compounds can be delivered in the form of an aerosol spray from a pressurized container or dispenser which contains a suitable propellant, e.g., a gas such as carbon dioxide, or a nebulizer. A non-limiting example of a non-propellant is a pump spray that is ejected from a closed container by means of mechanical force (i.e., pushing down a piston with one's finger or by compression of the container, such as by a compressive force applied to the container wall or an elastic force exerted by the wall itself, e.g., by an elastic bladder).

Suppositories disclosed herein can be prepared by mixing a compound disclosed herein with any of a variety of bases such as emulsifying bases or water-soluble bases. Embodiments of this pharmaceutical formulation of a compound disclosed herein can be administered rectally via a suppository. The suppository can include vehicles such as cocoa butter, carbowaxes and polyethylene glycols, which melt at body temperature, yet are solidified at room temperature.

Unit dosage forms for oral or rectal administration, such as syrups, elixirs, and suspensions, may be provided wherein each dosage unit, for example, teaspoonful, tablespoonful, tablet or suppository, contains a predetermined amount of the composition containing one or more compounds disclosed herein. Similarly, unit dosage forms for injection or intravenous administration may comprise a compound disclosed herein in a composition as a solution in sterile water, normal saline or another pharmaceutically acceptable carrier.

Embodiments of the pharmaceutical formulations disclosed herein include those in which one or more of an isolated polypeptide disclosed herein, an isolated polynucleotide disclosed herein, a vector disclosed herein, a small molecule for use in the disclosure, an isolated host cell disclosed herein, or an antibody disclosed herein is formulated in an injectable composition. Injectable pharmaceutical formulations disclosed herein are prepared as liquid solutions or suspensions; or as solid forms suitable for solution in, or suspension in, liquid vehicles prior to injection. The preparation may also be emulsified or the active ingredient encapsulated in liposome vehicles in accordance with other embodiments of the pharmaceutical formulations disclosed herein.

In an embodiment, one or more of an isolated polypeptide disclosed herein, an isolated polynucleotide disclosed herein, a vector disclosed herein, an isolated host cell disclosed herein, or an antibody disclosed herein is formulated for delivery by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present disclosure. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of a compound disclosed herein can be accomplished using any of a variety of refillable, pump systems. Pumps provide consistent, controlled release over time. In some embodiments, a compound disclosed herein is in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to, a subdermal, subcutaneous, intramuscular, or other suitable site within a subject's body. Subcutaneous implantation sites are used in some embodiments because of convenience in implantation and removal of the drug delivery device.

Drug release devices suitable for use in the disclosure may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use with the present disclosure. Examples of such devices include those described in, for example, U.S. Pat. Nos. 4,692,147; 4,360,019; 4,487,603; 4,360,019; 4,725,852; and the like. In general, a subject treatment method can be accomplished using any of a variety of refillable, non-exchangeable pump systems. Pumps and other convective systems may be utilized due to their generally more consistent, controlled release over time. Osmotic pumps are used in some embodiments due to their combined advantages of more consistent controlled release and relatively small size (see, e.g., PCT International Application Publication No. WO 97/27840 and U.S. Pat. Nos. 5,985,305 and 5,728,396). Exemplary osmotically-driven devices suitable for use in the disclosure include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like. A further exemplary device that can be adapted for the present disclosure is the Synchromed infusion pump (Medtronic).

In some embodiments, the drug delivery device is an implantable device. The drug delivery device can be implanted at any suitable implantation site using methods and devices well known in the art. As noted herein, an implantation site is a site within the body of a subject at which a drug delivery device is introduced and positioned. Implantation sites include, but are not necessarily limited to a subdermal, subcutaneous, intramuscular, or other suitable site within a subject's body.

Suitable excipient vehicles for a compound disclosed herein are, for example, water, saline, dextrose, glycerol, ethanol, or the like, and combinations thereof. In addition, if desired, the vehicle may contain minor amounts of auxiliary substances such as wetting or emulsifying agents or pH buffering agents. Methods of preparing such dosage forms are known, or will be apparent upon consideration of this disclosure, to those skilled in the art. See, e.g., Remington's Pharmaceutical Sciences, Mack Publishing Company, Easton, Pa., 17th edition, 1985. The composition or formulation to be administered will, in any event, contain a quantity of the compound adequate to achieve the desired state in the subject being treated.

Compositions of the present disclosure include those that comprise a sustained-release or controlled release matrix. In addition, embodiments of the present disclosure can be used in conjunction with other treatments that use sustained-release formulations. As used herein, a sustained-release matrix is a matrix made of materials, usually polymers, which are degradable by enzymatic or acid-based hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxcylic acids, fatty acids, phospholipids, polysaccharides, nucleic acids, polyamino acids, amino acids such as phenylatanine, tyrosine, isoleucine, polynucleotides, polyvinyl propylene, polyvinylpyrrolidone and silicone. Illustrative biodegradable matrices include a polylactide matrix, a polyglycolide matrix, and a polylactide co-glycolide (co-polymers of lactic acid and glycolic acid) matrix.

In another embodiment, the interfering agent (as well as combination compositions) is delivered in a controlled release system. For example, a compound disclosed herein may be administered using intravenous infusion, an implantable osmotic pump, a transdermal patch, liposomes, or other modes of administration. In one embodiment, a pump may be used (Sefton (1987) CRC Crit. Ref. Biomed. Eng. 14:201; Buchwald et al. (1980) Surgery 88:507; Saudek et al. (1989) N. Engl. J. Med. 321:574). In another embodiment, polymeric materials are used. In yet another embodiment a controlled release system is placed in proximity of the therapeutic target, i.e., the liver, thus requiring only a fraction of the systemic dose. In yet another embodiment, a controlled release system is placed in proximity of the therapeutic target, thus requiring only a fraction of the systemic. Other controlled release systems are discussed in the review by Langer (1990) Science 249:1527-1533.

In another embodiment, the compositions of the present disclosure (as well as combination compositions separately or together) include those formed by impregnation of an inhibiting agent described herein into absorptive materials, such as sutures, bandages, and gauze, or coated onto the surface of solid phase materials, such as surgical staples, zippers and catheters to deliver the compositions. Other delivery systems of this type will be readily apparent to those skilled in the art in view of the instant disclosure.

The present disclosure provides methods and compositions for the administration of a one or more of an interfering agent to a host (e.g., a human) for the treatment of a microbial infection. In various embodiments, these methods disclosed herein span almost any available method and route suitable for drug delivery, including in vivo and ex vivo methods, as well as systemic and localized routes of administration.

Screening Assays

The present disclosure provides methods for screening for equivalent agents, such as equivalent monoclonal antibodies to a polyclonal antibody as described herein and various agents that modulate the activity of the active agents and pharmaceutical compositions disclosed herein or the function of a polypeptide or peptide product encoded by the polynucleotide disclosed herein. For the purposes of this disclosure, an "agent" is intended to include, but not be limited to a biological or chemical compound such as a simple or complex organic or inorganic molecule, a peptide, a protein (e.g., antibody), a polynucleotide anti-sense) or a ribozyme. A vast array of compounds can be synthesized, for example polymers, such as polypeptides and polynucleotides, and synthetic organic compounds based on various core structures, and these are also included in the term "agent." In addition, various natural sources can provide compounds for screening, such as plant or animal extracts, and the like. It should be understood, although not always explicitly stated that the agent is used alone or in combination with another agent, having the same or different biological activity as the agents identified by the inventive screen.

One embodiment is a method for screening agents capable of interacting with, binding to, or inhibiting the DNA-DNABII (e.g., IHF) interaction. The present disclosure provides in FIG. 6B the three-dimensional structure of the microbial DNA and IHF. Accordingly, the disclosure permits the use of virtual design techniques, also known as computer-aided, in silico design or modeling, to design, select, and synthesize agents capable of interacting with, binding to, or inhibiting the DNA-DNABII (e.g., IHF) interaction. In turn, the candidate agents may be effective in the treatment of biofilms and associated diseases or conditions (medical, industrial or veterinary) as described herein. Thus, the present disclosure also provides agents identified or designed by the in silico methods.

Three-dimensional structure of a IHF-DNA complex is illustrated in FIG. 6B and a representative structure, with X, Y and Z coordinates, are provided in Protein Data Bank Accession Number: 1IHF, with relevant details provided in Rice et al. (1996) Cell 87:1295-1306. The three-dimensional structure of the IHF protein in the IHF-DNA complex can be used for the screening method. A suitable agent is one that can be positioned relative to the IHF protein structure in the IHF-DNA complex with interactions at least one, or alternatively two, or three, or four, or five, or six, or seven, or eight, or nine, or at least ten of the amino acid residues that are identified to be involved in interacting with DNA.

FIG. 6A illustrates the amino acid residues involved in IHF-DNA interaction, using the *E. coli* IHF sequence (SEQ ID NO: 42) as an example. Such amino acid residues, indicated by the lower level of arrows in FIG. 6A, are further described below, indicated with bold and underlined letters. Namely, with the *E. coli* IHF, the amino acids involved in DNA binding are T4, K5, A6, E28, Q43, K45, S47, G48, N51, R55, K57, R60, R63, N64, P65, K66, R76, T80, R82 or Q85.

(SEQ ID NO: 42)
MAL TKA EMSE YLFDKLGLSK RDAKELV E LF FEEIRRALEN

GE Q V K L SG FG N FDL R D K NQ R PG RNPK TGED

IPITA R RVV T F R PG Q KLKSR VENASPKDE

Thus, one embodiment of the present disclosure provides a computer-implemented method for identifying an agent that inhibits, competes or titrates the binding of a DNABII polypeptide or protein to a microbial DNA, that inhibits, prevents or breaks down a microbial biofilm, that inhibits, prevents or breaks down a biofilm in a subject, or that inhibits, prevents or treats a microbial infection that produces a biofilm in a subject, comprising positioning a three-dimensional structure of a candidate agent against a three-dimensional structure of an integration host factor (IHF) protein, wherein the three-dimensional structure of the IHF protein is based on X, Y and Z atomic structure coordinates determined from a crystalline form of an IHF and DNA complex, wherein interaction of the agent with the IHF at two or more IHF amino acids selected from T4, K5, A6, E28, Q43, K45, S47, G48, N51, R55, K57, R60, R63, N64, P65, K66, R76, T80, R82 or Q85 as represented in SEQ ID NO: 42, or the equivalent of each, identifies that the agent inhibits, competes or titrates the binding of a DNABII polypeptide or protein to a microbial DNA, inhibits, prevents or breaks down a microbial biofilm, inhibits, prevents or breaks down a biofilm, or inhibits, prevents or treats a microbial infection that produces a biofilm.

In one aspect, a candidate agent interacts with the IHF protein at least one, or two, or three of amino acids 63, 64, 65, or 66. In one aspect, a candidate agent interacts with the IHF protein at least one, or two, or three of R63, N64, P65, K66. In another aspect, a candidate agent interacts with the IHF protein at least at one of 63 or 66. In another aspect, a candidate agent interacts with the IHF protein at least at one of R63 or K66.

It would be appreciated in the art that the exact locations and amino acid residues vary depending on the IHF sequence. One of the skill in the art, however, can readily identify such locations and amino acid residues based on the sequences. For instance, an IHF sequence can be aligned with the IHF sequence of E. coli (SEQ ID NO: 42), as illustrated in Table 9, to reveal those that correspond to the amino acids in E. coli IHF that interact with DNA. Likewise, the three-dimensional structure of such an IHF sequence in an IHF-DNA complex can be used for the screening.

In addition to the computer-implemented methods as provided herein, the present disclosure also provides custom computer system that includes, e.g., processor, memory and/or program, for performing the methods, as well as a computer readable medium, such as a non-transitory computer readable medium that stores suitable computer program or code for carrying out the methods.

Accordingly, another embodiment provides a custom computing apparatus comprising: at least one processor;
a memory coupled to the at least one processor;
a storage medium in communication with the memory and the at least one processor, the storage medium containing a set of processor executable instructions that, when executed by the processor configure the custom computing apparatus to identify an agent that inhibits, competes or titrates the binding of a DNABII polypeptide or protein to a microbial DNA, that inhibits, prevents or breaks down a microbial biofilm, that inhibits, prevents or breaks down a biofilm in a subject, or that inhibits, prevents or treats a microbial infection that produces a biofilm in a subject, wherein the configuration comprises:
positioning a three-dimensional structure of a candidate agent against a three-dimensional structure of an integration host factor (IHF) protein, wherein the three-dimensional structure of the IHF protein is based on X, Y and Z atomic structure coordinates determined from a crystalline form of an IHF and DNA complex, wherein interaction of the agent with the IHF at two or more IHF amino acids selected from T4, K5, A6, E28, Q43, K45, S47, G48, N51, R55, K57, R60, R63, N64, P65, K66, R76, T80, R82 or Q85 as represented in SEQ ID NO: 42, or the equivalent of each, identifies that the agent inhibits, competes or titrates the binding of a DNABII polypeptide or protein to a microbial DNA, inhibits, prevents or breaks down a microbial biofilm, inhibits, prevents or breaks down a biofilm, or inhibits, prevents or treats a microbial infection that produces a biofilm.

Yet another embodiment provides a non-transitory computer medium comprising a set of processor executable instructions that, when executed by a processor, identifying an agent that inhibits, competes or titrates the binding of a DNABII polypeptide or protein to a microbial DNA, that inhibits, prevents or breaks down a microbial biofilm, that inhibits, prevents or breaks down a biofilm in a subject, or that inhibits, prevents or treats a microbial infection that produces a biofilm in a subject, comprising positioning a three-dimensional structure of a candidate agent against a three-dimensional structure of an integration host factor (IHF) protein, wherein the three-dimensional structure of the IHF protein is based on X, Y and Z atomic structure coordinates determined from a crystalline form of an IHF and DNA complex, wherein interaction of the agent with the IHF at two or more IHF amino acids selected from T4, K5, A6, E28, Q43, K45, S47, G48, N51, R55, K57, R60, R63, N64, P65, K66, R76, T80, R82 or Q85 as represented in SEQ ID NO: 42, or the equivalent of each, identifies that the agent inhibits, competes or titrates the binding of a DNABII polypeptide or protein to a microbial DNA, inhibits, prevents or breaks down a microbial biofilm, inhibits, prevents or breaks down a biofilm, or inhibits, prevents or treats a microbial infection that produces a biofilm.

Methods of in silico molecule or drug designs are well known in the art, see generally Kapetanovic (2008) Chem Biol. Interact., 171(2):165-76. Briefly, the atomic coordinates of the three-dimensional structure are input into a computer so that images of the structure and various parameters are shown on the display. The design typically involves positioning a three-dimensional structure to the three-dimensional structure of the target molecule. The positioning can be controlled by the user with assistance from a computer's graphic interface, and can be further guided by a computer algorithm looking for potential good matches. Positioning also involves moving either or both of the three-dimensional structures around at any dimension.

Then, the resultant data are input into a virtual compound and/or agent library. Since a virtual library is contained in a virtual screening software such as DOCK-4 (Kuntz, UCSF), the above-described data may be input into such a software. Candidate agents may be searched for, using a three-dimensional structure database of virtual or non-virtual drug candidate compounds, such as MDDR (Prous Science, Spain).

A candidate agent is found to be able to bind to DNA and/or DNABII protein if a desired interaction between the candidate agent and either or both is found. The interaction can be quantitative, e.g., strength of interaction and/or number of interaction sites, or qualitative, e.g., interaction or lack of interaction. The output of the method, accordingly, can be quantitative or qualitative. In one aspect, therefore, the present disclosure also provides a method for identifying an agent that does not inhibit the interaction or alternatively, strengthens the interaction between the DNA and protein.

The potential inhibitory or binding effect (i.e., interaction or association) of an agent such as a small molecule compound may be analyzed prior to its actual synthesis and testing by the use of computer modeling techniques. If the theoretical structure of the given compound suggests insufficient interaction and association between it and microbial DNA in the biofilm and/or DNABII protein, synthesis and testing of the agent can be obviated. However, if computer modeling indicates a strong interaction, the agent can then be synthesized and tested for its ability to bind to or inhibit the interaction using various methods such as in vitro or in vivo experiments. Methods of testing an agent's ability to inhibit or titrate a biofilm, alone or in connection with another agent, are disclosed herein. In this manner, synthesis of inoperative agents and compounds can be avoided.

One skilled in the art may use any of several methods to screen chemical or biological entities or fragments for their ability to associate with DNABII or microbial DNA and more particularly with the specific binding sites. Selected fragments or chemical entities may then be positioned in a variety of orientations, or docked, within an individual binding site of DNA or DNABII polypeptide. Docking may be accomplished using software such as QUANTA, SYBYL, followed by energy minimization and molecular dynamics with standard molecular mechanics force fields, such as CHARMM and AMBER.

Commercial computer programs are also available for in silico design. Examples include, without limitation, GRID (Oxford University, Oxford, UK), MCSS (Molecular Simulations, Burlington, Mass.), AUTODOCK (Scripps Research Institute, La Jolla, Calif.), DOCK (University of California, San Francisco, Calif.), GLIDE (Schrodinger Inc.), FlexX (Tripos Inc.) and GOLD (Cambridge Crystallographic Data Centre).

Once an agent or compound has been designed or selected by the above methods, the efficiency with which that agent or compound may bind to each other can be tested and optimized by computational evaluation. For example, an effective DNABII fragment or may demonstrate a relatively small difference in energy between its bound and free states (i.e., a small deformation energy of binding).

A compound designed or selected can be further computationally optimized so that in its bound state it may optionally lack repulsive electrostatic interaction with the target protein. Such non-complementary (e.g., electrostatic) interactions include repulsive charge-charge, dipole-dipole, and charge-dipole interactions. Specifically, the sum of all electrostatic interactions between the agent and DNABII and/or microbial DNA in the biofilm when the agent or compound is bound to either agent, optionally making a neutral or favorable contribution to the enthalpy of binding.

Computer softwares are also available in the art to evaluate compound deformation energy and electrostatic interaction. Examples include, without limitation, Gaussian 92 [Gaussian, Inc., Pittsburgh, Pa.]; AMBER [University of California at San Francisco]; QUANTA/CHARMM [Molecular Simulations, Inc., Burlington, Mass.]; and Insight II/Discover [Biosysm Technologies Inc., San Diego, Calif.].

Once a binding agent has been optimally selected or designed, as described above, substitutions may then be made in some of its atoms or side groups in order to improve or modify its binding properties. Generally, initial substitutions are conservative, i.e., the replacement group will have approximately the same size, shape, hydrophobicity and charge as the original group. It should, of course, be understood that components known in the art to alter conformation should be avoided. Such substituted chemical compounds may then be analyzed for efficiency of fit to the DNABII protein and/or microbial DNA in the biofilm by the same computer methods described in detail, above.

Certain embodiments relate to a method for screening small molecules capable of interacting with the protein or polynucleotide disclosed herein. For the purpose of this disclosure, "small molecules" are molecules having low molecular weights (MW) that are, in one embodiment, capable of binding to a protein of interest thereby altering the function of the protein. In some embodiments, the MW of a small molecule is no more than 1,000. Methods for screening small molecules capable of altering protein function are known in the art. For example, a miniaturized arrayed assay for detecting small molecule-protein interactions in cells is discussed by You et al. (1997) Chem. Biol. 4:961-968.

To practice the screening method in vitro, suitable cell culture or tissue infected with the microbial to be treated are first provided. The cells are cultured under conditions (temperature, growth or culture medium and gas ($CO_2$)) and for an appropriate amount of time to attain exponential proliferation without density dependent constraints. It also is desirable to maintain an additional separate cell culture that is not infected as a control.

As is apparent to one of skill in the art, suitable cells can be cultured in micro-titer plates and several agents can be assayed at the same time by noting genotypic changes, phenotypic changes or a reduction in microbial titer.

When the agent is a composition other than a DNA or RNA, such as a small molecule as described above, the agent can be directly added to the cell culture or added to culture medium for addition. As is apparent to those skilled in the art, an "effective" a mount must be added which can be empirically determined, When the agent is an antibody or antigen binding fragment, the agent can be contacted or incubated with the target antigen and polyclonal antibody as described herein under conditions to perform a competitive ELISA. Such methods are known to the skilled artisan.

The assays also can be performed in a subject. When the subject is an animal such as a rat, chinchilla, mouse or simian, the method provides a convenient animal model system that can be used prior to clinical testing of an agent in a human patient. In this system, a candidate agent is a potential drug if symptoms of the disease or microbial infection is reduced or eliminated, each as compared to untreated, animal having the same infection. It also can be useful to have a separate negative control group of cells or animals that are healthy and not treated, which provides a basis for comparison.

The agents and compositions can be used in the manufacture of medicaments and for the treatment of humans and other animals by administration in accordance with conventional procedures, such as an active ingredient in pharmaceutical compositions.

Combination Therapy

The compositions and related methods of the present disclosure may be used in combination with the administration of other therapies. These include, but are not limited to, the administration of DNase enzymes, antibiotics, antimicrobials, or other antibodies.

In some embodiments, the methods and compositions include a deoxyribonuclease (DNase) enzyme that acts synergistically with the anti-DNABII antibody. A DNase is any enzyme that catalyzes the cleavage of phosphodiester linkages in the DNA backbone. Three non-limiting examples of DNase enzymes that are known to target not only cruciform structures, but also a variety of secondary structure of DNA include DNAse I, T4 EndoVII and T7 Endo I. In certain embodiments, the effective amount of anti-DNABII antibody needed to destabilize the biofilm is reduced when combined with a DNase. When administered in vitro, the DNase can be added directly to the assay or in a suitable buffer known to stabilize the enzyme. The effective Unit dose of DNase and the assay conditions may vary, and can be optimized according to procedures known in the art.

In other embodiments, the methods and compositions can be combined with antibiotics and/or antimicrobials. Antimicrobials are substances that kill or inhibit the growth of microorganisms such as bacteria, fungi, or protozoans. Although biofilms are generally resistant to the actions of antibiotics, compositions and methods described herein can be used to sensitize the infection involving a biofilm to traditional therapeutic methods for treating infections. In other embodiments, the use of antibiotics or antimicrobials in combination with methods and compositions described herein allow for the reduction of the effective amount of the antimicrobial and/or biofilm reducing agent. Some non-limiting examples of antimicrobials and antibiotics useful in combination with methods of the current disclosure include amoxicillin, amoxicillin-clavulanate, cefdinir, azithromycin, and sulfamethoxazole-trimethoprim. The therapeutically effective dose of the antimicrobial and/or antibiotic in combination with the biofilm reducing agent can be readily determined by traditional methods. In some embodiments the dose of the antimicrobial agent in combination with the biofilm reducing agent is the average effective dose which has been shown to be effective in other bacterial infections, for example, bacterial infections wherein the etiology of the infection does not include a biofilm. In other embodiments, the dose is 0.1, 0.15, 0.2, 0.25, 0.30, 0.35, 0.40, 0.45, 0.50, 0.55, 0.60, 0.65, 0.70, 0.75, 0.8, 0.85, 0.9, 0.95, 1.1, 1.2, 1.3, 1.4, 1.5, 1.6, 1.7, 1.8, 1.9, 2.0, 2.5, 3.0 or 5 times the average effective dose. The antibiotic or antimicrobial can be added prior to, concurrent with, or subsequent to the addition of the anti-DNABII antibody.

In other embodiments, the methods and compositions can be combined with antibodies that treat the bacterial infection. One example of an antibody useful in combination with the methods and compositions described herein is an antibody directed against an unrelated outer membrane protein (i.e., OMP P5). Treatment with this antibody alone does not debulk a biofilm in vitro. Combined therapy with this antibody and a biofilm reducing agent results in a greater effect than that which could be achieved by either reagent used alone at the same concentration. Other antibodies that may produce a synergistic effect when combined with a biofilm reducing agent or methods to reduce a biofilm include anti-rsPilA anti-OMP26, anti-OMP P2, and anti-whole OMP preparations.

The compositions and methods described herein can be used to sensitize the bacterial infection involving a biofilm to common therapeutic modalities effective in treating bacterial infections without a biofilm but are otherwise ineffective in treating bacterial infections involving a biofilm. In other embodiments, the compositions and methods described herein can be used in combination with therapeutic modalities that are effective in treating bacterial infections involving a biofilm, but the combination of such additional therapy and biofilm reducing agent or method produces a synergistic effect such that the effective dose of either the biofilm reducing agent or the additional therapeutic agent can be reduced. In other instances the combination of such additional therapy and biofilm reducing agent or method produces a synergistic effect such that the treatment is enhanced. An enhancement of treatment can be evidenced by a shorter amount of time required to treat the infection.

The additional therapeutic treatment can be added prior to, concurrent with, or subsequent to methods or compositions used to reduce the biofilm, and can be contained within the same formation or as a separate formulation.

Kits

Kits containing the agents and instructions necessary to perform the in vitro and in vivo methods as described herein also are claimed. Accordingly, the disclosure provides kits for performing these methods which may include an interfering disclosed herein as well as instructions for carrying out the methods disclosed herein such as collecting tissue and/or performing the screen, and/or analyzing the results, and/or administration of an effective amount of an interfering agent as defined herein. These can be used alone or in combination with other suitable antimicrobial agents.

For example, a kit can comprise, or alternatively consist essentially of, or yet further consist of any one or more agent identified above, e.g., an agent of the group of an isolated or recombinant DNABII polypeptide, an integration host factor (IHF) polypeptide or a fragment or an equivalent of each thereof; an isolated or recombinant protein polypeptide identified in Table 8, Table 9, Table 9 a DNA binding peptide identified in FIGS. 6A-6B, or a fragment or an equivalent of each thereof; an isolated or recombinant polypeptide of SEQ ID NO: 1 through 33, or a fragment or an equivalent of each thereof; an isolated or recombinant polypeptide of SEQ ID NO: 342 through 353, or a fragment or an equivalent of each thereof; an isolated or recombinant C-terminal polypeptide of SEQ ID NO: 5 through 11, 28, 29, 340 or those identified in Table 8, Table 9 or a fragment or an equivalent of each thereof; a polypeptide that competes with an integration host factor on binding to a microbial DNA; a four-way junction polynucleotide resembling a Holliday junction, a 3 way junction polynucleotide resembling a replication fork, a polynucleotide that has inherent flexibility or bent polynucleotide; an isolated or recombinant polynucleotide encoding any one of the above noted polypeptides; an antibody that specifically recognizes or binds any one of the above noted polypeptides, or an equivalent or fragment thereof; or a small molecule that competes with the binding of a DNABII protein or polypeptide to a microbial DNA, and instructions for use. The kit can further comprising one or more of an adjuvant, an antigenic peptide or an antimicrobial. Examples of carriers include a liquid carrier, a pharmaceutically acceptable carrier, a solid phase carrier, a pharmaceutically acceptable carrier, a pharmaceutically acceptable polymer, a liposome, a micelle, an implant, a stent, a paste, a gel, a dental implant, or a medical implant.

TABLE 8

| Gram (+)-only HU, Gram (−)-all have HU some also IHF | | | |
|---|---|---|---|
| Bacteria strain | Abbreviation | Protein name(s) | |
| S. sobrinus 6715 | Ss | 1310 | (HU) (not fully sequenced) |

TABLE 8-continued

Gram (+)-only HU, Gram (−)-all have HU some also IHF

| Bacteria strain | Abbreviation | Protein name(s) | |
|---|---|---|---|
| S. pyogenes MGAS10270 | Spyog | Spy1239 | (HU) |
| S. gordonii Challis NCTC7868 | Sg | SGO_0701 | (HlpA) |
| S agalactiae (Group B Strep) 2603V/R | GBS | SAG_0505 | (Hup) |
| S. mutans UA159 | Sm | Smu_589 | (HU) |
| S. pneumoniae R6 | Spneu | spr1020 | (HU) |
| S. gallolyticus UCN34 (S. bovis) | Sgall | YP_003430069 | (HlpA) |
| S. aureus MW2 | Sa | MW1362 | (HU) |
| S. epidermidis RP62A | Se | SERP1041 | (Hup) |
| E. coli K12-MG1655 | Ec | b1712 | (HimA) |
| | | b0912 | (HimD) |
| | | | (HupA) |
| | | | (HupB) |
| H. influenza KW20 Rd | Hi | HI1221 | (HimA) |
| | | HI1313 | (HimD) |
| | | HI0430 | (HupA) |
| Salmonella enteric serovar typhi CT18 | Salm | Sty1771 | (HimA) |
| Aggregatibacter actinomycetemcomitans DHS-1 | Aa | YP_003255965 | (IHFalpha) |
| | | YP_003256209 | (IhfB) |
| | | YP_003255304 | (HU) |
| P. gingivalis W83 | Pg | PG 0121 | (Hup-1) |
| | | PG_1258 | (Hup-2) |
| N. gonorrhoeae FA 1090 (Oklahoma) | Ng | NGO603 | (IHFβ) |
| | | NGO030 | (IHFα) |
| N. meningitides MC58 | Nm | NMB_0729 | (HimA) |
| | | NMB_1302 | (HimA) |
| P. aeruginosa | Pa | PA3161 | (HimD) |
| | | PA 1804 | (HupB) |
| | | PA2758 | (HimA) |
| H. pylori 26695 | Hp | Hp0835 | (Hup) |
| B. burgdorferi B31 | Bb | BB_0232 | (Hbb) |
| Moraxella catarrhalis RH4 | Mc | YP_003626307 | (HimA) |
| | | YP_003627027 | (HimD) |
| | | YP_003626775 | (HupB) |
| V. cholera El Tor N16961 | Vc | VC_0273 | (HupA) |
| | | VC_1914 | (HipB) |
| | | VC_1919 | (HupB) |
| | | VC_1222 | (HimA) |
| Burkholderia cenocepacia HI2424 | Bc | Bcen2424_1048 | (IHFB) |
| | | Bcen2424_1481 | (IHFA) |
| Burkholderia pseudomallei 668 | Bp | BURPS668_2881 | (IHFB) |
| | | BURPS668_1718 | (IHFA) |
| Mycobacterium tuberculosis CDC1551 | Mtb | MT_3064 | (HU) |
| Mycobacterium smegmatis MC2 | Ms | MSMEG_2389 | (Hup) |
| Treponema denticola ATCC 35405 | Td | TDE_1709 | (HU) |
| Treponema palladum Nichols | Tp | TP_0251 | (DNA binding protein II) |
| Prevotella melaninogenica ATCC 25845 | Pm | PREME0022_2103 | (HupB) |
| | | PREME0022_0268 | (HupA) |
| | | PREME0022_0341 | (Hup) |
| | | PREME0022_0340 | (HimA) |
| Prevotella intermedia 17 | Pi | PIN_A0704 | (Hup) |
| | | PIN_A1504 | (Hup-2) |
| | | PIN_0345 | (HimA) |
| | | PIN_0343 | (Hypothetical protein) |
| Bordetella pertusis Tohama 1 | Bpert | BP2572 | (IhfA) |
| | | BP3530 | (HupB) |
| | | BP0951 | (IhfB) |
| Enterococcus faecalis V583 | Ef | Ef1550 | (hup) |

TABLE 9

(SEQ ID NOS 160-336, respectively, in order of appearance)

| Bacteria strain, protein name | β3 sequence | α3 sequence C-terminal 20 aa |
|---|---|---|
| S. pyogenes MGAS10270, HU | AFKAGKALKDAVK | IAASKVPAFKAGKALKDAVK |
| S. gallolyticus UCN34 (S. bovis), Hlp A | AFKAGKALKDAVK | IAASKVPAFKAGKALKDAVK |
| S. sobrinus 6715 HU | AFKAGKALKDAVK | IAASKVPAFKAGKALKDAVK |

TABLE 9-continued (SEQ ID NOS 160-336, respectively, in order of appearance)

| Bacteria strain, protein name | β3 sequence | α3 sequence C-terminal 20 aa |
|---|---|---|
| S. agalactiae (Group B Strep)2603V/R Hup | AFKAGKALKDAVK | IAASKVPAFKAGKALKDAVK |
| S. pneumoniae R6 HU | AFKAGKALKDAVK | IAASKVPAFKAGKALKDAVK |
| S. gordonii Challis NCTC7868, HlpA | AFKAGKALKDAVK | IAASKVPAFKAGKALKDAVK IKASKVPAFKAGKALKDAVK |
| S. mutans UA159, HU | AFKAGKALKDAVK | |
| Enterococcus faecalis V583, Hup | AFKPGKALKDAVK | IAASKVPAFKPGKALKDAVK |
| S. aureus MW2, HU | AFKAGKALKDAVK | IPASKVPAFKAGKALKDAVK |
| S. epidermidis RP62A Hup | AFKAGKALKDAVK | IPASKVPAFKAGKALKDAVK |
| H. influenza KW20 Rd HupA | AFVSGK ALKDAIK | IAASKVPAFVSGKALKDAIK |
| Aggregatibacter actinomycetemcomitans D11S-1 HU | AFVSGK ALKDAVK | IAASKVPAFVSGKALKDAVK |
| V. cholera El Tor N16961, HupA | AFVAGKALKDAIK | IAAANVPAFVAGKALKDAIK |
| E. coli K12-MG1655 hupA | AFVSGK ALKDAVK | IAAANVPAFVSGKALKDAVK |
| P. aeruginosa HupB | GFKAGKALKDAVN | 1AAAKIPGFKAGKALKDAVN |
| E. coli K12-MG1655 hupB | SFRAGK ALKDAVN | IAAAKVPSFRAGKALKDAVN |
| V. cholera El Tor N16961, HupB | SFKAGK ALKDACN | IAEAKVPSFKAGKALKDACN |
| Bordetella pertusis Tohama 1 HupB | KFRPGK ALKDAVN | IKKAKVPKFRPGKALKDAVN |
| Prevotella melaninogenica ATCC 25845 HupB | KFKAGAELADAVNK | AAKKVAKFKAGAELADAVNK |
| Prevotella intermedia 17 Hup | KFKPGA ELADAVNA | AAKKVAKFKPGAELADAVNA |
| Moraxella catarrhalis RH4 HupB | SFKAGK VLKESVN | IAASKVPSFKAGKVLKESVN |
| P. gingivalis W83 Hup-1 | RFKPGS TLELK | ISIPARKVVRFKPGSTLELK |
| H. pylori 2669 Hup | KFKPGK TLKQKVEEGK | KRVPKFKPGKTLKQKVEEGK |
| Prevotella melaninogenica ATCC 25845 HupA | SFKPAK TFIEDMKK | PAHDFPSFKPAKTFIEDMKK |
| Prevotella intermedia 17 Hup-2 | SFKPAK TFIEDMKK | PAHDFPSFKPAKTFIEDMKK |
| P. gingivalis W83 Hup-2 | AFKPSK IFMSQMKQD | KRNIPAFKPSKIFMSQMKQD |
| Mycobacterium tuberculosis CDC1551 HU | AFRPGA QFKAVVSGAQRLPAEGPAVKRG | AKRPATKAPAKKATARRGRK |
| Mycobacterium smegmatis MC2 Hup | AFRPGA QFKAVISGAQKLPADGPAVKRG | TKAPAKKAAAKKAPAKKGRR |
| Prevotella melaninogenica ATCC 25845 HimA | NFKPAA TIKGHVRKGGQDNG | NFKPAATIKGHVRKGGQDNG |
| Prevotella intermedia 17 HimA | NFRATA SVKEKLKKGGAE | VLNFRATASVKEKLKKGGAE |
| E. coli K12-MG1655 HimA | TFRPGQ KLKSRVENASPKDE | TFRPGQKLKSRVENASPKDE |
| Salmonella enteric serovar typhi CT18 HimA | TFRPGQ KLKSRVENASPKEE | TFRPGQKLKSRVENASPKEE |
| V. cholera El Tor N1696 HimA | TFRPGQ KLKARVENIKVEK | VTFRPGQKLKARVENIKVEK |

TABLE 9-continued (SEQ ID NOS 160-336, respectively, in order of appearance)

| Bacteria strain, protein name | β3 sequence | α3 sequence C-terminal 20 aa |
|---|---|---|
| *P. aeruginosa* HimA | TFRPGQ KLKARVEAYAGTKS | TFRPGQKLKARVEAYAGTKS |
| *Burkholderia cenocepacia* HI2424 IHFA | TFHASQ KLKALVENGAE | RVVTFHASQKLKALVENGAE |
| *Burkholderia pseudomallei* 668 IHFA | TFHASQ KLKALVENGAEPDLAR | HASQKLKALVENGAEPDLAR |
| *Bordetella pertusis* Tohama 1 IhfA | TFHASQ KLKSVVEQPNSPPDPASAE | QKLKSVVEQPNSPPDPASAE |
| *N. gonorrhoeae* FA1090 (Oklahoma) IHFα | TFHASQ KLKGMVEHYYDKQR | TFHASQKLKGMVEHYYDKQR |
| *N meningitides* MC58 HimA | TFHASQ KLKSMVEHYYDKQR | TFHASQKLKSMVEHYYDKQR |
| *H. influenza* KW20 Rd HimA | TFKPGQ KLRARVEKTK | RRVVTFKPGQKLRARVEKTK |
| *Aggregatibacter actinomycetemcomitans* D11S-1 HimA | VFKPGQ KLRNRVEKVKPKA | VVFKPGQKLRNRVEKVKPKA |
| *Moraxella catarrhalis* RH4 HimA | TFKAGQKLRGWIDSQNEG | VVTFKAGQKLRGWIDSQNEG |
| *Treponema palladium* Nichols DNA_binding_protein_II | VFRPSK RLKSAVRGYRSGEVGAD | PSKRLKSAVRGYRSGEVGAD |
| *Prevotella melaninogenica* ATCC 25845 Hup | SFTPDT VMKELVNKPFSQFETVVINDGV | MQAGDTMKVPKVELRPEYRK |
| *Prevotella intermedia* 17 hypothetical | SFTPDA TMKELVNKPFAQFETVVLNDGV | SAGDTMKVPKVELRPQYRTK |
| *E. coli* K12-MG1655 HimD | HFKPGK ELRDRANIYG | KYVPHFKPGKELRDRANIYG |
| *Salmonella enteric serovar typhi* CT18 bHimD | HFKPGK ELRDRANIYG | KYVPHFKPGKELRDRANIYG |
| *V. cholera* El Tor N1696 HipB | HFKPGK ELRERVNL | EGKYVPHFKPGKELRERVNL |
| *P. aeruginosa* HimD | HFKPGK ELRDRVNEPE | KFVPHFKPGKELRDRVNEPE |
| *H. influenza* KW20 Rd HimD | YFKAGKELKARVDVQA | KSVPYFKAGKELKARVDVQA |
| *Aggregatibacter actinomycetemcomitans* D11S-1 IHFB | YFKAGKELRERVDVYAA | CVPYFKAGKELRERVDVYAA |
| *N. gonorrhoeae* FA1090 (Oklahoma) IHFβ | HFKPGK ELRERVDLALKENAN | FKPGKELRERVDLALKENAN |
| *N. meningitides* MC58 HimD | HFKPGK ELRERVDLALKENAN | FKPGKELRERVDLALKENAN |
| *Burkholderia cenocepacia* HI2424 IHFB | HFKPGK ELRERVDGRAGEPLKADDPDDDR | ERVDGRAGEPLKADDPDDDR |
| *Burkholderia pseudomallei* 668 IHFB | HFKPGK ELRERVDGRAGEPLKNDEPEDAQ | ERVDGRAGEPLKNDEPEDAQ |
| *Bordetella pertusis* Tohama 1 IhfB | HFKAGKELREWVDLVGNDQGDDSSNGSS | DSSNGSSDPLQSVMDMHAMH |
| *Moraxella catarrhalis* RH4 HimD | YFKPGK ALRESVNLVND | ATPYFKPGKALRESVNLVND |
| *B. burgdorferi* B31 Hbb | YFRPGK DLKERVWGIKG | HVAYFRPGKDLKERVWGIKG |
| *Treponema denticola* ATCC 35405 HU | RFKPGK ELKEALHKIDTQELIES | PGKELKEALHKIDTQELIES |

The following examples are intended to illustrate, and not limit the embodiments disclosed herein.

EXPERIMENTAL

Experiment No. 1

Some of the IHF antibodies, proteins and polypeptides were a generous gift from Nash. The methods to produce them are well known to the skilled artisan, e.g., as described in Granston and Nash (1993) J. Mol. Biol. 234:45-59; Nash et al. (1987) Journal of Bacteriology 169(9):4124-4127; and Rice et al. (1996) Cell 87:1295-1306. Briefly, to overproduce IHF-α, the himA gene was inserted downstream from the $P_L$ promoter in the bacterial plasmid pAD284. Transformants of strain K5607, a lambda lysogen of strain C600himA42 that had received the desired plasmid, were identified by screening ampicillin-resistant transformants for the ability to grow bacteriophage Mu (13). DNA was prepared from himA$^+$ transformants according to standard DNA isolation techniques, and the orientation of the himA gene was determined by restriction enzyme cleavage. Plasmid pPLhimA-1, which has the himA gene in the proper orientation for expression by the $P^L$ promoter, was transformed into strain N5271, which contains a cryptic lambda prophage expressing the cI857 thermoinducible repressor, to yield strain K5770.

To overproduce IHF-β, plasmid pKT23-hip323, which contains a fusion of the IHF-β coding sequence to the bacteriophage lambda $P_L$ promoter was used. pKT23-hip323 was introduced into N5271 to give strain E443. To facilitate the selection of pKT23-hip323 in the presence of another plasmid, changed its selectable marker was changed from ampicillin resistance (bla$^+$) to chloramphenicol resistance (cat$^-$). A cat-containing fragment was isolated from plasmid pBR325 as described by Flamm and Weisberg and was inserted into the unique ScaI site in bla. The ligated DNA was introduced into strain E403, which carries a hip mutation and which synthesizes temperature-sensitive X repressor, and chloramphenicol-resistant transformants were selected at low temperature. One such transformant (E735) was hip$^+$ and ampicillin sensitive; it therefore appears to carry a bla cat$^+$ derivative of pKT23-hip323 (pE735).

To generate a strain that overproduces both subunits of IHF, E735 was transformed with plasmid pP$_L$himA-1, selecting transformant (E738) that had become ampicillin resistant and had retained chloramphenicol resistance. The generation of a second strain that overproduces both subunits of depended on the construction of plasmid pP$_L$hip himA-5, which was made by ligating blunted (SstII restriction enzyme site) containing the pheT and himA genes into the pKT23-hip323 plasmid. This is described in further detail in (Nash et al. (1987) J. Bacteriology 169(9):4124-4127. himA$^+$ transformants of strain K5607 were identified by screening for HimA$^+$, and the plasmid DNA was analyzed by restriction digestion. In all cases where the plasmid structure was obvious, two copies of himA had been ligated as a tandem direct repeat into the vector. It is not known if the presence of two copies of the himA gene on this plasmid is demanded by the selection, but it should be recalled that a single copy of the himA gene in plasmid pP$_L$himA-1 is sufficient to complement a himA mutant. Plasmid pP$_L$hiphimA-5 was used to transform strain N5271 to yield strain K5746.

Cells were grown in shaking water bath at 31° C. in TBY medium (10 g of tryptone, 5 g of yeast extract, and 5 g of sodium chloride per liter). At mid-log phase (optical density at 650 nm, ca. 0.6), the cells were shifted to a 42° C. water bath and shaking was continued. Typically, 300 ml of culture was centrifuged and suspended in 0.6 to 0.9 ml of TEG (20 mM Tris hydrochloride (pH 7.4), 1 mM sodium EDTA, 10% glycerol) containing 20 mM NaCl. The cells were disrupted with six 20-s bursts of sonication, with 40 s between each burst. A portion of the sonic extract was centrifuged in a Sorvall SS34 rotor for 20 min at 15,000 rpm. Samples of the sonic extract were analyzed by sodium dodecyl sulfate (SDS) gel electrophoresis according to standard molecular biology techniques.

Purification of was done according to the following: A 3.6-liter batch of cells was induced for 3 h. All subsequent steps were carried out at 0 to 4° C. The cell pellet from 3.3-liters was suspended in 10 ml of TEG containing 20 mM NaCl to give a total volume of 29 ml; this suspension was disrupted in two batches, each receiving six bursts of 3 min of sonication separated by 90-s intervals. The sonic extract was centrifuged for 20 min at 15,000 rpm, yielding 16.9 ml of clarified extract. A 10% (vol/vol) solution (1.1 ml) of polymin P (BDH Chemicals Ltd.) was added slowly to the clarified extract; after being stirred for 20 mm, the mixture was centrifuged for 30 mm at 10,000 rpm. The resulting pellet was suspended in 10 ml of TEG containing 500 mM NaCl; after being stirred for 15 min, the mixture was centrifuged for 20 min at 12,000 rpm. The supernatant (10.3 ml) was adjusted to 50% saturation by the addition of 3.2 g of ammonium sulfate, stirred for 20 min, and centrifuged for 15 min at 15,000 rpm. The resulting supernatant was adjusted to 70% saturation by the addition of 1.64 g of ammonium sulfate, stirred for 20 min, and centrifuged for 15 min at 15,000 rpm. The resulting pellet was suspended in 1 ml of TG (50 mM Tris hydrochloride (pH 7.4) containing 10% glycerol) and dialyzed against two changes of TG. The dialyzed material (2.0 ml) was loaded onto a 1-ml column (0.5 by 5.8 cm) of phosphocellulose (P11; Whatman, Inc.) that had been equilibrated with TG. The column was washed with 3 ml of TG and developed with 20 ml of a linear gradient (0 to 1.2 M) of KCl in TG. Fractions of 0.5 ml were collected, stored at −20° C., and assayed for IHF activity.

Polyclonal anti-IHF was prepared as follows. Rabbits were injected with 250 μg of purified IHF with Freund's complete adjuvant. Booster immunizations of 250 μg of IHF with Freund's incomplete adjuvant were given 1, 7, and 12 weeks later. As determined by immunoblotting of IHF, sera collected 13 weeks after the initial injection had a high titer of IHF-reactive material. The animals were maintained for several years and, when necessary, given further booster immunization in order to maintain a high titer of anti-IHF in their sera. The antibody was not purified further. Crude sera was stored at −70° C.

Antibodies specific to each subunit were generated by using synthetic polypeptides corresponding to the most C-terminal 20 amino acid residues of each subunit (SEQ ID NO: 34 and 35), to immunize rabbits according to Ditto et al. (1994) J. Bacteriology 176(12):3738-3748.

Experiment 2

This experiment describes an in vitro model for reversal of an established biofilm in 8-well chamber slide. The materials used in this experiment were: Chocolate Agar; sBHI (BHI with 2 mg heme/mL and 2 mg b-NAD/mL); 8-well Chamber slides (Nunc*Lab-Tek*Fisher catalog #12-565-18); Sterile 0.9% saline; LIVE/DEAD BacLight Bacterial Viability Kit (Fisher catalog #NC9439023) and Formalin.

On day 1, NTHI was struck for isolation on chocolate agar. It was then incubated for 20 hrs at 37° C. and 5% $CO_2$. The next day, bacteria were suspended in 5 mL equilibrated (37° C., 5% $CO_2$) and optical density was adjusted to $OD_{490}$=0.65 in sBHI. Bacteria were diluted 1:6 in equilibrated sBHI (1 mL bacterial suspension+5 mL sBHI). Bacteria was then incubated for 3 hours at 37° C. in 5% $CO_2$, static ($OD_{490}$ should be approx 0.65). Next, the bacteria were again diluted 1:2500 in equilibrated sBHI and 200 mL of the bacterial suspension was added to each well of the chamber slide. For dilution, 10 µL bacteria was added to 990 µL sBHI in an eppendorf tube and 8 µL dilution was added to 192 µL sBHI in each chamber and incubated at 37° C., 5% $CO_2$, static.

On the third day after 16 hours of incubation medium was aspirated from chamber by aspirating medium from the corner of the well so as not to disturb biofilm. Then 200 mL of equilibrated sBHI was added to each chamber and incubated for 37° C., 5% $CO_2$, static for 8 hours. After 8 hours, the medium was aspirated and 200 mL equilibrated sBHI was added to each untreated chamber; and 200 mL of interfering agent such as Rabbit anti-rsPilA; diluted 1:50 in sBHI and 200 mL Naive rabbit serum (or other appropriate serum control) diluted 1:50 in sBHI was added. They were then incubate at 37° C. and 5% $CO_2$, static.

On day 4, after approximately 16 hours of incubation, aspirate sBHI was aspirated and the biofilm was washed twice with 200 mL sterile saline. The saline was aspirated and 200 mL Live/Dead stain was added. Next, 3 mL component A plus 3 mL component B in 1 mL sterile 10 mM phosphate buffered saline was added. It was then incubated for 15 minutes at room temperature, static, protected from light. Stain was aspirated and biofilm was washed twice with 200 mL sterile saline. Saline was aspirated and 200 mL formalin was added to fix biofilm. It was then incubated 15 minutes at room temperature, static, protected from light. Formalin was aspirated and biofilm was washed twice with 200 mL sterile saline. Gasket was removed and coverslip were placed on slide; coverslip were sealed with nail polish and dried prior to viewing by confocal microscopy.

Using this method and anti-IHF antibody described in Experiment No. 1, Applicants reduced a biofilm produced by *Haemophilus influenzae* which is prevalent in sinusitis, bronchitis, otitis media and exacerbations of chronic obstructive pulmonary disease (COPD). Untreated biofilm mass was measured to be 4.24 $\mu m^3/\mu m^2$ with a mean thickness of 11.68 After treatment, the biofilm mass was reduced to 0.53 $\mu m^3/\mu m^2$ with a mean thickness of 1.31 µm. Thus, this shows an 88.8% reduction in mean thickness and an 87.5% reduction in biomass.

Polyclonal antisera directed against the *E. coli* IHF raised against an IHF promoter purified from *E. coli* K12 was prepared in rabbits according to standard techniques using purified Integration Host Factor (IHF). Experiment 1 describes the expression and purification of IHF from *E. coli*. This antibody is the anti-IHF antibody used to generate the data in the experiments disclosed below.

Using this method and anti-IHF antibody, Applicants reduced a biofilm produced by *Streptococcus mutans* which is prevalent in initiation and progression of dental caries. Untreated biofilm mass was measured to be 1.17 $\mu m^3/\mu m^2$ with a mean thickness of 5.43 After treatment, the biofilm mass was reduced to 0.1 $\mu m^3/\mu m^2$ with a mean thickness of 0.47 Thus, this shows a 91.3% reduction in mean thickness and an 91.6 % reduction in biomass. In vitro biofilm assays were repeated 3 times, on separate days. The percent reduction in the max height, average thickness, and biomass is depicted in Table 1 below.

TABLE 1

|  |  | Assay 1 | Assay 2 | Assay 3 |
|---|---|---|---|---|
| S. mutans | Max height (µm) | 56 | 24 | 41 |
|  | Ave thickness (µm) | 65 | 65 | 67 |
|  | biomass ($\mu m^3/\mu m^2$) | 37 | 58 | 66 |

Figure 7:
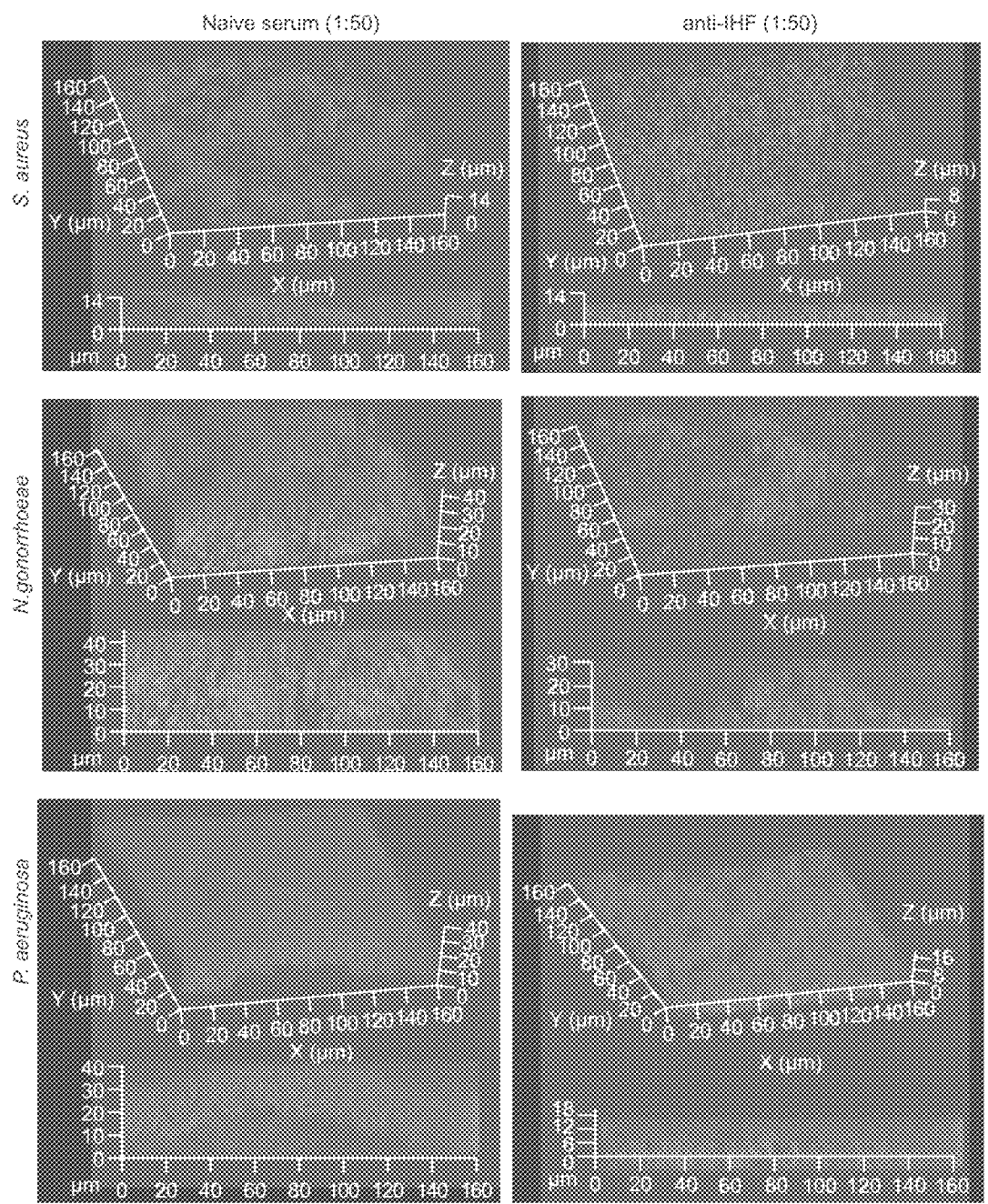
FIG. 7 depicts the reduction of biofilms formed by S. aureus, N. gonorrhoeae and P. aeruginosa upon incubation with rabbit anti-IHF compared to incubation with naïve rabbit serum.

Using this method and anti-IHF antibody, Applicants reduced a biofilm produced by *Staphylococcus aureus* which is prevalent in localized and diffuse skin infections, chronic rhinosinusitis and nosocomial infections. Untreated biofilm mass was measured to be 0.3 $\mu m^3/\mu m^2$ with a mean thickness of 2.2 µm and a biofilm height of 17.5 After treatment, the biofilm mass was reduced to 0.3 $\mu m^3/\mu m^2$ with a mean thickness of 1.1 µm and a biofilm height of 8 Thus, this shows a 48.8% reduction in mean thickness and a 2.7% reduction in biomass (FIG. 7).

Using this method and anti-IHF antibody, Applicants reduced a biofilm produced by *Moraxella catarrhalis* which is prevalent in exacerbation of COPD and otitis media. Untreated biofilm mass was measured to be 0.72 $\mu m^3/\mu m^2$ with a mean thickness of 1.48 After treatment, the biofilm mass was reduced to 0.13 $\mu m^3/\mu m^2$ with a mean thickness of 0.65 µm. Thus, this shows a 55.8% reduction in mean thickness and an 82.1% reduction in biomass. In vitro biofilm assays were repeated 3 times, on separate days. The percent reduction in the max height, average thickness, and biomass is depicted in Table 2 below.

TABLE 2

|  |  | Assay 1 | Assay 2 | Assay 3 |
|---|---|---|---|---|
| M. catarrhalis | Max height (µm) | 61 | 33 | 36 |
|  | Ave thickness (µm) | 92 | 34 | 84 |
|  | biomass ($\mu m^3/\mu m^2$) | 92 | 35 | 92 |

Using this method and anti-IHF antibody, Applicants reduced a biofilm produced by *Streptococcus pneumoniae* which is prevalent in sinusitis, pneumonia and otitis media. Untreated biofilm mass was measured to be 0.64 $\mu m^3/\mu m^2$ with a mean thickness of 3.99 After treatment, the biofilm mass was reduced to 0.14 $\mu m^3/\mu m^2$ with a mean thickness of 0.82 µm. Thus, this shows a 79.5% reduction in mean thickness and a 78.6% reduction in biomass. In vitro biofilm assays were repeated 3 times, on separate days. The percent reduction in the max height, average thickness, and biomass is depicted in Table 3 below.

TABLE 3

|  |  | Assay 1 | Assay 2 | Assay 3 |
|---|---|---|---|---|
| S. pneumoniae | Max height (µm) | 49 | 51 | 44 |
|  | Ave thickness (µm) | 25 | 64 | 79 |
|  | biomass ($\mu m^3/\mu m^2$) | 51 | 61 | 79 |

Using this method and anti-IHF antibody, Applicants reduced a biofilm produced by *Pseudomonas aeruginosa* which is prevalent in cystic fibrosis, pneumonia, skin and soft tissue infections and on medical devices. Untreated biofilm mass was measured to be 7.0 $\mu m^3/\mu m^2$ with a mean thickness of 25.70 µm and a biofilm height of 40 After treatment, the biofilm mass was reduced to 3.4 $\mu m^3/\mu m^2$ with a mean thickness of 10.3 µm and a biofilm height of 27.5 Thus, this shows a 60.1% reduction in mean thickness and a 50.8% reduction in biomass (FIG. 7).

Using this method and anti-IHF antibody, Applicants reduced a biofilm produced by *Neisseria gonorrhoeae* which is in gonorrhea. Untreated biofilm mass was measured to be 9.5 $\mu m^3/\mu m^2$ with a mean thickness of 22.02 $\mu m$ and a biofilm height of 40 After treatment, the biofilm mass was reduced to 0.8 $\mu m^3/\mu m^2$ with a mean thickness of 3.4 $\mu m$ and a biofilm height of 27.5 Thus, this shows an 84.5% reduction in mean thickness and a 92.1% reduction in biomass (FIG. 7).

Using this method and anti-IHF antibody, Applicants reduced a biofilm produced by Uropathogenic *E. coli* which is prevalent in urinary tract infections. Untreated biofilm mass was measured to be 1.75 $\mu m^3/\mu m^2$ with a mean thickness of 31.73 After treatment, the biofilm mass was reduced to 0.75 $\mu m^3/\mu m^2$ with a mean thickness of 1.62 Thus, this shows a 94.9% reduction in mean thickness and a 56.9% reduction in biomass. In vitro biofilm assays were repeated 3 times, on separate days. The percent reduction in the max height, average thickness, and biomass is depicted in Table 4 below.

TABLE 4

| | | Assay 1 | Assay 2 | Assay 3 |
|---|---|---|---|---|
| UPEC | Max height ($\mu m$) | 69 | 65 | 76 |
| | Ave thickness ($\mu m$) | 97 | 33 | 95 |
| | biomass ($\mu m^3/\mu m^2$) | 98 | 96 | 57 |

Using this method and anti-IHF antibody, Applicants reduced a biofilm produced by *Staphylococcus epidermidis* which is prevalent in infections of the skin. In vitro biofilm assays were repeated 3 times, on separate days. The percent reduction in the max height, average thickness, and biomass is depicted in Table 5 below.

TABLE 5

| | | Assay 1 | Assay 2 | Assay 3 |
|---|---|---|---|---|
| S. epidermidis | Max height ($\mu m$) | 42 | 38 | 56 |
| | Ave thickness ($\mu m$) | 62 | 71 | 92 |
| | biomass ($\mu m^3/\mu m^2$) | 62 | 76 | 88 |

Experiment No. 3

Middle ear infection (or otitis media, OM) is a highly prevalent disease worldwide, afflicting 50-330 million children globally each year. The socioeconomic burden of OM is also great, with cost estimates between $5-6 billion in the United States alone annually. All three of the predominant bacterial pathogens of OM are known to form biofilms both in vitro and in vivo and recently, clinicians have come to appreciate that the chronicity and recurrence of OM is due, at least in part, to the formation of bacterial biofilms within the middle ear cavity. In one chinchilla model of OM, juvenile chinchillas are first given a viral 'cold', followed a week later by their being challenged intranasally with an inoculum viable bacteria. Similar to the human condition wherein "my child has a cold and a week later gets an ear infection" chinchillas will also develop a bacterial OM approximately one week after a challenge, and while experiencing the viral upper respiratory tract infection. Once bacteria gain access to the middle ear (either via ascension of the Eustachian tube or following direct challenge to the middle ear space), they will form a robust biofilm. Applicants thus contemplated and indeed have already used chinchilla models as reported herein to demonstrate the protective efficacy of IHF immunization which results in rapid resolution of existing biofilms. This model is also useful for therapeutic approaches via either passive delivery of anti-DNABII antibody or via delivery of a small molecule or other agent known to bind to IHF or other DNABII family members.

Because the chinchilla model is used for development and pre-clinical testing of human vaccines, it is important to establish meaningful immunological parallels with the human host, particularly the child. Applicants have shown that effusions recovered from children with AOM due to NTHI, and middle ear fluids from chinchillas with experimental NTHI-induced OM, recognized immunodominant regions of OMP P5 in a similar hierarchical manner (see for e.g., Novotny, L. A. et al. (2000) Infect 68(4):2119-28; Novotny, L. A. et al. (2007) 9th International Symposium on Recent Advances in Otitis Media; St. Pete Beach, Fla.; Novotny, L. A. et al. (2002) Vaccine 20(29-30):3590-97). Applicants have also shown that chinchillas with experimental OM, children with natural OM, and adults with exacerbations of COPD, all recognized peptides representing PilA in a highly analogous manner (see for e.g., Adams, L. D. et al. (2007) 107th General Meeting, American Society for Microbiology; 2007; Toronto, ON; Adams, L. D. et al. (2007) 9th International Symposium on Recent Advances in Otitis Media; St. Pete Beach, Fla.). Thus, chinchillas with experimental OM and children with natural disease respond similarly immunologically to at least two unrelated NTHI protein adhesins. This parallel was put to the ultimate test recently, when the chinchilla AV-NTHI superinfection model was used to conduct pre-clinical efficacy testing of a novel 11-valent Protein D-pneumococcal polysaccharide conjugate vaccine. Data obtained in the chinchilla predicted an efficacy of 34% whereas, when tested in children, the efficacy obtained against *H. influenzae*-induced OM was 35.6% (see for e.g., Novotny, L. A. et al. (2006) Vaccine 24(22):4804-11 and Prymula, R. et al. (2006) Lancet. 367 (9512):740-8), thus lending strong support to the relevancy of this model for the development and testing of OM vaccine candidates.

Applicants have shown a dramatic reduction in the preformed biofilm remaining within the middle ears of chinchillas after receipt of 2 weekly TC immunizations with an IHF promoter purified from *E. coli* K12 (the full length combination of both IHF subunits) delivered with a mucosal/systemic adjuvant.

48 adults were ordered from Rauscher's Chinchilla Ranch (LaRue, Ohio) and were acclimated to the vivarium for 7-10 days prior to the beginning of the study. Prior to TB [transbullar or direct challenge into the middle ear cavity] challenge, baseline otoscopy and tympanometry were performed as well as a limited volume prebleed to collect serum. Chinchillas were anesthetized and 300 $\mu l$ of NTHI (strain #86-028NP) suspension containing approximately 1000 cfu were introduced into the middle ear space via transbullar challenge. Animals were allowed to recover, then monitored daily for adverse reactions as per IACUC accepted animal use protocols. Routine otoscopy and tympanometry were performed every 2-3 days throughout the study.

Four days after challenge (day +4), chinchillas were anesthetized and a CT scan was performed to visualize biofilms present within the middle ear and to obtain pre-immunization images. The surface of the pinnae were cleaned and hydrated by wiping with a sterile gauze pad moistened with sterile pyrogen free saline. After ~2 minutes (to allow the pinnae to dry), 50 μl of either the dmLT, IHF (purified *E. coli* IHF according to Experiment 1)+dmLT, or IHF+rsPiLA+dmLT solution will be added to the pinna and gently massaged in. Three chinchillas per cohort were sacrificed and tissues/samples collected (on days +4, and +11) to begin to determine mechanism of action.

Eleven days after challenge (day +11), the secondary immunization occurred as described above wherein the pinnae are cleaned/hydrated and immunogens were topically administered. Three chinchillas per cohort were sacrificed and tissues/samples collected to begin to determine mechanism of action.

Eighteen days after challenge (day +18), chinchillas were anesthetized and a CT scan were performed to identify any biofilms present, as well as to compare to the pre-immunization CT scans. The animals were then bled to collect serum and euthanized. The bullae are dissected and any fluids present were aseptically collected, the bullae were then opened to visualize the inferior bulla and any biofilm present. Images were collected and the bulla were washed with 1 ml of sterile saline and re-imaged. The mucosa, along with any biofilm present, were collected from the right bulla and placed in a preweighed tube. These tissues were homogenized, serially diluted, and plated to determine cfu NTHI/mg wet weight tissue. The left bullae were filled with OCT compound and snap frozen for histological analysis.

Images of the left and right middle ear cavities, with resident biofilms, were scrambled and two images per animal were compiled into a single file for ranking by blinded evaluators. The relative amount of biomass remaining within the middle ear of each animal was ranked on a 0 to 4+ scale by blinded reviewers using the scale shown in Table 6 below. Titer ELISAs, cytokine arrays, and Biacore were run on the serum as well as on the collected middle ear effusions. The OCT embedded middle ears were sectioned and stained either for basic morphology and architecture (H&E) or for the presence of IHF using immunohistochemistry and/or immunofluorescence.

TABLE 6

| Score | Criteria |
|---|---|
| 0 | No evidence of biomass. |
| 1+ | Biomass fills ≤25% of middle ear space. Junction of the bony septa to inferior bulla is visible. |
| 2+ | Biomass tills >25% to ≤50% of middle ear space. Unable to visualize where the bony septa meet the inferior bulla. |
| 3+ | Biomass fills >50% to ≤75% of middle ear space. Biomass covers >50% of the length of bony septa. |
| 4+ | Biomass tills >75% to ≤100% of middle ear space. Bony septa ot visible; obscured by biomass. |

Immunofluorescence imaging of frozen sections of biofilms formed in vivo was preformed according to the following. After dissection, the middle ear of each chinchilla was filled with OCT embedding compound (Fisher Scientific, Pittsburgh, Pa.) and flash frozen over liquid nitrogen. The bone which forms the inferior bulla was removed to leave the middle ear mucosa and existing biofilm intact. The resulting block was then bisected to reveal a cross section of the biofilm and re-embedded in OCT. Ten micron serial sections were cut using a Microm rotary cryotome, adhered to glass slides (Mercedes Medical, Sarasota, Fla.) and stored at −80° C. Sections were later stained to determine the relative incorporation of IHF within biofilms that had formed in vivo. Briefly, slides were air-dried, fixed in cold acetone, then equilibrated in buffer (0.05M Tris-HCl, 0.15M NaCl and 0.05% Tween 20, pH 7.4). Sections were blocked with image-iT FX signal enhancer (Molecular Probes, Eugene, Oreg.) and with Background Sniper (BioCare Medical, Concord, Calif.) per manufacturer's instructions. Sections were then incubated with a 1:200 dilution of polyclonal rabbit anti-IHF overnight at 4° C., in a humidified chamber. Slides were further rinsed and incubated with goat anti-rabbit IgG conjugated to AlexaFluor 594 (Invitrogen) for 30 minutes at room temp. As a counterstain, sections were incubated with DAPI and cover-slipped using ProLong Gold antifade reagent (Molecular Probes, Eugene, Oreg.). Naive rabbit serum served as the negative control. Sections were viewed with a Zeiss LSM 510 Meta confocal system attached to a Zeiss Axiovert 200 inverted microscope (Carl Zeiss Inc., Thornwood, N.Y.).

Significant differences in mean CFU/mg tissue and mean CFU NTHI/ml supernatant were determined by paired t-test. A p-value ≤0.05 was considered significant. Significance in relative biomass among cohorts was assessed by unpaired t-test. A p-value ≤0.05 was considered significant.

Figure 10A:
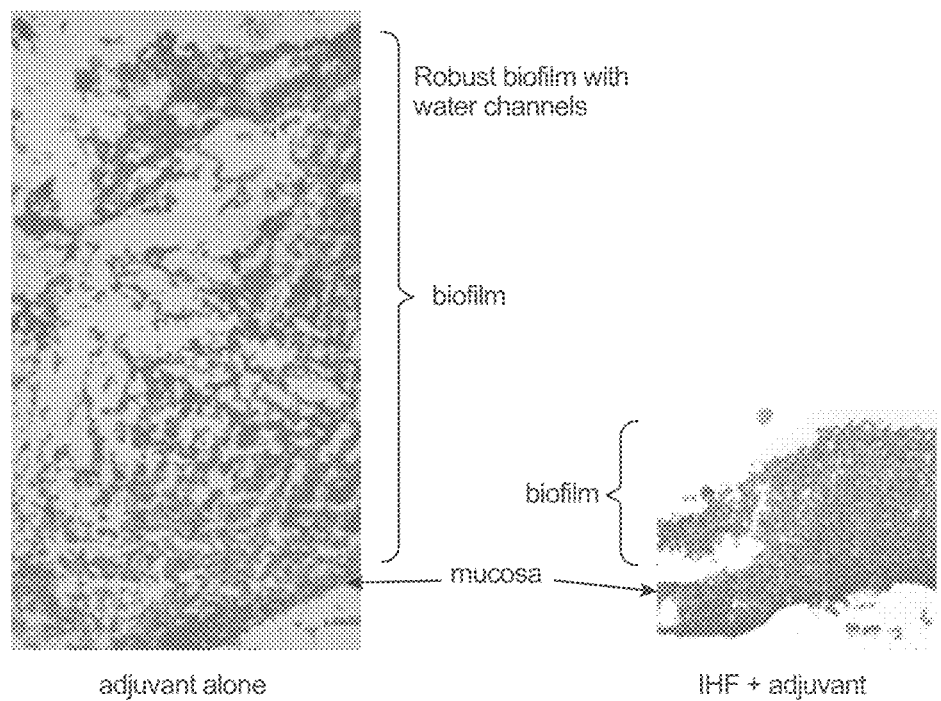
FIG. 10A shows H&E staining of a frozen section of a biofilm recovered from the middle ear of a chinchilla that had been immunized via TCI with adjuvant alone versus immunization with IHF+adjuvant. Note condensed and collapsed appearance of biofilm recovered from the animal immunized with IHF+adjuvant compared to that immunized with adjuvant alone. Images shown in FIG. 10A are shown at identical magnifications to illustrate the differences in height and density between the two representative biomasses.
Figure 10B:
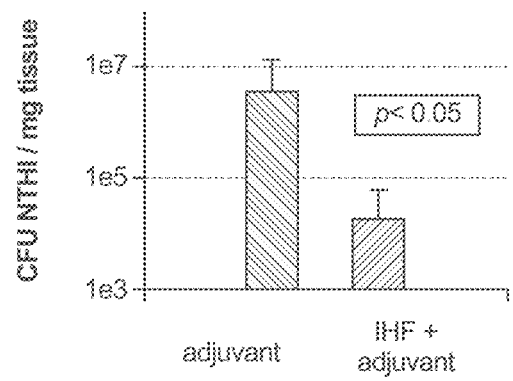
FIG. 10B demonstrates that there is a significant reduction of bacterial load present in the middle ears of animals immunized with adjuvant alone versus those immunized with IHF+adjuvant ($p<0.05$).

As shown in FIG. 9A, the mean score for remaining biomass within the middle ears of chinchillas immunized with adjuvant only was 2.8 which indicated significant remaining disease and a lack of resolution of pre-formed biomass in most animals by day 18 after bacterial challenge of the middle ear. In contrast, the mean score for an *E. coli* IHF+ adjuvant immunized animal was 1.5. Representative images of a residual biomass that received a mean score of +2.8 and one that received a mean score of +1.5 are shown in FIG. 9B. Also, as shown in FIGS. 10A-10B, the disease resolution was additionally measured by both histological evidence of altered biomass architecture within the middle ear (see FIG. 10A) as well as a statistically significant reduction of bacterial load present within remaining biomass as measured by homogenization of the biomass and culture on chocolate agar (see FIG. 10B). Furthermore, all animals immunized with isolated *E. coli* IHF mounted a strong local and systemic immune response and no animal presented with obvious secondary sequelae as the result of immunization as noted upon necropsy (data not shown).

The notable observed efficacy when anti-IHF raised against an IHF promoter purified from *E. coli* K12 (the full length combination of both IHF subunits) used in vitro to debulk biofilms and also of purified *E. coli* IHF, when used as an immunogen in vivo to induce the formation of polyclonal antibodies that could resolve an ongoing biofilm disease, created a conundrum as to why mammalian hosts do not naturally mount an effective immune response to DNABII proteins that are associated with eDNA within the bacterial biofilms of recurrent and/or chronic disease states. In review of the solved structure of IHF when it is bound to DNA (Rice et al. (1996) Cell 87(7):1295-1306), it is clear that a significant portion of the protein structure is occluded by bound DNA, which suggested the potential for occlusion of protective epitopes or domains of IHF and/or HU when bound to eDNA within a bacterial biofilm. It was hypothesized that use of native IHF, to which no DNA was bound, as the immunogen might provide a mechanism to overcome such occlusion and thereby foster production of protective antibodies.

To determine if eDNA could indeed prevent the development of protective antibodies directed against a DNABII family member upon immunization, whereas use of native protein was effective, a second larger cohort study was performed wherein the chinchilla study as detailed previously was essentially repeated.

For the second animal immunization study, twenty adult chinchillas (body mass between 500-700 g), shown to have no evidence of middle ear disease by tympanometry and video otoscopy, were enrolled and divided into four cohorts of 5 animals each. All animals were again challenged transbullarly with approximately 1000 CFU NTHI strain 86-028NP per bulla. Four days later, after a biofilm formed in the middle ear cavities of these animals, they were immunized by a transcutaneous route (TCI) as described above. Formulations consisted of either: 10 µg IHF admixed with 10 µg dmLT, 10 µg IHF that had been pre-bound to DNA+dmLT, DNA+dmLT, or 10 µg dmLT alone.

To determine if TCI with IHF pre-bound to DNA resulted in a similar immune response to that induced when the same nucleoprotein complex was delivered subcutaneously (SQ), and compared to that induced by IHF alone, two adult chinchillas were immunized to generate antisera. Each animal received a priming dose followed by two identical boosts delivered at 30-day intervals. Immunogens were admixed with the adjuvant monophosphoryl lipid A (MPL) (10 µg/dose) (Sigma-Aldrich, St. Louis, Mo.) due to its demonstrated strong adjuvant properties in the chinchilla host (See for example Bakaletz et al. (1999) Infect Immun. 67(6):2746-2762 and Kennedy et al. (2000) Infect. Immun. 68(5):2756-2765. One chinchilla was immunized with 10 µg of IHF+MPL and the other received 10 µg IHF bound to DNA+MPL. All doses were delivered SQ in a total volume of 200 µl. Fifteen days after receiving the final boost, animals were bled to procure serum and sera were assayed via Western blot and ELISA to determine both reciprocal titer and specificity of antibody reactivity to IHF.

Figure 11:
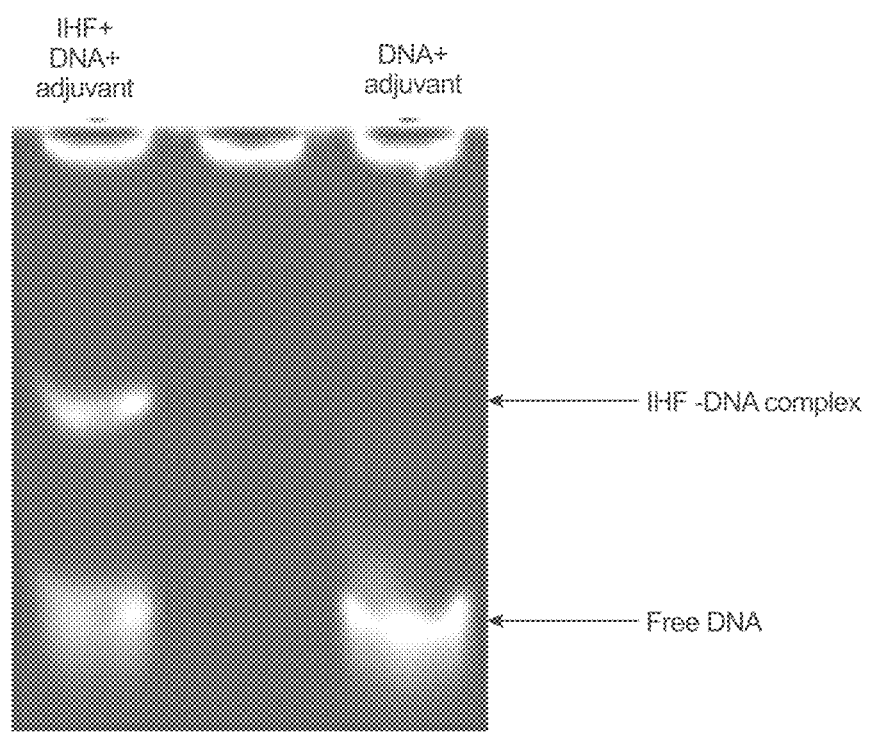
FIG. 11 depicts an electrophoretic mobility shift assay which demonstrated that IHF formed specific complexes with dsDNA under conditions used to immunize chinchillas.

Middle ears were again subsequently scored from 0 to 4+ for disease severity upon completion of the study. To better assure that the IHF and DNA remained in complex for immunization, synthetic oligonucleotides identical to those used in the published co-crystallization study (see for e.g., Rice et al. (1996) Cell 87(7):1295-1306) of a high affinity IHF binding site from the bacteriophage lambda recombination site attP at a molar ratio of 2:1 [DNA (10 µM) to IHF (5 µM)] was used. This amount was at least 3 orders of magnitude over the $K_d$ of IHF bound to this DNA target. As shown in FIG. 11, IHF indeed bound dsDNA as demonstrated by its reduced mobility in an electrophoretic mobility shift assay.

Figure 12:
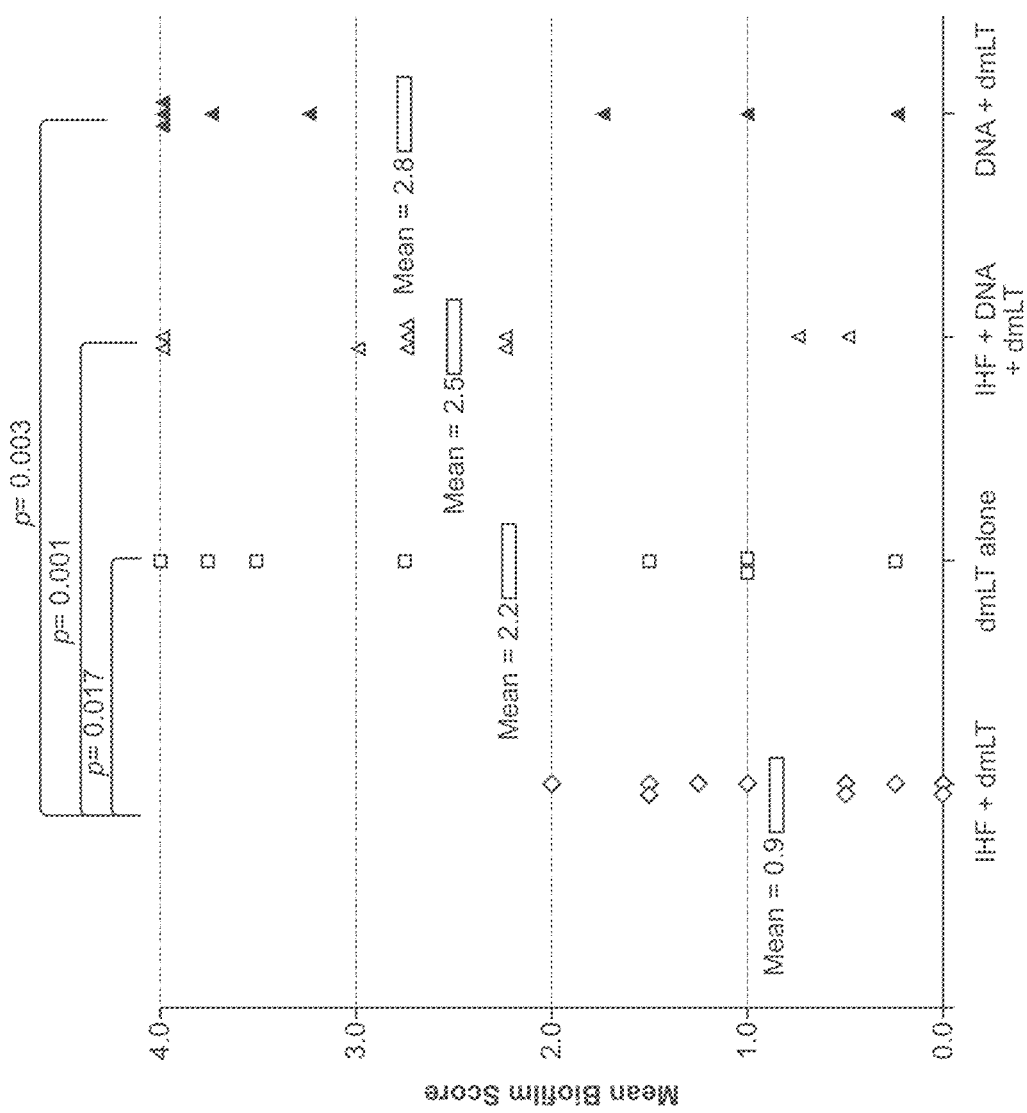
FIG. 12 graphically represents transcutaneous immunization with native IHF+adjuvant induced the formation of antibodies that significantly reduced the biomass resident within the middle ears of chinchillas compared to receipt of either adjuvant alone ($p<0.017$), dsDNA alone ($p<0.003$) or IHF to which dsDNA was already bound+adjuvant ($p<0.001$). This outcome suggested that binding of dsDNA to native IHF masked protective epitopes of this DNABII family member.

As shown in FIG. 12, animals immunized with isolated *E. coli* IHF showed a dramatic reduction in disease state with a mean residual middle ear biomass score of 0.9 as compared to the controls that had been immunized with adjuvant alone (mean biomass score=2.2) or to those that had been immunized with DNA that had been admixed with adjuvant (mean biomass score=2.8). Interestingly, those animals that had been immunized with the IHF-DNA complex also demonstrated middle ears with significant remaining bacterial biomass, yielding a mean biomass score of 2.5 which was not statistically significantly different from cohorts that received either the adjuvant alone or DNA that had been admixed with adjuvant. This outcome strongly suggested that if sufficient eDNA fragments were present, as one could hypothesize would be the case during natural disease, this situation could result in occlusion of critical IHF epitopes necessary for the generation of neutralizing antibodies.

Figure 13:
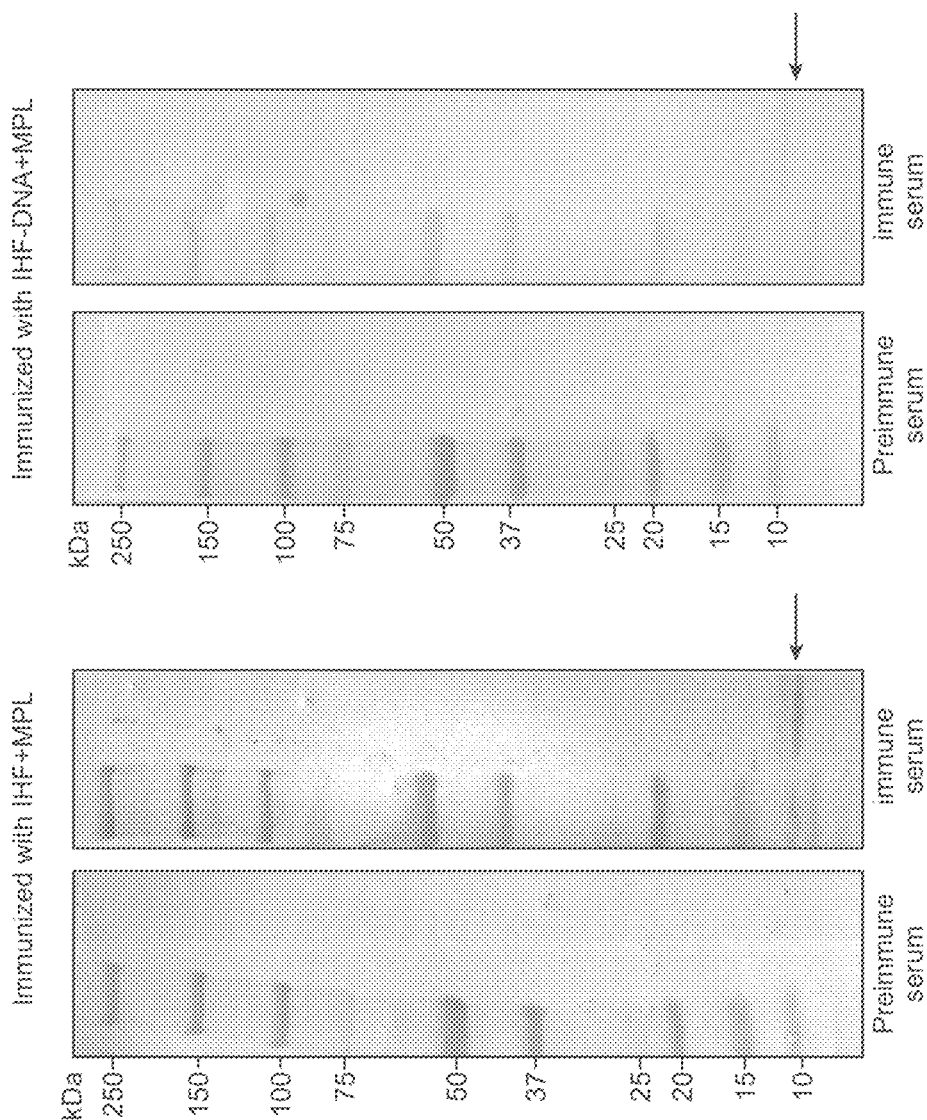
FIG. 13 depicts the recognition of IHF (arrows) by antibody in serum after subcutaneous immunization with IHF or with IHF to which dsDNA was bound.'
Figure 15:
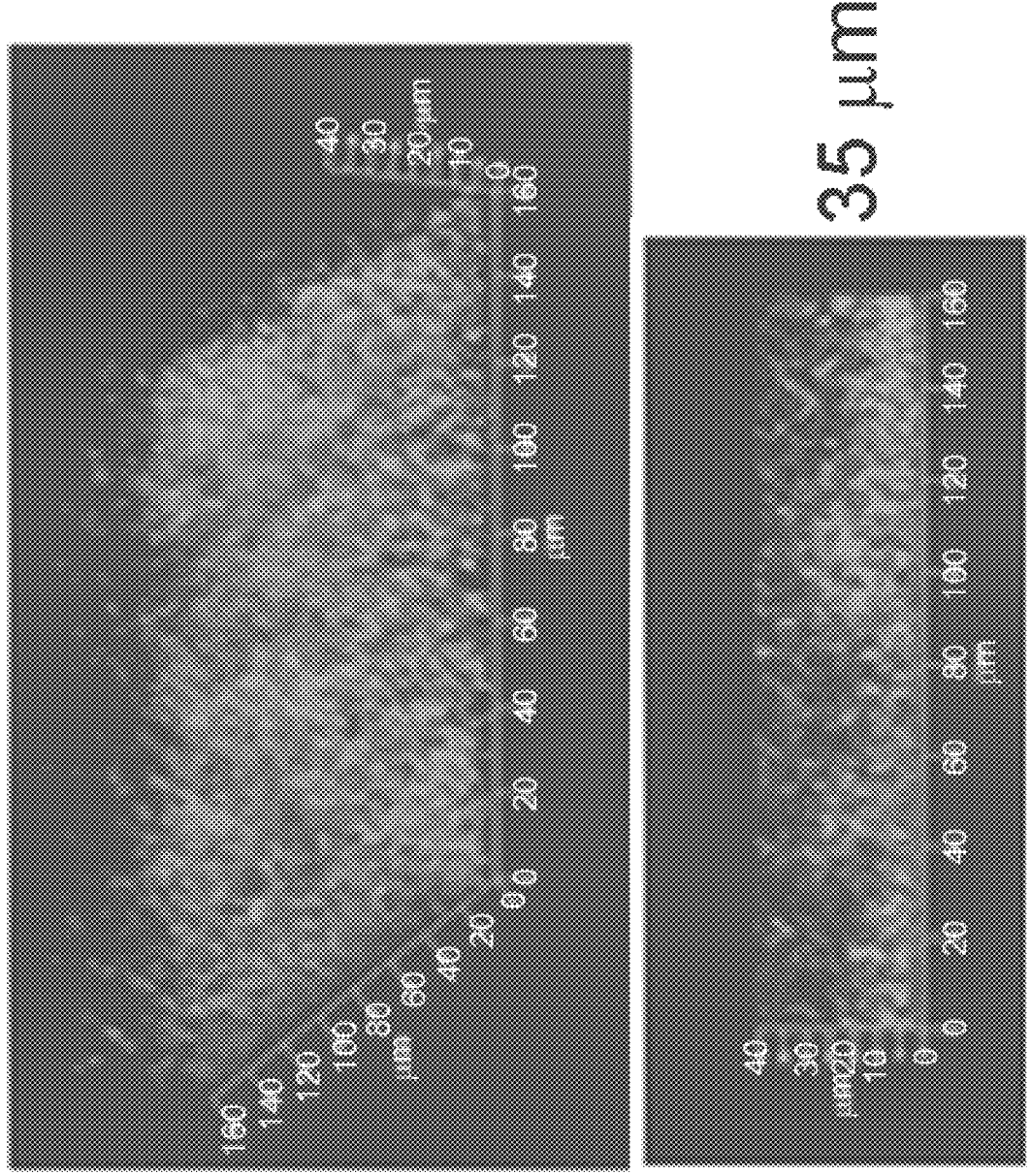
FIG. 15 is a comparison of E. coli treated with either naïve rabbit serum or rabbit anti-IHF serum (top row of images); with naive rat serum or rat anti-HNS serum (middle row of images); or with naive mouse serum or with mouse anti-DPS serum (bottom row of images). Note marked reduction in biomass following treatment with anti-IHF serum, however neither anti-HNS nor anti-DPS serum induced a reduction in biomass as used herein. Treatment with anti-IHF resulted in a 48.2% reduction in the biofilm height, an 81% reduction in the biofilm average thickness, and a 64.5% reduction in the biomass. In contrast treatment with the anti-HNS or anti-DPS resulted in a nominal height reduction of 0.7% and 4.2%, respectively, a reduction in the average thickness of 5.8% and 6.4% respectively, and a reduction in the biomass of 0.3% and −17.4% respectively.
Figure 15:
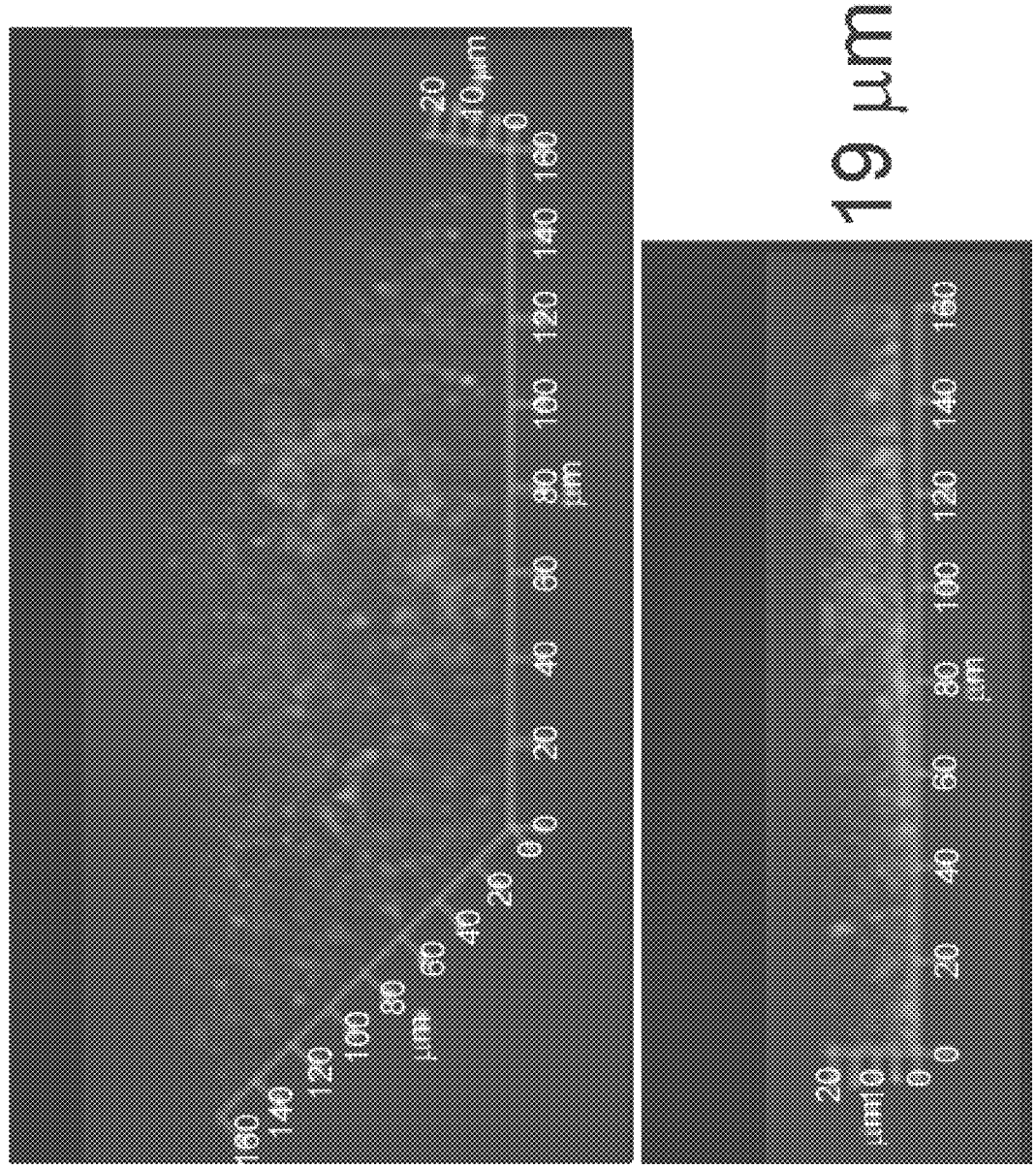
Figure 15:
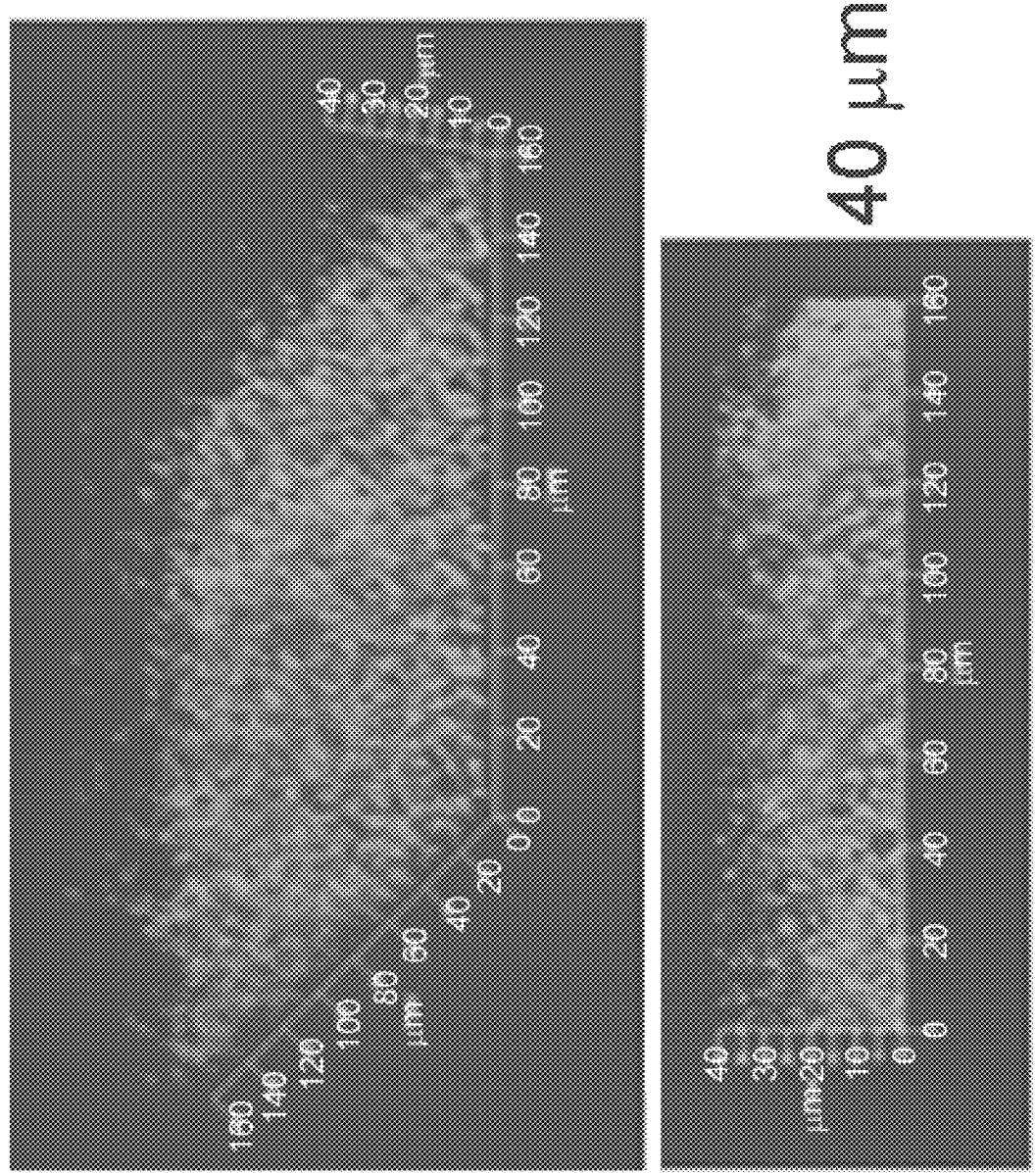
Figure 15:
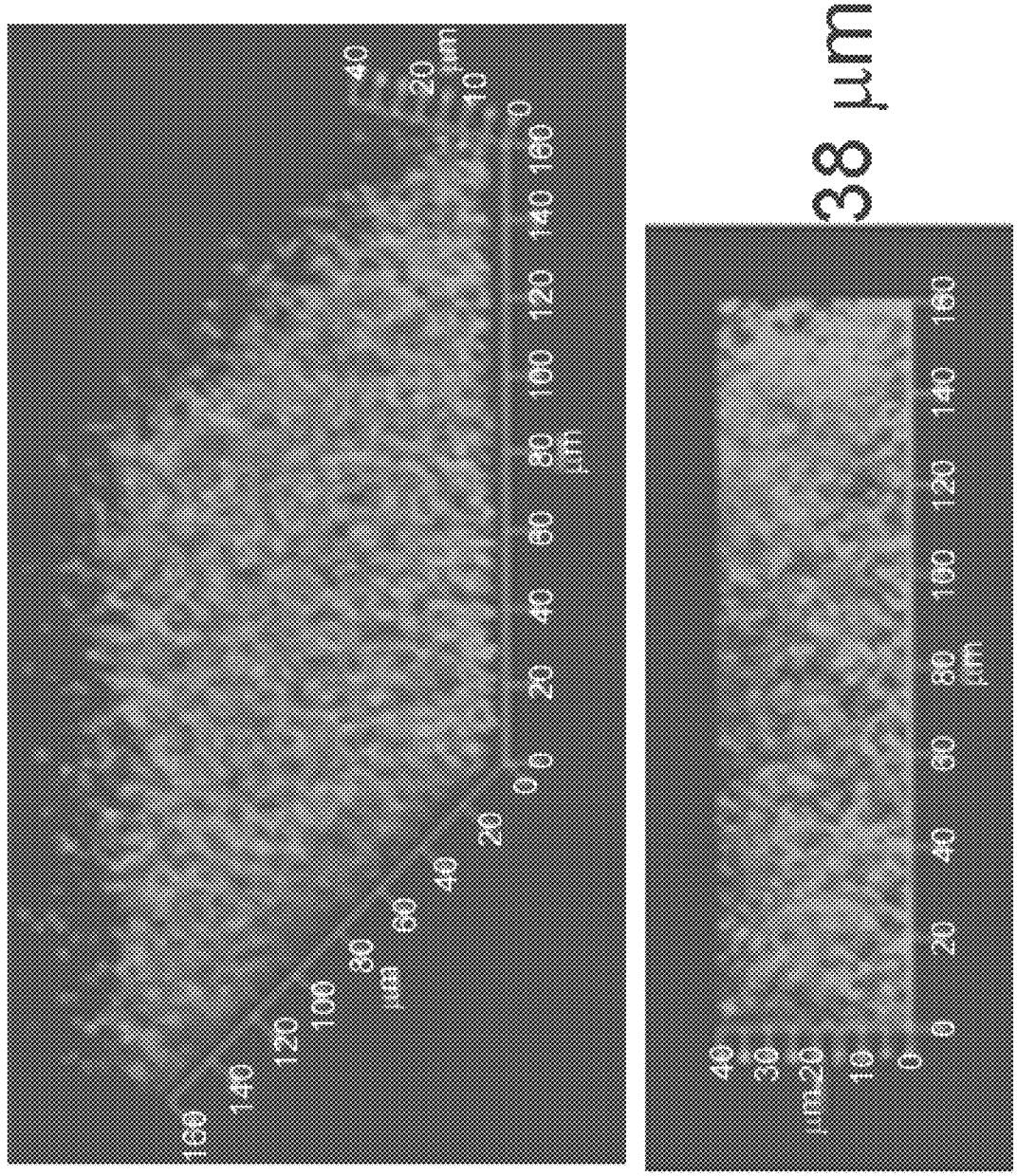
Figure 15:
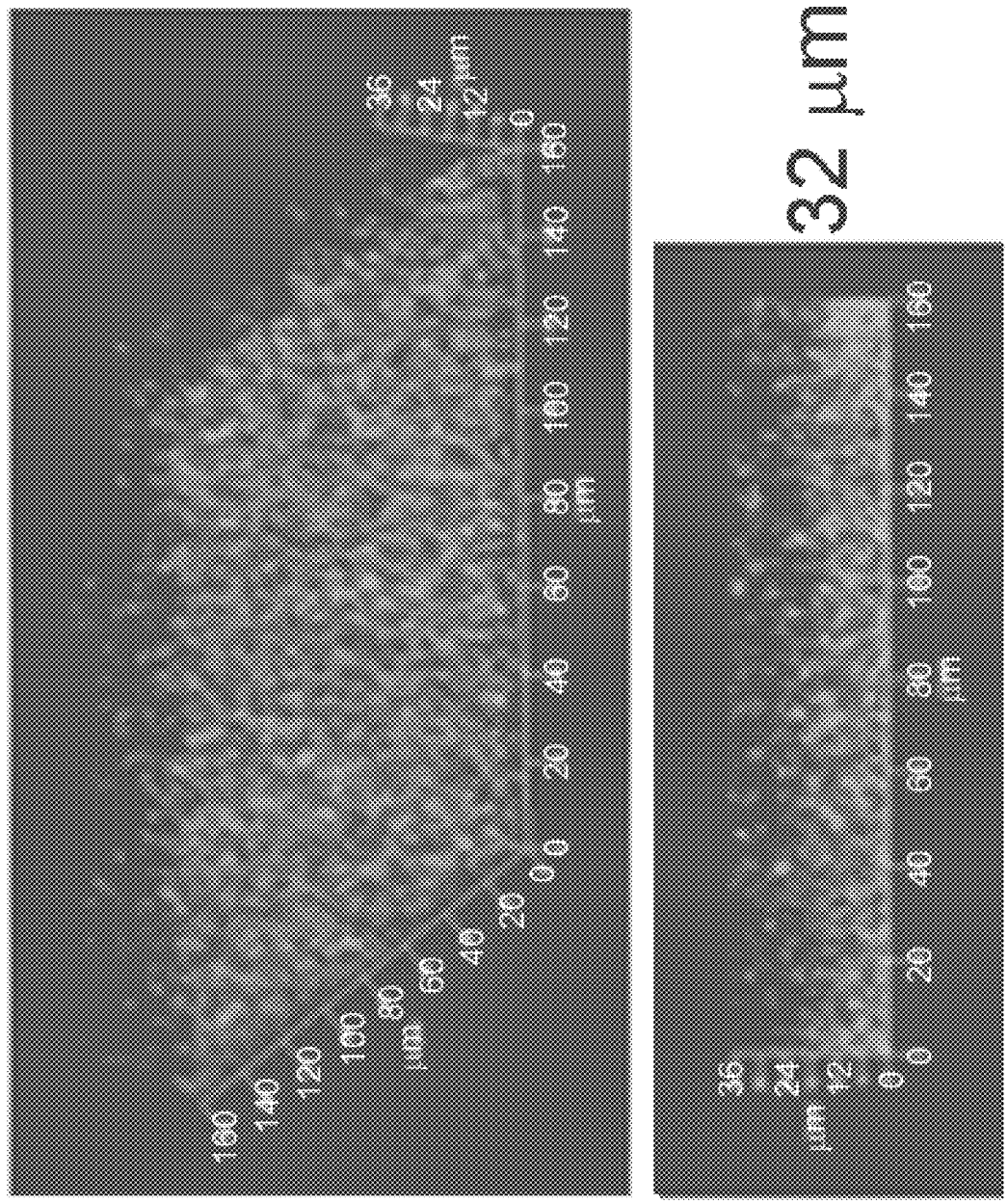
Figure 16:
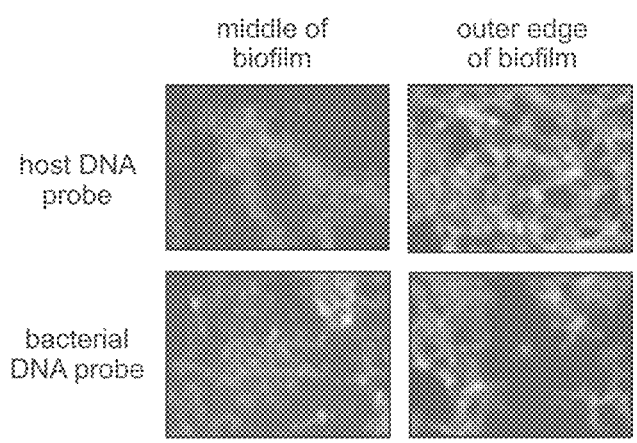
FIG. 16 shows in situ hybridization to demonstrate relative spatial distribution of DNA from either a host organism or from the bacterium when organized within a biofilm. In each circumstance, DNA appears as brighter, whiter areas within the foreground of these black and white images. DNA from the host is more densely labeled within the upper right hand image, demonstrating its more heavy distribution on the outer periphery of the biofilm, whereas DNA from the bacterium is more densely labeled in the lower left hand image of this 4-panel composite, thereby demonstrating its more dense distribution within the inner reaches of the biofilm.

To be assured that the observed DNA occlusion result was not specific to the use of a transcutaneous immunization route, these immunizations using a subcutaneous (SQ) immunization route to ensure delivery of the antigens to antigen presenting cells within the chinchilla host were repeated. As shown in FIG. 13, whereas SQ immunization with isolated *E. coli* IHF yielded the generation of a strong immune response to isolated IHF, immunization with *E. coli* IHF that had been pre-bound to an excess of DNA failed to induce detectable antibodies that recognized IHF when assayed by Western blot. When assayed by ELISA, reciprocal titer versus isolated IHF was 1000 for the animal immunized with IHF that had been pre-bound to oligonucleotides, whereas that for the animal immunized with native IHF was 8000 (both animal's pre-immune reciprocal titers against IHF were 100). Collectively, these results are consistent with our hypothesis that the binding of IHF to eDNA, as would occur during a natural disease state, has the potential to block epitopes or domains of IHF necessary for generation of a protective acquired immune response. Further, immunization with native IHF (to which no DNA is bound) appeared to allow for the effective direction of the immune response toward the generation of protective or neutralizing antibodies, as demonstrated in both pre-clinical chinchilla studies described here.

Experiment No. 4

A number of oral bacteria (e.g., *Aggregatibacter actinomycetemcomitans, Porphyromonas gingivalis*) have been implicated in the pathogenesis of inflammatory diseases such as periodontitis and peri-implantitis, which destroy alveolar bone and gingiva. Investigations of the pathogenesis of these bacteria are hampered by lack of effective animal models. One of the challenges of investigating the pathogenicity of specific bacteria is the difficulty of establishing a biofilm when exogenous bacteria are introduced into the oral cavity of animals. Though animal models of periodontitis have been developed, cultivable bacteria are rarely recovered from the oral cavity of inoculated animals. Developing an effective animal model which can assess the pathogenicity of specific bacteria wilt greatly aid in elucidating their pathogenic mechanisms.

The surface of machined titanium dental implants (1.2× 4.5 mm) was modified by grit blasting with A103 (100 µm) and HCl etching (pH 7.8 for 20 min at 80° C.). Machined and nano-textured implants were incubated in TSB medium inoculated with D7S clinical strain of *Aggregatibacter actinomycetemcomitans* (Aa) for 1 to 3 days at 37° C. The bacterial biofilm on the implants were analyzed by SEM, as well as by confocal laser scanning microscopy following staining with LIVE/DEAD® BacLight™. Implants with and without established Aa biofilm were transmucosally placed into the alveolar bone of female rats between premolar and incisor region of the maxillae. To detect the presence of Aa biofilm on the implants placed in vivo, bacterial samples were collected from saliva and the oral surfaces of implants after 2 days. Aa was detected by culture, as well as by PCR analysis. Micro-CT and histological analysis of peri-implant bone and mucosal tissues was performed six weeks after implantation.

After one day of cultivation, agglomerates of coccoid-shaped Aa cells were found scattered throughout the implant. After two days, the number and size of the agglomerates decreased and more cells of varying lengths were observed ranging between bacteria with coccoid morphology. After three days of incubation, the agglomerates had almost disappeared, while large areas of the implant surface were covered with bacteria with rod-shaped morphology, forming a densely packed biofilm. LIVE/DEAD® staining of such three days Aa biofilm on the implants showed green signal for 75-80% of all biofilm bacteria, indicating living cells with uncompromised membrane integrity. Microbiological and PCR detection of Aa biofilm on implants placed in vivo were positive for samples from die implant surfaces and negative for the saliva samples as well as control implants. Clinical examination demonstrated significant peri-implant mucosal inflammation around implants with Aa biofilm, compared with control untreated implants. Micro-CT and histological analysis of peri-implant bone and mucosal tissues is pending. Nano-textured implant surfaces favor the establishment of Aa biofilm and increase risk of peri-implantitis.

Experiment No. 5

This experiment provides a mouse model for pre-clinical testing of interfering agents to treat lyme disease. See Dresser et al. Pathogens 5(12)e1000680, Epub 2009 Dec. 4. Lyme disease is the most common tick-borne disease in the United States. Reported cases have more than doubled between 1992 and 2006, with approximately 29,000 new cases confirmed in 2008. Estimates are that the actual number of cases of Lyme disease may exceed that reported by a factor of 6-12 in endemic areas. By definition, these endemic areas are expanding as populations continue to move from cities to suburban and rural areas and whitetail deer (which carry the tick species *Ixodes*) increasingly roam these areas. Lyme disease is caused by the microorganism *Borrelia burgdorferi*, a spirochete. *B. burgdorferi* is transmitted via the bite of the *Ixodes* tick and subsequently disseminates, via the bloodstream, to other tissues and organs.

In this animal model, C3H/HeN mice are injected with spirochetes via dorsal subcutaneous and intraperitoneal injection, or via intravenous injection. Blood and biopsy specimens are recovered at approximately 7 days post infection for evaluation of microbial burden and assessment of pathology in tissues and organs. The methods and compositions disclosed herein are contemplated to develop both therapeutic as well as preventative strategies for reduction and/or elimination of the resulting *B. burgdorferi* biofilms which form subsequent to challenge and are believed to contribute to both the pathogenesis and chronic nature of the disease.

Experiment No. 6

This experiment provides a porcine model for pre-clinical testing of interfering agents to treat cystic fibrosis. See Stoltz et al. (2010) Science Translational Medicine 2(29):29-31. Cystic fibrosis is an autosomal recessive disease due to mutations in a gene that encodes the CF transmembrane conductance regulator (called CFTR) anion channel. In this model, pigs which have been specifically bred to carry a defect in the genes called "CFTR" and called CF pigs spontaneously develop hallmark features of CF lung disease that includes infection of the lower airway by multiple bacterial species. The pigs can be immunized with the interfering agents to either 1) immunize these CF pigs with a polypeptide or other immunogenic agent thereby inducing the formation of antibodies which will eradicate bacterial biofilms in the lungs (similarly to how antibodies to IHF eradicated biofilms resident within the middle ears of chinchillas following active immunization as shown in Experiment No. 1, to deliver anti-IHF (or other interfering agent) to the lungs of these animals by nebulization to assess the amelioration of the signs of disease and associated pathologies.

Experiment No. 7

Applicants also provide a pre-clinical model for tuberculosis (TB). See Ordway et al. (2010) Anti. Agents and Chemotherapy 54:1820. The microorganism *Mycobacterium tuberculosis* is responsible for a growing global epidemic. Current figures suggest that there are approximately 8 million new cases of TB and about 2.7 million deaths due to TB annually. In addition to the role of this microbe as a co-infection of individuals with HIV (of the ~45 million infected with HIV, estimates are that ~⅓ are also co-infected with *M. tuberculosis*), its particularly troublesome that isolates have become highly resistant to multiple drugs and no new drug for TB has been introduced in over a quarter of a century. In this animal model, SPF guinea pigs are maintained in a barrier colony and infected via aerosolized spray to deliver ~20 cfu of *M. tuberculosis* strain Erdman K01 bacilli into their lungs. Animals are sacrificed with determination of bacterial load and recovery of tissues for histopathological assessment on days 25, 50, 75, 100, 125 and 150 days post-challenge. Unlike mice which do not develop classic signs of TB, guinea pigs challenged in this manner develop well-organized granulomas with central necrosis, a hallmark of human disease. Further, like humans, guinea pigs develop severe pyogranulomatous and necrotizing lymphadenitis of the draining lymph nodes as part of the primary lesion complex. Use of this model will provide a pre-clinical screen to confirm and identify therapeutic as well as preventative strategies for reduction and/or elimination of the resulting *M. tuberculosis* biofilms which have been observed to form in the lungs of these animals subsequent to challenge and are believed to contribute to both the pathogenesis and chronicity of the disease.

Experiment No. 8

Multiple animal models of catheter/indwelling device biofilm infections are known. See Otto (2009) Nature Reviews Microbiology 7:555. While typically considered normal skin flora, the microbe *Staphylococcus epidermidis* has become what many regard as a key opportunistic pathogen, ranking first among causative agents of nosocomial infections. Primarily, this bacterium is responsible for the majority of infections that develop on indwelling medical devices which are contaminated by this common skin colonizer during device insertion. While not typically life-threatening, the difficulty associated with treatment of these biofilm infections, combined with their frequency, makes them a serious public health burden. Current costs associated with treatment of vascular catheter associated bloodstream infections alone that are due to *S. epidermidis* amount to $2 billion annually in the United States. In addition to *S. epidermidis*, *E. faecalis* and *S. aureus* are also contaminations found on indwelling medical devices. There are several animal models of catheter-associated *S. epidermidis* infections including rabbits, mice, guinea pigs and rats all of which are used to study the molecular mechanisms of pathogenesis and which lend themselves to studies of prevention and/or therapeutics. Rat jugular vein catheters have been used to evaluate therapies that interfere with *E. faecalis*, *S. aureus* and *S. epidermidis* biofilm formation. Biofilm reduction is often measured three ways—(i) sonicate catheter and calculate CFUs, (ii) cut slices of catheter or simply lay on a plate and score, or (iii) the biofilm can be stained with crystal violet or another dye, eluted, and OD measured as a proxy for CFUs.

Experiment No. 9

Methods described herein may be used to elicit immune responses in humans and animals. Immunogenic compositions may be administered to a human and animal subjects in the presence of adjuvants such as but not limited to aluminum salts and liposomes. Those skilled in the art will understand that any number of pharmaceutically acceptable adjuvants can also be used. Immunogenic compositions may be administered to a human or animal subjects intramuscularly, subdermally, intranasally, or through any other suitable route. Immunogenic compositions may be prepared in a manner consistent with the selected mode of administration. Immunogenic compositions may take the form of polypeptides, nucleic acids, or a combination thereof, and may comprise full-length or partial antigens. Additionally or alternatively, immunogenic compositions may take the form of APCs pulsed with a particular antigen, or APCs transfected with one or more polynucleotides encoding a particular antigen. Administration may comprise a single dose of an immunogenic composition, or an initial administration, followed by one or more booster doses. Booster doses may be provided a day, two days, three days, a week, two weeks, three weeks, one, two, three, six or twelve months, or at any other time point after an initial dose. A booster dose may be administered after an evaluation of the subject's antibody titer.

Experiment No. 10

Methods described herein may be used to confer passive immunity on a non-immune subject. Passive immunity against a given antigen may be conferred through the transfer of antibodies or antigen binding fragments that specifically recognize or bind to a particular antigen. Antibody donors and recipients may be human or non-human subjects. Additionally or alternatively, the antibody composition may comprise an isolated or recombinant polynucleotide encoding an antibody or antigen binding fragment that specifically recognizes or binds to a particular antigen.

Passive immunity may be conferred in cases where the administration of immunogenic compositions poses a risk for the recipient subject, the recipient subject is immunocompromised, or the recipient subject requires immediate immunity. Immunogenic compositions may be prepared in a manner consistent with the selected mode of administration. Compositions may comprise whole antibodies, antigen binding fragments, polyclonal antibodies, monoclonal antibodies, antibodies generated in vivo, antibodies generated in vitro, purified or partially purified antibodies, or whole serum. Administration may comprise a single dose of an antibody composition, or an initial administration followed by one or more booster doses. Booster doses may be provided a day, two days, three days, a week, two weeks, three weeks, one, two, three, six or twelve months, or at any other time point after an initial dose. A booster dose may be administered after an evaluation of the subject's antibody titer.

Experiment 11

Figure 8A:
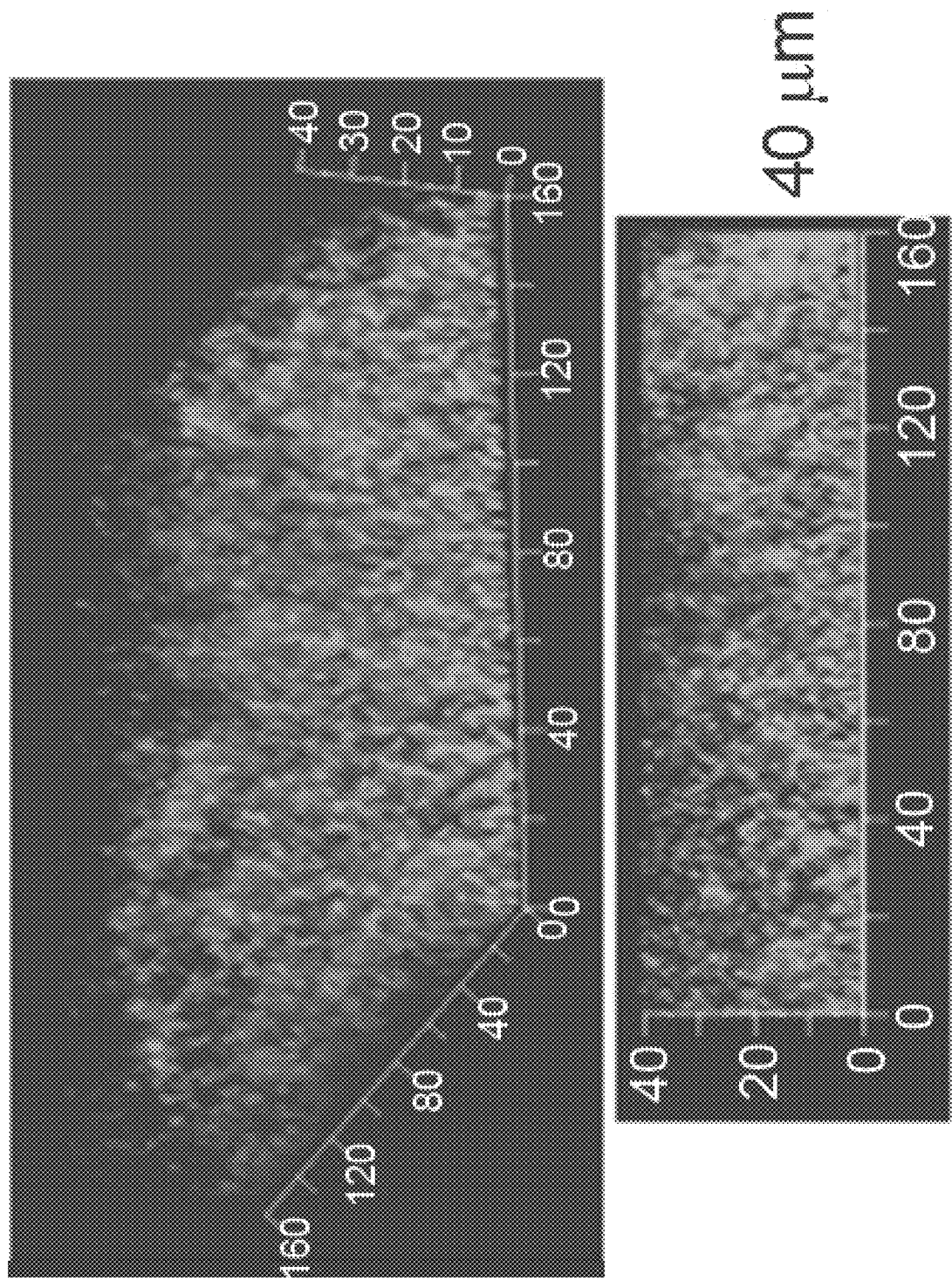
FIGS. 8A-8F show the effect of incubation of biofilms formed in vitro by E. coli with either naïve serum or with anti-IHF serum. Representative images of biofilms are shown in FIGS. 8A-8F with height of individual biofilms shown to the right of each image, whereas mean values in terms of percent reduction in biofilm height, biomass and mean thickness as mediated by incubation with anti-IHF are shown in the tables at the end of each row.
Figure 8B:
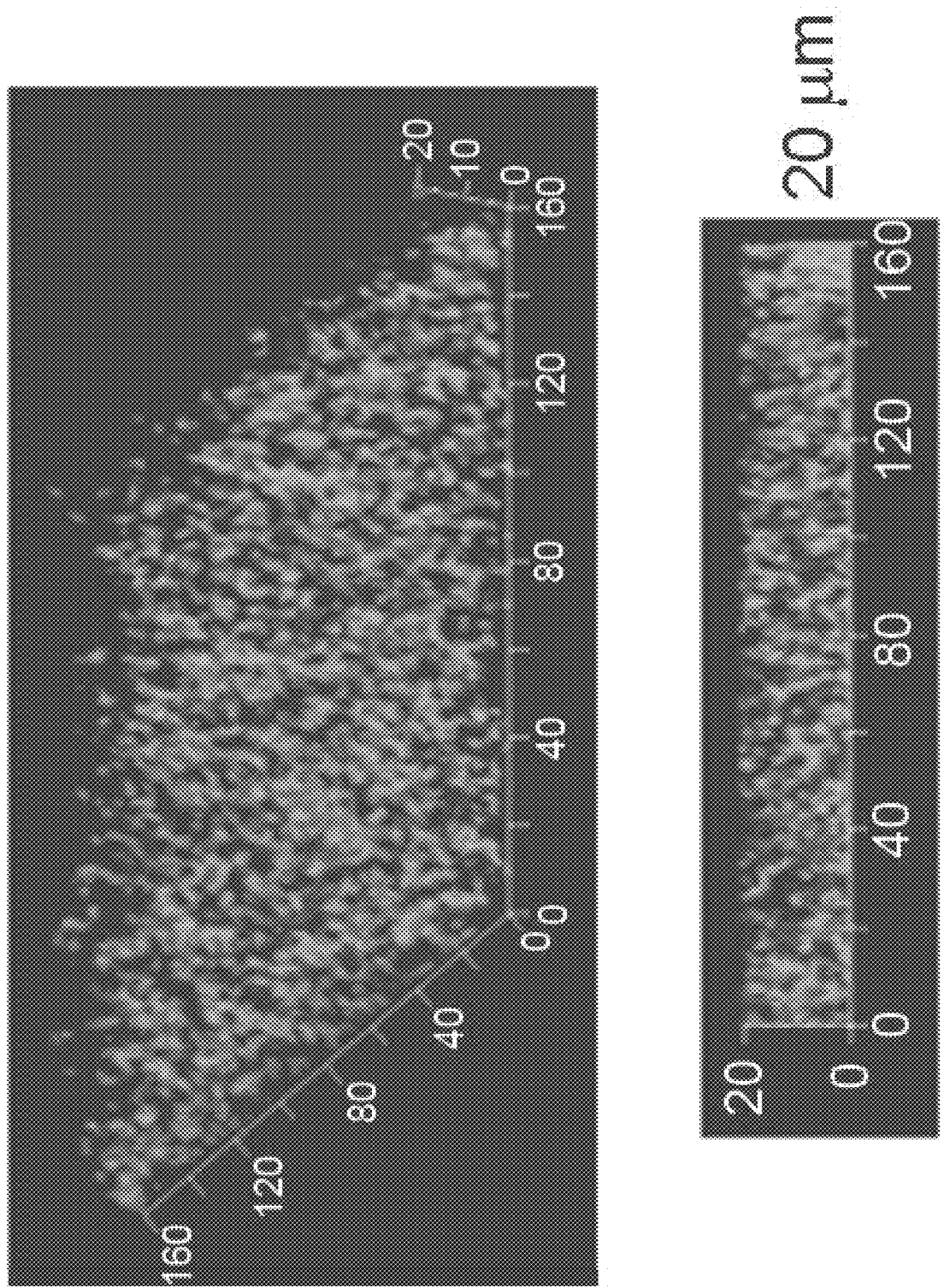
Figure 8C:
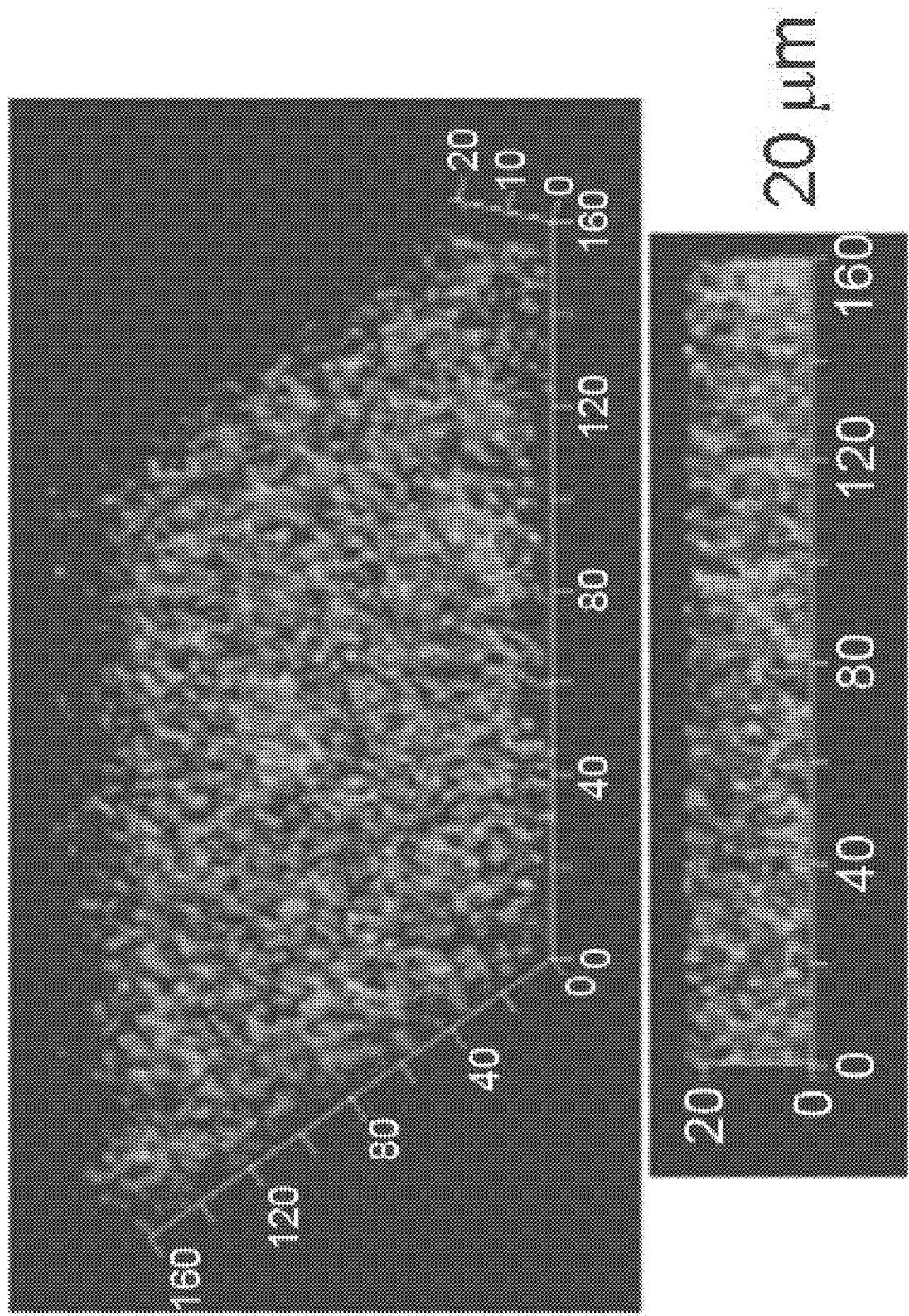
Figure 8D:
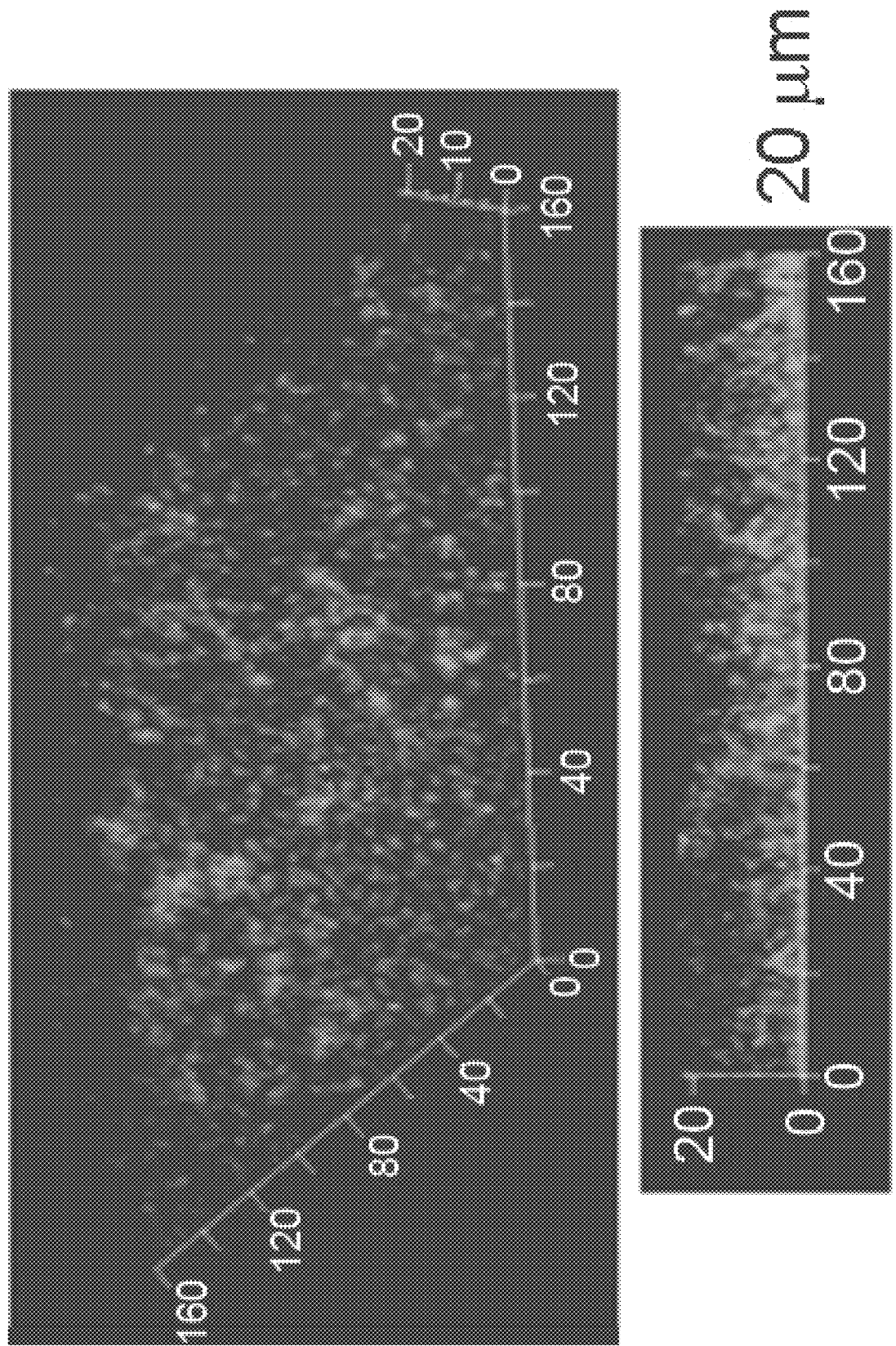
Figure 8E:
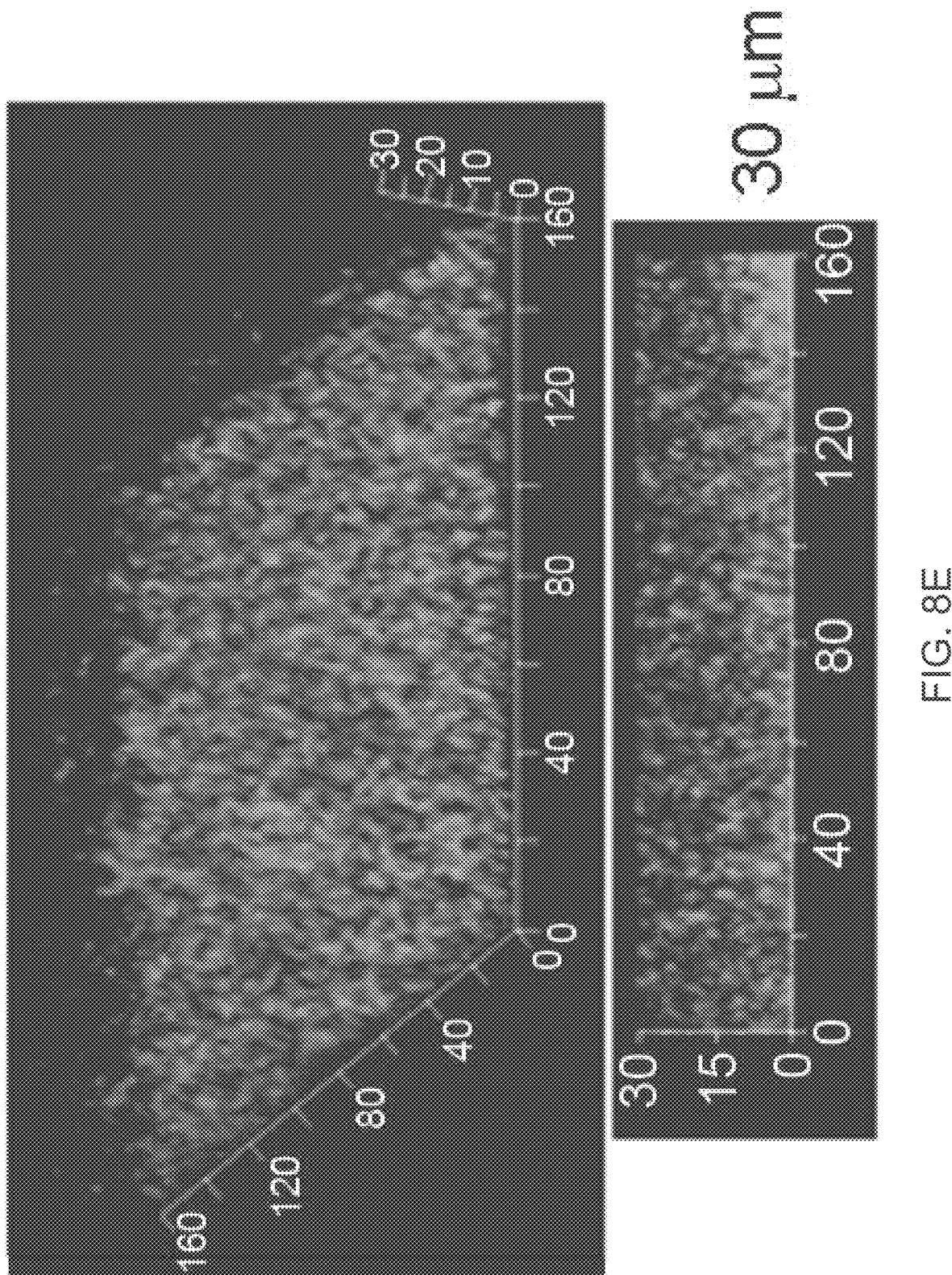
Figure 8F:
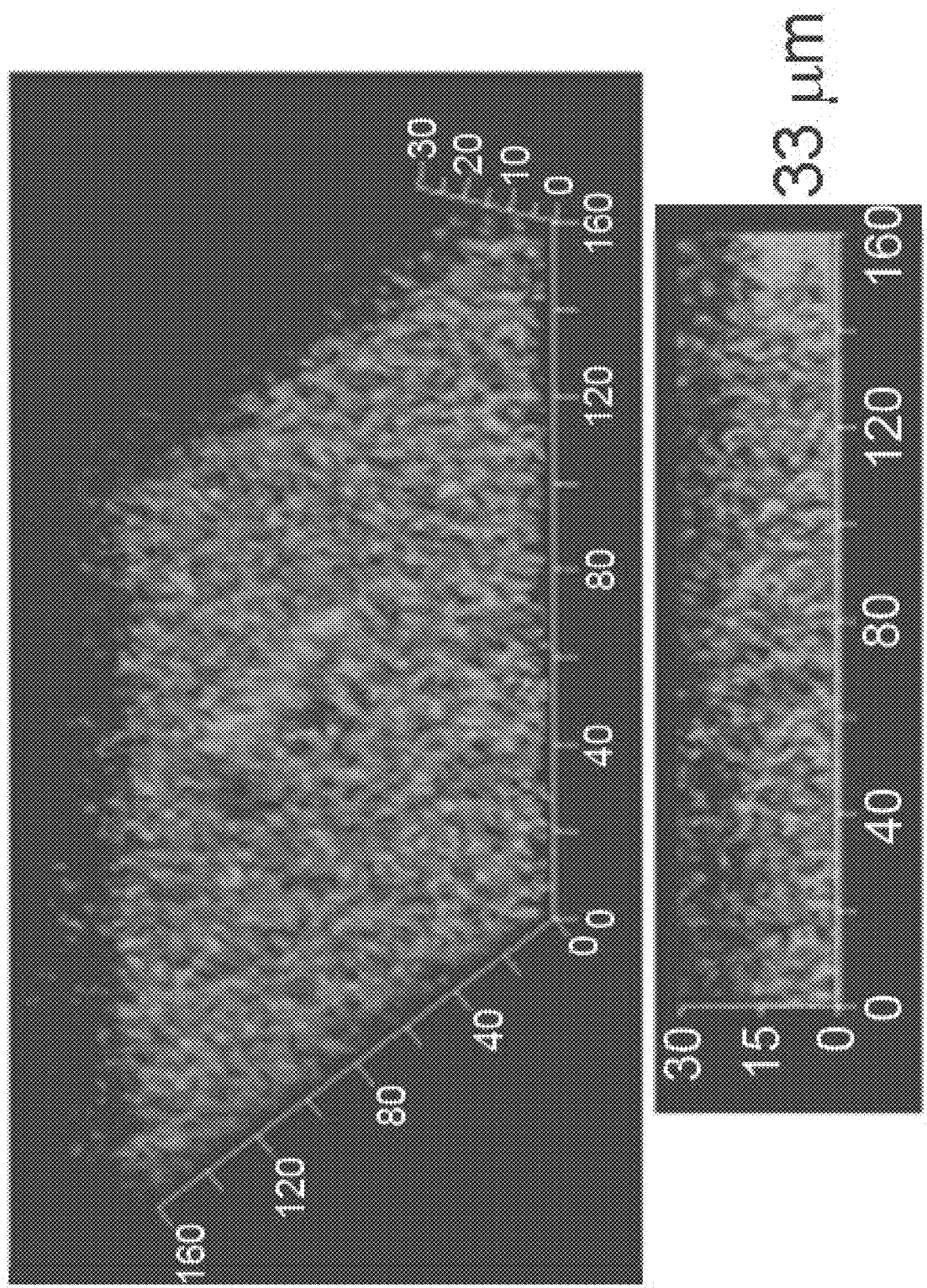

Members of the DNABII family are highly pleiotropic for multiple nucleoprotein systems including gene transcription, and moreover, are thus often essential. In contrast, both HU and IHF mutants have been generated in laboratory strains of E. coli and studied extensively. To determine what role IHF and HU have in eDNA formation, biofilms formed by E. coli strain MG1655 or its HU and IHF deficient derivatives were incubated with anti-IHF (prepared as described in Granston and Nash (1993) J. Mol. Biol. 234:45-59.) As shown in FIGS. 8A-8F, whereas the parental isolate, strain MG1655 produced a robust biofilm in vitro (FIG. 8A), both HU and IHF mutant strains were less robust (FIGS. 8C and 8E, respectively). An HU deficient mutant yielded a biofilm that was approximately ½ the height of the wild type biofilm, whereas IHF deficient strains produced a biofilm that was approximately ⅔ rds the height of the parental isolate. This result suggested that both proteins were involved in either the production and/or integrity of the E. coli biofilm EPS. After treatment with anti-IHF, the biofilm formed by the wild type isolate showed notable debulking and a mean percent reduction of 58.1% in height, 73.1% percent reduction in biomass and 87% reduction in mean thickness (FIG. 8B), whereas that formed by the HU mutant showed no reduction in height and only a 30.9% reduction on biomass and 37.2% reduction on mean thickness (FIG. 8D). In contrast, no effect on the biofilm formed by the IHF mutant was observed in terms of loss of height (−3.4% reduction), biomass (−20.5% reduction) or mean thickness (−19.8% reduction) (FIG. 8F). Collectively, these data indicated that for this strain of E. coli, IHF was likely the only structural element that could be targeted by use of the anti-IHF antibody. Since to date only the highly structured interwoven eDNA in biofilms that have been formed in vivo have been seen, confirmation of the expression of remaining DNABII family member by each respective mutant and any change in the resultant DNA structure awaits an in vivo immunofluorescent analysis.

Experiment 12

Whereas it was demonstrated in this application in vitro and in vivo that both anti-IHF and the use of IHF as an immunogen show utility in debulking biofilms and/or resolving biofilm disease respectively, it was unknown if dispersing of NTHI biofilms with anti-IHF might also allow synergism when used in conjunction with other therapeutic modalities. To this end the ability to induce augmented structural destabilization of pre-formed NTHI biofilms was assessed when a sub-optimal concentration of anti-IHF was used along with one of each of three unique reagents. These three reagents include 1) a DNA degrading enzyme (DNaseI) known to be able to degrade an NTHI biofilm in vitro (but used here at a suboptimal concentration), 2) antisera to an outer membrane protein of NTHI that did not destabilize a pre-formed NTHI biofilm when used alone (anti-OMP P5) (data not shown), and 3) an antibiotic typically used as a first line choice in children with chronic and/or recurrent OM (amoxicillin) but which has limited efficacy against bacteria resident within a biofilm community.

FIG. 14A shows that treatment of an NTHI biofilm with a concentration of DNase shown to be sub-optimal has a marginal effect (see FIG. 14A, Panel II). Likewise, a 1:200 dilution of anti-IHF had little effect on the pre-formed NTHI biofilm (see FIG. 14A, Panel III). In contrast however, when these two reagents were used in concert, the biofilm was notably diminished (see FIG. 14A, Panel IV). Upon repeat of this experiment three times, we found that the most marked synergistic effect of debulking of the biofilm was measured as a diminution in height. Table 7 below depicts these results.

TABLE 7

|  | DNase | Anti-IHF | DNase + anti-IHF | |
|---|---|---|---|---|
| Max height (μm) | 3.9 | 37.3 | 51.0 | Assay 1 |
| Max height (μm) | −11.5 | 16.4 | 37.7 | Assay 2 |
| Max height (μm) | −1.6 | 19.4 | 38.7 | Assay 3 |

One simple explanation for this outcome was that as the DNABII protein was being titrated away from the periphery of the biofilm, the eDNA became more accessible to the action of the DNase.

FIG. 14B shows the results of treatment with anti-OMP P5 on pre-formed NTHI biofilms. Although this antisera is strongly reactive with isolated NTHI OMP P5 (data not shown) and further, active immunization with isolated OMP P5 is effective in mediating significant protection against experimental OM in chinchilla models (see for e.g., Bakaletz et al. (1997) Vaccine 15(9):955-961; Bakaletz et al. (1999) Infect Immun 67(6):2746-2762; Kennedy et al. (2000) Infect Immun 68(5):2756-2765; Kyd, J. M. et al. (2003) Infect Immun 71(8):4691-4699; Novotny, L. A. et al. (2000) Infect Immun 68(4):2119-2128; Novotny, L. A. et al. (2002) Vaccine 20(29-30):3590-3597; Novotny, L. A. et al. (2003) J Immunol 171(4):1978-1983) this antiserum does not induce a change in the structural integrity of an NTHI biofilm that has been formed in vitro when used at a dilution of 1:50 (see FIG. 14B, Panel II). Likewise a marginal effect when these biofilms were incubated with a sub-optimal dilution of anti-IHF (used at a 1:100 dilution here) was observed (see FIG. 14B, Panel I). When combined, however, the use of anti-P5 plus anti-IHF resulted in a reduction in the height of the biofilm that exceeded the sum of the two antisera when used singly (see FIG. 14B, Panel III), thus indicating a synergistic outcome. Hence, it was concluded that use of anti-IHF to destabilize the NTHI EPS matrix resulted in the exposure of the targeted bacterial cell surface protein (e.g., OMP P5) that would otherwise be obscured by eDNA as well as perhaps other components of the EPS, thus allowing immune mediated bacterial clearance by as yet unknown mechanisms.

Figure 4A:
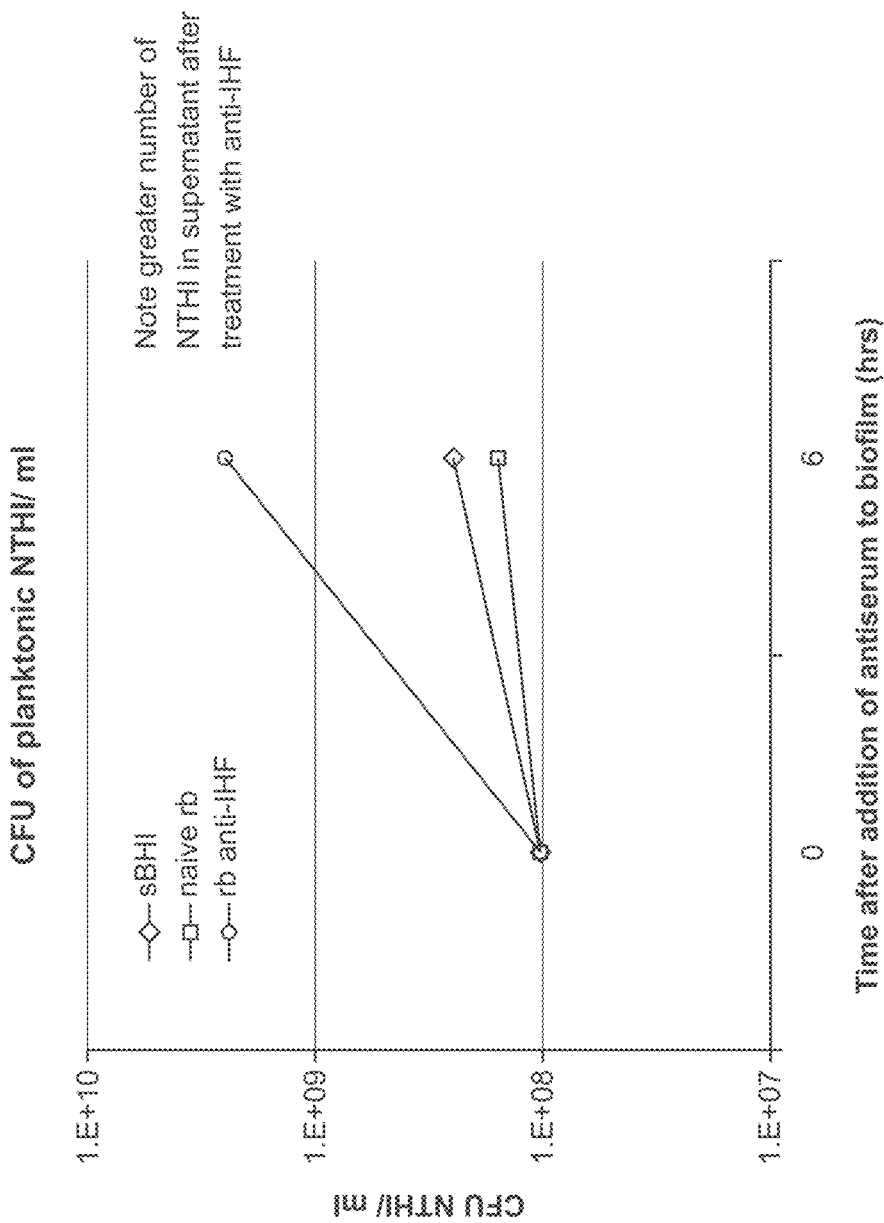
FIGS. 4A and 4B are graphs showing treatment of an established biofilm formed by NTHI with anti-IHF results in more NTHI released into the supernatant. Sixteen (16) hour NTHI biofilms grown in chamber slides were sham treated with sterile medium (sBHI) or treated with naïve rabbit serum or rabbit anti-IHF. Six hours later (FIG. 4A) or 10 hours later (FIG. 4B), supernatants were collected and analyzed. Note the greater number of NTHI in supernatant after treatment with anti-IHF. Incubation with anti-IHF resulted in a marked increase in planktonic bacteria available for culture from the medium within the chamber slide within approximately 6 hrs, and increasing notably at 10 hours of incubation. These results suggested release of bacteria from the biofilm matrix.
Figure 4B:
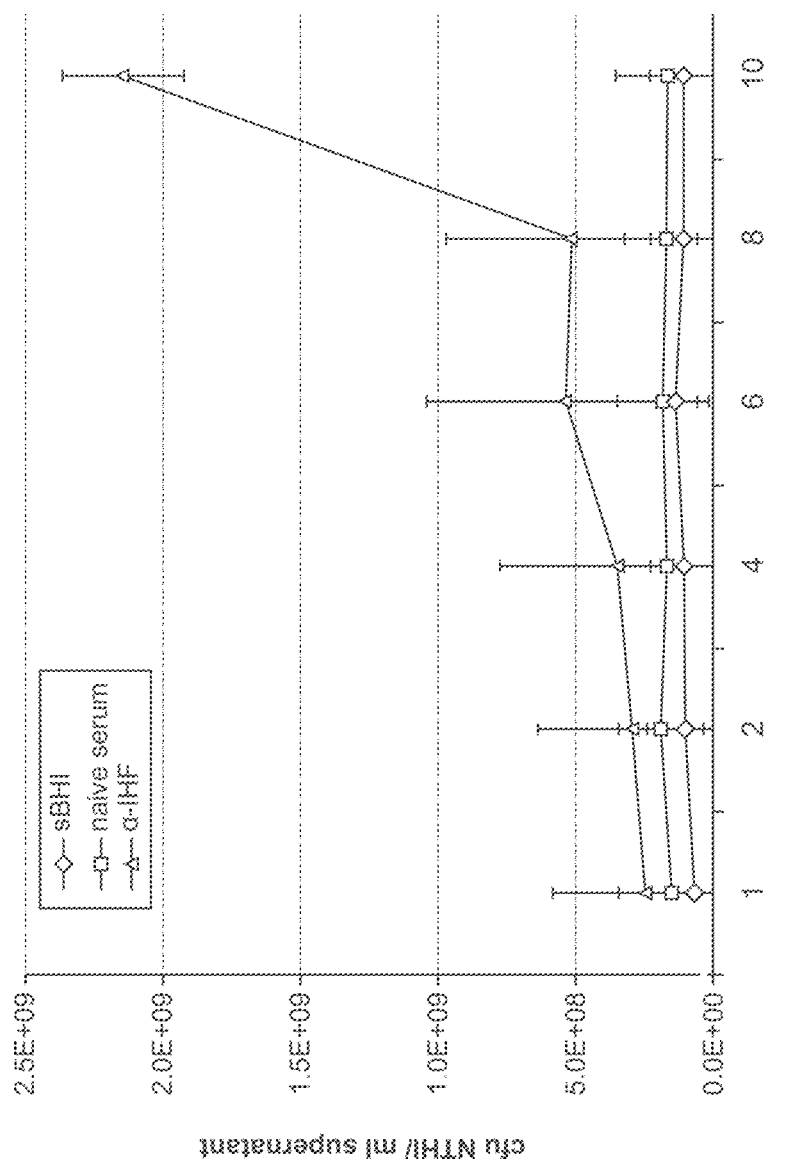

Lastly, FIG. 14C shows the results of treating pre-formed NTHI biofilms with amoxicillin. When used at a concentration of 64 μg/ml, amoxicillin had no measurable effect on the architecture of pre-formed NTHI biofilms (see FIG. 14C, Panel II) despite evidence of limited bacterial cell death. Treatment with IHF antisera at a 1:50 dilution substantially reduced the height of the biofilm as shown previously (see FIG. 14C, Panel III). Interestingly however, when the two reagents were used simultaneously, not only was there a dramatic reduction in the height of the biofilm (see FIG. 14C, Panel IV), but use of a vital dye indicated that the majority of the bacteria remaining in the biofilm were now dead as noted by the predominant fluorescence in the red channel within the imaged biofilm. This result showed that debulking of the biofilm with anti-IHF likely exposed the bacteria sufficiently so as to create conditions more akin to susceptibility to amoxicillin concentrations known to be effective when assayed against planktonic NTHI. This outcome may have been mediated by either increased physical exposure of bacteria within the remaining biofilm matrix to the action of amoxicillin and/or via increased release of bacteria into the planktonic phase as we showed earlier can occur during biofilm debulking by exposure to anti-IHF antibodies (see FIGS. 4A-4B).

Lastly, FIG. 14C shows the results of treating pre-formed NTHI biofilms with amoxicillin. When used at a concentration of 64 μg/ml, amoxicillin had no measurable effect on the architecture of pre-formed NTHI biofilms (see FIG. 14C, Panel II) despite evidence of limited bacterial cell death. Treatment with IHF antisera at a 1:50 dilution substantially reduced the height of the biofilm as shown previously (see FIG. 14C, Panel III). Interestingly however, when the two reagents were used simultaneously, not only was there a dramatic reduction in the height of the biofilm (see FIG. 14C, Panel IV), but use of a vital dye indicated that the majority of the bacteria remaining in the biofilm were now dead as noted by the predominant fluorescence in the red channel within the imaged biofilm. This result showed that debulking of the biofilm with anti-IHF likely exposed the bacteria sufficiently so as to create conditions more akin to susceptibility to amoxicillin concentrations known to be effective when assayed against planktonic NTHI. This outcome may have been mediated by either increased physical exposure of bacteria within the remaining biofilm matrix to the action of amoxicillin and/or via increased release of bacteria into the planktonic phase as we showed earlier can occur during biofilm debulking by exposure to anti-IHF antibodies (see FIGS. 4A-4B).

Experiment 13

Applicants sought to identify the immunodominant and immunoprotective domains of IHF 20-mer peptides with a 5-mer overlap were prepared from the deduced amino acid sequences of the genes that encode for IHF and HU in nontypeable *Haemophilus influenzae* (NTHI) strain 86-028NP (disclosed in FIG. 18). These peptides mimic the deduced amino acid sequence from N- to C-terminus but do not accommodate for either discontinuous or conformational epitopes within the properly folded native protein. Gross epitope mapping was performed using antiserum derived from chinchillas that had been parenterally immunized with native IHF isolated from *E. coli*+(the full length combination of both IHF subunits) and an adjuvant in order to determine if immunization with this protein would induce the formation of antibodies that could resolve pre-existing biofilms that had been formed in their middle ears by NTHI strain 86-028NP. The immunization was efficacious, thus inducing the formation of antibodies that eradicating experimental otitis media significantly earlier than controls which had received adjuvant only. Using BIACORE biosensor, the 20-mer peptides and antiserum from these animals, it was determined that the greatest immune recognition was to peptides that represented peptides A5 and B4 (from the alpha and beta subunit respectively). This was unexpected, as individuals suffering from biofilm diseases do not resolve biofilms thus suggesting that the observed result was a therapeutically induced environment Applicants considered how DNABII proteins would be available for responding to immunologically by the immune system in an individual with active disease wherein the DNABII proteins would most likely be complexed with eDNA within the biofilm matrix. Without being bound by theory, it was hypothesized that since IHF or HU would be complexed with eDNA in the biofilm during disease, this might mask the immunoprotective domains of the protein, thus making them unavailable to the immune system for recognition and generation of antibodies.

To test this hypothesis, additional cohorts of chinchillas were immunized with either native full length IHF from *E. coli* (obtained from Nash) or with native full length IHF from *E. coli* (obtained from Nash) that had been complexed to an excess of double stranded DNA in order to best mimic how it would be presented in nature. Again, using BIA-CORE biosensor, the 20-mer peptides and antiserum from these two cohorts of animals, it was again determined that for those animals immunized with native IHF, the greatest recognition was to peptides A5 and B4, however, when using serum derived from animals immunized with IHF that had been pre-complexed to an excess of DNA (to best mimic how the immune system "sees" this protein during disease, the greatest recognition was to peptides A3 and B2. Typically, for development of a novel vaccine or therapeutic, one epitope maps a protein based on how it is presented during disease, then one identifies the most immunodominant epitopes of that protein and uses these to attempt to design a vaccine candidate or immune target for treatment.

However, the epitope mapping data indicates that targeting the most immunodominant epitopes of IHF as available for responding to immunologically during disease for either vaccine or therapeutic development would be a flawed approach. Instead, it was necessary to immunize with epitopes that are not available for responding to immunologically during disease in order to redirect the immune system to the appropriate and immunoprotective targets. This would not have been determined had Applicants not immunized chinchillas with both native protein and protein that had been pre-complexed to an excess of DNA and performed both efficacy studies and comparative epitope mapping efforts.

Once these unexpected protective domains were identified, Applicants performed more fine mapping studies to better understand the mechanism(s) that underlined the results. To do so, the sequences of the 20-mer peptides were overlaid upon a theoretical 3D model of IHF or HU from NTHI (the deduced amino acid sequences of these NTHI proteins were substituted for those from *E. coli* for which a 3D crystal structure has already been obtained). It was found that the peptides A3 (amino acids 31 to 50 of IHF; SEQ ID NO: 350) and B2 (amino acids 16 to 35 of IHF; SEQ ID NO: 343) mapped to the "tails" of IHF whereas the peptides A5 (amino acids 61 to 80 of IHF; SEQ ID NO: 352) and B4 (46 to 65 of IHF; SEQ ID NO: 345) mapped to the 'tips' of the IHF protein. These data showed that during disease, the immune system likely only 'sees' the tails of these proteins as the tips are bound to eDNA and thus masked from the immune system. This observation would be counterintuitive to what is typically done to determine the most immunodominant epitope of a protein as presented by a bacterial pathogen during disease.

The generated 20-mer peptide were simply made in a sequence from N- to C-terminus, e.g., amino acids 1 to 20, 16 to 35, etc., and did not necessarily mimic the most optimal peptide sequence in terms of best reproducing either the structure of a discontinuous epitope or the 3-dimensional structure of these proteins (the latter of which is essential for their ability to bind to and bend DNA). Therefore, when needed, the amino acid sequence of a given 20-mer peptide was modified to better fit the new information obtained from the prior study on how these proteins interact with DNA, combined with our new understanding that the immunodominant epitopes of DNABII proteins bound to DNA were not the ones that would likely mediate a protective effect.

Experiment No. 14

Antibodies were raised in chinchillas against the IHFA and IHFB of *Haemophilus influenzae* according to the methods described in Experiment No. 1 specific to the polypeptide epitopes disclosed in SEQ ID NO: 342 to 353.

Figure 17:
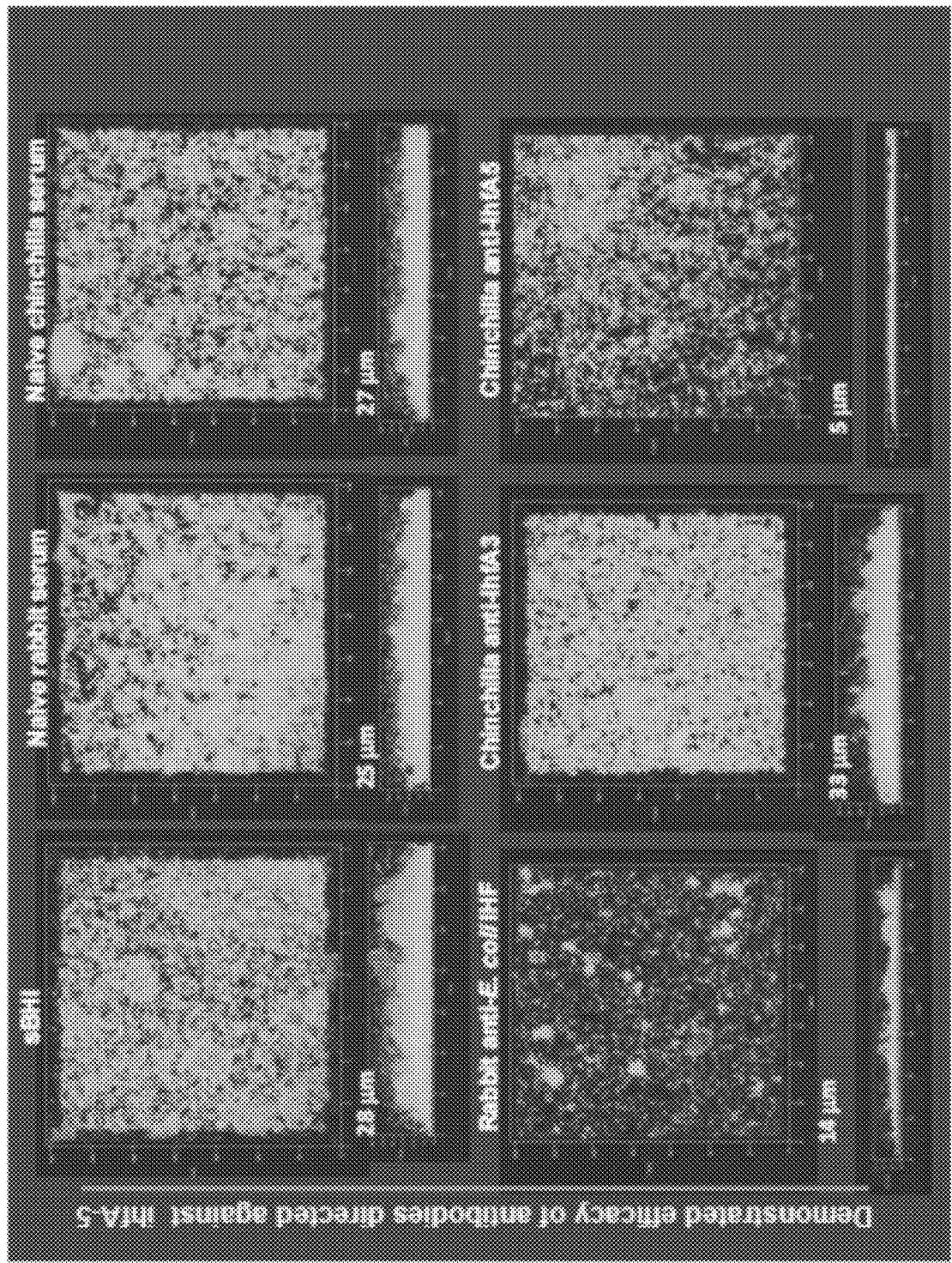
FIG. 17 depicts the reduction of biofilms formed by NTHI upon incubation with rabbit anti-IHF E. coli and chinchilla antibodies raised against IhfA, fragment A5 and A3, compared to incubation with naïve rabbit serum, chinchilla serum, and sBHI.

Using the in vitro model for reversal of an established biofilm described in Experiment 2 and these polyclonal antibodies, Applicants reduced a biofilm produced by NTHI. The disruption of the biofilm using the anti-IHF-A5 (raised against SEQ ID NO: 352) was significant (FIG. 17).

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

Unless otherwise defined, all technical and scientific terms used herein have the same meaning as commonly understood by one of ordinary skill in the art to which this disclosure belongs. All nucleotide sequences provided herein are presented in the 5' to 3' direction.

The embodiments illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure.

Thus, it should be understood that although the present disclosure has been specifically disclosed by specific embodiments and optional features, modification, improvement and variation of the embodiments therein herein disclosed may be resorted to by those skilled in the art, and that such modifications, improvements and variations are considered to be within the scope of this disclosure. The materials, methods, and examples provided here are representative of particular embodiments, are exemplary, and are not intended as limitations on the scope of the disclosure.

The scoped of the disclosure has been described broadly and generically herein. Each of the narrower species and subgeneric groupings falling within the generic disclosure also form part of the disclosure. This includes the generic description with a proviso or negative limitation removing any subject matter from the genus, regardless of whether or not the excised material is specifically recited herein.

In addition, where features or aspects of the disclosure are described in terms of Markush groups, those skilled in the art will recognize that embodiments of the disclosure may also thereby be described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

What is claimed is:

1. An isolated polypeptide consisting of (a) an amino acid sequence selected from MATITKLDIIEYLSDKYHLS (SEQ ID NO: 348), KYHLSKQDTKNVVENFLEEI (SEQ ID NO: 349), FLEEIRLSLESGQDVKLSGF (SEQ ID NO: 350), KLSGFGNFELRDKSSRPGRN (SEQ ID NO: 351), RPGRNPKTGDVVPVSARRVV (SEQ ID NO: 352), or ARRVVTFKPGQKLRARVEKTK (SEQ ID NO: 353), and
(b) a heterologous amino acid sequence selected from:
   (i) up to 20 random amino acids on the amine terminus of the amino acid sequence in (a); or
   (ii) up to 15 random amino acids on the carboxy terminus of the amino acid sequence in (a).

2. An isolated polypeptide consisting of
(a) an amino acid sequence selected from MATITKLDIIEYLSDKYHLS (SEQ ID NO: 348), KYHLSKQDTKNVVENFLEEI (SEQ ID NO: 349), FLEEIRLSLESGQDVKLSGF (SEQ ID NO: 350), KLSGFGNFELRDKSSRPGRN (SEQ ID NO: 351), RPGRNPKTGDVVPVSARRVV (SEQ ID NO: 352), or ARRVVTFKPGQKLRARVEKTK (SEQ ID NO: 353), and
(b) a heterologous amino acid sequence selected from:
   (i) up to 20 random amino acids on the amine terminus of the amino acid sequence in (a); or
   (ii) up to 15 random amino acids on the carboxy terminus of the amino acid sequence in (a); and
(c) a heterologous non-peptide domain.

3. An isolated polypeptide consisting of
(a) an amino acid sequence selected from MATITKLDIIEYLSDKYHLS (SEQ ID NO: 348), KYHLSKQDTKNVVENFLEEI (SEQ ID NO: 349), FLEEIRLSLESGQDVKLSGF (SEQ ID NO: 350), KLSGFGNFELRDKSSRPGRN (SEQ ID NO: 351), RPGRNPKTGDVVPVSARRVV (SEQ ID NO: 352), or ARRVVTFKPGQKLRARVEKTK (SEQ ID NO: 353),
(b) a heterologous amino acid sequence selected from:
   (i) up to 20 random amino acids on the amine terminus of the amino acid sequence in (a); or
   (ii) up to 15 random amino acids on the carboxy terminus of the amino acid sequence in (a); and
(c) a detectable label.

4. A composition consisting of an isolated polypeptide consisting of an amino acid sequence selected from: MATITKLDIIEYLSDKYHLS (SEQ ID NO: 348), KYHLSKQDTKNVVENFLEEI (SEQ ID NO: 349), FLEEIRLSLESGQDVKLSGF (SEQ ID NO: 350), KLSGFGNFELRDKSSRPGRN (SEQ ID NO: 351), RPGRNPKTGDVVPVSARRVV (SEQ ID NO: 352), or ARRVVTFKPGQKLRARVEKTK (SEQ ID NO: 353), and a pharmaceutically acceptable carrier.

5. A composition consisting of an isolated polypeptide consisting of an amino acid sequence and a detectable label, wherein the amino acid sequence is selected from: MATITKLDIIEYLSDKYHLS (SEQ ID NO: 348), KYHLSKQDTKNVVENFLEEI (SEQ ID NO: 349), FLEEIRLSLESGQDVKLSGF (SEQ ID NO: 350), KLSGFGNFELRDKSSRPGRN (SEQ ID NO: 351), RPGRNPKTGDVVPVSARRVV (SEQ ID NO: 352), or ARRVVTFKPGQKLRARVEKTK (SEQ ID NO: 353).

6. A composition consisting of an isolated polypeptide consisting of an amino acid sequence selected from: MATITKLDIIEYLSDKYHLS (SEQ ID NO: 348), KYHLSKQDTKNVVENFLEEI (SEQ ID NO: 349), FLEEIRLSLESGODVKLSGF (SEQ ID NO: 350), KLSGFGNFELRDKSSRPGRN (SEQ ID NO: 351), RPGRNPKTGDVVPVSARRVV (SEQ ID NO: 352), or ARRVVTFKPGQKLRARVEKTK (SEQ ID NO: 353) and an adjuvant.

7. The composition of claim 4, wherein the pharmaceutically acceptable carrier is selected from one or more of: an ion exchanger, a buffer, a saturated vegetable fatty acid, a salt, an electrolyte, a cellulose-based substance, an elixir, a buffering agent, a DNAse I, an antimicrobial, a preservative, a lubricant, a stabilizer, a glidant, or a flavoring agent.

8. A composition consisting of an isolated polypeptide consisting of an amino acid sequence selected from: MATITKLDIIEYLSDKYHLS (SEQ ID NO: 348), KYHLSKQDTKNVVENFLEEI (SEQ ID NO: 349), FLEEIRLSLESGODVKLSGF (SEQ ID NO: 350), KLSGFGNFELRDKSSRPGRN (SEQ ID NO: 351), RPGRNPKTGDVVPVSARRVV (SEQ ID NO: 352), or ARRVVTFKPGQKLRARVEKTK (SEQ ID NO: 353) and a pharmaceutically acceptable carrier and an adjuvant.

9. The composition of claim 8,
wherein the pharmaceutically acceptable carrier is selected from an ion exchanger, a buffer, a saturated vegetable fatty acid, a salt, an electrolyte, a cellulose-based substance, an elixir, a buffering agent, a DNAse I, an antimicrobial, a preservative, a lubricant, a stabilizer, a glidant, or a flavoring agent.

10. A composition consisting of an isolated polypeptide consisting of (a) an amino acid sequence selected from MATITKLDIIEYLSDKYHLS (SEQ ID NO: 348), KYHLSKQDTKNVVENFLEEI (SEQ ID NO: 349), FLEEIRLSLESGQDVKLSGF (SEQ ID NO: 350), KLSGFGNFELRDKSSRPGRN (SEQ ID NO: 351), RPGRNPKTGDVVPVSARRVV (SEQ ID NO: 352), or ARRVVTFKPGQKLRARVEKTK (SEQ ID NO: 353), and
(b) a heterologous amino acid sequence selected from:
   (i) up to 20 random amino acids on the amine terminus of the amino acid sequence in (a); or
   (ii) up to 15 random amino acids on the carboxy terminus of the amino acid sequence in (a) and a pharmaceutically acceptable carrier or an adjuvant.

11. The composition of claim 10, wherein the pharmaceutically acceptable carrier is selected from an ion exchanger, a buffer, a saturated vegetable fatty acid, a salt, an electrolyte, a cellulose-based substance, an elixir, a buffering agent, a DNAse I, an antimicrobial, a preservative, a lubricant, a stabilizer, a glidant, or a flavoring agent.

\* \* \* \* \*